(12) United States Patent
Oshima et al.

(10) Patent No.: US 8,664,217 B2
(45) Date of Patent: *Mar. 4, 2014

(54) BENZODIAZEPINE COMPOUND AND PHARMACEUTICAL COMPOSITION

(75) Inventors: Kunio Oshima, Osaka (JP); Takashi Oshiyama, Osaka (JP); Shinichi Taira, Osaka (JP); Yasuhiro Menjo, Osaka (JP); Hokuto Yamabe, Osaka (JP); Shuuji Matsumura, Osaka (JP); Masataka Ueda, Osaka (JP); Yasuo Koga, Osaka (JP); Kuninori Tai, Osaka (JP); Sunao Nakayama, Osaka (JP); Toshiyuki Onogawa, Osaka (JP); Kenji Tsujimae, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/591,361

(22) Filed: Aug. 22, 2012

(65) Prior Publication Data

US 2013/0040941 A1  Feb. 14, 2013

Related U.S. Application Data

(62) Division of application No. 12/918,226, filed as application No. PCT/JP2009/053623 on Feb. 20, 2009, now Pat. No. 8,338,406.

(30) Foreign Application Priority Data

Feb. 22, 2008 (JP) ................................. 2008-041296
Sep. 4, 2008 (JP) ................................. 2008-227368

(51) Int. Cl.
| | | |
|---|---|---|
| C07D 243/12 | (2006.01) | |
| C07D 401/12 | (2006.01) | |
| C07D 401/14 | (2006.01) | |
| C07D 491/04 | (2006.01) | |
| C07D 405/14 | (2006.01) | |
| C07D 417/14 | (2006.01) | |

(52) U.S. Cl.
USPC .......................................... 514/221; 540/518

(58) Field of Classification Search
USPC .......................................... 540/518; 514/221
See application file for complete search history.

(56) References Cited

U.S. PATENT DOCUMENTS

| | | | |
|---|---|---|---|
| 3,133,056 A | 5/1964 | Ash et al. | |
| 3,984,398 A | 10/1976 | Rossi | |
| 4,001,408 A | 1/1977 | Rossi | |
| 5,216,148 A | 6/1993 | Klaus et al. | |
| 7,321,001 B2 | 1/2008 | Fu et al. | |
| 2003/0158082 A1 | 8/2003 | Colclough et al. | |
| 2009/0264404 A1 | 10/2009 | Yamashita et al. | |

FOREIGN PATENT DOCUMENTS

| | | |
|---|---|---|
| EP | 0 504 695 A1 | 9/1992 |
| GB | 1 210 809 | 11/1970 |
| JP | 2-96133 | 4/1990 |
| WO | WO 96/40654 | 12/1996 |
| WO | WO 96/40655 | 12/1996 |
| WO | WO 01/10216 A1 | 2/2001 |
| WO | WO 01/77143 A2 | 10/2001 |
| WO | WO 2007/026959 A2 | 3/2007 |
| WO | WO 2009/104819 A1 | 8/2009 |

OTHER PUBLICATIONS

Alan S. Go et al.,"Prevalance of Diagnosed Atrial Fibrillation in Adults: National Implications for Rhythm Management and Stroke Prevention: the AnTicoagulation and Risk Factors in Atrial Fibrillation (ATRIA) Study," Journal of American Medical Association, 2001, vol. 285(18), pp. 2370-2375.

Yoko Miyasaka et al., "Secular Trends in Incidence of Atrial Fibrillation in Olmsted County, Minnesota, 1980 to 2000, and Implications on the Projections for Future Prevalance," Circulation, 2006, vol. 114, pp. 119-125.

Dan M. Roden, "Current Status of Class III Antiarrhythmic Drug Therapy," The American Journal of Cardiology, 1993, vol. 72, pp. 44B-49B.

(Continued)

*Primary Examiner* — Bruck Kifle
(74) *Attorney, Agent, or Firm* — Finnegan, Henderson, Farabow, Garrett & Dunner, L.L.P.

(57) ABSTRACT

The present invention provides a novel benzodiazepine compound that blocks the $I_{Kur}$ current or the Kv1.5 channel potently and more selectively than other K⁺ channels. The benzodiazepine compound of the invention is represented by General Formula (1)

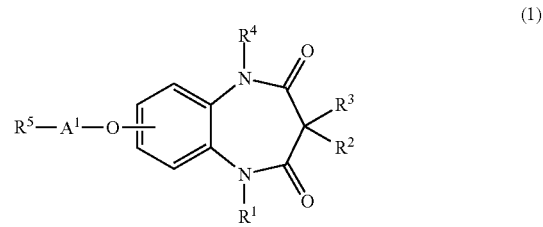

(1)

wherein $R^1$, $R^2$, $R^3$, and $R^4$ are each independently hydrogen or lower alkyl; $R^2$ and $R^3$ may be linked to form lower alkylene;
$A^1$ is lower alkylene optionally substituted with one or more hydroxy; and
$R^5$ is group represented by

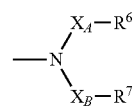

wherein $R^6$ and $R^7$ are each independently hydrogen or organic group;
$X_A$ and $X_B$ are each independently bond, lower alkylene, etc.

2 Claims, No Drawings

(56) References Cited

OTHER PUBLICATIONS

Richard L. Page et al., "Drug Therapy for Atrial Fibrillation: Where Do We Go From Here?," Nature Reviews/Drug Discovery, 2005, vol. 4, pp. 899-910.

Jamie I. Vandenberg et al., "HERG K+ channels: friend and foe," TRENDS in Pharmacological Sciences, 2001, vol. 22, No. 5, pp. 240-246.

Z. Wang et al., "Sustained depolarization-induced outward current in human atrial myocytes, Evidence for a novel delayed rectifier K+ current similar to Kv1.5 cloned channel currents," Circulation Research, 1993, vol. 73, pp. 1061-1076.

Gregory J. Amos et al., "Differences between outward currents of human atrial and subepicardial ventricular myocytes.," Journal of Physiology, 1996, vol. 491.1, pp. 31-50.

Jianlin Feng et al., "Antisense Oligodeoxynucleotides Directed Against Kv1.5 mRNA Specifiallly Inhibit Ultrarapaid Delayed Rectifier $K^+$ Current in Cultured Adult Human Atrial Myocytes," Circulation Research, 1997. vol. 80, No. 4, pp. 572-579.

G. Kraplvinsky et al., "The G-protein-gated atrial $K^+$ channel $I_{KACh}$ is a heteromultimer of two inwardly rectifying $K^+$-channel proteins," Nature, 1995, vol. 374, pp. 135-141.

Stanley Nattel et al., "Innovative approaches to anti-arrhythmic drug therapy," Nature Reviews/Drug Discovery, 2006, vol. 5, pp. 1034-1049, XP-002527589.

Examination Report issued in corresponding Pakistan patent application No. 719/2010.

European Patent Office, Supplementary European Search Report, dated Dec. 19, 2012, issued in European Patent Application No. EP 10 81 0017, 7 pages.

U.S. Patent and Trademark Office, "Office Action" in U.S. Appl. No. 13/391,466, dated May 20, 2013.

Bonsignore, L. et al., "Synthesis and Antimicrobial Activity of Coumarin and Benzodioxazepine-, Diazepine- and Benzoxazepine-substituted Penicillins," European Journal of Medicinal Chemistry, 1994, 29 (6), 479-485.

Office Action for U.S. Appl. No. 13/388,422 dated Sep. 20, 2013.

Office Action for U.S. Appl. No. 13/391,468 dated Oct. 9, 2013.

BENZODIAZEPINE COMPOUND AND PHARMACEUTICAL COMPOSITION

RELATED APPLICATIONS

This application is a divisional of U.S. application Ser. No. 12/918,226, filed Aug. 18, 2010 now U.S. Pat. No. 8,338,406, which is a §371 of International application No. PCT/JP2009/053623, filed Feb. 20, 2009, which claims priority of Japanese applications No. 2008-041296, filed Feb. 22, 2008, and No. 2008-227368, filed Sep. 4, 2008, the contents of all of which are incorporated herein by reference.

TECHNICAL FIELD

The present invention relates to a benzodiazepine compound and a pharmaceutical composition.

BACKGROUND ART

Atrial fibrillation (hereinafter referred to as "AF") is the most frequently observed type of arrhythmia in clinical examinations. Although not a lethal arrhythmia, AF causes cardiogenic cerebral embolism, and is therefore recognized as an arrhythmia that greatly affects vital prognoses and QOL. It is known that the onset of AF increases with age, and that repeated AF strokes lead to chronic (serious) AF (The Journal of American Medical Association, 285, 2370-2375 (2001) and Circulation, 114, 119-123 (2006)).

To prevent chronic AF, which causes difficulty in restoring sinus rhythm and increases the risk of cardiogenic cerebral embolism, early defibrillation and subsequent prevention of recurrence (maintenance of the sinus rhythm) are required. Antiarrhythmic drugs (classes I and III) are most commonly used as pharmacotherapy, but these drugs achieve insufficient therapeutic effects, while causing serious side effects such as a proarrhythmic effect (Am. J. Cardiol., 72, B44-B49 (1993)).

The onset of AF is triggered by atrial premature contraction with underlining causes such as intra-atrial conduction delay, shortening and heterogeneity of the atrial refractory period (Nature Reviews DRUG DISCOVERY 4, 899-910 (2005)). It is known that the prolongation of refractory period of atrial muscle can terminate AF (defibrillation) or prevent the occurrence of AF. The action potential duration of the mammalian cardiac muscle is predominantly determined by voltage-dependent $K^+$ channels. Inhibition of the $K^+$ channel prolongs myocardial action potential duration, which results in prolongation of the refractory period (Nature Reviews DRUG DISCOVERY 5, 1034-49 (2006)). The action mechanism of class III antiarrhythmic drugs (e.g., Dofetilide) is to inhibit rapid delayed rectifier $K^+$ current ($I_{Kr}$), $K^+$ current encoded by HERG. However, since $I_{Kr}$ is present in both the atria and ventricles, such drugs might cause ventricular arrhythmias, such as torsades de pointes (Trends Pharmacol. soc., 22, 240-246 (2001)).

Ultra-rapid delayed rectifier $K^+$ current ($I_{Kur}$), $K^+$ current encoded by Kv1.5, has been identified as $K^+$ channel that is specifically expressed only in human atria (Cric. Res., 73, 1061-1076 (1993), J. Physiol., 491, 31-50 (1996) and Cric. Res., 80, 572-579 (1997)). Muscarine potassium current ($I_{KACh}$) encoded by two genes called GIRK1 and GIRK4 is known as a $K^+$ channel specifically expressed in human atria (Nature 374, 135-141 (1995)). Accordingly, a pharmacologically acceptable substance that selectively blocks the $I_{Kur}$ current (the Kv1.5 channel) or the $I_{KACh}$ current (GIRK1/4 channel) can act selectively on the atrial muscle and is considered effective to exclude the proarrhythmic effect caused by prolonged action potential duration of the ventricular muscle.

DISCLOSURE OF THE INVENTION

The present inventors conducted extensive research to develop a compound that blocks the $I_{Kur}$ current (Kv1.5 channel) and/or the $I_{KACh}$ current (GIRK1/4 channel) potently and more selectively than other $K^+$ channels. As a result, the inventors found that a novel benzodiazepine compound represented by General Formula (1) below could be the desired compound. The present invention has been accomplished based on the above findings.

The present invention provides benzodiazepine compounds, and pharmaceutical compositions comprising the benzodiazepine compounds as summarized in items 1 to 13 below.

Item 1. A benzodiazepine compound represented by General Formula (1)

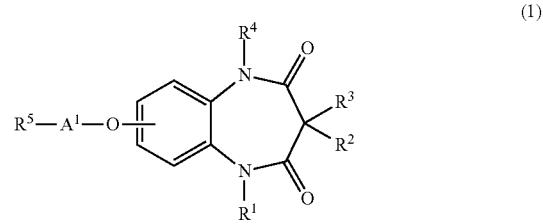

or a salt thereof,
wherein $R^1$, $R^2$, $R^3$, and $R^4$ are each independently hydrogen or lower alkyl;
$R^2$ and $R^3$ may be linked to form lower alkylene;
$A^1$ is lower alkylene optionally substituted with one or more hydroxy; and
$R^5$ is group represented by

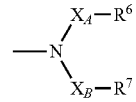

wherein $R^6$ and $R^7$ are each independently hydrogen or organic group;
$X_A$ and $X_B$ are each independently bond, lower alkylene, lower alkenylene, —CO—, —SO$_2$—, —SO$_2$-lower alkylene, —CO-lower alkylene, —CO-lower alkenylene, lower alkylene-N(lower alkyl)-CO-lower alkylene, lower alkylene-N(lower alkyl)-, lower alkylene-N(lower alkyl)-CO— or lower alkylene-O—.

Item 2. A benzodiazepine compound represented by General Formula (1) or a salt thereof according to item 1,
wherein $R^6$ and $R^7$ are each independently hydrogen, lower alkyl, cyclo lower alkyl, aryl or heterocyclic group.

Item 3. A benzodiazepine compound represented by General Formula (1) or a salt thereof according to item 2,
wherein $R^6$ and $R^7$ are each independently hydrogen, lower alkyl, cyclo lower alkyl, aryl or saturated or unsaturated monocyclic or polycyclic heterocyclic group containing at least one hetero atom selected from among oxygen, sulfur and nitrogen.

Item 4. A benzodiazepine compound represented by General Formula (1) or a salt thereof according to item 3,
wherein $R^6$ and $R^7$ are each independently hydrogen, lower alkyl, cyclo lower alkyl, phenyl, naphthyl, furyl, thienyl, pyrazolyl, oxazolyl, isoxazolyl, thiazolyl, pyrrolyl, triazolyl, pyridyl, pyrimidinyl, pyridazinyl, pyrazinyl, imidazo[2,1-b]thiazolyl, thieno[2,3-b]pyrazinyl, 2,3-dihydroimidazo[2,1-b]thiazolyl, benzothiazolyl, indolyl, imidazo[1,2-a]pyridyl, benzothienyl, benzimidazolyl, 2,3-dihydrobenzo[b]furyl, benzofuryl, indazolyl, furo[2,3-c]Pyridyl, furo[3,2-c]pyridyl, thieno[2,3-c]pyridyl, thieno[3,2-c]pyridyl, thieno[2,3-b]pyridyl, benzo[1,3]dioxolyl, benzisoxazolyl, pyrazolo[2,3-a]pyridyl, indolizinyl, 2,3-dihydroindolyl, isoquinolyl, 1,2,3,4-tetrahydro-1H-isoquinolyl, carbostyril, 3,4-dihydrocarbostyril, quinolyl, chromanyl, 5,6,7,8-tetrahydroisoquinolyl, 3,4-dihydro-1H-isoquinolyl, naphthyridinyl, 1,4-benzodioxanyl, cinnolinyl, quinoxalinyl, or 2,3-dihydrobenz-1,4-oxazinyl, each of which is optionally substituted.

Item 5. A benzodiazepine compound represented by General Formula (1) or a salt thereof according to item 4,
wherein $R^6$ and $R^7$ are each one of the following (1) to (52):
(1) hydrogen,
(2) lower alkyl,
(3) cyclo lower alkyl,
(4) phenyl optionally substituted with one or more substituents selected from the group consisting of the following (4-1) to (4-25):
(4-1) cyano,
(4-2) hydroxy,
(4-3) halogen,
(4-4) lower alkyl optionally substituted with one or more substituents selected from the group consisting of halogen, imidazolyl and morpholinyl,
(4-5) lower alkoxy optionally substituted with one or more substituents selected from the group consisting of amino and lower alkyl amino,
(4-6) pyridyl,
(4-7) thienyl,
(4-8) piperazinyl optionally substituted with one or more lower alkyl,
(4-9) phenyl,
(4-10) pyrazolyl optionally substituted with one or more lower alkyl,
(4-11) pyrimidinyl optionally substituted with one or more lower alkyl,
(4-12) piperidyl optionally substituted with one or more lower alkyl,
(4-13) furyl,
(4-14) carboxy,
(4-15) lower alkoxycarbonyl,
(4-16) amino optionally substituted with one or more substituents selected from the group consisting of lower alkanoyl and lower alkylsulfonyl,
(4-17) lower alkylthio,
(4-18) triazolyl,
(4-19) imidazolyl,
(4-20) pyrrolidinyl optionally substituted with one or more oxo,
(4-21) lower alkylsulfonyl,
(4-22) lower alkylenedioxy optionally substituted with one or more halogen,
(4-23) nitro,
(4-24) oxazolyl, and
(4-25) thiazolyl optionally substituted with one or more lower alkyl,
(5) naphthyl,
(6) furyl optionally substituted with one or more substituents selected from the group consisting of lower alkyl optionally substituted with halogen, carboxy, sulfo, pyridyloxy, lower alkoxycarbonyl and phenyl,
(7) thienyl optionally substituted with one or more substituents selected from the group consisting of lower alkyl, lower alkylenedioxy, carboxy, halogen, pyridyl, lower alkoxy, lower alkoxycarbonyl, oxazolyl and furyl,
(8) imidazolyl optionally substituted with one or more substituents selected from the group consisting of phenyl, lower alkyl and halogen,
(9) pyrazolyl optionally substituted with one or more substituents selected from the group consisting of lower alkyl optionally substituted with halogen, halogen, phenyl optionally substituted with lower alkoxy, furyl and thienyl,
(10) oxazolyl optionally substituted with one or more substituents selected from the group consisting of lower alkyl and phenyl,
(11) isoxazolyl optionally substituted with one or more substituents selected from the group consisting of phenyl, lower alkyl, thienyl and furyl,
(12) thiazolyl optionally substituted with one or more substituents selected from the group consisting of lower alkyl optionally substituted with lower alkoxy, phenyl and lower alkanoylamino,
(13) pyrrolyl optionally substituted with one or more substituents selected from the group consisting of lower alkyl and lower alkoxycarbonyl,
(14) triazolyl optionally substituted with one or more lower alkyl,
(15) pyridyl optionally substituted with one or more substituents selected from the group consisting of lower alkyl optionally substituted with halogen, oxo, hydroxy, lower alkoxy, halogen, pyrrolidinyl, morpholinyl and thienyl,
(16) pyrimidinyl optionally substituted with one or more substituents selected from the group consisting of lower alkyl and phenyl,
(17) pyridazinyl,
(18) pyrazinyl,
(19) imidazo[2,1-b]thiazolyl optionally substituted with one or more halogen,
(20) thieno[2,3-b]pyrazinyl,
(21) 2,3-dihydroimidazo[2,1-b]thiazolyl optionally substituted with one or more phenyl,
(22) benzothiazolyl optionally substituted with one or more lower alkyl,
(23) indolyl optionally substituted with one or more substituents selected from the group consisting of lower alkyl, lower alkanoyl and halogen,
(24) imidazo[1,2-a]pyridyl optionally substituted with one or more lower alkyl,
(25) benzothienyl optionally substituted with one or more lower alkyl,
(26) benzimidazolyl optionally substituted with one or more lower alkyl,
(27) 2,3-dihydrobenzo[b]furyl,
(28) benzofuryl optionally substituted with one or more halogen,
(29) indazolyl optionally substituted with one or more lower alkyl,
(30) furo[2,3-c]pyridyl optionally substituted with one or more substituents selected from the group consisting of oxo and lower alkyl,
(31) furo[3,2-c]pyridyl optionally substituted with one or more substituents selected from the group consisting of oxo, lower alkyl optionally substituted with halogen, halogen, furyl, pyridyl and phenyl optionally substituted with one or more substituents selected from the group consisting of amino and lower alkoxy,
(32) thieno[2,3-c]pyridyl optionally substituted with one or more substituents selected from the group consisting of oxo group and lower alkyl,
(33) thieno[3,2-c]pyridyl optionally substituted with one or more substituents selected from the group consisting of oxo and lower alkyl,
(34) thieno[2,3-b]pyridyl,
(35) benzo[1,3]dioxolyl optionally substituted with one or more halogen,
(36) benzisoxazolyl,
(37) pyrazolo[2,3-a]pyridyl,
(38) indolizinyl,
(39) 2,3-dihydroindolyl optionally substituted with one or more substituents selected from the group consisting of oxo, lower alkyl and lower alkanoyl,
(40) isoquinolyl optionally substituted with one or more substituents selected from the group consisting of lower alkyl, halogen and oxo,
(41) 1,2,3,4-tetrahydro-1H-isoquinolyl optionally substituted with one or more oxo,
(42) carbostyril optionally substituted with one or more lower alkoxy,
(43) 3,4-dihydrocarbostyril optionally substituted with one or more lower alkoxy,
(44) quinolyl optionally substituted with one or more substituents selected from the group consisting of amino optionally substituted with one or two lower alkyl, lower alkoxy, lower alkyl and oxo,
(45) chromanyl optionally substituted with one or more lower alkyl,
(46) 5,6,7,8-tetrahydroisoquinolyl optionally substituted with one or more oxo,
(47) 3,4-dihydro-1H-isoquinolyl optionally substituted with one or more oxo,
(48) naphthyridinyl,
(49) 1,4-benzodioxanyl,
(50) cinnolinyl,
(51) quinoxalinyl, or
(52) 2,3-dihydrobenz-1,4-oxazinyl optionally substituted with one or more substituents selected from the group consisting of lower alkyl and oxo.
Item 6. A benzodiazepine compound represented by General Formula (1) or a salt thereof according to item 5,
wherein $R^6$ and $R^7$ are each one of the following (4a), (6a), (7a), (15a), (30a), (31a), (32a), (33a), (40a) and (44a):
(4a) phenyl optionally substituted with one or more substituents selected from the group consisting of the following (4a-1), (4a-4) and (4a-6):
(4a-1) cyano,
(4a-4) lower alkyl optionally substituted with one or more halogen, and
(4a-6) pyridyl,
(6a) furyl,
(7a) thienyl,
(15a) pyridyl optionally substituted with one or more lower alkyl,
(30a) furo[2,3-c]pyridyl optionally substituted with one or more oxo,
(31a) furo[3,2-c]pyridyl optionally substituted with one or more substituents selected from the group consisting of oxo and lower alkyl,
(32a) thieno[2,3-c]pyridyl optionally substituted with one or more oxo,
(33a) thieno[3,2-c]pyridyl optionally substituted with one or more oxo,
(40a) isoquinolyl optionally substituted with one or more oxo, and
(44a) quinolyl optionally substituted with one or more oxo.
Item 7. A benzodiazepine compound represented by General Formula (1) or a salt thereof according to item 6, which is selected from the group consisting of the following compounds:
1-ethyl-3,3,5-trimethyl-7-{3-[(2-pyridin-3-ylethyl)pyridin-4-yl methylamino]propoxy}-1,5-dihydrobenzo[b][1,4]diazepine-2,4-dione trihydrochloride,
3,3,5-trimethyl-1-propyl-7-{3-[(2-pyridin-3-ylethyl)pyridin-4-yl methylamino]propoxy}-1,5-dihydrobenzo[b][1,4]diazepine-2,4-dione trihydrochloride,
1,5-diethyl-3,3-dimethyl-7-{3-[(2-pyridin-3-ylethyl)pyridin-4-yl methylamino]propoxy}-1,5-dihydrobenzo[b][1,4]diazepine-2,4-dione trihydrochloride,
1,3,3,5-tetramethyl-7-{3-[(2-pyridin-3-ylethyl)pyridin-4-ylmethyl amino]propoxy}-1,5-dihydrobenzo[b][1,4]diazepine-2,4-dione trihydrochloride,
1-ethyl-3,3,5-trimethyl-7-(3-{[2-(1-oxo-1H-isoquinolin-2-yl)ethyl]pyridin-4-ylmethylamino}propoxy)-1,5-dihydrobenzo[b][1,4]diazepine-2,4-dione dihydrochloride,
1-ethyl-3,3,5-trimethyl-7-(3-{[2-(7-oxo-7H-furo[2,3-c]pyridin-6-yl)ethyl]pyridin-4-ylmethylamino}propoxy)-1,5-dihydrobenzo[b][1,4]diazepine-2,4-dione dihydrochloride,
N-methyl-N-(2-{pyridin-4-ylmethyl-[3-(1,3,3,5-tetramethyl-2,4-dioxo-2,3,4,5-tetrahydro-1H-benzo[b][1,4]diazepin-7-yloxy)propyl]amino}ethyl)benzamide dihydrochloride,
1,3,3,5-tetramethyl-7-{3-[(2-methylbenzyl)-(2-pyridin-3-ylethyl)amino]propoxy}-1,5-dihydrobenzo[b][1,4]diazepine-2,4-dione dihydrochloride,
1,3,3,5-tetramethyl-7-{3-[(2-pyridin-3-ylethyl)-(quinolin-4-yl methyl)amino]propoxy}-1,5-dihydrobenzo[b][1,4]diazepine-2,4-dione trihydrochloride,
1-ethyl-3,3,5-trimethyl-7-{3-[(3-methylpyridin-4-ylmethyl)-(2-pyridin-3-ylethyl)amino]propoxy}-1,5-dihydrobenzo[b][1,4]diazepine-2,4-dione trihydrochloride,
1-ethyl-3,3,5-trimethyl-7-(3-{[2-(2-oxo-2H-quinolin-1-yl)ethyl]pyridin-4-ylmethylamino}propoxy)-1,5-dihydrobenzo[b][1,4]diazepine-2,4-dione dihydrochloride,
1-ethyl-3,3,5-trimethyl-7-(3-{[2-(7-oxo-7H-thieno[2,3-c]pyridin-6-yl)ethyl]pyridin-4-yl)methylamino}propoxy)-1,5-dihydrobenzo[b][1,4]diazepine-2,4-dione dihydrochloride,
4-({[3-(1-ethyl-3,3,5-trimethyl-2,4-dioxo-2,3,4,5-tetrahydro-1H-benzo[b][1,4]diazepin-7-yloxy)propyl]-[2-(1-oxo-1H-isoquinolin-2-yl)ethyl]amino}methyl)benzonitrile,
1-ethyl-3,3,5-trimethyl-7-(3-{[2-(1-oxo-1H-isoquinolin-2-yl)ethyl]thiophen-3-ylmethylamino}propoxy)-1,5-dihydrobenzo[b][1,4]diazepine-2,4-dione,
1-ethyl-7-(3-{furan-2-ylmethyl-[2-(1-oxo-1H-isoquinolin-2-yl)ethyl]amino}propoxy)-3,3,5-trimethyl-1,5-dihydrobenzo[b][1,4]diazepine-2,4-dione,
7-{3-[benzyl-(2-pyridin-3-ylethyl)amino]propoxy}-1-ethyl-3,3,5-trimethyl-1,5-dihydrobenzo[b][1,4]diazepine-2,4-dione,
3-{[[3-(1-ethyl-3,3,5-trimethyl-2,4-dioxo-2,3,4,5-tetrahydro-1H-benzo[b][1,4]diazepin-7-yloxy)propyl]-(2-pyridin-3-ylethyl)amino]methyl}benzonitrile,
1-ethyl-3,3,5-trimethyl-7-{3-[(2-pyridin-3-ylbenzyl)-(2-pyridin-3-ylethyl)amino]propoxy}-1,5-dihydrobenzo[b][1,4]diazepine-2,4-dione, 4-({[3-(1-ethyl-3,3,5-trimethyl-2,4-dioxo-2,3,4,5-tetrahydro-1H-benzo[b][1,4]diazepin-7-yloxy)propyl]-[2-(7-oxo-7H-furo[2,3-c]pyridin-6-yl)ethyl]amino}methyl)benzonitrile, 1-ethyl-3,3,5-trimethyl-7-{3-[[2-(7-oxo-7H-furo[2,3-c]pyridin-6-yl)ethyl]-(4-trifluoromethylbenzyl)amino]propoxy}-1,5-dihydrobenzo[b][1,4]diazepine-2,4-dione, 1-ethyl-3,3,5-trimethyl-7-(3-{(2-methylbenzyl)-[2-(7-oxo-7H-furo[2,3-c]pyridin-6-yl)ethyl]amino}propoxy)-1,5-dihydrobenzo[b][1,4]diazepine-2,4-dione, 1-ethyl-3,3,5-trimethyl-7-(3-{[2-(7-oxo-7H-furo[2,3-c]pyridin-6-yl)ethyl]thiophen-2-ylmethylamino}propoxy)-1,5-dihydrobenzo[b][1,4]diazepine-2,4-dione, 1-ethyl-3,3,5-trimethyl-7-(3-{[2-(2-methyl-4-oxo-4H-furo[3,2-c]pyridin-5-yl)ethyl]pyridin-4-ylmethylamino}propoxy)-1,5-dihydrobenzo[b][1,4]diazepine-2,4-dione dihydrochloride, 1-ethyl-3,3,5-trimethyl-7-(3-{[2-(4-oxo-4H-furo[3,2-c]pyridin-5-yl)ethyl]pyridin-3-ylmethylamino}propoxy)-1,5-dihydrobenzo[b][1,4]diazepine-2,4-dione, 1-ethyl-3,3,5-trimethyl-7-(3-{[2-(4-oxo-4H-thieno[3,2-c]pyridin-5-yl)ethyl]pyridin-3-ylmethylamino}propoxy)-1,5-dihydrobenzo[b][1,4]diazepine-2,4-dione, 1-ethyl-3,3,5-trimethyl-7-{3-[[2-(2-methyl-4-oxo-4H-furo[3,2-c]pyridin-5-yl)ethyl]-(4-methylpyridin-3-ylmethyl)amino]propoxy}-1,5-dihydrobenzo[b][1,4]diazepine-2,4-dione, 1-ethyl-3,3,5-trimethyl-7-(3-{(2-methylpyridin-3-ylmethyl)-[2-(4-oxo-4H-furo[3,2-c]pyridin-5-yl)ethyl]amino}propoxy)-1,5-dihydrobenzo[b][1,4]diazepine-2,4-dione, 1-ethyl-3,3,5-trimethyl-7-(3-{(4-methylpyridin-3-ylmethyl)-[2-(4-oxo-4H-furo[3,2-c]pyridin-5-yl)ethyl]amino}propoxy)-1,5-dihydrobenzo[b][1,4]diazepine-2,4-dione, 1-ethyl-3,3,5-trimethyl-7-(3-{(2-methylpyridin-3-ylmethyl)-[2-(4-oxo-4H-thieno[3,2-c]pyridin-5-yl)ethyl]amino}propoxy)-1,5-dihydro benzo[b][1,4]diazepine-2,4-dione, 1-ethyl-3,3,5-trimethyl-7-{3-[[2-(2-methyl-4-oxo-4H-furo[3,2-c]pyridin-5-yl)ethyl]-(2-propylpyridin-3-ylmethyl)amino]propoxy}-1,5-dihydrobenzo[b][1,4]diazepine-2,4-dione dihydrochloride, N-[3-(1-ethyl-3,3,5-trimethyl-2,4-dioxo-2,3,4,5-tetrahydro-1H-benzo[b][1,4]diazepin-7-yloxy)propyl]-N-(2-pyridin-3-ylethyl)benzenesulfonamide hydrochloride, 7-(3-{(2,6-dimethylpyridin-3-ylmethyl)-[2-(4-oxo-4H-furo[3,2-c]pyridin-5-yl)ethyl]amino}propoxy)-1-ethyl-3,3,5-trimethyl-1,5-dihydrobenzo[b][1,4]diazepine-2,4-dione dihydrochloride, N-[3-(1-ethyl-3,3,5-trimethyl-2,4-dioxo-2,3,4,5-tetrahydro-1H-benzo[b][1,4]diazepin-7-yloxy)propyl]-N-(2-pyridin-3-ylethyl)benzamide hydrochloride, and N-[3-(1-ethyl-3,3,5-trimethyl-2,4-dioxo-2,3,4,5-tetrahydro-1H-benzo[b][1,4]diazepin-7-yloxy)propyl]-N-[2-(1-oxo-1H-isoquinolin-2-yl)ethyl]benzenesulfonamide.

Item 8. A pharmaceutical composition comprising a benzodiazepine compound represented by Formula (1) or a salt thereof according to claim 1, and a pharmacologically acceptable carrier.

Item 9. A pharmaceutical composition according to item 8 for preventing and/or treating arrhythmia.

Item 10. A benzodiazepine compound represented by Formula (1) or a salt thereof according to item 1 for use in the pharmaceutical composition.

Item 11. Use of a benzodiazepine compound represented by Formula (1) or a salt thereof according to item 1 as a pharmaceutical composition.

Item 12. Use of a benzodiazepine compound represented by Formula (1) or a salt thereof according to item 1 for the production of a pharmaceutical composition.

Item 13. A method of preventing and/or treating arrhythmia, comprising administering to a patient a benzodiazepine compound represented by Formula (1) or a salt thereof according to item 1.

The groups represented by $R^1$, $R^2$, $R^3$, $R^4$, $R^5$, $R^6$, $R^7$, $A^1$, $X_A$ and $X_B$, in the specification are described below.

Examples of "organic group" include lower alkyl, cyclo lower alkyl, aryl such as phenyl and naphthyl, heterocyclic group such as the (6) to (52) for $R^6$ and $R^7$.

Examples of "heterocyclic group" include saturated or unsaturated monocyclic or polycyclic heterocyclic group containing at least one hetero atom selected from among oxygen, sulfur and nitrogen. More preferable heterocyclic group may be the group such as:

unsaturated 3 to 8-membered, preferably 5 or 6-membered heteromonocyclic group containing 1 to 4 nitrogen atom(s), for example, pyrrolyl, pyrrolinyl, imidazolyl, pyrazolyl, pyridyl, and its N-oxide, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.;

saturated 3 to 8-membered, preferably 5 or 6-membered heteromonocyclic group containing 1 to 4 nitrogen atom(s), for example, azetidinyl, pyrrolidinyl, imidazolidinyl, piperidinyl, pyrazolidinyl, piperazinyl, etc.;

unsaturated condensed 7 to 12-membered heterocyclic group containing 1 to 5 nitrogen atom(s), for example, indolyl, dihydroindolyl (e.g., 2,3-dihydroindolyl, etc.), isoindolyl, indolizinyl, benzimidazolyl, uinolyl, isoquinolyl, dihydroisoquinolyl (e.g., 3,4-dihydro-1H-isoquinolyl, etc.), tetrahydroisoquinolyl (e.g., 1,2,3,4-tetrahydro-1H-isoquinolyl, 5,6,7,8-tetrahydroisoquinolyl, etc.), carbostyril, dihydrocarbostyril (e.g., 3,4-dihydrocarbostyril, etc.), indazolyl, benzotriazolyl, tetrazolopyridyl, tetrazolopyridazinyl (e.g., tetrazolo[1,5-b]pyridazinyl, etc.), dihydrotriazolopyridazinyl, imidazopyridyl (e.g., imidazo[1,2-a]pyridyl, etc.,), naphthyridinyl, cinnolinyl, quinoxalinyl, pyrazolopyridyl (e.g., pyrazolo[2,3-a]pyridyl, etc.) etc.;

unsaturated 3 to 8-membered, preferably 5 or 6-membered heteromonocyclic group containing 1 to 2 oxygen atom(s), for example, furyl, etc.;

unsaturated condensed 7 to 12-membered heterocyclic group containing 1 to 3 oxygen atom(s), for example, benzofuryl, dihydrobenzofuryl (e.g. 2,3-dihydrobenzo[b]furyl, etc.), chromanyl, benzodioxanyl (e.g., 1,4-benzodioxanyl, etc.), dihydrobenzoxazinyl (e.g., 2,3-dihydrobenz-1,4-oxazinyl, etc.), benzodioxolyl (benzo[1,3]dioxolyl, etc.), etc.;

unsaturated 3 to 8-membered, preferably 5 or 6-membered heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered, preferably 5 or 6-membered heteromonocyclic group containing 1 to 2 oxygen atom(s) and 1 to 3 nitrogen atom(s), for example, morpholinyl, etc.;

unsaturated condensed 7 to 12-membered heterocyclic group containing 1 to 2 oxygen atom(s) and 1 to 3 nitrogen atom(s), for example, benzoxazolyl, benzoxadiazolyl, benzisoxazolyl, furopyridyl (e.g., furo[2,3-b]pyridyl, furo[3,2-c]pyridyl, etc.), etc.;

unsaturated 3 to 8-membered, preferably 5 or 6-membered heteromonocyclic group containing 1 to 2 sulfur atom(s) and 1 to 3 nitrogen atom(s), for example, thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl, etc.), etc.;

saturated 3 to 8-membered, preferably 5 or 6-membered heteromonocyclic group containing 1 to 2 sulfur atom(s) and 1 to 3 nitrogen atom(s), for example, thiazolidinyl, etc.;

unsaturated 3 to 8-membered, preferably 5 or 6-membered heteromonocyclic group containing a sulfur atom, for example, thienyl, etc.;

unsaturated condensed 7 to 12-membered heterocyclic group containing 1 to 3 sulfur atom(s), for example, benzothienyl (e.g. benzo[b]thienyl, etc.), unsaturated condensed 7 to 12-membered heterocyclic group containing 1 to 2 sulfur atom(s) and 1 to 3 nitrogen atom(s), for example, benzothiazolyl, benzothiadiazolyl, thienopyridyl (e.g., thieno[2,3-b]pyridyl, thieno[2,3-c]pyridyl, thieno[3,2-c]pyridyl, etc.), imidazothiazolyl (e.g., imidazo[2,1-b]thiazolyl, etc.), dihydroimidazothiazolyl (e.g., 2,3-dihydroimidazo[2,1-b]thiazolyl, etc.), thienopyrazinyl (e.g., thieno[2,3-b]pyrazinyl, etc.), etc. and the like; wherein said heterocyclic group may be substituted by one or more suitable substituent(s).

Examples of "lower alkyl" include linear or branched alkyl groups having 1 to 6 carbon atoms, such as methyl, ethyl, n-propyl, isopropyl, n-butyl, isobutyl, tert-butyl, sec-butyl, n-pentyl, neopentyl, n-hexyl, isohexyl, and 3-methylpentyl.

Examples of "lower alkylene" include linear or branched alkylene groups having 1 to 6 carbon atoms, such as methylene, ethylene, trimethylene, 2-methyltrimethylene, 2,2-dimethyltrimethylene, 1-methyltrimethylene, methylmethylene, ethylmethylene, tetramethylene, pentamethylene, and hexamethylene.

Examples of "cyclo lower alkyl" include linear or branched cyclo alkyl having 3 to 6 carbon atoms, such as cyclopropyl, cyclobutyl, cyclopentyl, and cyclohexyl.

Examples of "lower alkoxy" include linear or branched alkoxy groups having 1 to 6 carbon atoms, such as methoxy, ethoxy, n-propoxy, isopropoxy, n-butoxy, isobutoxy, tert-butoxy, sec-butoxy, n-pentyloxy, neopentyloxy, n-hexyloxy, isohexyloxy, and 3-methylpentyloxy.

Examples of "halogen" include fluorine, chlorine, bromine, and iodine.

Examples of "lower alkylenedioxy" include linear or branched alkylene groups having 1 to 4 carbon atoms, such as methylenedioxy, ethylenedioxy, trimethylenedioxy, and tetramethylenedioxy.

Examples of "lower alkanoyl" include linear or branched alkanoyl groups having 1 to 6 carbon atoms, such as formyl, acetyl, propionyl, butyryl, isobutyryl, pentanoyl, tert-butylcarbonyl, and hexanoyl.

The term "one or more" may be preferably 1 to 6, more preferably 1 to 3.

The benzodiazepine compound of the present invention represented by Formula (1) or its salt can be produced by, for example, the processes shown in the following reaction formulas.

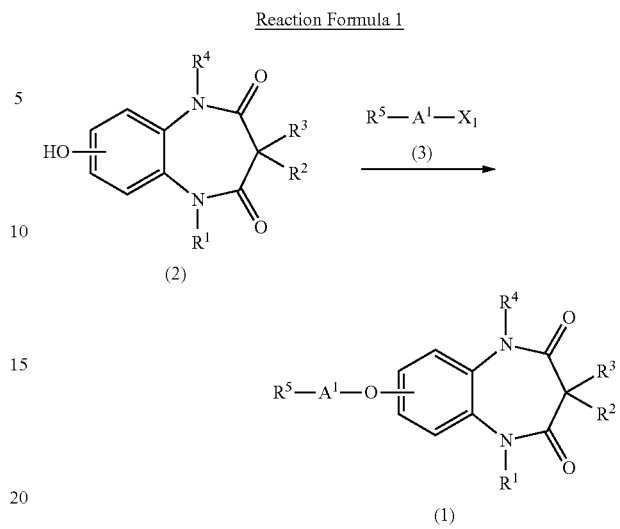

Reaction Formula 1 wherein $R^1$, $R^2$, $R^3$, $R^4$, $R^5$, and $A^1$ are the same as above, and $X_1$ is halogen or hydroxyl.

The reaction of the compound of Formula (2) with the compound of Formula (3) wherein $X_1$ is halogen can be performed in a usual inert solvent or without using any solvents in the presence or absence of a basic compound.

Examples of inert solvents include water; ethers such as dioxane, tetrahydrofuran, diethyl ether, diethylene glycol dimethyl ether, and ethylene glycol dimethyl ether; aromatic hydrocarbons such as benzene, toluene, and xylene; halogenated hydrocarbons such as dichloromethane, dichloroethane, chloroform, and carbon tetrachloride; lower alcohols such as methanol, ethanol, and isopropanol; ketones such as acetone and methyl ethyl ketone; polar solvents such as dimethylformamide (DMF), dimethyl sulfoxide (DMSO), hexamethylphosphoric triamide, and acetonitrile; and mixed solvents of such solvents.

The basic compound may be selected from various known compounds. Examples of such compounds include inorganic bases, for example, alkali metal hydroxides such as sodium hydroxide, potassium hydroxide, cesium hydroxide, and lithium hydroxide; alkali metal carbonates such as sodium carbonate, potassium carbonate, cesium carbonate, lithium carbonate, lithium hydrogencarbonate, sodium hydrogencarbonate, and potassium hydrogencarbonate; alkali metals such as sodium and potassium; sodium amide; sodium hydride; and potassium hydride; and organic bases, for example, alkali metal alcoholates such as sodium methoxide, sodium ethoxide, potassium methoxide, and potassium ethoxide; triethylamine; tripropylamine; pyridine; quinoline; 1,5-diazabicyclo[4.3.0]nonene-5 (DBN); 1,8-diazabicyclo[5.4.0]undecene-7 (DBU); and 1,4-diazabicyclo[2.2.2]octane (DABCO). These basic compounds can be used singly or in a combination of two or more.

The above reaction may be performed by adding an alkali metal iodide such as potassium iodide or sodium iodide to the reaction system, as required.

The compound of Formula (3) is usually used in an amount of at least 0.5 moles, and preferably 0.5 to 10 moles, per mole of the compound of Formula (2).

The basic compound is usually used in an amount of 0.5 to 10 moles, and preferably 0.5 to 6 moles, per mole of the compound of Formula (2).

The reaction is usually performed at a temperature of 0° C. to 250° C., and preferably 0° C. to 200° C., and is usually completed in about 1 to about 80 hours.

The reaction of the compound of Formula (2) with the compound of Formula (3) wherein $X_1$ is hydroxyl is performed in an appropriate solvent in the presence of a condensing agent.

Examples of solvents usable herein include water; halogenated hydrocarbons such as chloroform, dichloromethane, dichloroethane, and carbon tetrachloride; aromatic hydrocarbons such as benzene, toluene, and xylene; ethers such as diethyl ether, diisopropyl ether, tetrahydrofuran, and dimethoxyethane; esters such as methyl acetate, ethyl acetate, and isopropyl acetate; alcohols such as methanol, ethanol, isopropanol, propanol, butanol, 3-methoxy-1-butanol, ethyl cellosolve, and methyl cellosolve; aprotic polar solvents such as acetonitrile, pyridine, acetone, N,N-dimethyl formamide, dimethyl sulfoxide, and hexamethylphosphoric triamide; and mixtures of such solvents.

Examples of condensing agents include azocarboxylates such as di-tert-butyl azodicarboxylate, N,N,N',N'-tetramethyl azodicarboxamide, 1,1'-(Azodicarbonyl)dipiperidine, diethyl azodicarboxylate; and phosphorus compounds such as triphenylphosphine and tri-n-butylphosphine.

In this reaction, the compound (3) is usually used in an amount of at least 1 mole, and preferably 1 to 2 moles, per mole of the compound (2).

The condensing agent is usually used in an amount of at least 1 mole, and preferably 1 to 2 moles, per mole of the compound (2).

The reaction proceeds usually at 0 to 200° C., and preferably at about 0 to about 150° C., and is completed in about 1 to about 10 hours.

ethane; esters such as methyl acetate and ethyl acetate; and aprotic polar solvents such as N,N-dimethylformamide, dimethylsulfoxide, and hexamethylphosphoric triamide; and mixtures of such solvents. Other examples of solvents used for the reaction include alcohols such as methanol, ethanol, propanol, butanol, 3-methoxy-1-butanol, ethyl cellosolve or methyl cellosolve; acetonitrile, pyridine, acetone, and mixtures of such solvents.

The hydrazine is usually used in an amount of at least about 1 mole, and preferably about 1 to about 5 moles, per mole of the compound (1a).

The reaction proceeds usually at about 0 to about 120° C., and preferably at about 0 to about 100° C., and is usually completed in about 0.5 to about 5 hours.

The hydrolysis of the compound of Formula (1a) is performed in an appropriate solvent or without using any solvents in the presence of an acid or a basic compound.

Examples of solvents usable herein include water; lower alcohols such as methanol, ethanol, and isopropanol; ketones such as acetone and methyl ethyl ketone; ethers such as dioxane, tetrahydrofuran and ethylene glycol dimethyl ether; fatty acids such as acetic acid and formic acid; and mixtures of such solvents.

Examples of acids include mineral acids such as hydrochloric acids, sulfuric acid and hydrobromic acid; aliphatic acids such as formic acid, acetic acid; and sulfonic acids such as p-toluenesulfonic acid.

Examples of basic compounds include metal carbonates such as sodium carbonate and potassium carbonate; and metal hydroxides such as sodium hydroxide and potassium hydroxide.

The reaction proceeds usually at room temperature to about 200° C., and preferably at room temperature to about 150° C., and is usually completed in about 10 minutes to 25 hours.

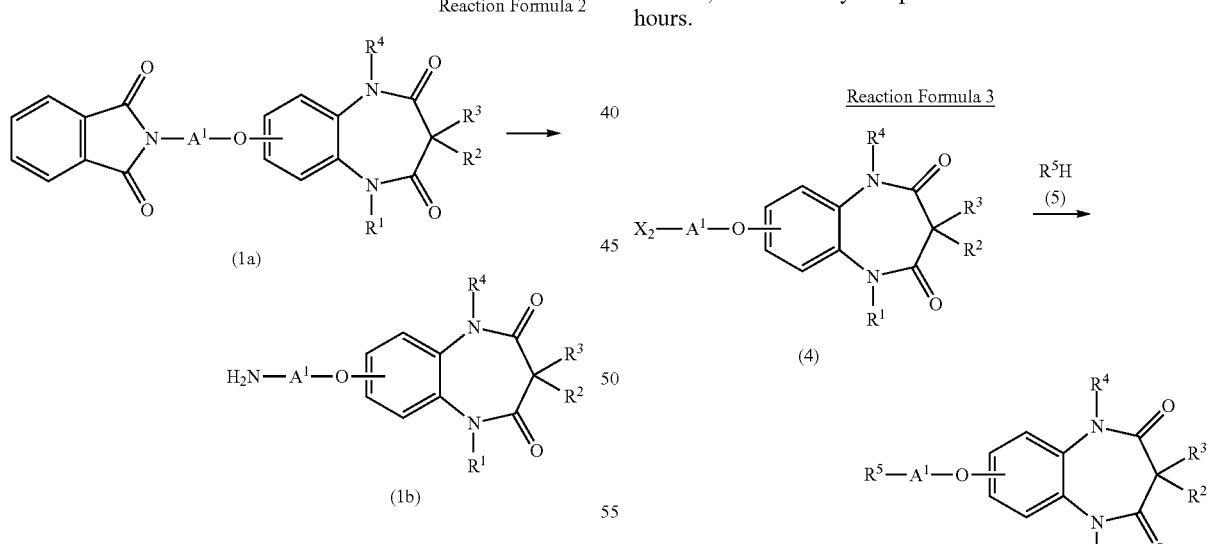

Reaction Formula 2

(1a)

(1b)

wherein $R^1$, $R^2$, $R^3$, $R^4$ and $A^1$ are the same as above.

The reaction converting the compound of Formula (1a) to the compound of Formula (1b) can be carried out by either reacting the compound (1a) with hydrazine in a suitable solvent, or by hydrolysis. Here, hydrazine hydrate may be used as the hydrazine.

Examples of solvents used for reaction of the hydrazine include water; halogenated hydrocarbons such as chloroform dichloromethane and dichloroethane; aromatic hydrocarbons such as benzene, toluene, and xylene; ethers such as diethyl ether, diisopropyl ether, tetrahydrofuran, and dimethoxy- Reaction Formula 3

(4)

(1)

wherein $R^1$, $R^2$, $R^3$, $R^4$, $R^5$, and $A^1$ are the same as above, and $X_2$ is halogen, alkanesulfonyloxy, or arylsulfonyloxy.

The reaction of the compound of Formula (4) with the compound of Formula (5) is performed under the same reaction conditions as those for the reaction of the compound of Formula (3), in which $X_1$ is halogen, with the compound of Formula (2) in Reaction Formula 1.

Reaction Formula 4

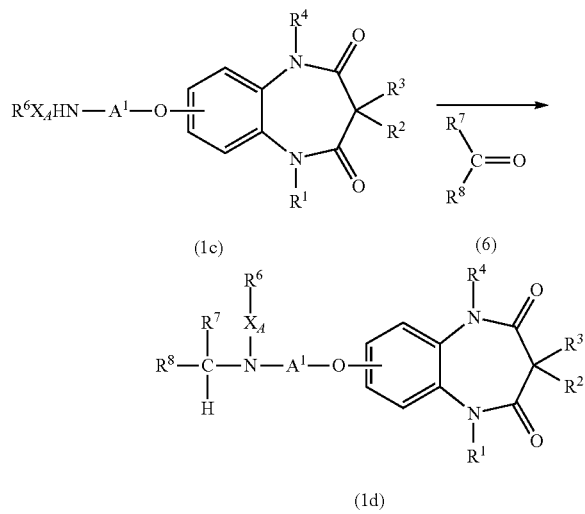

wherein $R^1$, $R^2$, $R^3$, $R^4$, $R^6$, $R^7$ and $A^1$ are the same as above; and $R^8$ is hydrogen or lower alkyl;
provided that the alkylene moiety of —$CHR^7R^8$ contains no more than 6 carbon atoms, and —$CHR^8$ is the same as $X_B$ in which alkylene is contained.

The reaction of the compound of Formula (1c) and the compound of Formula (6) is carried out, for example, in the presence of a reducing agent in a suitable solvent or without using any solvents.

Examples of solvents usable herein are water; lower alcohols such as methanol, ethanol, isopropanol, butanol, tert-butanol and ethylene glycol; acetonitrile; aliphatic acids such as formic acid and acetic acid; ethers such as diethyl ether, tetrahydrofuran, dioxane, monoglyme and diglyme; aromatic hydrocarbons such as benzene, toluene and xylene; halogenated hydrocarbons such as dichloromethane, dichloroethane, chloroform, and carbon tetrachloride; and mixtures of such solvents, etc.

Examples of reducing agents are aliphatic acids such as formic acid and acetic acid; aliphatic acid alkali metal salts such as sodium formate and sodium acetate; hydride reducing agents such as sodium borohydride, sodium cyanoborohydride, sodium triacetoxyborohydride and aluminium lithium hydride; mixtures of such hydride reducing agents; mixtures of aliphatic acids or aliphatic acid alkali metal salts with hydride reducing agents; catalytic hydrogenation reducing agents such as palladium black, palladium carbon, platinum oxide, platinum black, Raney nickel, etc.

When an aliphatic acid such as formic acid, or an aliphatic acid alkali metal salt such as sodium formate or sodium acetate is used as a reducing agent, a suitable reaction temperature is usually about room temperature to about 200° C., and preferably about 50 to about 150° C. The reaction is usually completed in about 10 minutes to about 10 hours. Such aliphatic acids and aliphatic acid alkali metal salts are usually used in a large excess relative to the compound of Formula (1c).

When a hydride reducing agent is used, a suitable reaction temperature is usually about −80 to about 100° C., and preferably about −80 to about 70° C. The reaction is usually completed in about 30 minutes to about 60 hours. The hydride reducing agent is usually used in an amount of about 1 to about 20 moles, and preferably about 1 to about 10 moles, per mole of the compound of Formula (1c). In particular, when aluminium lithium hydride is used as a hydride reducing agent, it is preferable to use diethyl ether, tetrahydrofuran, dioxane, monoglyme, diglyme, or like ethers; or benzene, toluene, xylene, or like aromatic hydrocarbons as a solvent. Trimethylamine, triethylamine, N-ethyldiisopropylamine, or like amines; or molecular sieves 3A (MS-3A), molecular sieves 4A (MS-4A), or like molecular sieves may be introduced into the reaction system of the reaction.

When a catalytic hydrogenation reducing agent is used, the reaction is usually carried out at about −30 to about 100° C., and preferably about 0 to about 60° C., in a hydrogen atmosphere usually about 1 to about 20 atm, and preferably about 1 to about 10 atm, or in the presence of formic acid, ammonium formate, cyclohexene, hydrazine hydrate, or like hydrogen donor. The reaction is usually completed in about 1 to about 12 hours. The catalytic hydrogenation reducing agent is usually used in an amount of about 0.1 to about 40 wt. %, and preferably about 1 to about 20 wt. %, relative to the compound of Formula (1c).

In the reaction of the compound of Formula (1c) with the compound of Formula (6), the compound of Formula (6) is usually used in an amount at least 1 mole, and preferably 1 to 5 moles, per mole of the compound of Formula (1c).

Reaction Formula 5

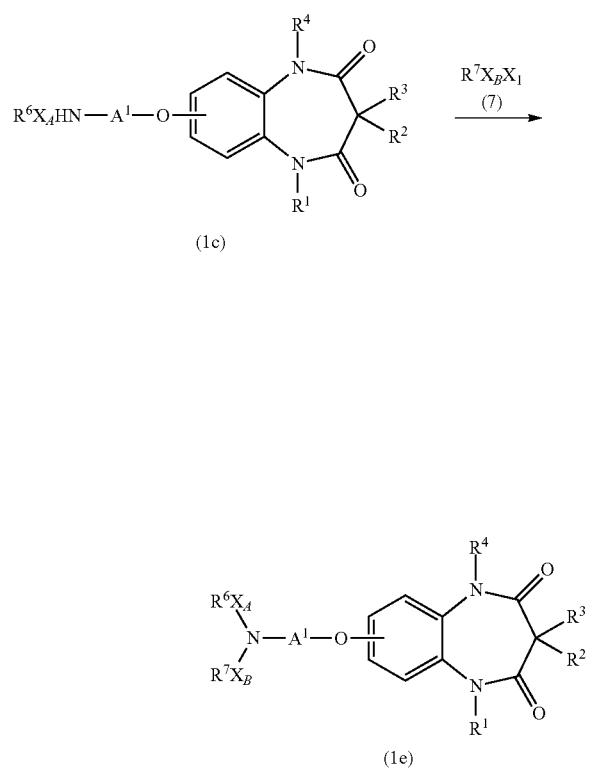

wherein $R^1$, $R^2$, $R^3$, $R^4$, $R^6$, $R^6$, $X_A$, $X_B$, $A^1$ and $X_1$ are the same as above.

The reaction of the compound of Formula (1c) with the compound of Formula (7) is performed under the same reaction conditions as those for the reaction of the compound of Formula (3) with the compound of Formula (2) in Reaction Formula 1.

Reaction Formula 6

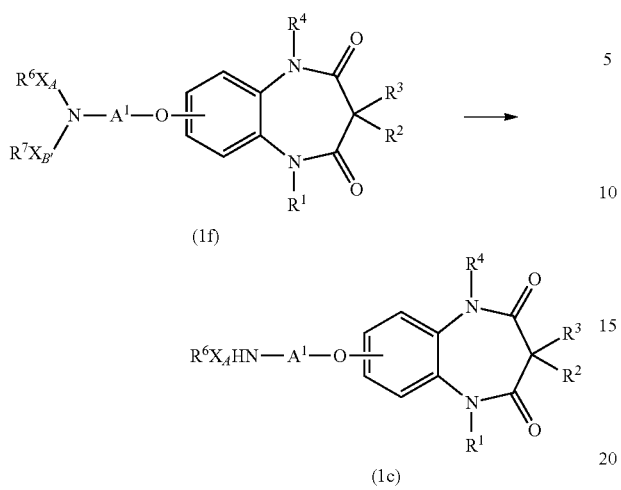

wherein $R^1$, $R^2$, $R^3$, $R^4$, $R^6$, $R^7$, $X_A$, and $A^1$ are the same as above, and $X_{B'}$ is —$SO_2$— or —CO—.

The reaction converting the compound of Formula (1f) to the compound of Formula (1c) can be carried out by hydrolysis. The hydrolysis reaction is performed in an appropriate solvent or without using any solvents in the presence of an acid or a basic compound.

Examples of useful solvents include water; lower alcohols such as methanol, ethanol, isopropanol and tert-butanol; ketones such as acetone and methylethyl ketone; ethers such as diethyl ether, dioxane, tetrahydrofuran, monoglyme and diglyme; aliphatic acids such as acetic acid and formic acid; esters such as methyl acetate and ethyl acetate; halogenated hydrocarbons such as chloroform, dichloromethane, dichloroethane and carbon tetrachloride; dimethyl sulfoxide; N,N-dimethylformamide; and hexamethylphosphoric triamide; and mixtures of such solvents.

Examples of useful acids include mineral acids such as hydrochloric acid, sulfuric acid and hydrobromic acid; and organic acids such as formic acid, acetic acid, thioglycolic acid, trifluoroacetic acid and sulfonic acid (e.g., p-toluenesulfonic acid). Such acids can be used singly or in a combination.

Examples of useful basic compounds include carbonates such as sodium carbonate, potassium carbonate, sodium hydrogencarbonate and potassium hydrogencarbonate; and metal hydroxides such as sodium hydroxide, potassium hydroxide, calcium hydroxide and lithium hydroxide. Such basic compounds can be used singly or in a combination.

An acid or basic compound is usually used in an amount of at least about 1 mole, and preferably about 1 to about 10 moles, per mole of the compound of Formula (1f).

The reaction advantageously proceeds usually at about 0 to about 200° C., and preferably at about 0 to about 150° C., and usually finishes in about 10 minutes to about 80 hours.

In Reaction Formula 6, when $X_{B'}$ in the compound of Formula (1f) is —$SO_2$—, the compound of Formula (1c) can be easily produced from the compound of Formula (1f) when thiol acts on the compound under basic conditions. Any basic compound used in the aforementioned hydrolysis reaction can be used. Examples of thiols include aromatic mercaptans such as thiophenol; lower alkyl thiols such as thioglycolic acid; etc. The reaction is performed under the same reaction conditions as those for the aforementioned hydrolysis reaction, except that thiol is usually used in an amount of at least 0.5 moles, and preferably about 1 to about 3 moles per mole of the compound of Formula (1f).

Reaction Formula 7

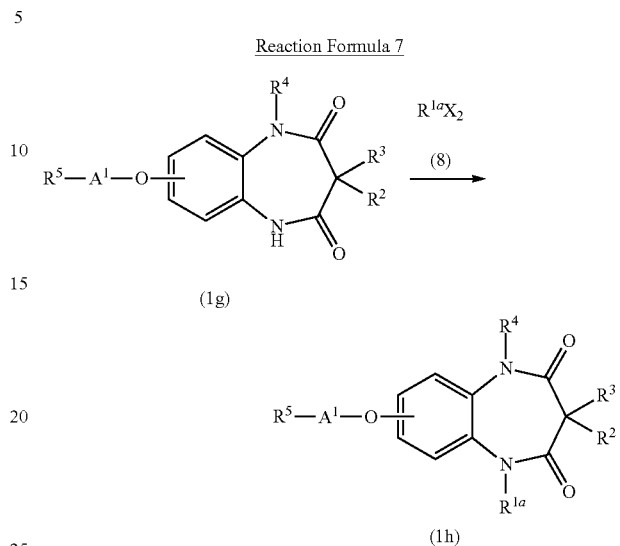

wherein $R^2$, $R^3$, $R^4$, $R^5$, $A^1$, and $X_2$ are the same as above, and $R^{1a}$ is lower alkyl.

The reaction of the compound of Formula (1g) with the compound of Formula (8) is performed under the same reaction conditions as those for the reaction of the compound of Formula (3), in which $X_1$ is halogen, with the compound of Formula (2) in Reaction Formula 1.

When $R^4$ in the compound of Formula (1g) is hydrogen in the reaction, a compound in which the first and fifth positions of the benzodiazepine skeleton are simultaneously substituted with $R^{1a}$ may be produced.

Reaction Formula 8

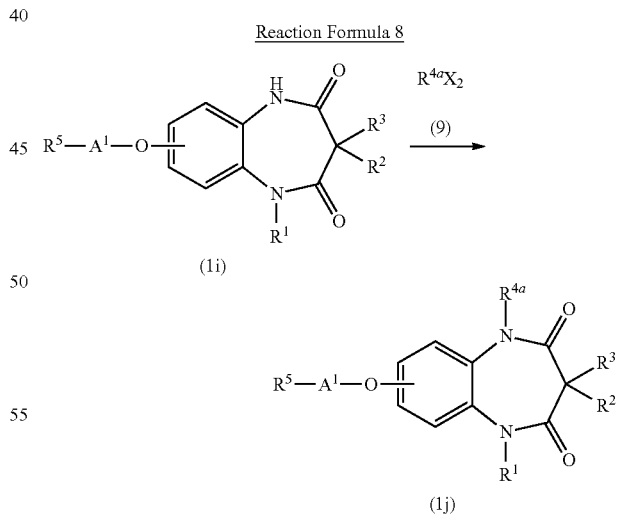

wherein $R^1$, $R^2$, $R^3$, $R^5$, $A^1$, and $X_2$ are the same as above, and $R^{4a}$ is lower alkyl.

The reaction of the compound of Formula (1i) with the compound of Formula (9) is performed under the same reaction conditions as those for the reaction of the compound of Formula (3), in which $X_1$ is halogen, with the compound of Formula (2) in Reaction Formula 1.

When $R^1$ in the compound of Formula (1i) is hydrogen in the reaction, a compound in which the first and fifth positions of the benzodiazepine skeleton are simultaneously substituted with $R^{4a}$ may be produced.

Reaction Formula 9

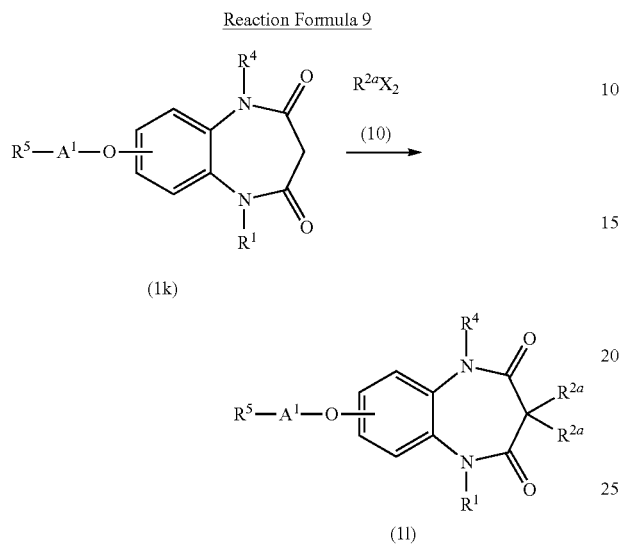

(1k)

(1l)

wherein $R^1$, $R^4$, $R^5$, $A^1$, and $X_2$ are the same as above, and $R^{2a}$ is lower alkyl.

The reaction of the compound of Formula (1k) with the compound of Formula (10) is performed under the same reaction conditions as those for the reaction of the compound of Formula (3), in which $X_1$ is halogen, with the compound of Formula (2) in Reaction Formula 1.

When $R^1$ and/or $R^4$ is hydrogen in the reaction of the compound of Formula (1k) and the compound of Formula (10), the hydrogen may be replaced with $R^{2a}$.

The compound of Formula (2), which is used as a starting material in the above-mentioned reaction formula, can be easily produced by the process shown in the following reaction formulae.

Reaction Formula 10

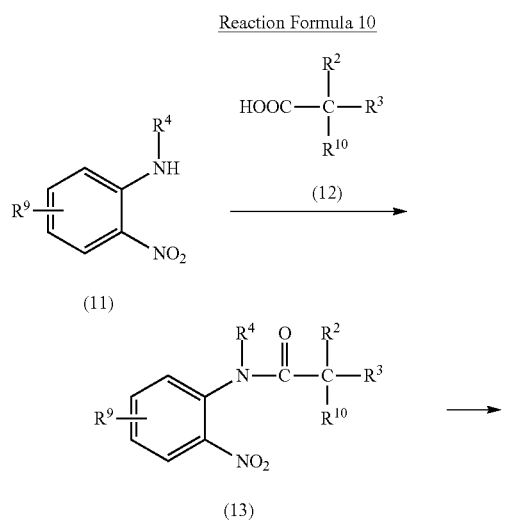

(11)

(13)

(14)

(15)

(16a)

wherein $R^2$, $R^3$, $R^4$, $R^{1a}$, and $X_2$ are the same as above. $R^9$ is lower alkoxy, and $R^{10}$ is lower alkoxycarbonyl.

In the reaction of the compound of Formula (11) and the compound of Formula (12), the compound of Formula (11) is reacted with carboxylic acid of the compound of Formula (12) through a usual amide bond formation reaction. Conditions for known amide bond formation reactions can be easily employed in the above amide formation reaction. For example, the following reaction methods can be employed: (A) a mixed acid anhydride method, in which Carboxylic Acid (12) is reacted with an alkyl halocarboxylate to form a mixed acid anhydride, which is then reacted with Amine (11); (B) an active ester method, in which Carboxylic Acid (12) is converted to an activated ester such as a phenyl ester, p-nitrophenyl ester, N-hydroxysuccinimide ester, 1-hydroxybenzotriazole ester or the like, or an activated amide with benzoxazoline-2-thione, and the activated ester or amide is reacted with Amine (11); (C) a carbodiimide method, in which Carboxylic Acid (12) is subjected to a condensation reaction with Amine (11) in the presence of an activating agent such as dicyclohexylcarbodiimide, 1-(3-dimethylaminopropyl)-3-ethylcarbodiimide (WSC), carbonyldiimidazole or the like; (D) other methods, for example, a method in which Carboxylic Acid (12) is converted to a carboxylic anhydride using a dehydrating agent such as acetic anhydride, and the carboxylic anhydride is then reacted with Amine (11), a method in which an ester of Carboxylic Acid (12) with a lower alcohol is reacted with Amine (11) at a high pressure and a high temperature, a method in which an acid halide of Carboxylic Acid (12), i.e., a carboxylic acid halide, is reacted with Amine (11), etc.

The mixed acid anhydride used in the mixed acid anhydride method (A) can be obtained by the known Schotten-Baumann reaction, and the obtained mixed acid anhydride is reacted with Amine (11), usually without being isolated, to thereby produce the compound of Formula (13). The Schotten-Baumann reaction is performed in the presence of a basic compound. Usable basic compounds include compounds conventionally used in the Schotten-Baumann reaction, such as triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and other organic bases; sodium carbonate, potassium carbonate, sodium hydrogencarbonate, potassium hydrogencarbonate and other carbonates; sodium hydroxide, potassium hydroxide, calcium hydroxide and other metal hydroxides; potassium hydride, sodium hydride, potassium, sodium, sodium amide, metal alcoholates such as sodium methylate and sodium ethylate, and other inorganic bases; etc. The reaction is usually performed at about −20 to about 150° C., and preferably at about 0 to about 100° C., usually for about 5 minutes to about 10 hours, and preferably for about 5 minutes to about 5 hours. The reaction of the obtained mixed acid anhydride with Amine (11) is usually carried out at about −20 to about 150° C., and preferably at about 10 to about 50° C., usually for about 5 minutes to about 30 hours, and preferably for about 5 minutes to about 25 hours. Generally, the mixed acid anhydride method is performed in a solvent. Solvents used for conventional mixed acid anhydride methods are usable. Examples of usable solvents include chloroform, dichloromethane, dichloroethane, carbon tetrachloride and other halogenated hydrocarbons; benzene, toluene, xylene and other aromatic hydrocarbons; diethyl ether, diisopropyl ether, tetrahydrofuran, dimethoxyethane and other ethers; methyl acetate, ethyl acetate, isopropyl acetate and other esters; N,N-dimethylformamide, dimethylsulfoxide, hexamethylphosphoric triamide and other aprotic polar solvents; mixtures thereof; etc. Examples of alkyl halocarboxylates usable in the mixed acid anhydride method include methyl chloroformate, methyl bromoformate, ethyl chloroformate, ethyl bromoformate, isobutyl chloroformate, etc. In this method, Carboxylic Acid (12), an alkyl halocarboxylate, and Amine (11) are preferably used in equimolear amounts, but each of the alkyl halocarboxylate and Carboxylic Acid (12) can also be used in an amount of about 1 to about 1.5 moles per mole of Amine (11).

Method (C), in which a condensation reaction is carried out in the presence of an activating agent, can be performed in a suitable solvent in the presence or absence of a basic compound. Solvents and basic compounds usable in this method include those mentioned hereinafter as solvents and basic compounds usable in the method in which a carboxylic acid halide is reacted with Amine (11) mentioned above as one of the other methods (D). A suitable amount of activating agent is at least 1 mole, and preferably 1 to 5 moles per mole of Amine (11). When using WSC as an activating agent, addition of 1-hydroxybenzotriazol to the reaction system enables the reaction to proceed advantageously. The reaction is usually performed at about −20 to about 180° C., and preferably at about 0 to about 150° C., and is usually completed in about 5 minutes to about 90 hours.

When the method in which a carboxylic acid halide is reacted with Amine (11), mentioned above as one of the other methods (D), is employed, the reaction is performed in the presence of a basic compound in a suitable solvent. Usable basic compounds include a wide variety of known basic compounds, such as those for use in the Schotten-Baumann reaction described above. Usable solvents include, in addition to those usable in the mixed acid anhydride method, methanol, ethanol, isopropanol, propanol, butanol, 3-methoxy-1-butanol, ethylcellosolve, methylcellosolve and other alcohols; acetonitrile; pyridine; acetone; water; etc. The ratio of the carboxylic acid halide to Amine (11) is not limited and can be suitably selected from a wide range. It is usually suitable to use, for example, at least about 1 mole, and preferably about 1 to about 5 moles of the carboxylic acid halide per mole of Amine (11). The reaction is usually performed at about −20 to about 180° C., and preferably at about 0 to about 150° C., and usually completed in about 5 minutes to about 30 hours.

The amide bond formation reaction shown in Reaction Formula 10 can also be performed by reacting Carboxylic Acid (12) with Amine (11) in the presence of a phosphorus compound serving as a condensing agent, such as triphenylphosphine, diphenylphosphinyl chloride, phenyl-N-phenylphosphoramide chloridate, diethyl chlorophosphate, diethyl cyanophosphate, diphenylphosphoric azide, bis(2-oxo-3-oxazolidinyl)phosphinic chloride or the like.

The reaction is carried out in the presence of a solvent and a basic compound usable for the method in which a carboxylic acid halide is reacted with Amine (11), usually at about −20 to about 150° C., and preferably at about 0 to about 100° C., and is usually completed in about 5 minutes to about 30 hours. It is suitable to use each of the condensing agent and Carboxylic Acid (12) in amounts of at least about 1 mole, and preferably about 1 to about 2 moles per mole of Amine (11).

The reaction converting the compound of Formula (13) to the compound of Formula (14) can be carried out by, for example, (1) reducing the compound of Formula (13) in a suitable solvent using a catalytic hydrogenation reducing agent, or (2) reducing the compound of Formula (13) in a suitable inert solvent using as a reducing agent a mixture of an acid with a metal or metal salt, a mixture of a metal or metal salt with an alkali metal hydroxide, sulfide, or ammonium salt, or the like.

When using Method (1) in which a catalytic hydrogenation reducing agent is used, examples of usable solvents are water; acetic acid; alcohols such as methanol, ethanol and isopropanol; hydrocarbons such as n-hexane and cyclohexane; ethers such as dioxane, tetrahydrofuran, diethyl ether and diethylene glycol dimethyl ether; esters such as ethyl acetate and methyl acetate; aprotic polar solvents such as N,N-dimethylformamide; mixtures of such solvents; etc. Examples of usable catalytic hydrogenation reducing agents include palladium, palladium black, palladium carbon, platinum carbon, platinum, platinum black, platinum oxide, copper chromite, Raney nickel, etc. A reducing agent is usually used in an amount of about 0.02 times to equal to the weight of the compound of Formula (13). The reaction temperature is usually about −20 to about 150° C., and preferably about 0 to about 100° C. The hydrogen pressure is usually about 1 to 10 atm. The reaction is usually completed in about 0.5 to about 100 hours. An acid such as hydrochloric acid may be introduced into the reaction system of the reaction.

When using Method (2) above, a mixture of iron, zinc, tin, or tin (II) chloride, with a mineral acid such as hydrochloric acid, or sulfuric acid; or a mixture of iron, iron (II) sulfate, zinc, or tin, with an alkali metal hydroxide such as sodium hydroxide, a sulfide such as ammonium sulfide, aqueous ammonia solution, or an ammonium salt such as ammonium chloride, or the like can be used as a reducing agent. Examples of inert solvents are water; acetic acid; alcohols such as methanol and ethanol; ethers such as dioxane; mixtures of such solvents, etc. Conditions for the reduction reaction can be suitably selected according to the reducing agent to be used. For example, when a mixture of tin (II) chloride and hydrochloric acid is used as a reducing agent, it is advantageous to carry out the reaction at about 0 to about 150° C. for about 0.5 to about 10 hours. A reducing agent is used in an amount of at least 1 mole, and preferably about 1 to 5 moles, per mole of the compound of Formula (13).

The reaction converting the compound of Formula (14) to the compound of Formula (15) is performed under the same reaction conditions as those for the reaction of the compound of Formula (11) with the compound of Formula (12).

The reaction of the compound of Formula (15) with the compound of Formula (8) is performed under the same reaction conditions as those for the reaction of the compound of Formula (1g) with the compound of Formula (8) in Reaction Formula 7.

Reaction Formula 11

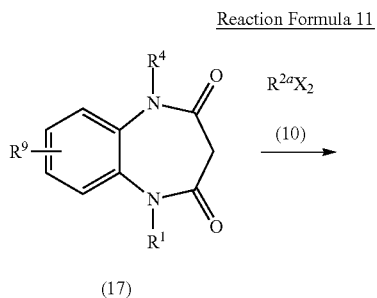

(17)

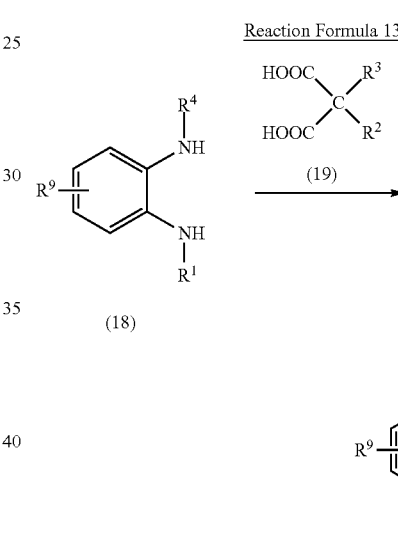

(16b)

wherein $R^1$, $R^{2a}$, $R^4$, $R^9$, and $X_2$ are the same as above.

The reaction of the compound of Formula (17) with the compound of Formula (10) is performed under the same reaction conditions as those for the reaction of the compound of Formula (3), in which $X_1$ is halogen, with the compound of Formula (2) in Reaction Formula 1.

When $R^1$ and/or $R^4$ is hydrogen in the reaction of the compound of Formula (17) and the compound of Formula (10), the hydrogen atom may be replaced with $R^{2a}$.

Reaction Formula 12

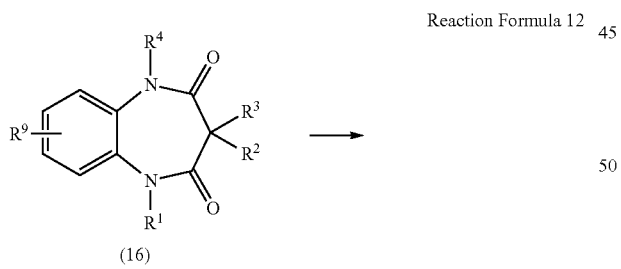

wherein $R^1$, $R^2$, $R^3$, $R^4$, and $R^9$ are the same as above.

The reaction converting the compound of Formula (16) to the compound of Formula (2) can be carried out in a suitable solvent in the presence of an acid. Examples of solvents include water; lower alcohols such as methanol, ethanol, and isopropanol; ethers such as dioxane, tetrahydrofuran, and diethyl ether; halogenated hydrocarbons such as dichloromethane, chloroform, and carbon tetrachloride; polar solvents such as acetonitrile; and mixtures of such solvents. Examples of acids include mineral acids such as hydrochloric acid, sulfuric acid, and hydrobromic acid; aliphatic acids such as formic acid, and acetic acid; sulfonic acids such as p-toluenesulfonic acid; Lewis acids such as boron fluoride, aluminium chloride, and boron tribromide; iodides such as sodium iodide, and potassium iodide; mixtures of such iodides and Lewis acids. The reaction is usually performed at about 0 to about 200° C., and preferably at about 0 to about 150° C., and is usually completed in about 0.5 to about 25 hours. An acid is usually used in an amount of 1 to 10 moles, and preferably about 1 mole to about 2 moles per mole of the compound of Formula (16).

The compound of Formula (16) can be prepared using the processes shown in Reaction Formulae 13 and 14 below.

Reaction Formula 13

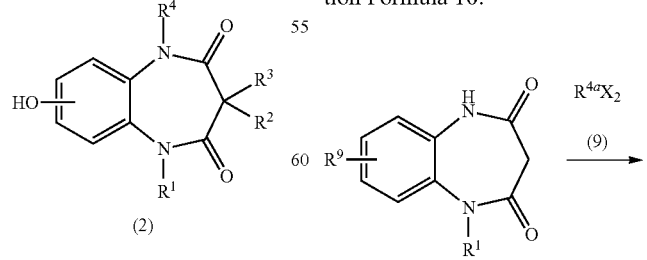

wherein $R^1$, $R^2$, $R^3$, $R^4$, and $R^9$ are the same as above.

The reaction of the compound of Formula (18) with the compound of Formula (19) is performed under the same reaction conditions as those for the reaction of the compound of Formula (11) with the compound of Formula (12) in Reaction Formula 10.

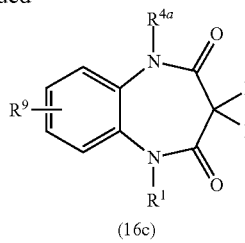

(16c)

wherein $R^1$, $R^2$, $R^3$, $R^{4a}$, and $R^9$ are the same as above.

The reaction of the compound of Formula (20) with the compound of Formula (9) is performed under the same reaction conditions as those for the reaction of the compound of Formula (1i) with the compound of Formula (9) in Reaction Formula 8.

When $R^1$ in the compound of Formula (20) is hydrogen in the reaction, a compound in which the first and fifth positions of the benzodiazepine skeleton are simultaneously substituted with $R^{4a}$ may be produced.

The compound of Formula 4, which is used as a starting material in the above-mentioned reaction formula, can be easily prepared by the process shown in the following reaction formula.

Reaction Formula 15

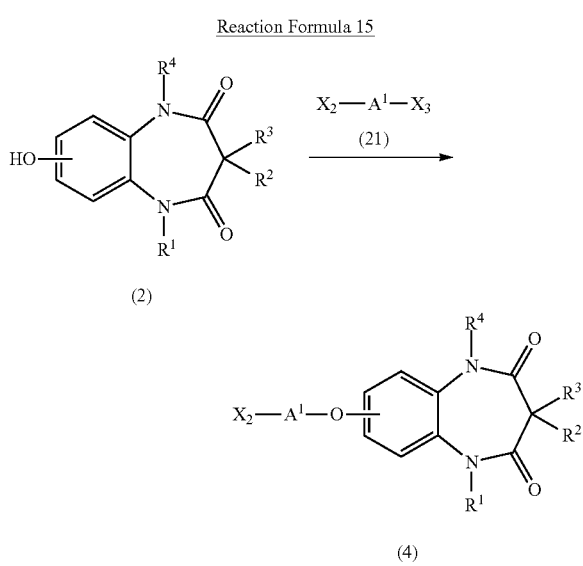

wherein $R^1$, $R^2$, $R^3$, $R^4$, $A^1$, and $X_2$ are the same as above, and $X_3$ is halogen.

The reaction of the compound of Formula (2) with the compound of Formula (21) is performed under the same reaction conditions as those for the reaction of the compound of Formula (3), in which $X_1$ is halogen, with the compound of Formula (2) in Reaction Formula 1.

$X_2$ in the compound of Formula (4) can be replaced with another halogen atom by adding it to an appropriate solvent with an alkali metal halide, and heating under reflux. Examples of alkali metal halides include sodium iodide, sodium bromide, sodium fluoride, sodium chloride, potassium iodide, potassium bromide, potassium fluoride, potassium chloride, etc. Examples of solvents for halogen exchange include ketones such as acetone, 2-butanone; ethers such as dioxane, tetrahydrofuran, diethyl ether, diethylene glycol dimethyl ether, and ethylene glycol dimethyl ether; and esters such as methyl acetate and ethyl acetate. Such solvents can be used singly or in a combination of two or more. An alkali metal halide is usually used in an amount at least 1 mole, and preferably about 1 mole to about 10 moles, per mole of the compound of Formula (4). Heat-reflux is continued until the reaction finishes. For example, heat-reflux is preferably continued for about 1 to about 15 hours. The heat-reflux temperature varies according to the solvent to be used, and is usually about 0 to about 150° C., and preferably about 0 to about 100° C.

The compound of Formula (5), which is used as a starting material, can be easily prepared by the process shown in the following reaction formula.

Reaction Formula 16

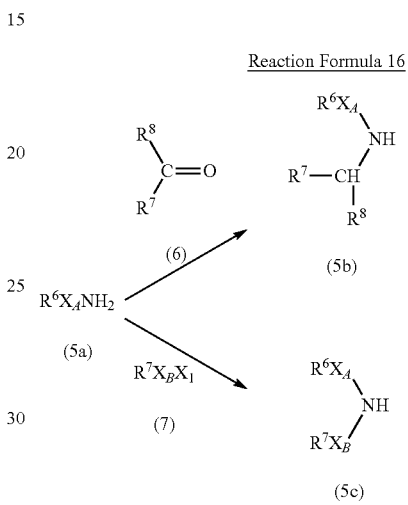

wherein $R^6$, $R^7$, $X_A$, $X_B$, $X_1$, and $R^8$ are the same as above.

The reaction of the compound of Formula (5a) with the compound of Formula (6) is performed under the same reaction conditions as those for the reaction of the compound of Formula (1c) with the compound of Formula (6) in Reaction Formula 4.

The reaction of the compound of Formula (5a) with the compound of Formula (7) is performed under the same reaction conditions as those for the reaction of the compound of Formula (1c) with the compound of Formula (7) in Reaction Formula 5.

The compound of Formula (3), which is used as a starting material, can be easily prepared by the process shown in the following reaction formula.

Starting material (24) used in the following Reaction Formula 18 can be easily prepared by the process shown in Reaction Formula 17.

Reaction Formula 17

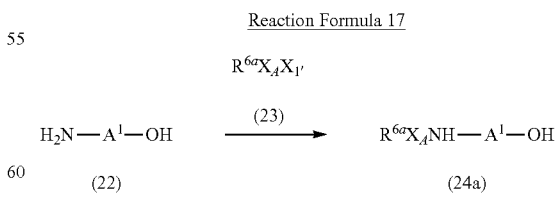

wherein $A^1$ and $X_A$ are the same as above, $X_{1'}$ is halogen, and $R^{6a}$ is the same as $R^6$ as defined above, excluding the hydrogen atom.

The reaction of the compound of Formula (22) with the compound of Formula (23) is performed under the same reaction conditions as those for the reaction of the compound of Formula (2) with the compound of Formula (3) in Reaction Formula 1.

The reaction of the compound of Formula (5c) with the compound of Formula (28) is performed under the same reaction conditions as those for the reaction of the compound of Formula (3), in which $X_1$ is halogen, with the compound of Formula (2) in Reaction Formula 1.

Reaction Formula 18

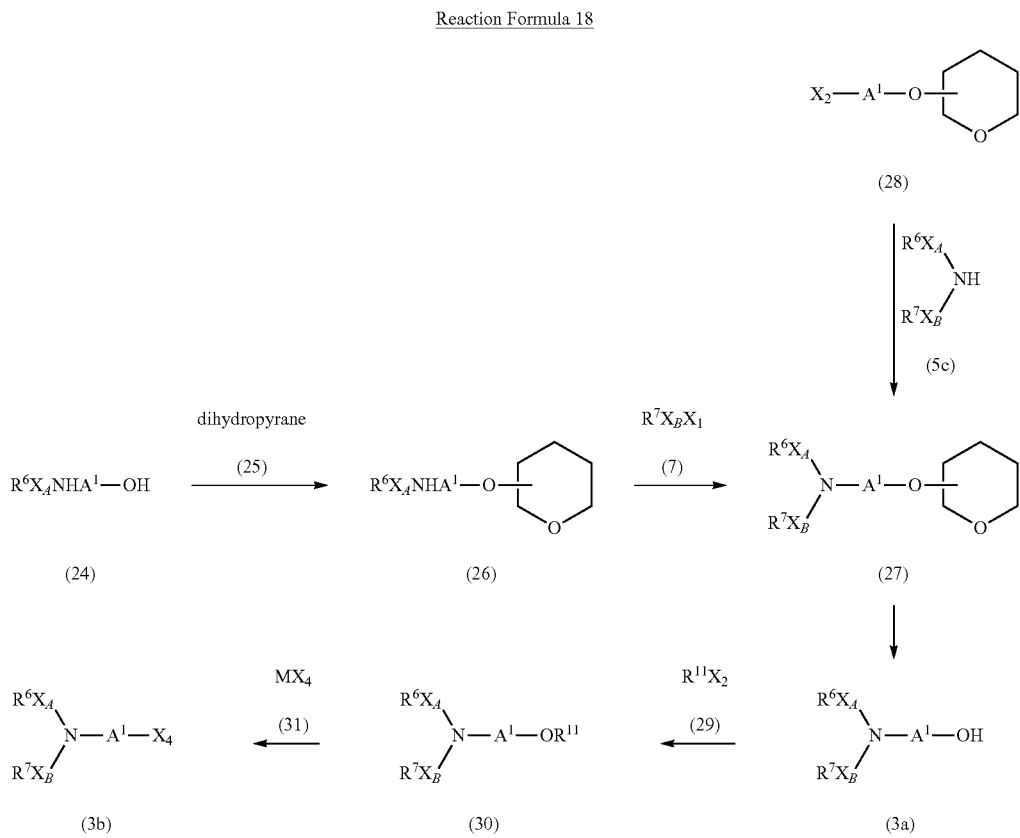

wherein $R^6$, $R^7$, $X_A$, $X_B$, $A^1$, $X_1$ and $X_2$ are the same as above, and $R^{11}$ is lower alkylsulfonyl. $X_4$ is halogen, and M is alkali metal such as sodium, potassium, etc.

Examples of the lower alkylsulfonyl groups represented by $R^{11}$ include linear or branched $C_{1-6}$ alkylsulfonyl groups, such as methylsulfonyl, ethylsulfonyl, n-propylsulfonyl, isopropylsulfonyl, n-butylsulfonyl, isobutylsulfonyl, tert-butylsulfonyl, sec-butylsulfonyl, n-pentylsulfonyl, isopentylsulfonyl, neopentylsulfonyl, n-hexylsulfonyl, isohexylsulfonyl, and 3-methylpentylsulfonyl.

The reaction of the compound of Formula (24) and the compound of Formula (25) is performed in a suitable solvent or without using any solvents in the presence of an acid. Examples of solvents include the solvents used in the reaction of the compound of Formula (2) and the compound of Formula (3) in Reaction Formula 1. Examples of usable acids include mineral acids such as hydrochloric acid, sulfuric acid, and hydrobromic acid; and organic acids such as formic acid, acetic acid, thioglycolic acid, trifluoroacetic acid, and sulfonic acid (e.g., p-toluenesulfonic acid). Such acids can be used singly or in a combination. Conditions other than those described above may be the same as those of the reaction between the compound of Formula (2) and the compound of Formula (3) in Reaction Formula 1.

The reaction of the compound of Formula (26) with the compound of Formula (7) is performed under the same reaction conditions as those for the reaction of the compound of Formula (2) with the compound of Formula (3) in Reaction Formula 1.

The reaction converting the compound of Formula (27) to the compound of Formula (3a) can be carried out in an appropriate solvent or without using any solvents in the presence of an acid or a basic compound.

Examples of useful solvents include water; lower alcohols such as methanol, ethanol, isopropanol, and tert-butanol; ketones such as acetone, and methyl ethyl ketone; ethers such as diethyl ether, dioxane, tetrahydrofuran, monoglyme and diglyme; aliphatic acids such as acetic acid and formic acid; esters such as methyl acetate and ethyl acetate; halogenated hydrocarbons such as chloroform, dichloromethane, dichloroethane, and carbon tetrachloride; dimethyl sulfoxide; N,N-dimethylformamide; and hexamethylphosphoric triamide; and mixtures of such solvents.

Examples of acids include mineral acids such as hydrochloric acid, sulfuric acid, and hydrobromic acid; and organic acids such as formic acid, acetic acid, trifluoroacetic acid, and sulfonic acid (e.g., p-toluenesulfonic acid and pyridinium p-toluenesulfonate); Lewis acids such as boron tribromide and boron trichloride. Such acids can be used singly or in a combination.

Examples of useful basic compounds include carbonates such as sodium carbonate, potassium carbonate, sodium hydrogencarbonate, and potassium hydrogencarbonate; and metal hydroxides such as sodium hydroxide, potassium hydroxide, calcium hydroxide, and lithium hydroxide. Such basic compounds can be used singly or in a combination.

The reaction advantageously proceeds usually at about 0 to about 200° C., and preferably at about 0 to about 150° C., and is usually completed in about 10 minutes to about 50 hours.

The reaction of the compound of Formula (3a) with the compound of Formula (29) is performed under the same reaction conditions as those for the reaction of the compound of Formula (5c) with the compound of Formula (28).

The reaction converting the compound of Formula (30) to the compound of Formula (3b) is performed under the same reaction conditions as those for the reaction of the compound of Formula (3), in which $X_1$ is halogen, with the compound of Formula (2) in Reaction Formula 1.

The compound of Formula (7), which is used as a starting material, can be easily prepared by the process shown in the following reaction formula.

Reaction Formula 19

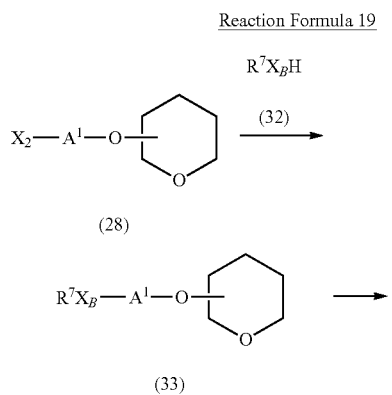

wherein $R_7$, $X_B$, $X^2$ and $A^1$ are the same as above.

The reaction of the compound of Formula (32) with the compound of Formula (28) is performed under the same reaction conditions as those for the reaction of the compound of Formula (5c) with the compound of Formula (28) in Reaction Formula 18.

The reaction converting the compound of Formula (33) to the compound of Formula (7a) can be carried out under the same reaction conditions as those for the reaction converting the compound of Formula (27) to the compound of Formula (3a) in Reaction Formula 18.

The compound of Formula (5), which is used as a starting material, can be easily prepared by the process shown in the following reaction formula.

Reaction Formula 20

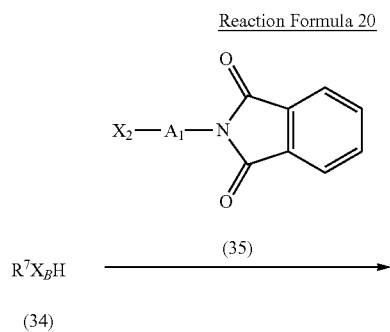

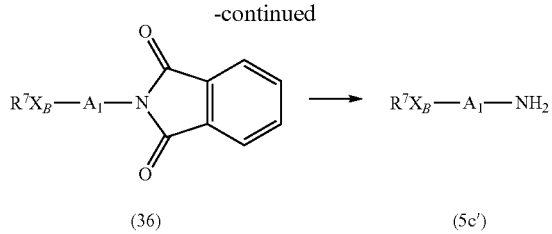

wherein $A^1$, $R^7$, $X_B$, and $X_2$ are the same as above.

The reaction of the compound of Formula (34) with the compound of Formula (35) is performed under the same reaction conditions as those for the reaction of the compound of Formula (3), in which $X_1$ is halogen, with the compound of Formula (2) in Reaction Formula 1.

The reaction converting the compound of Formula (36) to the compound of Formula (5c) can be carried out under the same reaction conditions as those for the reaction converting the compound of Formula (1a) to the compound of Formula (1b) in Reaction Formula 2

Reaction Formula 21

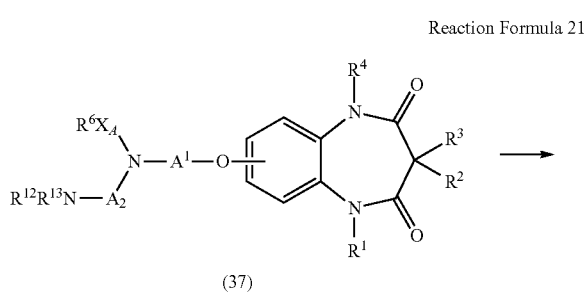

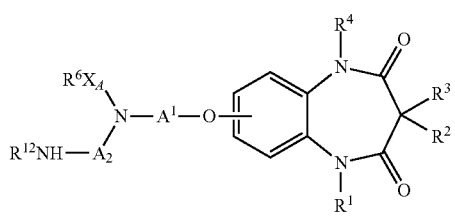

wherein $R^1$, $R^2$, $R^3$, $R^4$, $R^6$, $X_A$ and $A^1$ are the same as above. $R^{12}$ is hydrogen, lower alkyl, lower alkoxycarbonyl, 2,3-dihydrobenzo[b]furylcarbonyl, or benzoyl. $R^{13}$ is lower alkoxycarbonyl, 2,3-dihydrobenzo[b]furyl carbonyl, or benzoyl, and $A^2$ is lower alkylene.

The reaction converting the compound of Formula (37) to the compound of Formula (38) can be carried out under the same reaction conditions as those for the reaction converting the compound of Formula (1f) to the compound of Formula (1c) in Reaction Formula 6.

Reaction Formula 22

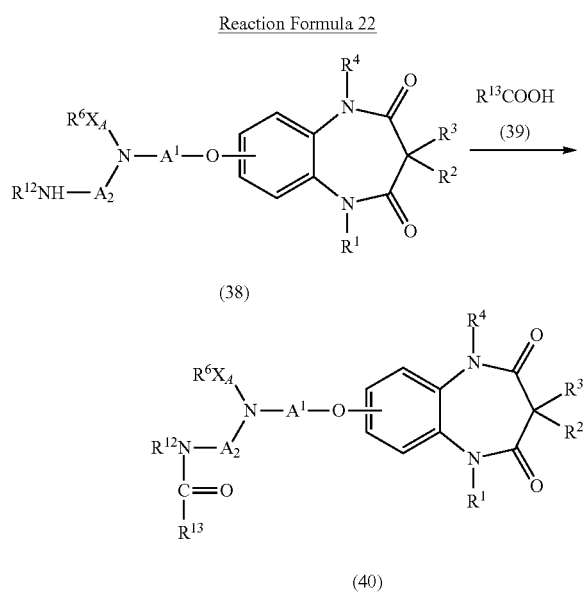

wherein $R^1$, $R^2$, $R^3$, $R^4$, $R^6$, $X_4$, $R^{12}$, $A^1$, and $A^2$ are the same as above. $R^{13}$ is 2,3-dihydrobenzo[b]furyl or phenyl.

The reaction of the compound of Formula (38) with the compound of Formula (39) is performed under the same reaction conditions as those for the reaction of the compound of Formula (11) with the compound of Formula (12) in Reaction Formula 10.

In addition, compounds in the form in which a solvate (for example, a hydrate, ethanolate, etc.) was added to the starting material compounds and object compounds shown in each of the reaction formulae are included in each of the formulae.

The compound of Formula (1) according to the present invention includes stereoisomers and optical isomers.

The starting material compounds and object compounds represented by each of the reaction formulae can be used in an appropriate salt form.

Each of the object compounds obtained according to the above reaction formulae can be isolated and purified from the reaction mixture by, for example, after cooling the reaction mixture, performing an isolation procedure such as filtration, concentration, extraction, etc., to separate a crude reaction product, and then subjecting the crude reaction product to a usual purification procedure such as column chromatography, recrystallization, etc.

Among the compounds of the present invention, those having a basic group or groups can easily form salts with common pharmaceutically acceptable acids. Examples of such acids include hydrochloric acid, hydrobromic acid, nitric acid, sulfuric acid, phosphoric acid and other inorganic acids, methansulfonic acid, p-toluenesulfonic acid, acetic acid, citric acid, tartaric acid, maleic acid, fumaric acid, malic acid, lactic acid and other organic acids, etc.

Among the compounds of the present invention, those having an acidic group or groups can easily form salts by reacting with pharmaceutically acceptable basic compounds. Examples of such basic compounds include sodium hydroxide, potassium hydroxide, calcium hydroxide, sodium carbonate, potassium carbonate, sodium hydrogencarbonate, potassium hydrogencarbonate, etc.

The following is an explanation of pharmaceutical preparations comprising the compound of the present invention as an active ingredient.

Such pharmaceutical preparations are obtained by formulating the compound of the present invention into usual pharmaceutical preparations, using usually employed diluents or excipients such as fillers, extenders, binders, wetting agents, disintegrants, surfactants, lubricants, etc.

The form of such pharmaceutical preparations can be selected from various forms according to the purpose of therapy. Typical examples include tablets, pills, powders, solutions, suspensions, emulsions, granules, capsules, suppositories, injections (solutions, suspensions, etc.) and the like.

To form tablets, any of various known carriers can be used, including, for example, lactose, white sugar, sodium chloride, glucose, urea, starch, calcium carbonate, kaolin, crystalline cellulose and other excipients; water, ethanol, propanol, simple syrup, glucose solutions, starch solutions, gelatin solutions, carboxymethylcellulose, shellac, methylcellulose, potassium phosphate, polyvinylpyrrolidone and other binders; dry starch, sodium alginate, agar powder, laminaran powder, sodium hydrogencarbonate, calcium carbonate, fatty acid esters of polyoxyethylenesorbitan, sodium laurylsulfate, stearic acid monoglyceride, starch, lactose and other disintegrants; white sugar, stearin, cacao butter, hydrogenated oils and other disintegration inhibitors; quaternary ammonium base, sodium lauryl sulfate and other absorption promoters; glycerin, starch and other wetting agents; starch, lactose, kaolin, bentonite, colloidal silicic acid and other adsorbents; purified talc, stearates, boric acid powder, polyethylene glycol and other lubricants; etc.

Such tablets may be coated with usual coating materials as required, to prepare, for example, sugar-coated tablets, gelatin-coated tablets, enteric-coated tablets, film-coated tablets, double- or multi-layered tablets, etc.

To form pills, any of various known carriers can be used, including, for example, glucose, lactose, starch, cacao butter, hydrogenated vegetable oils, kaolin, talc and other excipients; gum arabic powder, tragacanth powder, gelatin, ethanol and other binders; laminaran, agar and other disintegrants; etc.

To form suppositories, any of various known carriers can be used, including, for example, polyethylene glycol, cacao butter, higher alcohols, esters of higher alcohols, gelatin, semisynthetic glycerides, etc.

To form an injection, a solution, emulsion or suspension is sterilized and preferably made isotonic with blood. Any of various known widely used diluents can be employed to prepare the solution, emulsion or suspension. Examples of such diluents include water, ethanol, propylene glycol, ethoxylated isostearyl alcohol, polyoxylated isostearyl alcohol, fatty acid esters of polyoxyethylene sorbitan, etc. In this case, the pharmaceutical preparation may contain sodium chloride, glucose or glycerin in an amount sufficient to prepare an isotonic solution, and may contain usual solubilizers, buffers, analgesic agents, etc., and further, if necessary, coloring agents, preservatives, flavors, sweetening agents, etc., and/or other medicines.

The proportion of the compound of the present invention in the pharmaceutical preparation is not limited and can be suitably selected from a wide range. It is usually preferable that the pharmaceutical preparation contain the compound of the present invention in a proportion of 1 to 70 wt. %.

The route of administration of the pharmaceutical preparation according to the present invention is not limited, and the preparation can be administered by a route suitable for the form of the preparation, the patient's age and sex, the conditions of the disease, and other conditions.

For example, tablets, pills, solutions, suspensions, emulsions, granules and capsules are administered orally.

Injections are intravenously administered singly or as mixed with usual injection transfusions such as glucose solutions, amino acid solutions or the like, or singly administered intramuscularly, intracutaneously, subcutaneously or intraperitoneally, as required. Suppositories are administered intrarectally.

The dosage of the pharmaceutical preparation is suitably selected according to the method of use, the patient's age and sex, the severity of the disease, and other conditions, and is usually about 0.001 to about 100 mg/kg body weight/day, and preferably 0.001 to 50 mg/kg body weight/day, in single or divided doses.

Since the dosage varies depending on various conditions, a dosage smaller than the above range may be sufficient, or a dosage larger than the above range may be required.

When administered to the human body as a pharmaceutical, the compound of the present invention may be used concurrently with, or before or after, antithrombotics such as blood clotting inhibitors and antiplatelet agents (e.g., warfarin, aspirin, etc.). Further, the present compound may be used concurrently with, or before or after, drugs for treating chronic diseases, such as antihypertensive drugs (ACE inhibitors, beta blockers, angiotensin II receptor antagonists), heart failure drugs (cardiotonic agents, diuretics), and diabetes treatment agents.

The compound of the present invention has potent blocking effects on human Kv1.5 and/or GIRK1/4 channels, and weak blocking effects on HERG channels. Thus, the compound of the invention has characteristics as an atrial-selective $K^+$ channel-blocking agent.

Therefore, the compound of the invention can be used as a pharmacologically active substance that is safer and provides a more potent effect on the prolongation of the atrial refractory period than conventional antiarrhythmic agents. The compound of the invention is preferably used as a therapeutic agent for arrhythmia such as atrial fibrillation, atrial flutter, and atrial tachycardia (elimination of arrhythmia and/or prevention of the occurrence of arrhythmia). The compound of the invention is particularly preferably used as a therapeutic agent for atrial fibrillation (defibrillation and maintenance of sinus rhythm). The compound of the invention can also be used as a prophylactic agent for thromboembolism such as cerebral infarction and as a therapeutic agent for heart failure.

The compound having potent blocking effects on both human Kv1.5 and human GIRK1/4 channels has more potent atrial refractory period prolongation effects and is highly safe, compared to compounds inhibiting either one of the channels. Furthermore, this compound has greater therapeutic effects on atrial fibrillation (defibrillation and maintenance of sinus rhythm) than compounds inhibiting either one of the channels. Therefore, the compound having potent blocking effects on both the human Kv1.5 and human GIRK1/4 channels is particularly useful as a therapeutic agent for arrhythmia such as atrial fibrillation, atrial flutter, and atrial tachycardia (termination of arrhythmia and/or prevention of the occurrence of arrhythmia). This compound is particularly useful as a therapeutic agent for atrial fibrillation (defibrillation and maintenance of sinus rhythm).

BEST MODE FOR CARRYING OUT THE INVENTION

The following Examples are intended to illustrate the present invention in future detail.

Reference Example 1

Synthesis of ethyl N-(5-methoxy-2-nitrophenyl)-N-methyl malonamate

Sodium hydride (60% in oil, 96 mg, 2.4 mmol) was suspended in 10 ml of dimethylformamide (DMF). N-Methyl-5-methoxy-2-nitroaniline (364 mg, 2 mmol) was added thereto at 0° C., and stirring was conducted for 30 minutes at room temperature. Ethyl malonyl chloride (0.38 ml, 3 mmol) was added at 0° C. to the stirred mixture, and the reaction mixture was stirred at room temperature overnight. Water was added thereto, and extraction with ethyl acetate was performed. The organic layer was dried over sodium sulfate, and concentrated under reduced pressure. The residue was purified by silica gel column chromatography (n-hexane: ethyl acetate=2:1→1:2).

The purified product was concentrated under reduced pressure to thereby obtain 554 mg (yield: 90%) of ethyl N-(5-methoxy-2-nitrophenyl)-N-methyl malonamate as a yellow oil.

$^1$H-NMR (CDCl$_3$) δppm:
1.24 (3H, t, J=7.1 Hz), 3.15-3.17 (2H, m), 3.25 (3H, s), 3.92 (3H, s), 4.13 (2H, q, J=7.1 Hz), 6.93 (1H, d, J=2.8 Hz), 7.02 (1H, dd, J=2.8 and 9.2 Hz), 8.15 (1H, d, J=9.2 Hz).

Reference Example 2

Synthesis of ethyl N-ethyl-N-(5-methoxy-2-nitrophenyl)malonamate

Using an appropriate starting material and following the procedure of Reference Example 1, the object compound was synthesized.

$^1$H-NMR (CDCl$_3$) δppm:
1.11 (3H, t, J=7.2 Hz), 1.24 (3H, t, J=7.1 Hz), 3.11-3.25 (2H, m), 3.39-3.46 (1H, m), 3.92 (3H, s), 3.98-4.17 (3H, m), 6.89 (1H, d, J=2.8 Hz), 7.03 (1H, dd, J=9.2 and 2.8 Hz), 8.13 (1H, d, J=9.2 Hz).

Reference Example 3

Synthesis of ethyl N-(2-amino-5-methoxyphenyl)-N-methyl malonamate

Palladium carbon (10%, 0.5 g) was added to an ethanol solution (150 ml) of ethyl N-(5-methoxy-2-nitrophenyl)-N-methyl malonamate (3.0 g, 10 mmol), and catalytic reduction was conducted at room temperature and normal pressure. The reaction mixture was filtered through Celite to remove the catalyst. The filtrate was concentrated under reduced pressure to thereby obtain 2.68 g (yield: quantitative) of ethyl N-(2-amino-5-methoxyphenyl)-N-methyl malonamate as a yellow oil.

$^1$H-NMR (CDCl$_3$) δppm:
1.22 (3H, t, J=7.1 Hz), 3.19-3.27 (5H, m), 3.52-3.68 (2H, br), 3.74 (3H, s), 4.11 (2H, q, J=7.1 Hz), 6.62 (1H, d, J=2.7 Hz), 6.73 (1H, d, J=8.7 Hz), 6.79 (1H, dd, J=2.7 and 8.7 Hz).

Reference Example 4

Synthesis of 8-methoxy-1-methyl-1,5-dihydrobenzo[b][1,4]diazepine-2,4-dione

Sodium ethoxide (204 mg, 3.0 mmol) was added to an ethanol solution (15 ml) of ethyl N-(2-amino-5-methoxyphenyl)-N-methyl malonamate (266 mg, 1.0 mmol), and stirred at 65° C. for 2.5 hours. The reaction mixture was cooled to room temperature, and concentrated under reduced pressure. The residue was purified by silica gel column chromatography (dichloromethane:methanol=1:0→10:1). The purified product was concentrated to dryness under reduced pressure to thereby obtain 176.3 mg (yield: 80%) of 8-methoxy-1-methyl-1,5-dihydrobenzo[b][1,4]diazepine-2,4-dione as a white powder.

$^1$H-NMR (CDCl$_3$) δppm:
3.36 (2H, s), 3.43 (3H, s), 3.84 (3H, s), 6.79-6.83 (1H, m), 7.06-7.09 (1H, m), 8.72 (1H, br-s).

Reference Example 5

Synthesis of 1-ethyl-8-methoxy-1,5-dihydrobenzo[b][1,4]diazepine-2,4-dione

Palladium carbon (10%, 1.1 g) was added to an ethanol solution (250 ml) of ethyl N-ethyl-N-(5-methoxy-2-nitrophenyl)malonamate (21.05 g, 67.8 mmol), and cooled in an ice water bath. Catalytic reduction was conducted at about room temperature. Celite filtration was conducted to remove the catalyst, and the filtrate was concentrated under reduced pressure. The residue was dissolved in tetrahydrofuran (THF) (200 ml). Sodium ethoxide (6.9 g, 102 mmol) was added thereto, and then heating was conducted under reflux for 15 minutes. The reaction mixture was cooled to room temperature, and the precipitated insoluble matter was collected by filtration. The filtrate was concentrated under reduced pressure. Water was added to the residue and the collected insoluble matter, and the mixture was neutralized with hydrochloric acid. Extraction with ethyl acetate was then performed. The organic layer was washed with a saturated sodium chloride aqueous solution, dried over anhydrous sodium sulfate, and concentrated under reduced pressure. The residue was recrystallized from ethanol to thereby obtain 7.9 g (yield: 50%) of 1-ethyl-8-methoxy-1,5-dihydrobenzo[b][1,4]diazepine-2,4-dione as a white powder. The mother liquor was then concentrated, and the residue was purified using a silica gel flash column (n-hexane:ethyl acetate=1:1→0:1) to thereby obtain 2.9 g of object compound.

$^1$H-NMR (CDCl$_3$) δppm:
1.19 (3H, t, J=7.1 Hz), 3.33 (2H, s), 3.78-3.84 (1H, m), 3.84 (3H, s), 4.13-4.25 (1H, m), 6.82 (1H, dd, J=8.8 and 2.7 Hz), 6.87 (1H, d, J=2.7 Hz), 7.09 (1H, d, J=8.8 Hz), 8.82 (1H, br-s).

Reference Example 6

Synthesis of 1-ethyl-7-methoxy-5-methyl-1,5-dihydrobenzo[b][1,4]diazepine-2,4-dione Sodium hydride (60% in oil, 44 mg, 1.1 mmol) was suspended in dimethylformamide (DMF) (8 ml), and cooled in an ice water bath to 0° C. 8-Methoxy-1-methyl-1,5-dihydrobenzo[b][1,4]diazepine-2,4-dione (220 mg, 1.0 mmol) was added to the suspension at the same temperature, and stirred at 0° C. for 1 hour. Ethyl iodide (187 mg, 1.2 mmol) was added to the mixture and stirred at room temperature overnight. Water was added to the reaction mixture, and extraction with ethyl acetate was performed. The organic layer was dried over sodium sulfate, and concentrated under reduced pressure. The residue was purified by silica gel column chromatography (n-hexane:ethyl acetate=4:1→1:1). The purified product was concentrated to dryness under reduced pressure to thereby obtain 190.2 mg (yield: 77%) of 1-ethyl-7-methoxy-5-methyl-1,5-dihydrobenzo[b][1,4]diazepine-2,4-dione as a yellow solid.

$^1$H-NMR (CDCl$_3$) δppm:
1.11 (3H, t, J=7.1 Hz), 3.31-3.32 (2H, m), 3.40 (3H, s), 3.59-3.68 (1H, m), 3.85 (3H, s), 4.18-4.30 (1H, m), 6.78 (1H, d, J=2.8 Hz), 6.84 (1H, dd, J=9.0 and 2.8 Hz), 7.26 (1H, d, J=9.0 Hz).

Reference Example 7

Synthesis of 1,5-diethyl-7-methoxy-1,5-dihydrobenzo[b][1,4]diazepine-2,4-dione

Using an appropriate starting material and following the procedure of Reference Example 6, the object compound was synthesized.

$^1$H-NMR (CDCl$_3$) δppm:
1.04-1.14 (6H, m), 3.28 (2H, s), 3.50-3.64 (2H, m), 3.85 (3H, s), 4.35-4.47 (2H, m), 6.83-6.88 (2H, m), 7.25-7.27 (1H, m).

Reference Example 8

Synthesis of 7-methoxy-5-methyl-1-propyl-1,5-dihydrobenzo[b][1,4]diazepine-2,4-dione Using an appropriate starting material and following the procedure of Reference Example 6, the object compound was synthesized.

$^1$H-NMR (CDCl$_3$) δppm:
0.76 (3H, t, J=7.3 Hz), 1.35-1.62 (2H, m), 3.32 (2H, s), 3.40 (3H, s), 3.33-3.51 (1H, m), 3.49 (3H, s), 4.21-4.38 (1H, m), 6.78 (1H, d, J=2.8 Hz), 6.84 (1H, dd, J=9.0 and 2.8 Hz), 7.25 (1H, d, J=9.0 Hz).

Reference Example 9

Synthesis of 1-isobutyl-7-methoxy-5-methyl-1,5-dihydrobenzo[b][1,4]diazepine-2,4-dione Using an appropriate starting material and following the procedure of Reference Example 6, the object compound was synthesized.

$^1$H-NMR (CDCl$_3$) δppm:
0.69 (3H, d, J=6.7 Hz), 0.77 (3H, d, J=6.7 Hz), 1.56-1.90 (1H, m), 3.24 (1H, dd, J=13.6 and 5.9 Hz), 3.33 (2H, s), 3.40 (3H, s), 3.85 (3H, s), 4.32 (1H, dd, J=13.6 and 9.0 Hz), 6.78 (1H, d, J=2.8 Hz), 6.84 (1H, dd, J=9.0 and 2.9 Hz), 7.24 (1H, d, J=9.0 Hz).

Reference Example 10

Synthesis of 7-methoxy-5-methyl-1-(3-methylbutyl)-1,5-dihydrobenzo[b][1,4]diazepine-2,4-dione Using an appropriate starting material and following the procedure of Reference Example 6, the object compound was synthesized.

$^1$H-NMR (CDCl$_3$) δppm:
0.80 (3H, d, J=6.3 Hz), 0.86 (3H, d, J=6.3 Hz), 1.22-1.53 (3H, m), 3.32 (2H, s), 3.39 (3H, s), 3.36-3.62 (1H, m), 3.85

(3H, s), 4.31-4.48 (1H, m), 6.78 (1H, d, J=2.8 Hz), 6.85 (1H, dd, J=8.8 and 2.8 Hz), 7.25 (1H, d, J=8.8 Hz).

Reference Example 11

Synthesis of 7-methoxy-5-methyl-1-(3-methylbut-2-enyl)-1,5-dihydrobenzo[b][1,4]diazepine-2,4-dione Using an appropriate starting material and following the procedure of Reference Example 6, the object compound was synthesized.
$^1$H-NMR (CDCl$_3$) δppm:
1.63 (6H, s), 3.32-3.34 (2H, m), 3.38 (3H, s), 3.84 (3H, s), 4.33 (1H, dd, J=13.6 and 6.2 Hz), 4.51 (1H, dd, J=13.6 and 6.9 Hz), 5.14-5.19 (1H, m), 6.76 (1H, d, J=2.8 Hz), 6.81 (1H, dd, J=9.0 and 2.8 Hz), 7.27 (1H, d, J=9.0 Hz).

Reference Example 12

Synthesis of 1-ethyl-7-methoxy-3,3,5-trimethyl-1,5-dihydrobenzo[b][1,4]diazepine-2,4-dione Sodium hydride (60% in oil, 76 mg, 1.9 mmol) was suspended in DMF (8 ml).
1-Ethyl-7-methoxy-5-methyl-1,5-dihydrobenzo[b][1,4]diazepine-2,4-dione (190 mg, 0.76 mmol) was added thereto at 0° C., and stirring was conducted at the same temperature for 1 hour. Methyl iodide (0.19 ml, 3.1 mmol) was added to the mixture, and stirred at room temperature for 3 days. Water was added to the reaction mixture, and extraction with ethyl acetate was performed. The organic layer was dried over sodium sulfate, and concentrated under reduced pressure. The residue was purified by silica gel column chromatography (ethyl acetate). The purified product was concentrated to dryness under reduced pressure to thereby obtain 169 mg (yield: 80%) of 1-ethyl-7-methoxy-3,3,5-trimethyl-1,5-dihydrobenzo[b][1,4]diazepine-2,4-dione as a yellow powder.
$^1$H-NMR (CDCl$_3$) δppm:
0.86 (3H, s), 1.15 (3H, t, J=7.1 Hz), 1.53 (3H, s), 3.40 (3H, s), 3.65-3.76 (1H, m), 3.85 (3H, s), 4.12-4.24 (1H, m), 6.73 (1H, d, J=2.8 Hz), 6.83 (1H, dd, J=9.0 and 2.8 Hz), 7.22 (1H, d, J=9.0 Hz).

Reference Example 13

Synthesis of 7-methoxy-3,3,5-trimethyl-1-propyl-1,5-dihydrobenzo[b][1,4]diazepine-2,4-dione Using an appropriate starting material and following the procedure of Reference Example 12, the object compound was synthesized.
$^1$H-NMR (CDCl$_3$) δppm:
0.76 (3H, t, J=7.3 Hz), 0.85 (3H, s), 1.52 (3H, s), 1.38-1.68 (2H, m), 3.41 (3H, s), 3.42-3.58 (1H, m), 3.85 (3H, s), 4.19-4.31 (1H, m), 6.72 (1H, d, J=2.8 Hz), 6.81 (1H, dd, J=9.0 and 2.8 Hz), 7.20 (1H, d, J=9.0 Hz).

Reference Example 14

Synthesis of 7-methoxy-3,3,5-trimethyl-1-(3-methylbutyl)-1,5-dihydrobenzo[b][1,4]diazepine-2,4-dione Using an appropriate starting material and following the procedure of Reference Example 12, the object compound was synthesized.
$^1$H-NMR (CDCl$_3$) δppm:
0.82 (3H, d, J=6.2 Hz), 0.85 (3H, s), 0.86 (3H, d, J=6.2 Hz), 1.30-1.49 (3H, m), 1.52 (3H, s), 3.40 (3H, s), 3.49-3.62 (1H, m), 3.85 (3H, s), 4.21-4.36 (1H, m), 6.71 (1H, d, J=2.8 Hz), 6.80 (1H, dd, J=9.0 and 2.8 Hz), 7.20 (1H, d, J=9.0 Hz).

Reference Example 15

Synthesis of 1,5-diethyl-7-methoxy-3,3-dimethyl-1,5-dihydrobenzo[b][1,4]diazepine-2,4-dione Using an appropriate starting material and following the procedure of Reference Example 12, the object compound was synthesized.
$^1$H-NMR (CDCl$_3$) δppm:
0.84 (3H, s), 1.06-1.18 (6H, m), 1.51 (3H, s), 3.56-3.83 (2H, m), 3.85 (3H, s), 4.29-4.42 (2H, m), 6.79-6.86 (2H, m), 7.21 (1H, d, J=8.9 Hz).

Reference Example 16

Synthesis of 1,3-diethyl-7-methoxy-5-methyl-1,5-dihydrobenzo[b][1,4]diazepine-2,4-dione Using an appropriate starting material and following the procedure of Reference Example 12, the object compound was synthesized.
$^1$H-NMR (CDCl$_3$) δppm:
0.86 (3H, t, J=7.3 Hz), 1.06 (3H, t, J=7.0 Hz), 1.94-2.05 (2H, m), 2.97 (1H, t, J=6.9 Hz), 3.40 (3H, s), 3.55-3.66 (1H, m), 3.86 (3H, s), 4.20-4.33 (1H, m), 6.79 (1H, d, J=2.8 Hz), 6.84-6.88 (1H, m), 7.26-7.29 (1H, m).

Reference Example 17

Synthesis of 3,3-diethyl-7-methoxy-1,5-dihydrobenzo[b][1,4]diazepine-2,4-dione

Diethylmalonyl dichloride (0.95 ml, 5.5 mmol) was added to a dichloromethane solution (20 ml) of 4-methoxy-o-phenylenediamine (691 mg, 5 mmol) and triethylamine (1.7 ml, 12.5 mmol) at 0° C., and stirred at room temperature overnight. Water was added to the reaction mixture, and extraction with dichloromethane was performed. The organic layer was washed with a saturated sodium chloride aqueous solution, dried over sodium sulfate, and concentrated under reduced pressure. The residue was purified by silica gel column chromatography (n-hexane:ethyl acetate=9:1→1:1). The purified product was concentrated to dryness under reduced pressure to thereby obtain 452.3 mg (yield: 34%) of 3,3-diethyl-7-methoxy-1,5-dihydrobenzo[b][1,4]diazepine-2,4-dione as a yellow oil.
$^1$H-NMR (CDCl$_3$) δppm:
1.10 (6H, t, J=7.5 Hz), 1.86 (4H, q, J=7.5 Hz), 3.76 (3H, s), 4.18 (2H, br), 6.30 (1H, d, J=2.7 Hz), 6.35 (1H, dd, J=8.7 and 2.7 Hz), 7.23 (1H, d, J=8.7 Hz).

Reference Example 18

Synthesis of 3,3-diethyl-7-methoxy-1,5-dimethyl-1,5-dihydrobenzo[b][1,4]diazepine-2,4-dione Sodium hydride (60% in oil, 170 mg, 4.3 mmol) was suspended in DMF (15 ml).
3,3-Diethyl-7-methoxy-1,5-dihydrobenzo[b][1,4]diazepine-2,4-dione (452 mg, 1.7 mmol) was added thereto at 0° C., and stirring was conducted at the same temperature for 1 hour. Methyl iodide (0.42 ml, 6.8 mmol) was added to the mixture, and stirred at room temperature for 3 days. Water was added to the reaction mixture and extraction with ethyl acetate was performed. The organic layer was dried over sodium sulfate, and concentrated under reduced pressure. The residue was purified by silica gel column chromatography (n-hexane:ethyl acetate=2:1→1:1). The purified product was concentrated to dryness under reduced pressure to thereby obtain 373 mg (yield: 76%) of 3,3-diethyl-7-methoxy-1,5-dimethyl-1,5-dihydrobenzo[b][1,4]diazepine-2,4-dione as a white powder.

$^1$H-NMR (CDCl$_3$) δppm:

0.56 (3H, t, J=7.4 Hz), 1.02 (3H, t, J=7.3 Hz), 1.20-1.31 (2H, m), 2.15 (2H, q, J=7.3 Hz), 3.38 (3H, s), 3.41 (3H, s), 3.85 (3H, s), 6.71 (1H, d, J=2.8 Hz), 6.81 (1H, dd, J=9.0 and 2.8 Hz), 7.14 (1H, d, J=9.0 Hz).

Reference Example 19

Synthesis of 7-methoxy-1,3,3,5-tetramethyl-1,5-dihydrobenzo[b][1,4]diazepine-2,4-dione Sodium hydride (60% in oil, 128 mg, 3.2 mmol) was suspended in DMF (10 ml).

8-Methoxy-1-methyl-1,5-dihydrobenzo[b][1,4]diazepine-2,4-dione (176 mg, 0.8 mmol) was added thereto at 0° C., and stirring was conducted at the same temperature for 1 hour. Methyl iodide (0.25 ml, 4.0 mmol) was added to the mixture, and stirred at room temperature overnight. Water was added to the reaction mixture, and extraction with ethyl acetate was performed. The organic layer was washed with water, dried over sodium sulfate, and concentrated under reduced pressure. The residue was recrystallized from n-hexane to thereby obtain 161.6 mg (yield: 77%) of 7-methoxy-1,3,3,5-tetramethyl-1,5-dihydrobenzo[b][1,4]diazepine-2,4-dione as a white powder.

$^1$H-NMR (CDCl$_3$) δppm:

0.87 (3H, s), 1.54 (3H, s), 3.40 (3H, s), 3.42 (3H, s), 3.84 (3H, s), 6.73 (1H, s), 6.84 (1H, d, J=8.9 Hz), 7.14 (1H, d, J=8.9 Hz).

Reference Example 20

Synthesis of 5-ethyl-7-methoxy-1,3,3-trimethyl-1,5-dihydrobenzo[b][1,4]diazepine-2,4-dione Using an appropriate starting material and following the procedure of Reference Example 19, the object compound was synthesized.

$^1$H-NMR (CDCl$_3$) δppm:

0.86 (3H, s), 1.19 (3H, t, J=7.1 Hz), 1.53 (3H, s), 3.38 (3H, s), 3.75-3.82 (1H, m), 3.84 (3H, s), 4.12-4.19 (1H, m), 6.80-6.85 (2H, m), 7.16 (1H, dd, J=8.6 and 0.5 Hz).

Reference Example 21

Synthesis of 1,3,3,5-tetraethyl-7-methoxy-1,5-dihydrobenzo[b][1,4]diazepine-2,4-dione Using an appropriate starting material and following the procedure of Reference Example 19, the object compound was synthesized.

$^1$H-NMR (CDCl$_3$) δppm:

0.56 (3H, t, J=7.4 Hz), 0.98 (3H, t, J=7.4 Hz), 1.07-1.26 (6H, m), 2.10-2.17 (2H, m), 3.59-3.74 (2H, m), 3.85 (3H, s), 4.24-4.32 (2H, m), 6.78-6.85 (2H, m), 7.20 (1H, d, J=8.9 Hz).

Reference Example 22

Synthesis of 1,3,3-triethyl-7-methoxy-5-methyl-1,5-dihydrobenzo[b][1,4]diazepine-2,4-dione Using an appropriate starting material and following the procedure of Reference Example 19, the object compound was synthesized.

$^1$H-NMR (CDCl$_3$) δppm:

0.57 (3H, t, J=7.4 Hz), 1.00 (3H, t, J=7.3 Hz), 1.16 (3H, t, J=7.2 Hz), 1.21-1.29 (2H, m), 2.10-2.19 (2H, m), 3.40 (3H, s), 3.72-3.83 (1H, m), 3.85 (3H, s), 4.06-4.14 (1H, m), 6.71 (1H, d, J=2.8 Hz), 6.82 (1H, dd, J=9.0 and 2.8 Hz), 7.21 (1H, d, J=9.0 Hz).

Reference Example 23

Synthesis of 1,3,5-triethyl-7-methoxy-1,5-dihydrobenzo[b][1,4]diazepine-2,4-dione Using an appropriate starting material and following the procedure of Reference Example 19, the object compound was synthesized.

$^1$H-NMR (CDCl$_3$) δppm:

0.85 (3H, t, J=7.5 Hz), 0.88-1.11 (6H, m), 2.92-2.97 (1H, m), 3.50-3.65 (2H, m), 3.86 (3H, s), 4.12 (2H, q, J=7.2 Hz), 4.38-4.45 (2H, m), 6.84-6.89 (2H, m), 7.25-7.28 (1H, m).

Reference Example 24

Synthesis of 1-ethyl-7-hydroxy-3,3,5-trimethyl-1,5-dihydrobenzo[b][1,4]diazepine-2,4-dione A 1.0 M boron tribromide/dichloromethane solution (1.22 ml) was added to a dichloromethane solution (3 ml) of 1-ethyl-7-methoxy-3,3,5-trimethyl-1,5-dihydrobenzo[b][1,4]diazepine-2,4-dione (169 mg, 1.0 mmol) at 0° C., and stirred at room temperature overnight. Water and methanol were added to the reaction mixture and extraction with the mixture solvent (dichloromethane:methanol=10:1) was performed. The organic layer was dried over anhydrous sodium sulfate, and concentrated to dryness under reduced pressure to thereby obtain 156.4 mg (yield: 98%) of 1-ethyl-7-hydroxy-3,3,5-trimethyl-1,5-dihydrobenzo[b][1,4]diazepine-2,4-dione as a white powder.

$^1$H-NMR (CDCl$_3$) δppm:

0.90 (3H, s), 1.16 (3H, t, J=7.0 Hz), 1.55 (3H, s), 3.41 (3H, s), 3.66-3.78 (1H, m), 4.12-4.23 (1H, m), 6.79 (1H, d, J=2.7 Hz), 6.84 (1H, dd, J=8.8 and 2.7 Hz), 6.88 (1H, d, J=2.7 Hz), 7.18 (1H, d, J=8.8 Hz).

Reference Example 25

Synthesis of 3,3-diethyl-7-hydroxy-1,5-dimethyl-1,5-dihydrobenzo[b][1,4]diazepine-2,4-dione Using an appropriate starting material and following the procedure of Reference Example 24, the object compound was synthesized.

¹H-NMR (CDCl₃) δppm:
0.55 (3H, t, J=7.3 Hz), 1.00 (3H, t, J=7.3 Hz), 1.15-1.29 (2H, m), 2.12 (2H, q, J=7.3 Hz), 3.37 (3H, s), 3.38 (3H, s), 6.69 (1H, d, J=2.7 Hz), 6.76 (1H, dd, J=8.8 and 2.7 Hz), 7.06 (1H, d, J=8.8 Hz).

Reference Example 26

Synthesis of 1,3,3-triethyl-7-hydroxy-5-methyl-1,5-dihydrobenzo[b][1,4]diazepine-2,4-dione Using an appropriate starting material and following the procedure of Reference Example 24, the object compound was synthesized.
¹H-NMR (CDCl₃) δppm:
0.59 (3H, t, J=7.3 Hz), 1.01 (3H, t, J=7.3 Hz), 1.18 (3H, t, J=7.1 Hz), 1.21-1.34 (2H, m), 2.13-2.24 (2H, m), 3.40 (3H, s), 3.71-3.82 (1H, m), 4.05-4.16 (1H, m), 6.78 (1H, d, J=2.7 Hz), 6.84 (1H, dd, J=8.8 and 2.7 Hz), 7.04 (1H, br-s), 7.17 (1H, d, J=8.8 Hz).

Reference Example 27

Synthesis of 1,3-diethyl-7-hydroxy-5-methyl-1,5-dihydrobenzo[b][1,4]diazepine-2,4-dione Using an appropriate starting material and following the procedure of Reference Example 24, the object compound was synthesized.
¹H-NMR (CDCl₃) δppm:
0.87 (3H, t, J=7.4 Hz), 1.07 (3H, t, J=7.1 Hz), 1.95-2.05 (2H, m), 3.00 (1H, t, J=6.9 Hz), 3.39 (3H, s), 3.58-3.64 (1H, m), 4.22-4.29 (1H, m), 5.87 (1H, br-s), 6.80-6.84 (2H, m), 7.21-7.24 (1H, m).

Reference Example 28

Synthesis of 1,3-diethyl-7-hydroxy-3,5-dimethyl-1,5-dihydrobenzo[b][1,4]diazepine-2,4-dione Using an appropriate starting material and following the procedure of Reference Example 24, the object compound was synthesized.
¹H-NMR (CDCl₃) δppm:
0.64 (3H, t, J=7.3 Hz), 1.11-1.26 (5H, m), 1.54 (3H, s), 3.40 (3H, s), 3.70-3.82 (1H, m), 4.06-4.17 (1H, m), 6.39 (1H, br-s), 6.75-6.83 (2H, m), 7.17-7.24 (1H, d, J=8.8 Hz).

Reference Example 29

Synthesis of 5-ethyl-7-hydroxy-1,3,3-trimethyl-1,5-dihydrobenzo[b][1,4]diazepine-2,4-dione Using an appropriate starting material and following the procedure of Reference Example 24, the object compound was synthesized.
¹H-NMR (CDCl₃) δppm:
0.88 (3H, s), 1.20 (3H, t, J=7.1 Hz), 1.53 (3H, s), 3.38 (3H, s), 3.73-3.84 (1H, m), 4.07-4.19 (1H, m), 6.76-6.81 (2H, m), 7.11 (1H, d, J=8.7 Hz).

Reference Example 30

Synthesis of 7-hydroxy-3,3,5-trimethyl-1-propyl-1,5-dihydrobenzo[b][1,4]diazepine-2,4-dione Using an appropriate starting material and following the procedure of Reference Example 24, the object compound was synthesized.
¹H-NMR (CD₃OD) δppm:
0.74 (3H, t, J=7.4 Hz), 0.85 (3H, s), 1.43 (3H, s), 1.38-1.61 (2H, m), 3.36 (3H, s), 3.53-3.61 (1H, m), 4.21-4.29 (1H, m), 6.76-6.82 (2H, m), 7.26 (1H, d, J=8.5 Hz).

Reference Example 31

Synthesis of 7-hydroxy-3,3,5-trimethyl-1-(3-methyl-butyl)-1,5-dihydrobenzo[b][1,4]diazepine-2,4-dione Using an appropriate starting material and following the procedure of Reference Example 24, the object compound was synthesized.
¹H-NMR (CD₃OD) δppm:
0.79 (3H, d, J=6.1 Hz), 0.85 (3H, s), 0.85 (3H, d, J=6.1 Hz), 1.26-1.40 (3H, m), 1.42 (3H, s), 3.35 (3H, s), 3.56-3.63 (1H, m), 4.34-4.41 (1H, m), 6.76-6.82 (2H, m), 7.28 (1H, d, J=8.7 Hz).

Reference Example 32

Synthesis of 1,3,3,5-tetraethyl-7-hydroxy-1,5-dihydrobenzo[b][1,4]diazepine-2,4-dione Using an appropriate starting material and following the procedure of Reference Example 24, the object compound was synthesized.
¹H-NMR (CDCl₃) δppm:
0.58 (3H, t, J=7.4 Hz), 0.98 (3H, t, J=7.3 Hz), 1.08-1.29 (8H, m), 2.12-2.19 (2H, m), 3.57-3.76 (2H, m), 4.20-4.34 (2H, m), 6.09 (1H, br-s), 6.78-6.82 (2H, m), 7.14-7.17 (1H, m).

Reference Example 33

Synthesis of 1,5-diethyl-7-hydroxy-3,3-dimethyl-1,5-dihydrobenzo[b][1,4]diazepine-2,4-dione Using an appropriate starting material and following the procedure of Reference Example 24, the object compound was synthesized.
¹H-NMR (CDCl₃) δppm:
0.87 (3H, s), 1.08-1.17 (6H, m), 1.54 (3H, s), 3.57-3.73 (2H, m), 4.27-4.39 (2H, m), 6.85-6.87 (2H, m), 7.15-7.18 (1H, m).

Reference Example 34

Synthesis of 1,3,5-triethyl-7-hydroxy-1,5-dihydrobenzo[b][1,4]diazepine-2,4-dione Using an appropriate starting material and following the procedure of Reference Example 24, the object compound was synthesized.
¹H-NMR (CDCl₃) δppm:
0.84 (3H, t, J=7.4 Hz), 1.02-1.12 (6H, m), 1.95-2.19 (2H, m), 3.03 (1H, t, J=6.9 Hz), 3.51-3.70 (2H, m), 4.33-4.46 (2H, m), 6.89-6.93 (2H, m), 7.23 (1H, d, J=8.5 Hz), 7.57 (1H, s).

Reference Example 35

Synthesis of 7-hydroxy-1,3,3,5-tetramethyl-1,5-dihydrobenzo[b][1,4]diazepine-2,4-dione Using an appropriate starting material and following the procedure of Reference Example 24, the object compound was synthesized.

¹H-NMR (CDCl₃) δppm:
0.90 (3H, s), 1.49 (3H, s), 3.39 (3H, s), 3.40 (3H, s), 6.73 (1H, d, J=2.7 Hz), 6.80 (1H, dd, J=8.9 and 2.7 Hz), 7.13 (1H, d, J=8.9 Hz).

Reference Example 36

Synthesis of 7-hydroxy-1-isobutyl-3,3,5-trimethyl-1,5-dihydrobenzo[b][1,4]diazepine-2,4-dione Using an appropriate starting material and following the procedure of Reference Example 24, the object compound was synthesized.
¹H-NMR (CDCl₃) δppm:
0.69 (3H, d, J=6.7 Hz), 0.75 (3H, d, J=6.7 Hz), 0.87 (3H, s), 1.53 (3H, s), 1.72-1.91 (1H, m), 3.24 (1H, dd, J=6.3 and 13.5 Hz), 3.40 (3H, s), 4.35 (1H, dd, J=8.6 and 13.5 Hz), 6.72-6.79 (2H, m), 7.13 (1H, d, J=8.6 Hz).

Reference Example 37

Synthesis of 7-(3-chloropropoxy)-1-ethyl-3,3,5-trimethyl-1,5-dihydrobenzo[b][1,4]diazepine-2,4-dione 1-Ethyl-7-hydroxy-3,3,5-trimethyl-1,5-dihydrobenzo[b][1,4]diazepine-2,4-dione (1.85 g, 7.1 mmol) and potassium carbonate (1.2 g, 8.5 mmol) were added to 50% water-containing acetonitrile (40 ml), and dissolved by heating to 70° C. 1-Bromo-3-chloropropane (2.1 ml, 21 mmol) was added thereto, and heating was conducted under reflux for 6 hours. The reaction mixture was cooled to room temperature. Water was added, and extraction with ethyl acetate was performed. The organic layer was dried over sodium sulfate, and concentrated under reduced pressure. The residue was purified by silica gel column chromatography (n-hexane:ethyl acetate=2:1→1:1). The purified product was concentrated to dryness under reduced pressure to thereby obtain 2.18 g (yield: 91%) of 7-(3-chloropropoxy)-1-ethyl-3,3,5-trimethyl-1,5-dihydrobenzo[b][1,4]diazepine-2,4-dione as a colorless oil.
¹H-NMR (CDCl₃) δppm:
0.86 (3H, s), 1.15 (3H, t, J=7.1 Hz), 1.53 (3H, s), 2.21-2.38 (2H, m), 3.40 (3H, s), 3.63-3.89 (4H, m), 4.10-4.26 (2H, m), 6.74 (1H, d, J=2.8 Hz), 6.83 (1H, dd, J=2.8 and 9.0 Hz), 7.21 (1H, d, J=9.0 Hz).

Reference Example 38

Synthesis of 7-(3-chloropropoxy)-1,3,3,5-tetramethyl-1,5-dihydrobenzo[b][1,4]diazepine-2,4-dione Using an appropriate starting material and following the procedure of Reference Example 37, the object compound was synthesized.
¹H-NMR (CDCl₃) δppm:
0.88 (3H, s), 1.53 (3H, s), 2.20-2.32 (2H, m), 3.40 (3H, s), 3.42 (3H, s), 3.77 (2H, t, J=6.1 Hz), 4.15 (2H, t, J=5.8 Hz), 6.74 (1H, d, J=2.7 Hz), 6.83 (1H, dd, J=2.7 and 9.0 Hz), 7.15 (1H, d, J=9.0 Hz).

Reference Example 39

Synthesis of 1-ethyl-7-(3-iodopropoxy)-3,3,5-trimethyl-1,5-dihydrobenzo[b][1,4]diazepine-2,4-dione 7-(3-Chloropropoxy)-1-ethyl-3,3,5-trimethyl-1,5-dihydrobenzo[b][1,4]diazepine-2,4-dione (2.18 g, 6.4 mmol) and sodium iodide (4.8 g, 32 mmol) were added to acetone (50 ml), and heated under reflux for 8.5 hours. The reaction mixture was cooled to room temperature, water was added, and extraction with ethyl acetate was performed. The organic layer was dried over sodium sulfate, and concentrated under reduced pressure. The residue was purified by silica gel column chromatography (n-hexane:ethyl acetate=1:1). The purified product was concentrated under reduced pressure to thereby obtain 2.76 g (yield: 100%) of 1-ethyl-7-(3-iodopropoxy)-3,3,5-trimethyl-1,5-dihydrobenzo[b][1,4]diazepine-2,4-dione as a colorless oil.
¹H-NMR (CDCl₃) δppm:
0.87 (3H, s), 1.15 (3H, t, J=7.1 Hz), 1.53 (3H, s), 2.26-2.34 (2H, m), 3.39 (2H, t, J=6.6 Hz), 3.65-3.76 (1H, m), 3.41 (3H, s), 4.07 (2H, t, J=5.8 Hz), 4.12-4.24 (1H, m), 6.74 (1H, d, J=2.8 Hz), 6.83 (1H, dd, J=9.0 and 2.8 Hz), 7.22 (1H, d, J=9.0 Hz).

Reference Example 40

Synthesis of 7-(3-iodopropoxy)-1,3,3,5-tetramethyl-1,5-dihydrobenzo[b][1,4]diazepine-2,4-dione Using an appropriate starting material and following the procedure of Reference Example 39, the object compound was synthesized.
¹H-NMR (CDCl₃) δppm:
0.88 (3H, s), 1.54 (3H, s), 2.22-2.34 (2H, m), 3.39 (2H, t, J=6.6 Hz), 3.40 (3H, s), 3.42 (3H, s), 4.07 (2H, t, J=5.8 Hz), 6.74 (1H, d, J=2.8 Hz), 6.83 (1H, dd, J=2.8 and 9.0 Hz), 7.15 (1H, d, J=9.0 Hz).

Reference Example 41

Synthesis of (2-pyridin-3-ylethyl)pyridin-4-ylmethylamine

4-Pyridinecarbaldehyde (5.36 g, 50 mmol) and 3-(2-aminoethyl)pyridine (6.5 ml, 50 mmol) were added to methanol (100 ml), and stirred at room temperature for 7 hours. The resulting mixture was cooled to 0° C. Sodium borohydride (2.8 g, 74 mmol) was added to the mixture, and stirred at 0° C. for 1 hour. Water was then added to the reaction mixture to distill the methanol off under reduced pressure. The residue was extracted with dichloromethane. The organic layer was washed with a saturated sodium chloride aqueous solution, dried over anhydrous sodium sulfate, and concentrated under reduced pressure. The residue was purified by basic silica gel column chromatography (ethyl acetate:methanol=95:5→85:5). The purified product was concentrated under reduced pressure to thereby obtain 10.03 g (yield: 94%) of (2-pyridin-3-ylethyl)pyridin-4-ylmethylamine as a colorless oil.
¹H-NMR (CDCl₃) δppm:
2.79-2.98 (4H, m), 3.82 (2H, s), 7.21-7.25 (3H, m), 7.51-7.55 (1H, m), 8.47-8.50 (2H, m), 8.52-8.54 (2H, m)

Reference Example 42

Synthesis of (2-pyridin-3-ylethyl)pyridin-4-ylmethyl-[3-(tetrahydropyran-2-yloxy)propyl]amine Sodium iodide (1.5 g, 10 mmol) was added to a DMF solution (20 ml) of 2-(3-bromopropoxy)tetrahydropyran (0.85 ml, 5 mmol), and stirred at 70° C. for 7 hours. The reaction mixture was cooled to room temperature. (2-Pyridin-3-ylethyl)pyridin-4-ylmethylamine (1.28 g, 6 mmol) and N-ethyl diisopropylamine (1.3 ml, 7.5 mmol) were then added to the reaction mixture and stirred at room temperature overnight. Water was added to the reaction mixture, and extraction with ethyl acetate was performed. The organic layer was washed with water, and a saturated sodium chloride aqueous solution, in this order. The organic layer was dried over anhydrous sodium sulfate, and concentrated under reduced pressure. The residue was purified by silica gel column chromatography (ethyl acetate:methanol=20:1→4:1). The purified product was concentrated under reduced pressure to thereby obtain 236 mg (yield: 13%) of (2-pyridin-3-ylethyl)pyridin-4-ylmethyl-[3-(tetrahydropyran-2-yloxy)propyl]amine as a colorless oil.

$^1$H-NMR (CDCl$_3$) δppm:
1.40-1.92 (8H, m), 2.52-2.83 (6H, m), 3.30-3.56 (2H, m), 3.62 (2H, s), 3.66-3.90 (2H, m), 4.51-4.53 (1H, m), 7.16 (2H, d, J=6.0 Hz), 7.19 (1H, d, J=4.8 Hz), 7.42 (1H, d, J=6.6 Hz), 8.41-8.49 (4H, m)

Reference Example 43

Synthesis of 3-[(2-pyridin-3-ylethyl)pyridin-4-ylmethylamino]propan-1-ol

A 2N-hydrogen chloride methanol solution (1.2 ml) was added to a methanol solution (4 ml) of (2-pyridin-3-ylethyl)pyridin-4-ylmethyl-[3-(tetrahydropyran-2-yloxy)propyl]amine (236 mg, 0.66 mmol), and stirred at room temperature overnight. A 2N-hydrogen chloride methanol solution (0.5 ml) was added to the mixture, and stirred at 50° C. for 3 hours. Triethylamine (0.64 ml) was then added to the reaction mixture, and concentrated under reduced pressure. The residue was purified by basic silica gel column chromatography (dichloromethane). The purified product was concentrated under reduced pressure to thereby obtain 186.3 mg (yield: quantitative) of 3-[(2-pyridin-3-ylethyl)pyridin-4-ylmethylamino]propan-1-ol as an orange oil.

$^1$H-NMR (CDCl$_3$) δppm:
1.70-1.86 (2H, m), 2.67-2.78 (4H, m), 2.81 (2H, t, J=6.0 Hz), 3.65 (2H, s), 3.72 (2H, t, J=5.5 Hz), 7.18 (2H, d, J=5.9 Hz), 7.21 (1H, d, J=4.9 Hz), 7.42 (1H, dt, J=1.8 and 7.8 Hz), 8.42-8.54 (2H, m), 8.54 (2H, d, J=5.9 Hz).

Reference Example 44

Synthesis of 6-[2-(tetrahydropyran-2-yloxy)ethyl]-6H-furo[2,3-c]pyridin-7-one

Sodium hydride (60% in oil, 138 mg, 3.5 mmol) was suspended in DMF (10 ml). A DMF solution (5 ml) of 6H-furo[2,3-c]pyridin-7-one (310 mg, 2.3 mmol) was added thereto at 0° C., and stirring was conducted at the same temperature for 1 hour. A DMF solution (5 ml) of 2-(2-iodoethoxy)tetrahydropyran (1175 mg, 4.6 mmol) was added thereto, and stirring was conducted at room temperature overnight. Water was added to the reaction mixture and extraction with ethyl acetate was performed. The organic layer was washed with water, dried over sodium sulfate, and concentrated under reduced pressure. The residue was purified by silica gel column chromatography (n-hexane:ethyl acetate=2:1→1:1). The purified product was concentrated under reduced pressure to thereby obtain 450 mg (yield: 74%) of 6-[2-(tetrahydropyran-2-yloxy)ethyl]-6H-furo[2,3-c]pyridin-7-one as a yellow oil.

$^1$H-NMR (CDCl$_3$) δppm:
1.46-1.81 (6H, m), 3.40-3.47 (1H, m), 3.63-3.79 (2H, m), 4.00-4.07 (1H, m), 4.16-4.24 (1H, m), 4.34-4.41 (1H, m), 4.54 (1H, t, J=3.1 Hz), 6.43 (1H, d, J=7.0 Hz), 6.65 (1H, d, J=1.9 Hz), 7.26 (1H, d, J=7.0 Hz), 7.73 (1H, d, J=1.9 Hz).

Reference Example 45

Synthesis of 7-methyl-2-[2-(tetrahydropyran-2-yloxy)ethyl]-2H-isoquinolin-1-one

Using an appropriate starting material and following the procedure of Reference Example 44, the object compound was synthesized.

$^1$H-NMR (CDCl$_3$) δppm:
1.39-1.88 (6H, m), 2.49 (3H, s), 3.33-3.48 (1H, m), 3.61-3.81 (2H, m), 4.00-4.21 (2H, m), 4.28-4.39 (1H, m), 4.53-4.56 (1H, m), 6.43 (1H, d, J=7.4 Hz), 7.15 (1H, d, J=7.4 Hz), 7.41 (1H, d, J=8.1 Hz), 7.45 (1H, dd, J=1.7 and 8.1 Hz), 8.23 (1H, s).

Reference Example 46

Synthesis of 6-(2-hydroxyethyl)-6H-furo[2,3-c]pyridin-7-one

Pyridinium p-toluenesulfonate (0.21 g, 0.85 mmol) was added to a methanol solution (20 ml) of 6-[2-(tetrahydropyran-2-yloxy)ethyl]-6H-furo[2,3-c]pyridin-7-one (0.45 g, 1.7 mmol), and stirred at room temperature for 2 days. An aqueous sodium hydrogen carbonate solution was added to the reaction mixture, and extracted with dichloromethane. The organic layer was dried over anhydrous sodium sulfate, and concentrated under reduced pressure. Diethyl ether was added to the residue to precipitate crystals. The crystals were collected by filtration and dried to thereby obtain 223 mg (yield: 73%) of 6-(2-hydroxyethyl)-6H-furo[2,3-c]pyridin-7-one as a white powder.

$^1$H-NMR (CDCl$_3$) δppm:
3.15 (1H, t, J=5.3 Hz), 3.96-4.01 (2H, m), 4.25 (2H, t, J=5.3 Hz), 6.49 (1H, d, J=7.0 Hz), 6.66 (1H, d, J=2.0 Hz), 7.18 (1H, d, J=7.0 Hz), 7.75 (1H, d, J=2.0 Hz).

Reference Example 47

Synthesis of 2-(2-hydroxyethyl)-7-methyl-2H-isoquinolin-1-one

Using an appropriate starting material and following the procedure of Reference Example 46, the object compound was synthesized.

$^1$H-NMR (CDCl$_3$) δppm:
2.48 (3H, s), 3.29 (1H, t, J=5.2 Hz), 3.96-4.01 (2H, m), 4.16-4.19 (2H, m), 6.49 (1H, d, J=7.3 Hz), 7.05 (1H, d, J=7.3 Hz), 7.41 (1H, d, J=8.1 Hz), 7.46 (1H, dd, J=1.7 and 8.1 Hz), 8.20 (1H, d, J=1.7 Hz).

Reference Example 48

Synthesis of 2-nitro-N-[3-(tetrahydropyran-2-yloxy)propyl]benzenesulfonamide

2-Nitrobenzenesulfonyl chloride (22.1 g, 0.10 mol) was added to a dichloromethane solution (400 ml) of 3-aminopropanol (8.2 g, 0.11 mol) and triethylamine (21 ml, 0.15 mol) at 0° C., and stirred at room temperature overnight. Water was added to the reaction mixture and extraction with dichloromethane was performed. The organic layer was dried over anhydrous sodium sulfate, and concentrated under reduced pressure. The residue was dissolved in dichloromethane (400 ml), and 3,4-dihydro-2H-pyrane (9.3 g, 0.11 mol) and p-toluenesulfonic acid (1.9 g, 0.01 mol) were added thereto. Stirring was conducted at room temperature overnight. A 1N-sodium hydroxide aqueous solution was added to the reaction mixture, and extraction with dichloromethane was performed. The organic layer was washed with water, dried over sodium sulfate, and concentrated under reduced pressure. The residue was purified by silica gel column chromatography (n-hexane:ethyl acetate=2:1→1:2). The purified product was concentrated under reduced pressure to thereby obtain 27.56 g (yield: 80%) of 2-nitro-N-[3-(tetrahydropyran-2-yloxy)propyl]benzenesulfonamide as a pale brown oil.

$^1$H-NMR (CDCl$_3$) δppm:
1.40-1.93 (6H, m), 3.12-3.38 (2H, m), 3.38-3.58 (2H, m), 3.75-3.92 (2H, m), 4.11-4.17 (1H, m), 4.51-4.54 (1H, m), 5.85-5.93 (1H, m), 7.63-7.79 (2H, m), 7.79-7.92 (1H, m), 8.07-8.20 (1H, m).

Reference Example 49

Synthesis of 2-nitro-N-[2-(7-oxo-7H-furo[2,3-c]pyridin-6-yl)ethyl]-N-[3-(tetrahydropyran-2-yloxy)propyl]benzenesulfonamide Triphenylphosphine (393 mg, 1.5 mmol) and azodicarboxylic acid di-tert-butyl ester (345 mg, 1.5 mmol) were added to a tetrahydrofuran (THF) solution (10 ml) of 6-(2-hydroxyethyl)-6H-furo[2,3-c]pyridin-7-one (179 mg, 1.0 mmol) and 2-nitro-N-[3-(tetrahydropyran-2-yloxy)propyl]benzenesulfonamide (413 mg, 1.2 mmol), and stirred overnight. The resulting reaction mixture was concentrated under reduced pressure. The residue was purified by silica gel column chromatography (n-hexane:ethyl acetate=1:1→0:1). The purified product was concentrated to dryness under reduced pressure to thereby obtain 286 mg (yield: 57%) of 2-nitro-N-[2-(7-oxo-7H-furo[2,3-c]pyridin-6-yl)ethyl]-N-[3-(tetrahydropyran-2-yloxy)propyl]benzenesulfonamide as a white amorphous solid.

$^1$H-NMR (CDCl$_3$) δppm:
1.37-1.91 (8H, m), 3.25-3.59 (4H, m), 3.61-3.88 (4H, m), 4.27 (2H, t, J=6.5 Hz), 4.45-4.49 (1H, m), 6.43 (1H, d, J=7.0 Hz), 6.64 (1H, s), 7.19 (1H, d, J=7.0 Hz), 7.49-7.69 (3H, m), 7.72 (1H, s), 7.92-8.02 (1H, m).

Reference Example 50

Synthesis of 2-nitro-N-[2-(1-oxo-1H-isoquinolin-2-yl)ethyl]-N-[3-(tetrahydropyran-2-yloxy)propyl]benzenesulfonamide Using an appropriate starting material and following the procedure of Reference Example 49, the object compound was synthesized.
$^1$H-NMR (CDCl$_3$) δppm:
1.40-1.91 (8H, m), 3.21-3.61 (4H, m), 3.61-3.86 (4H, m), 4.21 (2H, t, J=6.6 Hz), 4.45-4.48 (1H, m), 6.45 (1H, d, J=7.3 Hz), 7.14 (1H, d, J=7.3 Hz), 7.38-7.79 (6H, m), 7.91-8.01 (1H, m), 8.34 (1H, d, J=7.5 Hz).

Reference Example 51

Synthesis of 2-nitro-N-[2-(1-oxo-3,4-dihydro-1H-isoquinolin-2-yl)ethyl]-N-[3-(tetrahydropyran-2-yloxy)propyl]benzenesulfonamide Using an appropriate starting material and following the procedure of Reference Example 49, the object compound was synthesized.

$^1$H-NMR (CDCl$_3$) δppm:
1.44-1.98 (8H, m), 3.01 (2H, t, J=6.6 Hz), 3.28-3.82 (12H, m), 4.46-4.49 (1H, m), 7.18 (1H, d, J=7.6 Hz), 7.29-7.72 (5H, m), 7.98-8.07 (2H, m).

Reference Example 52

Synthesis of N-(3-hydroxypropyl)-2-nitro-N-[2-(7-oxo-7H-furo[2,3-c]pyridin-6-yl)ethyl]benzenesulfonamide Using an appropriate starting material and following the procedure of Reference Example 46, the object compound was synthesized.
$^1$H-NMR (CDCl$_3$) δppm:
1.73-1.87 (2H, m), 3.51 (2H, t, J=6.9 Hz), 3.63 (2H, t, J=5.7 Hz), 3.71 (2H, t, J=6.8 Hz), 4.27 (2H, t, J=6.8 Hz), 6.46 (1H, d, J=7.0 Hz), 6.65 (1H, d, J=1.9 Hz), 7.20 (1H; d, J=7.0 Hz), 7.50-7.69 (3H, m), 7.73 (1H, d, J=1.9 Hz), 7.92-8.01 (1H, m).

Reference Example 53

Synthesis of N-(3-hydroxypropyl)-2-nitro-N-[2-(1-oxo-1H-isoquinolin-2-yl)ethyl]benzenesulfonamide Using an appropriate starting material and following the procedure of Reference Example 46, the object compound was synthesized.
$^1$H-NMR (CDCl$_3$) δppm:
1.72-1.89 (2H, m), 3.54 (2H, t, J=6.7 Hz), 3.65 (2H, t, J=5.5 Hz), 3.72 (2H, t, J=6.7 Hz), 4.23 (2H, t, J=6.8 Hz), 6.49 (1H, d, J=7.3 Hz), 7.15 (1H, d, J=7.3 Hz), 7.42-7.70 (6H, m), 7.90-8.00 (1H, m), 8.34 (1H, d, J=7.9 Hz).

Reference Example 54

Synthesis of N-(3-hydroxypropyl)-2-nitro-N-[2-(1-oxo-3,4-dihydro-1H-isoquinolin-2-yl)ethyl]benzenesulfonamide Using an appropriate starting material and following the procedure of Reference Example 46, the object compound was synthesized.
$^1$H-NMR (CDCl$_3$) δppm:
1.75-2.05 (2H, m), 3.01 (2H, t, J=6.2 Hz), 3.46-3.88 (10H, m), 7.18 (1H, d, J=7.6 Hz), 7.34 (1H, d, J=7.7 Hz), 7.39-7.42 (1H, m), 7.57-7.70 (3H, m), 7.97-8.06 (2H, m).

Reference Example 55

Synthesis of 3-{(2-nitrobenzenesulfonyl)-[2-(7-oxo-7H-furo[2,3-c]pyridin-6-yl)ethyl]amino}propyl methanesulfonate Methanesulfonyl chloride (0.14 ml, 1.8 mmol) was added to a THF solution (30 ml) of N-(3-hydroxypropyl)-2-nitro-N-[2-(7-oxo-7H-furo[2,3-c]pyridin-6-yl)ethyl]benzenesulfonamide (644 mg, 1.5 mmol) and triethylamine (0.34 ml, 2.3 mmol), and stirred at room temperature overnight. Water was added to the reaction mixture, and extraction with dichloromethane was performed. The organic layer was dried over anhydrous sodium sulfate, and concentrated under reduced pressure. The residue was purified by silica gel column chromatography (ethyl acetate:methanol=1:0→10:1). The purified product was concentrated to dryness under reduced pressure to thereby obtain 480 mg (yield: 64%) of 3-{(2- nitrobenzenesulfonyl)-[2-(7-oxo-7H-furo [2,3-c]pyridin-6-yl)ethyl]amino}propyl methanesulfonate as a white amorphous solid.

$^1$H-NMR (CDCl$_3$) δppm:
1.95-2.05 (2H, m), 3.04 (3H, s), 3.50 (2H, t, J=7.1 Hz), 3.70 (2H, t, J=6.7 Hz), 4.18 (2H, t, J=5.8 Hz), 4.26 (2H, t, J=6.7 Hz), 6.47 (1H, d, J=7.0 Hz), 6.66 (1H, d, J=1.9 Hz), 7.19 (1H, d, J=7.0 Hz), 7.50-7.74 (4H, m), 7.94-8.02 (1H, m).

Reference Example 56

Synthesis of 3-{(2-nitrobenzenesulfonyl)-[2-(1-oxo-1H-isoquinolin-2-yl)ethyl]amino}propyl methanesulfonate Using an appropriate starting material and following the procedure of Reference Example 55, the object compound was synthesized.

$^1$H-NMR (CDCl$_3$) δppm:
1.98-2.09 (2H, m), 3.01 (3H, s), 3.52 (2H, t, J=6.9 Hz), 3.71 (2H, t, J=6.6 Hz), 4.17 (2H, t, J=5.8 Hz), 4.21 (2H, t, J=6.9 Hz), 6.47 (1H, d, J=7.4 Hz), 7.13 (1H, d, J=7.4 Hz), 7.45-7.70 (6H, m), 7.90-8.00 (1H, m), 8.33 (1H, d, J=7.7 Hz).

Reference Example 57

Synthesis of 3-{(2-nitrobenzenesulfonyl)-[2-(1-oxo-3,4-dihydro-1H-isoquinolin-2-yl)ethyl]amino}propyl methanesulfonate Using an appropriate starting material and following the procedure of Reference Example 55, the object compound was synthesized.

$^1$H-NMR (CDCl$_3$) δppm:
2.04-2.19 (2H, m), 3.01 (2H, t, J=6.7 Hz), 3.02 (3H, s), 3.39-3.48 (6H, m), 3.75 (2H, t, J=7.2 Hz), 4.26 (2H, t, J=5.9 Hz), 7.17 (1H, d, J=7.4 Hz), 7.28-7.45 (2H, m), 7.60-7.74 (3H, m), 7.96-8.04 (2H, m).

Reference Example 58

Synthesis of N-(3-iodopropyl)-2-nitro-N-[2-(7-oxo-7H-furo[2,3-c]pyridin-6-yl)ethyl]benzenesulfonamide 3-{(2-Nitrobenzenesulfonyl)-[2-(7-oxo-7H-furo[2,3-c]pyridin-6-yl)ethyl]amino}propyl methanesulfonate (480 mg, 0.96 mmol) and sodium iodide (720 mg, 4.8 mmol) were added to acetone (20 ml), and heated under reflux for 5 hours. The reaction mixture was cooled to room temperature, water was added, and extraction with dichloromethane was performed. The organic layer was dried over sodium sulfate, and concentrated under reduced pressure to thereby obtain 474 mg (yield: 93%) of N-(3-iodopropyl)-2-nitro-N-[2-(7-oxo-7H-furo[2,3-c]pyridin-6-yl)ethyl]benzenesulfonamide as a yellow amorphous solid.

$^1$H-NMR (DMSO-D$_6$) δppm:
1.89-2.02 (2H, m), 3.12 (2H, t, J=6.9 Hz), 3.42 (2H, t, J=7.3 Hz), 3.66 (2H, t, J=5.8 Hz), 4.15 (2H, t, J=5.9 Hz), 6.49 (1H, d, J=7.0 Hz), 6.84 (1H, d, J=1.9 Hz), 7.37 (1H, d, J=7.0 Hz), 7.69-7.81 (2H, m), 7.87-7.99 (2H, m), 8.09 (1H, d, J=1.9 Hz).

Reference Example 59

Synthesis of N-(3-iodopropyl)-2-nitro-N-[2-(1-oxo-1H-isoquinolin-2-yl)ethyl]benzenesulfonamide Using an appropriate starting material and following the procedure of Reference Example 58, the object compound was synthesized.

$^1$H-NMR (CDCl$_3$) δppm:
2.02-2.18 (2H, m), 3.06 (2H, t, J=7.0 Hz), 3.44 (2H, t, J=7.2 Hz), 3.72 (2H, t, J=6.5 Hz), 4.21 (2H, t, J=6.5 Hz), 6.46 (1H, d, J=7.3 Hz), 7.13 (1H, d, J=7.3 Hz), 7.41-7.70 (6H, m), 7.95-8.06 (1H, m), 8.34 (1H, d, J=7.9 Hz).

Reference Example 60

Synthesis of N-(3-iodopropyl)-2-nitro-N-[2-(1-oxo-3,4-dihydro-1H-isoquinolin-2-yl)ethyl]benzenesulfonamide Using an appropriate starting material and following the procedure of Reference Example 58, the object compound was synthesized.

$^1$H-NMR (CDCl$_3$) δppm:
2.03-2.20 (2H, m), 3.02 (2H, t, J=6.6 Hz), 3.12 (2H, t, J=6.6 Hz), 3.50 (2H, t, J=7.1 Hz), 3.56-3.70 (4H, m), 3.76 (2H, t, J=7.0 Hz), 7.17 (1H, d, J=7.5 Hz), 7.28-7.45 (2H, m), 7.60-7.70 (3H, m), 8.00-8.11 (2H, m).

Reference Example 61

Synthesis of tert-butyl methyl-[2-(2-nitrobenzenesulfonylamino)ethyl]carbamate

2-Nitrobenzenesulfonyl chloride (4.9 g, 22 mmol) was added to a dichloromethane solution (100 ml) of tert-butyl (2-aminoethyl)methylcarbamate (3.5 g, 20 mmol) and triethylamine (3.3 ml, 24 mmol) at 0° C., and stirred at room temperature overnight. Water was added to the reaction mixture, and extraction with dichloromethane was performed. The organic layer was dried over anhydrous sodium sulfate, and concentrated under reduced pressure. The residue was purified by silica gel column chromatography (n-hexane:ethyl acetate=3:2→2:3). The purified product was concentrated under reduced pressure to thereby obtain 5.06 g (yield: 70%) of tert-butyl methyl-[2-(2-nitrobenzenesulfonylamino)ethyl]carbamate as a yellow oil.

$^1$H-NMR (CDCl$_3$) δppm:
1.45 (9H, s), 2.84 (3H, s), 3.26-3.41 (4H, m), 7.68-7.79 (2H, m), 7.79-7.90 (1H, m), 8.09-8.19 (1H, m).

Reference Example 62

Synthesis of 2-nitro-N-(2-pyridin-3-ylethyl)benzenesulfonamide

Using an appropriate starting material and following the procedure of Reference Example 61, the object compound was synthesized.

$^1$H-NMR (CDCl$_3$) δppm:
2.88 (2H, t, J=7.1 Hz), 3.41 (2H, q, J=7.1 Hz), 5.44 (1H, t, J=5.4 Hz), 7.18-7.22 (1H, m), 7.50 (1H, dt, J=7.8 and 1.8 Hz), 7.71-7.77 (2H, m), 7.82-7.88 (1H, m), 8.07-8.12 (1H, m), 8.35 (1H, d, J=1.8 Hz), 8.45 (1H, dd, J=4.8 and 1.8 Hz).

Example 1

Synthesis of 7-(3-(1,3-dioxo-1,3-dihydroisoindol-2-yl)propoxy)-1-ethyl-3,3,5-trimethyl-1,5-dihydrobenzo[b][1,4]diazepine-2,4-dione Potassium carbonate (2.99 g, 21.6 mmol) and N-(3-bromopropyl)phthalimide (2.32 g, 8.65 mmol) were added to a DMF solution (50 ml) of 1-ethyl-7-hydroxy-3,3,5-trimethyl-1,5-dihydrobenzo[b][1,4]diazepine-2,4-dione (1.89 g, 7.2 mmol), and stirred at room temperature overnight. Water was added to the reaction mixture, and extraction with ethyl acetate was performed. The organic layer was washed with water and a saturated sodium chloride aqueous solution, in this order. The organic layer was dried over anhydrous magnesium sulfate, and concentrated under reduced pressure. The residue was purified by silica gel column chromatography (n-hexane:ethyl acetate=2:1→3:7). The purified product was concentrated to dryness under reduced pressure to thereby obtain 2.70 g (yield: 83%) of 7-(3-(1,3-dioxo-1,3-dihydroisoindol-2-yl)propoxy)-1-ethyl-3,3,5-trimethyl-1,5-dihydrobenzo[b][1,4]diazepine-2,4-dione as a white powder.

$^1$H-NMR (CDCl$_3$) δppm:

0.84 (3H, s), 1.13 (3H, t, J=7.1 Hz), 1.52 (3H, s), 2.18-2.24 (2H, m), 3.33 (3H, s), 3.63-3.75 (1H, m), 3.93 (2H, t, J=6.8 Hz), 4.06 (2H, t, J=5.9 Hz), 4.10-4.10 (1H, m), 6.59 (1H, d, J=2.8 Hz), 6.73 (1H, dd, J=9.0 and 2.8 Hz), 7.16 (1H, d, J=9.0 Hz), 7.72-7.76 (2H, m), 7.82-7.88 (2H, m).

Example 2

Synthesis of 7-(3-aminopropoxy)-1-ethyl-3,3,5-trimethyl-1,5-dihydrobenzo[b][1,4]diazepine-2,4-dione Hydrazine hydrate (1.17 ml, 24 mmol) was added to a methanol solution (60 ml) of 7-[3-(1,3-dioxo-1,3-dihydroisoindol-2-yl)propoxy]-1-ethyl-3,3,5-trimethyl-1,5-dihydrobenzo[b][1,4]diazepine-2,4-dione (2.70 g, 6.0 mmol), and stirred while heating under reflux for 2 hours. The reaction mixture was concentrated under reduced pressure. A 1N-sodium hydroxide aqueous solution was added to the residue, and stirred for 30 minutes, and extraction with dichloromethane was performed. The organic layer was washed with water and a saturated sodium chloride aqueous solution, in this order. The organic layer was dried over anhydrous magnesium sulfate, and concentrated under reduced pressure to thereby obtain 1.48 g (yield: 77%) of 7-(3-aminopropoxy)-1-ethyl-3,3,5-trimethyl-1,5-dihydrobenzo[b][1,4]diazepine-2,4-dione as a colorless oil.

$^1$H-NMR (CDCl$_3$) δppm:

0.86 (3H, s), 1.14 (3H, t, J=7.1 Hz), 1.52 (3H, s), 1.90-2.00 (2H, m), 2.94 (2H, t, J=6.8 Hz), 3.40 (3H, s), 3.66-3.76 (1H, m), 4.08 (2H, t, J=6.2 Hz), 4.11-4.21 (1H, m), 6.73 (1H, d, J=2.8 Hz), 6.82 (1H, dd, J=9.0 and 2.8 Hz), 7.20 (1H, d, J=9.0 Hz).

Example 3

Synthesis of 7-(3-aminopropoxy)-1-ethyl-3,3,5-trimethyl-1,5-dihydrobenzo[b][1,4]diazepine-2,4-dione hydrochloride A 4N-hydrogen chloride ethyl acetate solution (0.42 ml) was added to an ethyl acetate solution (3 ml) of 7-(3-aminopropoxy)-1-ethyl-3,3,5-trimethyl-1,5-dihydrobenzo[b][1,4]diazepine-2,4-dione (264 mg), and stirred at room temperature for 30 minutes. The reaction mixture was concentrated to dryness under reduced pressure to thereby obtain 0.22 g of 7-(3-aminopropoxy)-1-ethyl-3,3,5-trimethyl-1,5-dihydrobenzo[b][1,4]diazepine-2,4-dione hydrochloride as a white amorphous solid.

$^1$H-NMR (DMSO-D$_6$) δppm:

0.77 (3H, s), 1.01 (3H, t, J=6.6 Hz), 1.33 (3H, s), 1.92-2.38 (4H, m), 3.33 (3H, s), 3.67-4.20 (6H, m), 6.95-7.00 (2H, m), 7.42 (1H, d, J=8.8 Hz), 8.28 (1H, br-s).

Example 4

Synthesis of N-(3-(1-ethyl-3,3,5-trimethyl-2,4-dioxo-2,3,4,5-tetrahydro-1H-benzo[b][1,4]diazepin-7-yloxy)propyl)-2-nitrobenzenesulfonamide Triethylamine (0.8 ml, 5.7 mmol) was added to a dichloromethane solution (50 ml) of 7-(3-aminopropoxy)-1-ethyl-3,3,5-trimethyl-1,5-dihydrobenzo[b][1,4]diazepine-2,4-dione (1.22 g, 3.8 mmol) and ice-cooled. o-Nitrobenzenesulfonyl chloride (1.03 g, 4.2 mmol) was added to the resulting mixture, and stirred at room temperature for 2 hours. Water was added to the reaction mixture, and extraction with dichloromethane was performed. The organic layer was washed with water and a saturated sodium chloride aqueous solution, in this order, then dried over anhydrous magnesium sulfate, and concentrated under reduced pressure. The residue was purified by silica gel column chromatography (n-hexane:ethyl acetate=1:1→0:1). The purified product was concentrated to dryness under reduced pressure to thereby obtain 1.86 g (yield: 97%) of N-(3-(1-ethyl-3,3,5-trimethyl-2,4-dioxo-2,3,4,5-tetrahydro-1H-benzo[b][1,4]diazepin-7-yloxy)propyl)-2-nitrobenzenesulfonamide as a white amorphous solid.

$^1$H-NMR (CDCl$_3$) δppm:

0.86 (3H, s), 1.15 (3H, t, J=7.1 Hz), 1.52 (3H, s), 2.05-2.13 (2H, m), 3.34-3.40 (2H, m), 3.40 (3H, s), 3.65-3.77 (1H, m), 4.07-4.21 (3H, m), 5.76 (1H, t, J=5.9 Hz), 6.77 (1H, d, J=2.7 Hz), 6.82 (1H, dd, J=8.9 and 2.8 Hz), 7.21 (1H, d, J=9.0 Hz), 7.73-7.79 (2H, m), 7.85-7.89 (1H, m), 8.14-8.18 (1H, m).

Example 5

Synthesis of 1-ethyl-3,3,5-trimethyl-7-[3-(2-pyridin-3-ylethylamino)propoxy]-1,5-dihydrobenzo[b][1,4]diazepine-2,4-dione 1-Ethyl-7-(3-iodopropoxy)-3,3,5-trimethyl-1,5-dihydrobenzo[b][1,4]diazepine-2,4-dione (5.3 mmol) was added to a methanol solution (100 ml) of 3-(2-aminoethyl)pyridine (3.3 g, 26.7 mmol), and stirred at 50° C. for 9 hours. The reaction mixture was cooled to room temperature, and concentrated under reduced pressure. Water was added to the residue, and extraction with dichloromethane was performed. The organic layer was dried over anhydrous sodium sulfate, and concentrated under reduced pressure. The residue was purified by silica gel column chromatography (dichloromethane:methanol=20:1→10:1). The purified product was concentrated under reduced pressure, and the residue was purified by basic silica gel column chromatography (ethyl acetate:methanol=1:0→10:1) again. The purified product was concentrated under reduced pressure to thereby obtain 1.57 g (yield: 70%) of 1-ethyl-3,3,5-trimethyl-7-[3-(2-pyridin-3-ylethylamino)propoxy]-1,5-dihydrobenzo[b][1,4]diazepine-2,4-dione as a yellow oil.

$^1$H-NMR (CDCl$_3$) δppm:

0.86 (3H, s), 1.14 (3H, t, J=7.1 Hz), 1.52 (3H, s), 1.93-2.00 (2H, m), 2.80-2.96 (6H, m), 3.39 (3H, s), 3.66-3.73 (1H, m), 4.04 (2H, t, J=6.1 Hz), 4.14-4.21 (1H, m), 6.70 (1H, d, J=2.8 Hz), 6.78 (1H, dd, J=9.0 and 2.0 Hz), 7.17-7.24 (2H, m), 7.54 (1H, dt, J=7.8 and 1.9 Hz), 8.46 (1H, dd, J=4.8 and 1.6 Hz), 8.49 (1H, d, J=2.0 Hz).

Example 6

Synthesis of 1-ethyl-3,3,5-trimethyl-7-[3-(2-pyridin-3-ylethyl amino)propoxy]-1,5-dihydrobenzo[b][1,4]diazepine-2,4-dione dihydrochloride A 4N-hydrogen chloride ethyl acetate solution (0.37 ml) was added to an ethyl acetate solution (10 ml) of 1-ethyl-3,3, 5-trimethyl-7-[3-(2-pyridin-3-ylethylamino)propoxy]-1,5-dihydrobenzo[b][1,4]diazepine-2,4-dione (207 mg, 0.49 mmol), and stirred for 30 minutes at room temperature. The precipitated insoluble matter was collected by filtration, washed with ethyl acetate, and dried to thereby obtain 208 mg (yield: 85%) of 1-ethyl-3,3,5-trimethyl-7-[3-(2-pyridin-3-ylethylamino)propoxy]-1,5-dihydrobenzo[b][1,4]diazepine-2,4-dione dihydrochloride as a pale yellow amorphous solid.

$^1$H-NMR (DMSO-D$_6$) δppm:
0.76 (3H, s), 1.01 (3H, t, J=7.0 Hz), 1.32 (3H, s), 2.14-2.20 (2H, m), 3.10 (2H, br-s), 3.25-3.33 (6H, m), 3.61-3.73 (1H, m), 3.99-4.18 (4H, m), 6.92-6.99 (2H, m), 7.42 (1H, d, J=8.9 Hz), 7.94-7.89 (1H, m), 8.46 (1H, d, J=8.0 Hz), 8.80 (1H, dd, J=5.5 and 1.0 Hz), 8.90 (1H, d, J=1.0 Hz), 9.46 (2H, br-s).

Example 7

Synthesis of 1-ethyl-3,3,5-trimethyl-7-{3-[(2-pyridin-3-ylethyl)pyridin-4-ylmethylamino]propoxy}-1,5-dihydrobenzo[b][1,4]diazepine-2,4-dione 4-Pyridinecarbaldehyde (1.18 ml, 12.5 mmol) and a catalytic amount of acetic acid were added to a 1,2-dichloroethane solution (40 ml) of 1-ethyl-3,3,5-trimethyl-7-[3-(2-pyridin-3-ylethylamino)propoxy]-1,5-dihydrobenzo[b][1,4]diazepine-2,4-dione (4.44 g, 10.5 mmol), and stirred for 30 minutes. Sodium triacetoxyhydroborate (3.33 g, 15.7 mmol) was added to the resulting mixture, and stirred at room temperature overnight. The reaction mixture was diluted with dichloromethane, washed with water and a saturated sodium chloride aqueous solution in this order, then dried over anhydrous magnesium sulfate, and concentrated under reduced pressure. The residue was purified by silica gel flash chromatography (ethyl acetate:methanol=1:0→9:1). The purified product was concentrated under reduced pressure to thereby obtain 4.73 g (yield: 88%) of 1-ethyl-3,3,5-trimethyl-7-{3-[(2-pyridin-3-ylethyl)pyridin-4-ylmethylamino]propoxy}-1,5-dihydrobenzo[b][1,4]diazepine-2,4-dione as a pale yellow oil.

$^1$H-NMR (CDCl$_3$) δppm:
0.86 (3H, s), 1.15 (3H, t, J=7.0 Hz), 1.52 (3H, s), 1.87-1.95 (2H, m), 2.67-2.80 (6H, m), 3.40 (3H, s), 3.66-3.77 (3H, m), 3.89 (2H, t, J=6.0 Hz), 4.09-4.21 (1H, m), 6.63 (1H, d, J=2.7 Hz), 6.72 (1H, dd, J=9.0 and 2.7 Hz), 7.12-7.22 (4H, m), 7.42 (1H, dt, J=7.8 and 1.9 Hz), 8.42-8.46 (4H, m).

Example 8

Synthesis of 1-ethyl-3,3,5-trimethyl-7-{3-[(2-pyridin-3-ylethyl)pyridin-4-ylmethylamino]propoxy}-1,5-dihydrobenzo[b][1,4]diazepine-2,4-dione trihydrochloride Triphenylphosphine (186 mg, 0.71 mmol) and di-tert-butyl azodicarboxylate (163 mg, 0.71 mmol) were added to a tetrahydrofuran (THF) solution (5 ml) of 1-ethyl-7-hydroxy-3,3,5-trimethyl-1,5-dihydrobenzo[b][1,4]diazepine-2,4-dione (156 mg, 0.59 mmol) and 3-[(2-pyridin-3-ylethyl)pyridin-4-ylmethylamino]propan-1-ol (161 mg, 0.59 mmol), and stirred overnight. The reaction mixture was concentrated under reduced pressure. The residue was purified by silica gel column chromatography (ethyl acetate:methanol=1:0→4:1), and the purified product was concentrated under reduced pressure. A 4N-hydrogen chloride ethyl acetate solution (0.29 ml) was added to the residue (ethyl acetate solution), stirred at room temperature for 30 minutes, and concentrated to dryness under reduced pressure to thereby obtain 206 mg (yield: 56%) of 1-ethyl-3,3,5-trimethyl-7-{3-[(2-pyridin-3-ylethyl)pyridin-4-ylmethylamino]propoxy}-1,5-dihydrobenzo[b][1,4]diazepine-2,4-dione trihydrochloride as a white amorphous solid.

$^1$H-NMR (DMSO-D$_6$) δppm:
0.75 (3H, s), 1.01 (3H, t, J=7.0 Hz), 1.32 (3H, s), 2.22-2.41 (2H, m), 3.15-3.53 (6H, m), 3.33 (3H, s), 3.64-3.71 (1H, m), 4.07-4.14 (3H, m), 4.62-4.86 (2H, m), 6.88-6.94 (2H, m), 7.42 (1H, d, J=8.8 Hz), 8.03 (1H, dd, J=8.0 and 5.7 Hz), 8.27-8.42 (2H, m), 8.54 (1H, d, J=8.0 Hz), 8.84 (1H, d, J=4.8 Hz), 8.94-9.02 (3H, m).

Example 9

Synthesis of 1-isobutyl-3,3,5-trimethyl-7-{3-[(2-pyridin-3-ylethyl)pyridin-4-ylmethylamino]propoxy}-1,5-dihydrobenzo[b][1,4]diazepine-2,4-dione trihydrochloride N,N,N',N'-Tetramethylazodicarboxamide(TMAD) (189 mg, 1.1 mmol) and tri-n-butyl phosphine (0.28 ml, 1.1 mmol) were added to a THF solution (5 ml) of 7-hydroxy-1-isobutyl-3,3,5-trimethyl-1,5-dihydrobenzo[b][1,4]diazepine-2,4-dione (213 mg, 0.73 mmol) and 3-[(2-pyridin-3-ylethyl)pyridin-4-ylmethylamino]propan-1-ol (199 mg, 0.73 mmol), and stirred at room temperature overnight. Water was added to the reaction mixture, and extraction with dichloromethane was performed. The organic layer was dried over anhydrous sodium sulfate, and concentrated under reduced pressure. The residue was purified by silica gel column chromatography (ethyl acetate:methanol=20:1→10:1). The purified product was concentrated under reduced pressure, and the residue was purified by silica gel column chromatography (dichloromethane:methanol=40:1→10:1) again. The purified product was concentrated under reduced pressure. A 4N-hydrogen chloride ethyl acetate solution (0.57 ml) was added to the residue (ethyl acetate solution), stirred at room temperature for 30 minutes, and concentrated to dryness under reduced pressure to thereby obtain 480 mg (yield: quantitative) of 1-isobutyl-3,3,5-trimethyl-7-{3-[(2-pyridin-3-ylethyl)pyridin-4-ylmethylamino]propoxy}-1,5-dihydrobenzo[b][1,4]diazepine-2,4-dione trihydrochloride as a white amorphous solid.

$^1$H-NMR (DMSO-D$_6$) δppm:
0.58 (3H, d, J=6.6 Hz), 0.71 (3H, d, J=6.6 Hz), 0.75 (3H, s), 1.33 (3H, s), 1.51-1.78 (2H, m), 2.19-2.38 (2H, m), 3.00-3.48 (7H, m), 3.34 (3H, s), 4.02-4.28 (2H, m), 4.38-4.59 (2H, m), 6.86-6.94 (2H, m), 7.45 (1H, d, J=9.0 Hz), 7.63-7.67 (1H, m), 7.87 (2H, d, J=5.2 Hz), 8.07 (1H, d, J=7.9 Hz), 8.62 (1H, d, J=1.3 Hz), 8.66-8.78 (3H, m).

Example 10

Synthesis of 3,3,5-trimethyl-1-propyl-7-{3-[(2-pyridin-3-ylethyl)pyridin-4-ylmethylamino]propoxy}-1,5-dihydrobenzo[b][1,4]diazepine-2,4-dione trihydrochloride Using an appropriate starting material and following the procedure of Example 9, the object compound was synthesized.

$^1$H-NMR (DMSO-D$_6$) δppm:
0.64 (3H, t, J=7.4 Hz), 0.75 (3H, s), 1.32 (3H, s), 1.28-1.51 (2H, m), 2.18-2.41 (2H, m), 3.09-3.61 (7H, m), 3.32 (3H, s), 4.02-4.26 (3H, m), 4.47-4.82 (2H, m), 6.82-6.97 (2H, m), 7.42 (1H, d, J=8.8 Hz), 7.92-8.03 (1H, m), 8.08-8.31 (2H, m), 8.41-8.50 (1H, m), 8.82 (1H, d, J=5.6 Hz), 8.83-8.98 (3H, m).

Example 11

Synthesis of 3,3,5-trimethyl-1-(3-methylbutyl)-7-{3-[(2-pyridin-3-ylethyl)pyridin-4-ylmethylamino]propoxy}-1,5-dihydrobenzo[b][1,4]diazepine-2,4-dione trihydrochloride Using an appropriate starting material and following the procedure of Example 9, the object compound was synthesized.

$^1$H-NMR (DMSO-D$_6$) δppm:
0.68-1.80 (15H, m), 2.28-2.48 (2H, m), 3.19-3.40 (2H, m), 3.31 (3H, s), 3.40-3.64 (5H, m), 4.03-4.18 (2H, m), 4.18-4.33 (1H, m), 4.70-4.92 (2H, m), 6.87-6.99 (2H, m), 7.44 (1H, d, J=8.9 Hz), 8.00-8.09 (1H, m), 8.38-8.50 (2H, m), 8.51-8.62 (1H, m), 8.86 (1H, d, J=5.5 Hz), 8.94-9.08 (3H, m).

Example 12

Synthesis of 5-ethyl-1,3,3-trimethyl-7-{3-[(2-pyridin-3-ylethyl)pyridin-4-ylmethylamino]propoxy}-1,5-dihydrobenzo[b][1,4]diazepine-2,4-dione trihydrochloride Using an appropriate starting material and following the procedure of Example 9, the object compound was synthesized.

$^1$H-NMR (DMSO-D$_6$) δppm:
0.75 (3H, s), 1.03 (3H, t, J=7.0 Hz), 1.32 (3H, s), 2.21-2.41 (2H, m), 3.15-3.32 (2H, m), 3.28 (3H, s), 3.32-3.58 (4H, m), 3.64-3.82 (1H, m), 4.01-4.18 (3H, m), 4.59-4.82 (2H, m), 6.86-7.00 (2H, m), 7.38 (1H, d, J=8.9 Hz), 8.02 (1H, dd, J=5.7 and 8.0 Hz), 8.32 (2H, s), 8.53 (1H, d, J=8.1 Hz), 8.83 (1H, d, J=5.2 Hz), 8.90-8.99 (3H, m).

Example 13

Synthesis of 1,3,3,5-tetraethyl-7-{3-[(2-pyridin-3-ylethyl)pyridin-4-ylmethylamino]propoxy}-1,5-dihydrobenzo[b][1,4]diazepine-2,4-dione trihydrochloride Using an appropriate starting material and following the procedure of Example 9, the object compound was synthesized.

$^1$H-NMR (DMSO-D$_6$) δppm:
0.47 (3H, t, J=7.1 Hz), 0.76-1.80 (13H, m), 1.80-2.00 (2H, m), 2.25-2.44 (2H, m), 3.22-3.40 (2H, m), 3.40-3.58 (2H, m), 3.58-3.79 (2H, m), 4.02-4.30 (4H, m), 4.70-4.92 (2H, m), 6.93 (2H, dd, J=2.5 and 9.0 Hz), 6.99 (1H, d, J=2.5 Hz), 7.44 (1H, d, J=9.0 Hz), 8.06 (1H, dd, J=5.8 and 7.9 Hz), 8.49 (1H, s), 8.60 (1H, d, J=8.1 Hz), 8.86 (1H, d, J=5.5 Hz), 8.96-9.09 (3H, m).

Example 14

Synthesis of 1,5-diethyl-3,3-dimethyl-7-{3-[(2-pyridin-3-ylethyl)pyridin-4-ylmethylamino]propoxy}-1,5-dihydrobenzo[b][1,4]diazepine-2,4-dione trihydrochloride Using an appropriate starting material and following the procedure of Example 9, the object compound was synthesized.

$^1$H-NMR (DMSO-D$_6$) δppm:
0.73 (3H, s), 0.79-1.01 (6H, m), 1.31 (3H, s), 2.20-2.45 (2H, m), 3.18-3.38 (2H, m), 3.38-3.52 (2H, m), 3.52-3.79 (2H, m), 4.09-4.16 (2H, m), 4.16-4.35 (2H, m), 4.63-4.89 (2H, m), 6.92 (1H, dd, J=2.6 and 9.0 Hz), 6.99 (1H, d, J=2.6 Hz), 7.43 (1H, d, J=9.0 Hz), 8.02 (1H, dd, J=5.7 and 8.0 Hz), 8.34 (2H, s), 8.55 (1H, d, J=8.0 Hz), 8.84 (1H, d, J=5.4 Hz), 8.94-8.97 (3H, m).

Example 15

Synthesis of 1,3,5-triethyl-7-{3-[(2-pyridin-3-ylethyl)pyridin-4-ylmethylamino]propoxy}-1,5-dihydrobenzo[b][1,4]diazepine-2,4-dione trihydrochloride Using an appropriate starting material and following the procedure of Example 9, the object compound was synthesized.

$^1$H-NMR (DMSO-D$_6$) δppm:
0.62-1.80 (11H, m), 2.22-2.41 (2H, m), 2.81-3.00 (1H, m), 3.12-3.37 (2H, m), 3.37-3.55 (4H, m), 3.55-3.85 (2H, m), 4.08-4.19 (2H, m), 4.19-4.38 (2H, m), 4.62-4.88 (2H, m), 6.92 (1H, d, J=9.1 Hz), 7.05 (1H, s), 7.50 (1H, d, J=9.1 Hz), 8.03 (1H, dd, J=5.9 and 7.9 Hz), 8.37 (2H, s), 8.56 (1H, d, J=8.0 Hz), 8.84 (1H, d, J=5.5 Hz), 8.92-9.02 (3H, m).

Example 16

Synthesis of 2-nitro-N-(2-pyridin-3-ylethyl)-N-[3-(1,3,3,5-tetramethyl-2,4-dioxo-2,3,4,5-tetrahydro-1H-benzo[b][1,4]diazepin-7-yloxy)propyl]benzenesulfonamide 2-Nitro-N-(2-pyridin-3-ylethyl)benzenesulfonamide (1.8 g, 5.8 mmol) and potassium carbonate (1.0 g, 7.2 mmol) were added to a DMF solution (30 ml) of 7-(3-iodopropoxy)-1,3,3,5-tetramethyl-1,5-dihydrobenzo[b][1,4]diazepine-2,4-dione (2.0 g, 4.8 mmol) and stirred at room temperature overnight. The reaction mixture was added to ice water, and extraction with ethyl acetate was performed. The organic layer was washed with water, dried over anhydrous sodium sulfate, concentrated under reduced pressure. The residue was purified by silica gel column chromatography (n-hexane:ethyl acetate=1:2→ethyl acetate→ethyl acetate:methanol=20:1). The purified product was concentrated to dryness under reduced pressure to thereby obtain 2.29 g (yield: 80%) of 2-nitro-N-(2-pyridin-3-ylethyl)-N-[3-(1,3,3,5-tetramethyl-2,4-dioxo-2,3,4,5-tetrahydro-1H-benzo[b][1,4]diazepin-7-yloxy)propyl]benzenesulfonamide as a yellow amorphous solid.

$^1$H-NMR (CDCl$_3$) δppm:
0.86 (3H, s), 1.53 (3H, s), 2.02-2.12 (2H, m), 2.91 (2H, t, J=8.1 Hz), 3.39 (3H, s), 3.41 (3H, s), 3.57 (2H, t, J=8.4 Hz), 3.60 (2H, t, J=7.4 Hz), 4.01 (2H, t, J=5.9 Hz), 6.71 (1H, d, J=2.7 Hz), 6.77 (1H, d, J=8.8 Hz), 7.14 (1H, d, J=8.9 Hz), 7.18-7.24 (1H, m), 7.48-7.64 (4H, m), 8.00 (1H, d, J=9.2 Hz), 8.41 (1H, d, J=2.1 Hz), 8.45 (1H, d, J=4.8 Hz).

Example 17

Synthesis of 2-nitro-N-(2-pyridin-3-ylethyl)-N-[3-(1,3,3,5-tetramethyl-2,4-dioxo-2,3,4,5-tetrahydro-1H-benzo[b][1,4]diazepin-7-yloxy)propyl]benzenesulfonamide hydrochloride A 4N-hydrogen chloride ethyl acetate solution (0.57 ml) was added to an ethyl acetate solution (1 ml) of 2-nitro-N-(2- pyridin-3-ylethyl)-N-[3-(1,3,3,5-tetramethyl-2,4-dioxo-2,3,4,5-tetrahydro-1H-benzo[b][1,4]diazepin-7-yloxy)propyl]benzenesulfonamide (236 mg), and stirred at room temperature for 1 minute. The precipitated insoluble matter was collected by filtration, washed with ethyl acetate, and dried to thereby obtain 163 mg (yield: 65%) of 2-nitro-N-(2-pyridin-3-ylethyl)-N-[3-(1,3,3,5-tetramethyl-2,4-dioxo-2,3,4,5-tetrahydro-1H-benzo[b][1,4]diazepin-7-yloxy)propyl]benzenesulfonamide hydrochloride as a white powder.

$^1$H-NMR (DMSO-D$_6$) δppm:

0.76 (3H, s), 1.33 (3H, s), 1.89-2.08 (2H, m), 3.10 (2H, t, J=7.0 Hz), 3.30 (3H, s), 3.33 (3H, s), 3.55 (2H, t, J=7.6 Hz), 3.69 (2H, t, J=6.8 Hz), 4.00 (2H, t, J=6.0 Hz), 6.82-6.95 (2H, m), 7.34 (1H, d, J=8.8 Hz), 7.76-7.96 (4H, m), 8.03 (1H, d, J=7.4 Hz), 8.40 (1H, d, J=7.8 Hz), 8.75 (1H, d, J=5.3 Hz), 8.85 (1H, s).

Example 18

Synthesis of 1,3,3,5-tetramethyl-7-[3-(2-pyridin-3-ylethylamino)propoxy]-1,5-dihydrobenzo[b][1,4]diazepine-2,4-dione Lithium hydroxide (0.36 g, 15 mmol) and thioglycolic acid (0.48 ml, 6.9 mmol) were added to a DMF solution (20 ml) of 2-nitro-N-(2-pyridin-3-ylethyl)-N-[3-(1,3,3,5-tetramethyl-2,4-dioxo-2,3,4,5-tetrahydro-1H-benzo[b][1,4]diazepin-7-yloxy)propyl]benzenesulfonamide (2.05 g, 3.4 mmol), and stirred at room temperature for 3 days. The reaction mixture was added to ice water, and extracted with ethyl acetate. The organic layer was washed with water, dried over anhydrous sodium sulfate, and concentrated under reduced pressure. The residue was purified by silica gel column chromatography (ethyl acetate:methanol=20:1→dichloromethane:methanol=10:1→4:1). The purified product was concentrated under reduced pressure to thereby obtain 1.13 g (yield: 81%) of 1,3,3,5-tetramethyl-7-[3-(2-pyridin-3-ylethylamino)propoxy]-1,5-dihydrobenzo[b][1,4]diazepine-2,4-dione as a yellow oil.

$^1$H-NMR (CDCl$_3$) δppm:

0.87 (3H, s), 1.53 (3H, s), 1.92-2.02 (2H, m), 2.78-2.90 (4H, m), 2.93 (2H, t, J=6.5 Hz), 3.39 (3H, s), 3.41 (3H, s), 4.04 (2H, t, J=6.2 Hz), 6.71 (1H, d, J=2.7 Hz), 6.78 (1H, dd, J=2.7 and 8.9 Hz), 7.13 (1H, d, J=9.0 Hz), 7.16-7.25 (1H, m), 7.54 (1H, d, J=7.8 Hz), 8.46 (1H, dd, J=1.6 and 4.8 Hz), 8.49 (1H, d, J=1.6 Hz).

Example 19

Synthesis of 1,3,3,5-tetramethyl-7-{3-[(2-pyridin-3-ylethyl)pyridin-4-ylmethylamino]propoxy}-1,5-dihydrobenzo[b][1,4]diazepine-2,4-dione trihydrochloride Using an appropriate starting material and following the procedure of Example 8, the object compound was synthesized.

$^1$H-NMR (DMSO-D$_6$) δppm:

0.76 (3H, s), 1.33 (3H, s), 2.18-2.40 (2H, m), 3.10-3.64 (6H, m), 3.30 (3H, s), 3.33 (3H, s), 3.97-4.14 (2H, m), 4.40-4.72 (2H, m), 6.81-6.92 (2H, m), 7.36 (1H, d, J=8.6 Hz), 7.73-8.02 (3H, m), 8.28 (1H, d, J=6.4 Hz), 8.68-8.82 (4H, m).

Example 20

Synthesis of 3,3-diethyl-1,5-dimethyl-7-{3-[(2-pyridin-3-ylethyl)pyridin-4-ylmethylamino]propoxy}-1,5-dihydrobenzo[b][1,4]diazepine-2,4-dione trihydrochloride Using an appropriate starting material and following the procedure of Example 8, the object compound was synthesized.

$^1$H-NMR (CDCl$_3$) δppm:

0.54 (3H, t, J=7.5 Hz), 1.01 (3H, t, J=7.5 Hz), 1.12-1.31 (4H, m), 2.09-2.24 (2H, m), 2.99-3.41 (6H, m), 3.38 (3H, s), 3.41 (3H, s), 3.97-4.08 (2H, m), 4.40-4.88 (2H, m), 6.67 (1H, d, J=2.6 Hz), 6.74 (1H, dd, J=9.0 and 2.6 Hz), 7.14 (1H, d, J=9.0 Hz), 7.51-7.62 (1H, m), 7.70 (2H, d, J=5.3 Hz), 7.96 (1H, d, J=7.1 Hz), 8.61 (1H, d, J=4.7 Hz), 8.70 (2H, d, J=5.3 Hz), 8.89 (1H, s).

Example 21

Synthesis of N-[3-(1-ethyl-3,3,5-trimethyl-2,4-dioxo-2,3,4,5-tetrahydro-1H-benzo[b][1,4]diazepin-7-yloxy)propyl]-2-nitro-N-[2-(1-oxo-1H-isoquinolin-2-yl)ethyl]benzenesulfonamide Potassium carbonate (0.22 g, 1.6 mmol) was added to a DMF solution (10 ml) of N-(3-iodopropyl)-2-nitro-N-[2-(1-oxo-1H-isoquinolin-2-yl)ethyl]benzenesulfonamide (0.57 g, 1.05 mmol) and 1-ethyl-7-hydroxy-3,3,5-trimethyl-1,5-dihydrobenzo[b][1,4]diazepine-2,4-dione (0.33 g, 1.26 mmol), and stirred at room temperature overnight. The reaction mixture was added to ice water, and extraction with ethyl acetate was performed. The organic layer was washed with 1N-sodium hydroxide aqueous solution and water, dried over anhydrous sodium sulfate, and concentrated under reduced pressure. The residue was purified by silica gel column chromatography (n-hexane:ethyl acetate=1:1→0:1). The purified product was concentrated to dryness under reduced pressure to thereby obtain 0.49 g (yield: 69%) of N-[3-(1-ethyl-3,3,5-trimethyl-2,4-dioxo-2,3,4,5-tetrahydro-1H-benzo[b][1,4]diazepin-7-yloxy)propyl]-2-nitro-N-[2-(1-oxo-1H-isoquinolin-2-yl)ethyl]benzenesulfonamide as a white amorphous solid.

$^1$H-NMR (CDCl$_3$) δppm:

0.84 (3H, s), 1.14 (3H, t, J=7.0 Hz), 1.52 (3H, s), 2.08-2.14 (2H, m), 3.39 (3H, s), 3.62 (2H, t, J=7.4 Hz), 3.66-3.77 (3H, m), 3.94 (2H, t, J=5.8 Hz), 4.13-4.22 (1H, m), 4.24 (2H, t, J=6.7 Hz), 6.46 (1H, d, J=7.3 Hz), 6.67 (1H, d, J=2.7 Hz), 6.72 (1H, dd, J=8.9 and 2.7 Hz), 7.12-7.19 (2H, m), 7.47-7.67 (6H, m), 7.95-7.98 (1H, m), 8.35 (1H, d, J=7.5 Hz).

Example 22

Synthesis of 1-ethyl-3,3,5-trimethyl-7-{3-[2-(1-oxo-1H-isoquinolin-2-yl)ethylamino]propoxy}-1,5-dihydrobenzo[b][1,4]diazepine-2,4-dione Using an appropriate starting material and following the procedure of Example 18, the object compound was synthesized.

$^1$H-NMR (CDCl$_3$) δppm:

0.84 (3H, s), 1.14 (3H, t, J=7.0 Hz), 1.52 (3H, s), 1.92-2.00 (2H, m), 2.87 (2H, t, J=6.7 Hz), 3.06 (2H, t, J=6.2 Hz), 3.38

(3H, s), 3.63-3.74 (1H, m), 4.02 (2H, t, J=6.1 Hz), 4.09-4.23 (3H, m), 6.46 (1H, d, J=7.3 Hz), 6.69 (1H, d, J=2.7 Hz), 6.74 (1H, dd, J=9.0 and 2.7 Hz), 7.10-7.16 (2H, m), 7.46-7.51 (2H, m), 7.64 (1H, t, J=8.1 Hz), 8.41 (1H, d, J=8.2 Hz).

Example 23

Synthesis of 1-ethyl-3,3,5-trimethyl-7-(3-{[2-(1-oxo-1H-isoquinolin-2-yl)ethyl]pyridin-4-ylmethylamino}propoxy)-1,5-dihydrobenzo[b][1,4]diazepine-2,4-dione dihydrochloride Using appropriate starting materials and following the procedures of Examples 7 and 6, the object compound was synthesized.

$^1$H-NMR (DMSO-D$_6$) δppm:

0.74 (3H, s), 1.01 (3H, t, J=7.0 Hz), 1.32 (3H, s), 2.01-2.39 (2H, m), 2.89-3.51 (2H, m), 3.30 (3H, s), 3.61-3.73 (1H, m), 3.89-4.12 (5H, m), 4.19-4.77 (4H, m), 6.67 (1H, d, J=7.0 Hz), 6.71-6.90 (2H, m), 7.37 (1H, d, J=9.0 Hz), 7.50-7.54 (2H, m), 7.66-7.76 (2H, m), 8.20 (1H, d, J=8.0 Hz), 7.87-8.13 (2H, m), 8.60-8.96 (2H, m).

Example 24

Synthesis of 1-ethyl-3,3,5-trimethyl-7-(3-{[2-(1-oxo-1H-isoquinolin-2-yl)ethyl]pyridin-4-ylmethylamino}propoxy)-1,5-dihydrobenzo[b][1,4]diazepine-2,4-dione Using an appropriate starting material and following the procedure of Example 7, the object compound was synthesized.

White Powder (ethyl acetate)

Melting point 119.8-121.6° C.

$^1$H-NMR (CDCl$_3$) δppm:

0.86 (3H, s), 1.16 (3H, t, J=7.0 Hz), 1.53 (3H, s), 1.87-1.96 (2H, m), 2.70-2.74 (2H, m), 2.83-2.93 (2H, m), 3.36 (3H, s), 3.36-3.74 (3H, m), 3.86 (2H, t, J=6.0 Hz), 4.10 (2H, t, J=6.1 Hz), 4.12-4.21 (1H, m), 6.41 (1H, d, J=7.3 Hz), 6.58-6.62 (2H, m), 6.98 (1H, d, J=7.3 Hz), 7.08-7.17 (3H, m), 7.47-7.52 (2H, m), 7.66 (1H, td, J=7.5 and 1.7 Hz), 8.27 (2H, dd, J=4.4 and 1.6 Hz), 8.59 (1H, dt, J=8.1 and 0.7 Hz).

Example 25

Synthesis of 2-nitro-N-[2-(7-oxo-7H-furo[2,3-c]pyridin-6-yl)ethyl]-N-[3-(1,3,3,5-tetramethyl-2,4-dioxo-2,3,4,5-tetrahydro-1H-benzo[b][1,4]diazepin-7-yloxy)propyl]benzenesulfonamide Using an appropriate starting material and following the procedure of Example 21, the object compound was synthesized.

$^1$H-NMR (CDCl$_3$) δppm:

0.85 (3H, s), 1.53 (3H, s), 2.03-2.15 (2H, m), 3.39 (3H, s), 3.42 (3H, s), 3.59 (2H, t, J=7.4 Hz), 3.73 (2H, t, J=6.9 Hz), 3.94 (2H, t, J=5.8 Hz), 4.29 (2H, t, J=6.7 Hz), 6.45 (1H, d, J=7.0 Hz), 6.64 (1H, d, J=2.0 Hz), 6.69-6.75 (2H, m), 7.12 (1H, d, J=8.8 Hz), 7.19 (1H, d, J=7.0 Hz), 7.56-7.66 (3H, m), 7.73 (1H, d, J=1.9 Hz), 7.98-8.02 (1H, m).

Example 26

Synthesis of 1,3,3,5-tetramethyl-7-{3-[2-(7-oxo-7H-furo[2,3-c]pyridin-6-yl)ethylamino]propoxy}-1,5-dihydrobenzo[b][1,4]diazepine-2,4-dione Using an appropriate starting material and following the procedure of Example 18, the object compound was synthesized.

$^1$H-NMR (CDCl$_3$) δppm:

0.86 (3H, s), 1.53 (3H, s), 1.90-2.02 (2H, m), 2.87 (2H, t, J=6.7 Hz), 3.07 (2H, t, J=6.2 Hz), 3.39 (3H, s), 3.41 (3H, s), 4.03 (2H, t, J=6.1 Hz), 4.20 (2H, t, J=6.5 Hz), 6.45 (1H, d, J=7.0 Hz), 6.65 (1H, d, J=2.0 Hz), 6.72 (1H, d, J=2.7 Hz), 6.78 (1H, dd, J=2.7 and 8.9 Hz), 7.12 (1H, d, J=8.9 Hz), 7.17 (1H, d, J=7.0 Hz), 7.74 (1H, d, J=2.0 Hz).

Example 27

Synthesis of 1,3,3,5-tetramethyl-7-(3-{[2-(7-oxo-7H-furo[2,3-c]pyridin-6-yl)ethyl]pyridin-4-ylmethylamino}propoxy)-1,5-dihydrobenzo[b][1,4]diazepine-2,4-dione dihydrochloride Using appropriate starting materials and following the procedures of Examples 7 and 6, the object compound was synthesized.

$^1$H-NMR (DMSO-D$_6$) δppm:

0.76 (3H, s), 1.33 (3H, s), 1.89-2.32 (2H, m), 2.89-3.51 (6H, m), 3.30 (3H, s), 3.33 (3H, s), 3.91-4.12 (2H, m), 4.22-4.61 (2H, m), 6.62 (1H, d, J=6.5 Hz), 6.72-6.98 (3H, m), 7.35 (1H, d, J=8.9 Hz), 7.56 (1H, d, J=7.0 Hz), 8.08 (2H, br-s), 8.13 (1H, s), 8.81 (2H, br-s).

Example 28

Synthesis of N-[3-(1-ethyl-3,3,5-trimethyl-2,4-dioxo-2,3,4,5-tetrahydro-1H-benzo[b][1,4]diazepin-7-yloxy)propyl]-2-nitro-N-[2-(7-oxo-7H-furo[2,3-c]pyridin-6-yl)ethyl]benzenesulfonamide Using an appropriate starting material and following the procedure of Example 21, the object compound was synthesized.

$^1$H-NMR (CDCl$_3$) δppm:

0.84 (3H, s), 1.14 (3H, t, J=7.1 Hz), 1.52 (3H, s), 2.06-2.13 (2H, m), 3.40 (3H, s), 3.57-3.75 (5H, m), 3.94 (2H, t, J=5.8 Hz), 4.11-4.20 (1H, m), 4.29 (2H, t, J=6.9 Hz), 6.45 (1H, d, J=7.0 Hz), 6.64 (1H, d, J=2.0 Hz), 6.70-6.76 (2H, m), 7.18 (1H, d, J=8.9 Hz), 7.20 (1H, d, J=7.0 Hz), 7.55-7.66 (3H, m), 7.74 (1H, d, J=2.0 Hz), 7.99-8.02 (1H, m).

Example 29

Synthesis of 1-ethyl-3,3,5-trimethyl-7-{3-[2-(7-oxo-7H-furo[2,3-c]pyridin-6-yl)ethylamino]propoxy}-1,5-dihydrobenzo[b][1,4]diazepine-2,4-dione Using an appropriate starting material and following the procedure of Example 18, the object compound was synthesized.

$^1$H-NMR (CDCl$_3$) δppm:

0.85 (3H, s), 1.14 (3H, t, J=7.1 Hz), 1.52 (3H, s), 1.92-2.01 (2H, m), 2.86 (2H, t, J=6.8 Hz), 3.05 (2H, t, J=6.2 Hz), 3.39 (3H, s), 3.66-3.75 (1H, m), 4.02 (2H, t, J=6.1 Hz), 4.12-4.24 (3H, m), 6.43 (1H, d, J=7.0 Hz), 6.64 (1H, d, J=2.0 Hz), 6.71

(1H, d, J=2.8 Hz), 6.78 (1H, dd, J=9.0 and 2.8 Hz), 7.14 (1H, d, J=7.0 Hz), 7.18 (1H, d, J=9.0 Hz), 7.73 (1H, d, J=2.0 Hz).

Example 30

Synthesis of 1-ethyl-3,3,5-trimethyl-7-(3-{[2-(7-oxo-7H-furo[2,3-c]pyridin-6-yl)ethyl]pyridin-4-ylmethylamino}propoxy)-1,5-dihydrobenzo[b][1,4]diazepine-2,4-dione Using an appropriate starting material and following the procedure of Example 7, the object compound was synthesized.

White Powder (ethyl acetate-n-hexane)
Melting point 80.7-82.8° C.
$^1$H-NMR (CDCl$_3$) δppm:
0.86 (3H, s), 1.15 (3H, t, J=7.1 Hz), 1.52 (3H, s), 1.89-1.97 (2H, m), 2.73 (2H, t, J=6.8 Hz), 2.87 (2H, t, J=4.9 Hz), 3.40 (3H, s), 3.66-3.77 (3H, m), 3.91 (2H, t, J=6.1 Hz), 4.09-4.22 (3H, m), 6.37 (1H, d, J=7.0 Hz), 6.64-6.72 (3H, m), 6.99 (1H, d, J=7.0 Hz), 7.09 (2H, d, J=5.9 Hz), 7.19 (1H, d, J=8.9 Hz), 7.75 (1H, d, J=2.0 Hz), 8.33 (2H, dd, J=4.5 and 1.5 Hz).

Example 31

Synthesis of 1-ethyl-3,3,5-trimethyl-7-(3-{[2-(7-oxo-7H-furo[2,3-c]pyridin-6-yl)ethyl]pyridin-4-ylmethylamino}propoxy)-1,5-dihydrobenzo[b][1,4]diazepine-2,4-dione dihydrochloride Using an appropriate starting material and following the procedure of Example 3, the object compound was synthesized.

$^1$H-NMR (DMSO-D$_6$) δppm:
0.75 (3H, s), 1.01 (3H, t, J=7.0 Hz), 1.32 (3H, s), 1.98-2.20 (2H, m), 2.92-3.40 (4H, m), 3.31 (3H, s), 3.63-3.71 (1H, m), 3.99-4.12 (4H, m), 4.22-4.66 (3H, m), 6.62 (1H, d, J=6.7 Hz), 6.82-6.90 (3H, m), 7.39 (1H, d, J=9.0 Hz), 7.55 (1H, d, J=6.8 Hz), 7.89-8.19 (3H, m), 8.65-8.94 (2H, m).

Example 32

Synthesis of 2-nitro-N-[2-(1-oxo-3,4-dihydro-1H-isoquinolin-2-yl)ethyl]-N-[3-(1,3,3,5-tetramethyl-2,4-dioxo-2,3,4,5-tetrahydro-1H-benzo[b][1,4]diazepin-7-yloxy)propyl]benzenesulfonamide Using an appropriate starting material and following the procedure of Example 21, the object compound was synthesized.

$^1$H-NMR (CDCl$_3$) δppm:
0.85 (3H, s), 1.53 (3H, s), 2.10-2.20 (2H, m), 2.95-3.07 (2H, m), 3.39 (3H, s), 3.41 (3H, s), 3.55-3.69 (6H, m), 3.79 (2H, t, J=6.9 Hz), 3.99 (2H, t, J=5.9 Hz), 6.65-6.77 (2H, m), 7.11 (1H, d, J=8.8 Hz), 7.18 (1H, d, J=7.8 Hz), 7.30-7.49 (2H, m), 7.58-7.69 (3H, m), 7.98-8.08 (2H, m).

Example 33

Synthesis of 1,3,3,5-tetramethyl-7-{3-[2-(1-oxo-3,4-dihydro-1H-isoquinolin-2-yl)ethylamino]propoxy}-1,5-dihydrobenzo[b][1,4]diazepine-2,4-dione Using an appropriate starting material and following the procedure of Example 18, the object compound was synthesized.

$^1$H-NMR (CDCl$_3$) δppm:
0.86 (3H, s), 1.53 (3H, s), 1.92-2.02 (2H, m), 2.87-3.02 (6H, m), 3.38 (3H, s), 3.40 (3H, s), 3.62 (2H, t, J=6.4 Hz), 3.72 (2H, t, J=6.5 Hz), 4.06 (2H, t, J=6.1 Hz), 6.72 (1H, d, J=2.7 Hz), 6.79 (1H, dd, J=2.7 and 9.0 Hz), 7.10 (1H, d, J=8.9 Hz), 7.17 (1H, d, J=7.4 Hz), 7.29-7.43 (2H, m), 8.05 (1H, d, J=7.6 Hz).

Example 34

Synthesis of 1,3,3,5-tetramethyl-7-(3-{[2-(1-oxo-3,4-dihydro-1H-isoquinolin-2-yl)ethyl]pyridin-4-ylmethylamino}propoxy)-1,5-dihydrobenzo[b][1,4]diazepine-2,4-dione dihydrochloride Using appropriate starting materials and following the procedures of Examples 7 and 6, the object compound was synthesized.

$^1$H-NMR (DMSO-D$_6$) δppm:
0.76 (3H, s), 1.33 (3H, s), 2.20-2.41 (2H, m), 2.98-3.08 (2H, m), 3.16-3.45 (4H, m), 3.29 (3H, s), 3.33 (3H, s), 3.53-3.71 (2H, m), 3.82-4.01 (2H, m), 4.03-4.20 (2H, m), 4.55-4.89 (2H, m), 6.81-6.97 (2H, m), 7.28-7.40 (3H, m), 7.42-7.54 (1H, m), 7.87 (1H, d, J=7.6 Hz), 8.28 (2H, d, J=4.9 Hz), 8.94 (2H, d, J=5.6 Hz).

Example 35

Synthesis of N-[3-(1-ethyl-3,3,5-trimethyl-2,4-dioxo-2,3,4,5-tetrahydro-1H-benzo[b][1,4]diazepin-7-yloxy)propyl]-2-nitro-N-[2-(1-oxo-3,4-dihydro-1H-isoquinolin-2-yl)ethyl]benzenesulfonamide Using an appropriate starting material and following the procedure of Example 21, the object compound was synthesized.

$^1$H-NMR (CDCl$_3$) δppm:
0.84 (3H, s), 1.14 (3H, t, J=7.0 Hz), 1.52 (3H, s), 2.10-2.24 (2H, m), 3.01 (2H, t, J=6.5 Hz), 3.39 (3H, s), 3.59-3.87 (9H, m), 3.99 (2H, t, J=5.9 Hz), 4.08-4.23 (1H, m), 6.69 (1H, d, J=2.9 Hz), 6.74 (1H, dd, J=2.7 and 8.8 Hz), 7.17 (2H, d, J=9.0 Hz), 7.29-7.48 (2H, m), 7.57-7.69 (3H, m), 8.00-8.05 (2H, m).

Example 36

Synthesis of 1-ethyl-3,3,5-trimethyl-7-{3-[2-(1-oxo-3,4-dihydro-1H-isoquinolin-2-yl)ethylamino]propoxy}-1,5-dihydrobenzo[b][1,4]diazepine-2,4-dione Using an appropriate starting material and following the procedure of Example 18, the object compound was synthesized.

$^1$H-NMR (CDCl$_3$) δppm:
0.85 (3H, s), 1.14 (3H, t, J=7.0 Hz), 1.52 (3H, s), 1.91-2.06 (2H, m), 2.82-3.02 (6H, m), 3.38 (3H, s), 3.53-3.78 (5H, m), 4.06 (2H, t, J=6.1 Hz), 4.09-4.25 (1H, m), 6.72 (1H, d, J=2.7 Hz), 6.78 (1H, dd, J=2.7 and 9.0 Hz), 7.16 (2H, d, J=8.9 Hz), 7.28-7.48 (2H, m), 8.05 (1H, d, J=7.6 Hz).

Example 37

Synthesis of 1-ethyl-3,3,5-trimethyl-7-(3-{[2-(1-oxo-3,4-dihydro-1H-isoquinolin-2-yl)ethyl]pyridin-4-ylmethylamino}propoxy)-1,5-dihydrobenzo[b][1,4]diazepine-2,4-dione dihydrochloride Using appropriate starting materials and following the procedures of Examples 7 and 6, the object compound was synthesized.

¹H-NMR (DMSO-D₆) δppm:
0.75 (3H, s), 1.01 (3H, t, J=7.0 Hz), 1.32 (3H, s), 2.22-2.43 (2H, m), 2.98-3.10 (2H, m), 3.20-3.49 (4H, m), 3.32 (3H, s), 3.57-3.75 (3H, m), 3.90-4.08 (3H, m), 4.08-4.20 (2H, m), 4.65-4.90 (2H, m), 6.80-6.97 (2H, m), 7.28-7.45 (3H, m), 7.45-7.55 (1H, m), 7.87 (1H, d, J=7.6 Hz), 8.38 (2H, d, J=5.7 Hz), 8.99 (2H, d, J=6.1 Hz).

Example 38

Synthesis of 2-nitro-N-[2-(1-oxo-1H-isoquinolin-2-yl)ethyl]-N-[3-(1,3,3,5-tetramethyl-2,4-dioxo-2,3,4,5-tetrahydro-1H-benzo[b][1,4]diazepin-7-yloxy)propyl]benzenesulfonamide Using an appropriate starting material and following the procedure of Example 21, the object compound was synthesized.
¹H-NMR (CDCl₃) δppm:
0.85 (3H, s), 1.53 (3H, s), 1.99-2.15 (2H, m), 3.39 (3H, s), 3.41 (3H, s), 3.61 (2H, t, J=6.9 Hz), 3.74 (2H, t, J=6.8 Hz), 3.94 (2H, t, J=5.6 Hz), 4.24 (2H, t, J=6.7 Hz), 6.45 (1H, d, J=7.3 Hz), 6.60-6.74 (2H, m), 7.02-7.18 (2H, m), 7.41-7.70 (6H, m), 7.88-8.00 (1H, m), 8.35 (1H, d, J=8.3 Hz).

Example 39

Synthesis of 1,3,3,5-tetramethyl-7-{3-[2-(1-oxo-1H-isoquinolin-2-yl)ethylamino]propoxy}-1,5-dihydrobenzo[b][1,4]diazepine-2,4-dione Using an appropriate starting material and following the procedure of Example 18, the object compound was synthesized.
¹H-NMR (CDCl₃) δppm:
0.86 (3H, s), 1.53 (3H, s), 1.89-2.04 (2H, m), 2.87 (2H, t, J=6.8 Hz), 3.07 (2H, t, J=6.2 Hz), 3.38 (3H, s), 3.39 (3H, s), 4.03 (2H, t, J=6.1 Hz), 4.08-4.21 (2H, m), 6.47 (1H, d, J=7.3 Hz), 6.70 (1H, d, J=2.7 Hz), 6.75 (1H, dd, J=2.7 and 9.0 Hz), 7.09 (1H, d, J=8.9 Hz), 7.13 (1H, d, J=7.4 Hz), 7.41-7.55 (2H, m), 7.60-7.70 (1H, m), 8.41 (1H, d, J=8.0 Hz).

Example 40

Synthesis of 1,3,3,5-tetramethyl-7-(3-{[2-(1-oxo-1H-isoquinolin-2-yl)ethyl]pyridin-4-ylmethylamino}propoxy)-1,5-dihydrobenzo[b][1,4]diazepine-2,4-dione dihydrochloride Using appropriate starting materials and following the procedures of Examples 7 and 6, the object compound was synthesized.
¹H-NMR (DMSO-D₆) δppm:
0.75 (3H, s), 1.33 (3H, s), 2.09-2.38 (2H, m), 3.01-3.56 (6H, m), 3.30 (3H, s), 3.32 (3H, s), 3.93-4.18 (2H, m), 4.30-4.54 (2H, m), 6.62-6.73 (1H, m), 6.73-6.96 (2H, m), 7.34 (1H, d, J=8.9 Hz), 7.48-7.62 (2H, m), 7.62-7.81 (2H, m), 8.12-8.38 (3H, m), 8.76-9.05 (2H, m).

Example 41

Synthesis of tert-butyl methyl-(2-{(2-nitrobenzenesulfonyl)-[3-(1,3,3,5-tetramethyl-2,4-dioxo-2,3,4,5-tetrahydro-1H-benzo[b][1,4]diazepin-7-yloxy)propyl]amino}ethyl)carbamate Using an appropriate starting material and following the procedure of Example 21, the object compound was synthesized.

¹H-NMR (CDCl₃) δppm:
0.86 (3H, s), 1.46 (9H, s), 1.53 (3H, s), 2.01-2.15 (2H, m), 2.87 (3H, s), 3.39 (3H, s), 3.41 (3H, s), 3.43-3.48 (4H, m), 3.58 (2H, t, J=6.9 Hz), 3.99 (2H, t, J=5.5 Hz), 6.69 (1H, d, J=2.7 Hz), 6.75 (1H, dd, J=2.7 and 8.9 Hz), 7.12 (1H, d, J=9.1 Hz), 7.57-7.72 (3H, m), 7.98-8.08 (1H, m).

Example 42

Synthesis of tert-butyl methyl-{2-[3-(1,3,3,5-tetramethyl-2,4-dioxo-2,3,4,5-tetrahydro-1H-benzo[b][1,4]diazepin-7-yloxy)propyl amino]ethyl}carbamate Using an appropriate starting material and following the procedure of Example 18, the object compound was synthesized.
¹H-NMR (CDCl₃) δppm:
0.87 (3H, s), 1.46 (9H, s), 1.53 (3H, s), 1.91-2.04 (2H, m), 2.80 (2H, t, J=6.5 Hz), 2.84 (2H, t, J=7.0 Hz), 2.88 (3H, s), 3.35 (2H, t, J=6.5 Hz), 3.39 (3H, s), 3.41 (3H, s), 4.06 (2H, t, J=6.2 Hz), 6.73 (1H, d, J=2.7 Hz), 6.81 (1H, dd, J=2.7 and 9.0 Hz), 7.13 (1H, d, J=9.0 Hz).

Example 43

Synthesis of tert-butyl methyl-(2-{pyridin-4-ylmethyl-[3-(1,3,3,5-tetramethyl-2,4-dioxo-2,3,4,5-tetrahydro-1H-benzo[b][1,4]diazepin-7-yloxy)propyl]amino}ethyl)carbamate Using an appropriate starting material and following the procedure of Example 7, the object compound was synthesized.
¹H-NMR (CDCl₃) δppm:
0.87 (3H, s), 1.44 (9H, br), 1.53 (3H, s), 1.90-2.02 (2H, m), 2.63 (2H, t, J=6.9 Hz), 2.67 (2H, t, J=6.9 Hz), 2.79 (3H, br), 3.33 (2H, br), 3.40 (3H, s), 3.41 (3H, s), 3.65 (2H, s), 4.00 (2H, t, J=6.1 Hz), 6.66 (1H, d, J=2.7 Hz), 6.75 (1H, dd, J=2.7 and 8.9 Hz), 7.13 (1H, d, J=8.9 Hz), 7.25 (2H, d, J=6.5 Hz), 8.48 (2H, d, J=5.7 Hz).

Example 44

Synthesis of 1,3,3,5-tetramethyl-7-{3-[(2-methylaminoethyl)-pyridin-4-ylmethylamino]propoxy}-1,5-dihydrobenzo[b][1,4]diazepine-2,4-dione A 4N-hydrogen chloride ethyl acetate solution (3.2 ml) was added to an ethyl acetate solution (30 ml) of tert-butyl methyl-(2-{pyridin-4-ylmethyl-[3-(1,3,3,5-tetramethyl-2,4-dioxo-2,3,4,5-tetrahydro-1H-benzo[b][1,4]diazepin-7-yloxy)propyl]amino}ethyl)carbamate (1.43 g, 2.5 mmol) and stirred at room temperature overnight. The reaction mixture was concentrated under reduced pressure. The residue was dissolved in dichloromethane, and trifluoroacetic acid (3 ml) was added thereto. Stirring was conducted at room temperature for 1 hour. The reaction mixture was concentrated under reduced pressure, and the residue was dissolved in a dichloromethane-methanol mixture solvent. Polymer-bonded quaternary ammonium carbonate (PL-HcO3MP) was added thereto to neutralize the mixture. The resulting reaction mixture was filtered. The filtrate was concentrated under reduced pressure to thereby obtain 1.44 g (yield: quantitative) of 1,3,3,5-tetramethyl-7-{3-[(2-methylaminoethyl)pyridin-4-ylmethylamino]propoxy}-1,5-dihydrobenzo[b][1,4]diazepine-2,4-dione as a pale brown oil.

¹H-NMR (CDCl₃) δppm:
0.85 (3H, s), 1.53 (3H, s), 1.92-2.06 (2H, m), 2.56 (3H, s), 2.72 (2H, t, J=7.0 Hz), 2.89 (2H, t, J=5.6 Hz), 3.03 (2H, t, J=5.6 Hz), 3.38 (3H, s), 3.39 (3H, s), 3.68 (2H, s), 4.00 (2H, t, J=5.6 Hz), 6.67 (1H, d, J=2.7 Hz), 6.75 (1H, dd, J=2.7 and 8.9 Hz), 7.12 (1H, d, J=8.9 Hz), 7.30 (2H, d, J=5.8 Hz), 8.51 (2H, d, J=4.6 Hz).

Example 45

Synthesis of N-methyl-N-(2-{pyridin-4-ylmethyl-[3-(1,3,3,5-tetramethyl-2,4-dioxo-2,3,4,5-tetrahydro-1H-benzo[b][1,4]diazepin-7-yloxy)propyl]amino}ethyl)benzamide dihydrochloride 1-(3-Dimethylaminopropyl)-3-ethyl carbodiimide hydrochloride (WSC) (144 mg, 0.75 mmol) and 1-hydroxybenzotriazole (HOBt) (115 mg, 0.75 mmol) were added to a DMF solution (5 ml) of 1,3,3,5-tetramethyl-7-{3-[(2-methylaminoethyl)pyridin-4-ylmethylamino]propoxy}-1,5-dihydrobenzo[b][1,4]diazepine-2,4-dione (227 mg, 0.5 mmol) and benzoic acid (92 mg, 0.75 mmol), and stirred at room temperature overnight. Water was added to the reaction mixture, and extraction with ethyl acetate was performed. The organic layer was washed with water, dried over anhydrous sodium sulfate, and concentrated under reduced pressure. The residue was purified by silica gel column chromatography (ethyl acetate:methanol=1:0→10:1). The purified product was concentrated under reduced pressure, and a 4N-hydrogen chloride ethyl acetate solution (0.14 ml) was added to the residue (an ethyl acetate solution). The precipitated insoluble matter was collected by filtration, washed with ethyl acetate, and dried to thereby obtain 120.5 mg (yield: 40%) of N-methyl-N-(2-{pyridin-4-ylmethyl-[3-(1,3,3,5-tetramethyl-2,4-dioxo-2,3,4,5-tetrahydro-1H-benzo[b][1,4]diazepin-7-yloxy)propyl]amino}ethyl)benzamide dihydrochloride as a white powder.
¹H-NMR (DMSO-D₆) δppm:
0.76 (3H, s), 1.34 (3H, s), 2.08-2.31 (2H, m), 2.94 (3H, s), 2.99-3.38 (4H, m), 3.29 (3H, s), 3.32 (3H, s), 3.66-3.89 (2H, m), 4.00-4.15 (2H, m), 4.29-4.55 (2H, m), 6.80-6.89 (2H, m), 7.32 (1H, d, J=8.7 Hz), 7.41 (5H, br-s), 8.02 (2H, br-s), 7.58-8.78 (2H, m).

Example 46

Synthesis of 2,3-dihydrobenzofuran-7-carboxylic acid methyl-(2-{pyridin-4-ylmethyl-[3-(1,3,3,5-tetramethyl-2,4-dioxo-2,3,4,5-tetrahydro-1H-benzo[b][1,4]diazepin-7-yloxy)propyl]amino}ethyl)amide dihydrochloride Using an appropriate starting material and following the procedure of Example 45, the object compound was synthesized.
¹H-NMR (DMSO-D₆) δppm:
0.77 (3H, s), 1.34 (3H, s), 2.08-2.34 (2H, m), 2.76-3.33 (8H, m), 3.29 (3H, s), 3.32 (3H, s), 3.69-3.92 (2H, m), 3.95-4.18 (3H, m), 4.39-4.63 (4H, m), 6.72-6.92 (3H, m), 6.92-7.10 (1H, m), 7.19-7.37 (2H, m), 7.80-8.18 (2H, m), 8.79 (2H, br-s).

Example 47

Synthesis of 2-nitro-N-(2-pyridin-3-ylethyl)-N-[3-(1-ethyl-3,3,5-trimethyl-2,4-dioxo-2,3,4,5-tetrahydro-1H-benzo[b][1,4]diazepin-7-yloxy)propyl]benzenesulfonamide Potassium carbonate (1.89 g, 13.7 mmol) was added to a DMF solution (50 ml) of 2-nitro-N-(2-pyridin-3-ylethyl)benzene sulfonamide (1.40 g, 4.56 mmol) and 1-ethyl-7-(3-iodopropoxy)-3,3,5-trimethyl-1,5-dihydrobenzo[b][1,4]diazepine-2,4-dione (2.16 g, 5.0 mmol), and stirred at room temperature overnight. Water was added to the reaction mixture, and extraction with ethyl acetate was performed. The organic layer was washed with water and a saturated sodium chloride aqueous solution in this order, dried over anhydrous magnesium sulfate, and concentrated under reduced pressure. The residue was purified by silica gel column chromatography (ethyl acetate:methanol=1:0→10:1). The purified product was concentrated under reduced pressure to thereby obtain 2.99 g (yield: quantitative) of 2-nitro-N-(2-pyridin-3-ylethyl)-N-[3-(1-ethyl-3,3,5-trimethyl-2,4-dioxo-2,3,4,5-tetrahydro-1H-benzo[b][1,4]diazepin-7-yloxy)propyl]benzenesulfonamide as a yellow oil.
¹H-NMR (CDCl₃) δppm:
0.84 (3H, s), 1.15 (3H, t, J=7.0 Hz), 1.52 (3H, s), 2.04-2.12 (2H, m), 2.88-2.96 (2H, m), 3.40 (3H, s), 3.55-3.62 (4H, m), 3.64-3.76 (1H, m), 4.01 (2H, t, J=5.9 Hz), 4.08-4.23 (1H, m), 6.70 (1H, d, J=2.7 Hz), 6.78 (1H, dd, J=9.0 and 2.0 Hz), 7.17-7.22 (2H, m), 7.53 (1H, dt, J=7.9 and 2.1 Hz), 7.59-7.70 (2H, m), 7.99-8.02 (2H, m), 8.42 (1H, d, J=1.7 Hz), 8.46 (1H, dd, J=4.8 and 1.7 Hz).

Example 48

Synthesis of 1-ethyl-7-{3-[(1H-imidazol-2-ylmethyl)-(2-pyridin-3-ylethyl)amino]propoxy}-3,3,5-trimethyl-1,5-dihydrobenzo[b][1,4]diazepine-2,4-dione Using an appropriate starting material and following the procedure of Example 7, the object compound was synthesized.
¹H-NMR (CDCl₃) δppm:
0.85 (3H, s), 1.15 (3H, t, J=7.0 Hz), 1.52 (3H, s), 1.91-1.99 (2H, m), 2.68-2.90 (6H, m), 3.39 (3H, s), 3.60-3.78 (1H, m), 3.78-4.02 (4H, m), 4.07-4.22 (1H, m), 6.67 (1H, d, J=2.5 Hz), 6.76 (1H, dd, J=2.5 and 9.0 Hz), 6.85-6.94 (2H, m), 7.12-7.28 (2H, m), 7.46 (1H, d, J=7.8 Hz), 8.44 (1H, d, J=4.5 Hz), 8.47 (1H, s).

Example 49

Synthesis of 1-ethyl-7-{3-[(3H-imidazol-4-ylmethyl)-(2-pyridin-3-ylethyl)amino]propoxy}-3,3,5-trimethyl-1,5-dihydrobenzo[b][1,4]diazepine-2,4-dione dihydrochloride Using appropriate starting materials and following the procedures of Examples 7 and 6, the object compound was synthesized.
¹H-NMR (DMSO-D₆) δppm:
0.76 (3H, s), 1.01 (3H, t, J=6.9 Hz), 1.32 (3H, s), 2.18-2.38 (2H, m), 3.17-3.42 (6H, m), 3.33 (3H, s), 3.58-3.72 (1H, m), 4.00-4.19 (3H, m), 4.40-4.52 (2H, m), 6.88-6.98 (2H, m), 7.42 (1H, d, J=8.8 Hz), 7.73 (1H, dd, J=5.3 and 7.5 Hz), 7.87 (1H, s), 8.21 (1H, d, J=7.5 Hz), 8.67 (1H, d, J=5.3 Hz), 8.78 (1H, s), 8.91 (1H, s).

Example 50

Synthesis of 1,3,3,5-tetramethyl-7-{3-[(2-methylbenzyl)-(2-pyridin-3-ylethyl)amino]propoxy}-1,5-dihydrobenzo[b][1,4]diazepine-2,4-dione dihydrochloride Using appropriate starting materials and following the procedures of Examples 7 and 6, the object compound was synthesized.

¹H-NMR (DMSO-D₆) δppm:
0.76 (3H, s), 1.33 (3H, s), 2.20-2.42 (2H, m), 2.50 (3H, s), 3.08-3.40 (2H, m), 3.30 (3H, s), 3.33 (3H, s), 3.49-3.62 (4H, m), 4.08-4.21 (2H, m), 4.37-4.61 (2H, m), 6.82-6.96 (2H, m), 7.17-7.41 (4H, m), 7.78 (1H, d, J=7.3 Hz), 7.99 (1H, dd, J=5.7 and 7.6 Hz), 8.49 (1H, d, J=8.0 Hz), 8.82 (1H, d, J=5.3 Hz), 8.94 (1H, s).

Example 51

Synthesis of 1,3,3,5-tetramethyl-7-{3-[(2-pyridin-3-ylethyl)-(quinolin-4-ylmethyl)amino]propoxy}-1,5-dihydrobenzo[b][1,4]diazepine-2,4-dione trihydrochloride Using appropriate starting materials and following the procedures of Examples 7 and 6, the object compound was synthesized.
¹H-NMR (DMSO-D₆) δppm:
0.74 (3H, s), 1.32 (3H, s), 2.13-2.45 (2H, m), 3.14-3.78 (6H, m), 3.29 (3H, s), 3.31 (3H, s), 3.98-4.17 (4H, m), 6.73-6.89 (2H, m), 7.33 (1H, d, J=8.8 Hz), 7.90 (1H, t, J=7.7 Hz), 7.98-8.12 (2H, m), 8.37 (1H, d, J=8.4 Hz), 8.53 (1H, d, J=8.2 Hz), 8.38-8.69 (2H, m), 8.83 (1H, d, J=5.6 Hz), 8.95 (1H, s), 9.22 (1H, d, J=4.9 Hz).

Example 52

Synthesis of 1,3,3,5-tetramethyl-7-{3-[(2-methylpyridin-4-ylmethyl)(2-pyridin-3-ylethyl)amino]propoxy}-1,5-dihydrobenzo[b][1,4]diazepine-2,4-dione trihydrochloride Using appropriate starting materials and following the procedures of Examples 7 and 6, the object compound was synthesized.
¹H-NMR (DMSO-D₆) δppm:
0.76 (3H, s), 1.33 (3H, s), 2.10-2.37 (2H, m), 2.69 (3H, s), 3.00-3.98 (6H, m), 3.30 (3H, s), 3.33 (3H, s), 3.98-4.22 (2H, m), 4.41-4.78 (2H, m), 6.82-6.95 (3H, m), 7.37 (1H, d, J=8.6 Hz), 7.88-8.26 (3H, m), 8.68-8.82 (2H, m), 8.85 (1H, s).

Example 53

Synthesis of 7-{3-[(3,5-dichloropyridin-4-ylmethyl)-(2-pyridin-3-ylethyl)amino]propoxy}-1-ethyl-3,3,5-trimethyl-1,5-dihydrobenzo[b][1,4]diazepine-2,4-dione trihydrochloride Using appropriate starting materials and following the procedures of Examples 7 and 6, the object compound was synthesized.
¹H-NMR (DMSO-D₆) δppm:
0.76 (3H, s), 1.02 (3H, t, J=7.0 Hz), 1.33 (3H, s), 2.09-2.44 (2H, m), 2.98-3.60 (6H, m), 3.33 (3H, s), 3.60-3.77 (1H, m), 3.98-4.18 (3H, m), 4.20-4.62 (2H, m), 6.80-7.00 (2H, m), 7.41 (1H, d, J=8.7 Hz), 7.97-8.10 (1H, m), 8.49-8.78 (3H, m), 8.84 (1H, d, J=5.4 Hz), 8.96 (1H, s).

Example 54

Synthesis of 1-ethyl-3,3,5-trimethyl-7-{3-[(3-methylpyridin-4-ylmethyl)-(2-pyridin-3-ylethyl)amino]propoxy}-1,5-dihydrobenzo[b][1,4]diazepine-2,4-dione trihydrochloride Using appropriate starting materials and following the procedures of Examples 7 and 6, the object compound was synthesized.
¹H-NMR (DMSO-D₆) δppm:
0.75 (3H, s), 1.01 (3H, t, J=6.9 Hz), 1.32 (3H, s), 2.11-2.42 (2H, m), 2.56 (3H, s), 3.08-3.59 (8H, m), 3.59-3.77 (1H, m), 3.95-4.18 (2H, m), 4.41-4.90 (4H, m), 6.82-6.97 (2H, m), 7.41 (1H, d, J=8.8 Hz), 8.03 (1H, dd, J=5.7 and 7.8 Hz), 8.30-8.69 (1H, m), 8.56 (1H, d, J=8.1 Hz), 8.72-8.88 (3H, m), 8.96 (1H, s).

Example 55

Synthesis of 1-ethyl-3,3,5-trimethyl-7-{3-[(2-pyridin-3-ylethyl)pyridin-3-ylmethylamino]propoxy}-1,5-dihydrobenzo[b][1,4]diazepine-2,4-dione trihydrochloride Using appropriate starting materials and following the procedures of Examples 7 and 6, the object compound was synthesized.
¹H-NMR (DMSO-D₆) δppm:
0.76 (3H, s), 1.01 (3H, t, J=6.9 Hz), 1.32 (3H, s), 2.27-2.41 (2H, m), 3.20-3.36 (2H, m), 3.33 (3H, s), 3.38-3.57 (4H, m), 3.67-3.76 (1H, m), 4.00-4.18 (3H, m), 4.52-4.75 (2H, m), 6.87-6.97 (2H, m), 7.42 (1H, d, J=8.8 Hz), 7.83 (1H, dd, J=5.3 and 7.9 Hz), 7.99 (1H, dd, J=5.7 and 8.0 Hz), 8.51 (1H, d, J=8.1 Hz), 8.65 (1H, d, J=7.9 Hz), 8.78-8.87 (2H, m), 8.95 (1H, s), 9.13 (1H, s).

Example 56

Synthesis of 1-ethyl-3,3,5-trimethyl-7-(3-{[2-(1-oxo-1H-isoquinolin-2-yl)ethyl]pyridin-3-ylmethylamino}propoxy)-1,5-dihydrobenzo[b][1,4]diazepine-2,4-dione dihydrochloride Using appropriate starting materials and following the procedures of Examples 7 and 6, the object compound was synthesized.
¹H-NMR (DMSO-D₆) δppm:
0.75 (3H, s), 1.01 (3H, t, J=7.0 Hz), 1.32 (3H, s), 2.19-2.40 (2H, m), 3.20-3.57 (4H, m), 3.32 (3H, s), 3.61-3.72 (1H, m), 3.99-4.10 (3H, m), 4.35-4.85 (4H, m), 6.70 (1H, d, J=7.4 Hz), 6.81-6.97 (2H, m), 7.39 (1H, d, J=9.0 Hz), 7.50-7.57 (2H, m), 7.66-7.92 (3H, m), 8.22 (1H, d, J=8.0 Hz), 8.50-8.71 (1H, m), 8.78-8.90 (1H, m), 9.02-9.18 (1H, m).

Example 57

Synthesis of 1-ethyl-3,3,5-trimethyl-7-(3-{[2-(1-oxo-1H-isoquinolin-2-yl)ethyl]thiazol-2-ylmethylamino}propoxy)-1,5-dihydrobenzo[b][1,4]diazepine-2,4-dione Using an appropriate starting material and following the procedure of Example 7, the object compound was synthesized.
¹H-NMR (CDCl₃) δppm:
0.84 (s, 3H), 1.15 (t, J=7.1 Hz, 3H), 1.53 (s, 3H), 1.88-2.00 (m, 2H), 2.82 (t, J=6.3 Hz, 2H), 3.01 (t, J=6.3 Hz, 2H), 3.36 (s, 3H), 3.61-3.74 (m, 1H), 3.88 (t, J=6.1 Hz, 2H), 4.07 (s, 2H), 4.08-4.23 (m, 3H), 6.42 (d, J=7.3 Hz, 1H), 6.60-6.68 (m, 2H), 7.06 (d, J=7.3 Hz, 1H), 7.12-7.15 (m, 2H), 7.48-7.49 (m, 2H), 7.64 (d, J=7.4 Hz, 1H), 7.67 (d, J=3.3 Hz, 1H), 8.39 (d, J=7.4 Hz, 1H).

Example 58

Synthesis of 1-ethyl-7-(3-{(3-fluorobenzyl)-[2-(1-oxo-1H-isoquinolin-2-yl)ethyl]amino}propoxy)-3,3,5-trimethyl-1,5-dihydrobenzo[b][1,4]diazepine-2,4-dione Using an appropriate starting material and following the procedure of Example 7, the object compound was synthesized.

$^1$H-NMR (CDCl$_3$) δppm:
0.85 (s, 3H), 1.15 (t, J=7.0 Hz, 3H), 1.53 (s, 3H), 1.80-1.96 (m, 2H), 2.70 (t, J=6.4 Hz, 2H), 2.70 (t, J=6.4 Hz, 2H), 3.35 (s, 3H), 3.67 (s, 2H), 3.66-3.76 (m, 1H), 3.83 (t, J=6.0 Hz, 2H), 4.08 (t, J=6.0 Hz, 2H), 4.00-4.21 (m, 1H), 6.40 (d, J=7.4 Hz, 1H), 6.55-6.61 (m, 2H), 6.80-6.95 (m, 1H), 6.88-7.00 (m, 3H), 7.05-7.18 (m, 2H), 8.41-8.50 (m, 2H), 7.64 (t, J=8.0 Hz, 1H), 8.39 (d, J=8.0 Hz, 1H).

Example 59

Synthesis of 1-ethyl-7-(3-{(3-methoxybenzyl)-[2-(1-oxo-1H-isoquinolin-2-yl)ethyl]amino}propoxy)-3,3,5-trimethyl-1,5-dihydrobenzo[b][1,4]diazepine-2,4-dione Using an appropriate starting material and following the procedure of Example 7, the object compound was synthesized.

$^1$H-NMR (CDCl$_3$) δppm:
0.84 (s, 3H), 1.15 (t, J=7.1 Hz, 3H), 1.52 (s, 3H), 1.80-1.96 (m, 2H), 2.70 (t, J=6.8 Hz, 2H), 2.90 (t, J=6.2 Hz, 2H), 3.36 (s, 3H), 3.65 (s, 2H), 3.68 (s, 3H), 3.65-3.72 (m, 1H), 3.84 (t, J=6.2 Hz, 2H), 4.06 (t, J=6.2 Hz, 2H), 4.10-4.20 (m, 1H), 6.38 (d, J=7.3 Hz, 1H), 6.55-6.60 (m, 2H), 6.67-6.73 (m, 1H), 6.79-6.81 (m, 2H), 6.95-7.30 (m, 3H), 7.39-7.50 (m, 2H), 7.60-7.67 (m, 1H), 8.40 (d, J=1.2 Hz, 1H).

Example 60

Synthesis of 1-ethyl-3,3,5-trimethyl-7-(3-{[2-(1-oxo-1H-isoquinolin-2-yl)ethyl]thiophen-2-ylmethylamino}propoxy)-1,5-dihydrobenzo[b][1,4]diazepine-2,4-dione Using an appropriate starting material and following the procedure of Example 7, the object compound was synthesized.

$^1$H-NMR (CDCl$_3$) δppm:
0.85 (s, 3H), 1.14 (t, J=7.1 Hz, 3H), 1.52 (s, 3H), 1.80-1.96 (m, 2H), 2.69 (t, J=6.8 Hz, 2H), 2.91 (t, J=6.2 Hz, 2H), 3.35 (s, 3H), 3.65-3.78 (m, 1H), 3.82 (t, J=6.2 Hz, 2H), 3.89 (s, 2H), 4.07 (t, J=6.2 Hz, 2H), 4.10-4.25 (m, 1H), 6.40 (d, J=7.3 Hz, 1H), 6.38-6.49 (m, 2H), 6.87-6.89 (m, 2H), 7.02-7.28 (m, 3H), 7.42-7.50 (m, 2H), 7.60-7.64 (m, 1H), 8.40 (d, J=1.2 Hz, 1H).

Example 61

Synthesis of 7-(3-{bis-[2-(1-oxo-1H-isoquinolin-2-yl)ethyl]amino}propoxy)-1-ethyl-3,3,5-trimethyl-1,5-dihydrobenzo[b][1,4]diazepine-2,4-dione (1-Oxo-1H-isoquinolin-2-yl)acetaldehyde (207 mg, 1.1 mmol) was added to a 1,2-dichloroethane solution (4 ml) of 7-(3-aminopropoxy)-1-ethyl-3,3,5-trimethyl-1,5-dihydrobenzo[b][1,4]diazepine-2,4-dione (329 mg, 1.0 mmol) and sodium triacetoxyhydroborate (381 mg, 1.8 mmol), and stirred at room temperature overnight. Water was added to the reaction mixture, and extraction with ethyl acetate was performed. The organic layer was washed with water, and a saturated sodium chloride aqueous solution, in this order, dried over anhydrous magnesium sulfate, and concentrated under reduced pressure. The residue was purified by silica gel column chromatography (dichloromethane:methanol=20:1). The purified product was concentrated under reduced pressure to thereby obtain 7-(3-{bis-[2-(1-oxo-1H-isoquinolin-2-yl)ethyl]amino}propoxy)-1-ethyl-3,3,5-trimethyl-1,5-dihydrobenzo[b][1,4]diazepine-2,4-dione.

$^1$H-NMR (CDCl$_3$) δppm:
0.84 (s, 3H), 1.14 (t, J=7.1 Hz, 3H), 1.52 (s, 3H), 1.74-1.82 (m, 2H), 2.75 (t, J=7.3 Hz, 2H), 2.94 (t, J=6.2 Hz, 4H), 3.34 (s, 3H), 3.62-3.75 (m, 3H), 4.02 (t, J=6.2 Hz, 4H), 4.12-4.23 (m, 1H), 6.16 (d, J=7.3 Hz, 2H), 6.50 (dd, J=8.9 and 2.7 Hz, 1H), 6.56 (d, J=2.7 Hz, 1H), 6.91 (d, J=7.3 Hz, 2H), 7.09 (d, J=8.9 Hz, 1H), 7.39-7.62 (m, 4H), 7.59-7.68 (m, 2H), 8.41 (d, J=7.9 Hz, 2H).

Example 62

Synthesis of 1-ethyl-7-(3-{[2-(7-methoxy-2-oxo-3,4-dihydro-2H-quinolin-1-yl)ethyl]pyridin-4-ylmethylamino}propoxy)-3,3,5-trimethyl-1,5-dihydrobenzo[b][1,4]diazepine-2,4-dione Using an appropriate starting material and following the procedure of Example 7, the object compound was synthesized.

$^1$H-NMR (CDCl$_3$) δppm:
0.84 (s, 3H), 1.14 (t, J=7.1 Hz, 3H), 1.51 (s, 3H), 1.90-2.00 (m, 4H), 2.58 (t, J=6.8 Hz, 2H), 2.68 (t, J=6.8 Hz, 2H), 3.38 (s, 3H), 3.61 (s, 2H), 3.62-3.72 (m, 1H), 3.95-4.00 (m, 4H), 4.08-4.22 (m, 1H), 6.44 (d, J=7.3 Hz, 1H), 6.68 (d, J=2.7 Hz, 1H), 6.75 (dd, J=9.0 and 2.7 Hz, 1H), 6.95 (d, J=7.3 Hz, 1H), 7.17 (d, J=9.0 Hz, 1H), 7.25-7.27 (m, 2H), 7.45-7.52 (m, 2H), 7.60-7.70 (m, 1H), 8.40 (d, J=7.9 Hz, 1H), 8.48 (d, J=1.5 Hz, 2H).

Example 63

Synthesis of 1-ethyl-3,3,5-trimethyl-7-(3-{[2-(2-oxo-2H-quinolin-1-yl)ethyl]pyridin-4-ylmethylamino}propoxy)-1,5-dihydrobenzo[b][1,4]diazepine-2,4-dione Using an appropriate starting material and following the procedure of Example 7, the object compound was synthesized.

$^1$H-NMR (CDCl$_3$) δppm:
0.87 (s, 3H), 1.17 (t, J=7.0 Hz, 3H), 1.54 (s, 3H), 1.92-2.04 (m, 2H), 2.80-2.86 (m, 4H), 3.41 (s, 3H), 3.76 (s, 2H), 3.68-3.78 (m, 1H), 4.01 (t, J=6.0 Hz, 2H), 4.10-4.22 (m, 1H), 4.44 (t, J=7.0 Hz, 2H), 6.66-6.70 (m, 2H), 6.76 (dd, J=8.9 and 2.9 Hz, 1H), 7.09 (d, J=8.3 Hz, 1H), 7.07-7.11 (m, 4H), 7.38-7.46 (m, 1H), 7.57 (d, J=6.5 Hz, 1H), 7.68 (d, J=9.5 Hz, 1H), 8.44 (d, J=5.9 Hz, 2H).

Example 64

Synthesis of 1-ethyl-7-{3-[(2-(6-methoxy-2-oxo-2H-quinolin-1-yl)ethyl)pyridin-4-ylmethylamino]propoxy}-3,3,5-trimethyl-1,5-dihydrobenzo[b][1,4]diazepine-2,4-dione Using an appropriate starting material and following the procedure of Example 7, the object compound was synthesized.

¹H-NMR (CDCl₃) δppm:

0.85 (s, 3H), 1.15 (t, J=7.1 Hz, 3H), 1.52 (s, 3H), 1.89-2.00 (m, 2H), 2.81 (m, 4H), 3.39 (s, 3H), 3.74 (s, 2H), 3.65-3.77 (m, 1H), 3.85 (s, 3H), 3.99 (t, J=6.0 Hz, 2H), 4.11-4.28 (m, 1H), 4.40 (t, J=6.9 Hz, 2H), 6.64-6.70 (m, 2H), 6.74 (dd, J=8.9 and 2.9 Hz, 1H), 6.96-7.04 (m, 3H), 7.16-7.20 (m, 3H), 7.60 (d, J=9.5 Hz, 1H), 8.43 (d, J=5.9 Hz, 2H).

Example 65

Synthesis of 1-ethyl-7-(3-{[2-(6-methoxyquinolin-2-yloxy)ethyl]pyridin-4-ylmethylamino}propoxy)-3,3,5-trimethyl-1,5-dihydrobenzo[b][1,4]diazepine-2,4-dione Using an appropriate starting material and following the procedure of Example 7, the object compound was synthesized.

¹H-NMR (CDCl₃) δppm:

0.82 (s, 3H), 1.12 (t, J=7.1 Hz, 3H), 1.51 (s, 3H), 1.90-2.05 (m, 2H), 2.77 (t, J=7.0 Hz, 2H), 2.97 (t, J=7.0 Hz, 2H), 3.34 (s, 3H), 4.58-5.59 (m, 1H), 3.77 (s, 2H), 3.90 (s, 3H), 3.95-4.04 (m, 2H), 4.04-4.19 (m, 1H), 4.50-4.63 (m, 2H), 6.59-6.66 (m, 2H), 6.83 (d, J=8.8 Hz, 1H), 7.04 (d, J=2.8 Hz, 1H), 7.11 (d, J=8.9 Hz, 1H), 7.24-7.27 (m, 3H), 7.67 (d, J=9.1 Hz, 1H), 7.89 (d, J=8.8 Hz, 1H), 8.42 (d, J=5.9 Hz, 2H).

Example 66

Synthesis of 1-ethyl-3,3,5-trimethyl-7-(3-{[2-(2-oxo-3,4-dihydro-2H-quinolin-1-yl)ethyl]pyridin-4-ylmethylamino}propoxy)-1,5-dihydrobenzo[b][1,4]diazepine-2,4-dione Using an appropriate starting material and following the procedure of Example 7, the object compound was synthesized.

¹H-NMR (CDCl₃) δppm:

0.85 (s, 3H), 1.14 (t, J=7.1 Hz, 3H), 1.52 (s, 3H), 1.89-1.97 (m, 2H), 2.53-2.64 (m, 2H), 2.68-2.77 (m, 4H), 2.86 (t, J=8.0 Hz, 2H), 3.38 (s, 3H), 3.69 (s, 2H), 3.60-3.78 (m, 1H), 3.93-4.20 (m, 5H), 6.67 (d, J=2.7 Hz, 1H), 6.72-6.84 (m, 2H), 6.79 (t, J=8.2 Hz, 1H), 7.10-7.22 (m, 5H), 8.44 (d, J=6.0 Hz, 2H).

Example 67

Synthesis of 1-ethyl-3,3,5-trimethyl-7-{3-[(2-(4-oxo-4H-thieno[3,2-c]pyridin-5-yl)ethyl)pyridin-4-ylmethylamino]propoxy}-1,5-dihydrobenzo[b][1,4]diazepine-2,4-dione Using an appropriate starting material and following the procedure of Example 7, the object compound was synthesized.

¹H-NMR (CDCl₃) δppm:

0.88 (s, 3H), 1.17 (t, J=7.1 Hz, 3H), 1.54 (s, 3H), 1.89-1.97 (m, 2H), 2.74 (t, J=6.8 Hz, 2H), 2.83-2.95 (m, 2H), 3.39 (s, 3H), 3.69 (s, 2H), 3.68-3.74 (m, 1H), 3.89 (t, J=6.0 Hz, 2H), 4.12 (t, J=6.0 Hz, 2H), 4.11-4.21 (m, 1H), 6.53-6.70 (m, 3H), 7.05 (d, J=7.2 Hz, 1H), 7.10 (d, J=5.9 Hz, 2H), 7.20 (d, J=8.9 Hz, 1H), 7.32 (d, J=5.3 Hz, 1H), 7.63 (d, J=5.3 Hz, 1H), 8.32 (d, J=5.9 Hz, 2H).

Example 68

Synthesis of 1-ethyl-3,3,5-trimethyl-7-(3-{[2-(7-oxo-7H-thieno[2,3-c]pyridin-6-yl)ethyl]pyridin-4-ylmethylamino}propoxy)-1,5-dihydrobenzo[b][1,4]diazepine-2,4-dione Using an appropriate starting material and following the procedure of Example 7, the object compound was synthesized.

¹H-NMR (CDCl₃) δppm:

0.88 (s, 3H), 1.17 (t, J=7.1 Hz, 3H), 1.54 (s, 3H), 1.89-1.97 (m, 2H), 2.74 (t, J=6.8 Hz, 2H), 2.83-2.95 (m, 2H), 3.39 (s, 3H), 3.68 (s, 2H), 3.68-3.74 (m, 1H), 3.90 (t, J=6.0 Hz, 2H), 4.05-4.21 (m, 3H), 6.56 (d, J=7.1 Hz, 1H), 6.60-6.70 (m, 2H), 7.03-7.10 (m, 3H), 7.16-7.23 (m, 2H), 7.73 (d, J=5.2 Hz, 1H), 8.31 (d, J=5.9 Hz, 2H).

Example 69

Synthesis of 1-ethyl-7-(3-{[2-(8-methoxy-2-oxo-2H-quinolin-1-yl)ethyl]pyridin-4-ylmethylamino}propoxy)-3,3,5-trimethyl-1,5-dihydrobenzo[b][1,4]diazepine-2,4-dione Using an appropriate starting material and following the procedure of Example 7, the object compound was synthesized.

¹H-NMR (CDCl₃) δppm:

0.87 (s, 3H), 1.17 (t, J=7.1 Hz, 3H), 1.54 (s, 3H), 1.89-1.97 (m, 2H), 2.78 (t, J=6.7 Hz, 2H), 2.88 (t, J=7.2 Hz, 2H), 3.41 (s, 3H), 3.75 (s, 3H), 3.68-3.79 (m, 3H), 3.98 (t, J=6.2 Hz, 2H), 4.05-4.21 (m, 1H), 4.80 (t, J=7.7 Hz, 2H), 6.65-6.78 (m, 3H), 6.96-7.03 (m, 1H), 7.11-7.23 (m, 5H), 7.62 (d, J=9.4 Hz, 1H), 8.41 (d, J=6.0 Hz, 2H).

Example 70

Synthesis of 1-ethyl-7-(3-{[2-(8-methoxyquinolin-2-yloxy)ethyl]pyridin-4-ylmethylamino}propoxy)-3,3,5-trimethyl-1,5-dihydrobenzo[b][1,4]diazepine-2,4-dione Using an appropriate starting material and following the procedure of Example 7, the object compound was synthesized.

¹H-NMR (CDCl₃) δppm:

0.83 (s, 3H), 1.14 (t, J=7.1 Hz, 3H), 1.51 (s, 3H), 1.89-2.03 (m, 2H), 2.76 (t, J=6.7 Hz, 2H), 3.00 (t, J=7.2 Hz, 2H), 3.35 (s, 3H), 3.59-3.67 (m, 1H), 3.80 (s, 2H), 3.99 (s, 3H), 3.95-4.07 (m, 2H), 4.10-4.19 (m, 1H), 4.70 (t, J=7.0 Hz, 2H), 6.58-6.70 (m, 2H), 6.89 (d, J=8.8 Hz, 1H), 6.95-7.05 (m, 1H), 7.11 (d, J=8.9 Hz, 1H), 7.23-7.38 (m, 4H), 7.97 (d, J=8.8 Hz, 1H), 8.41 (d, J=6.0 Hz, 2H).

Example 71

Synthesis of 1-ethyl-3,3,5-trimethyl-7-(3-{[2-(4-oxo-4H-furo[3,2-c]pyridin-5-yl)ethyl]pyridin-4-ylmethylamino}propoxy)-1,5-dihydrobenzo[b][1,4]diazepine-2,4-dione Using an appropriate starting material and following the procedure of Example 7, the object compound was synthesized.

¹H-NMR (CDCl₃) δppm:

0.87 (s, 3H), 1.16 (t, J=7.1 Hz, 3H), 1.53 (s, 3H), 1.82-1.95 (m, 2H), 2.72 (t, J=6.8 Hz, 2H), 2.76-2.89 (m, 2H), 3.38 (s, 3H), 3.68 (s, 2H), 3.63-3.78 (m, 1H), 3.87 (t, J=6.0 Hz, 2H), 4.10 (t, J=6.0 Hz, 2H), 4.11-4.20 (m, 1H), 6.43 (d, J=7.4 Hz, 1H), 6.60 (d, J=2.8 Hz, 1H), 6.67 (dd, J=9.0 and 2.8 Hz, 1H), 6.96 (d, J=2.9 Hz, 1H), 7.05-7.11 (m, 3H), 7.19 (d, J=9.0 Hz, 1H), 7.50 (d, J=2.9 Hz, 1H), 8.35 (d, J=6.0 Hz, 2H).

Example 72

Synthesis of 1-ethyl-7-(3-{[2-(6-methoxy-2-oxo-3,4-dihydro-2H-quinolin-1-yl)ethyl]pyridin-4-ylmethylamino}propoxy)-3,3,5-trimethyl-1,5-dihydrobenzo[b][1,4]diazepine-2,4-dione Using an appropriate starting material and following the procedure of Example 7, the object compound was synthesized.

¹H-NMR (CDCl₃) δppm:

0.87 (s, 3H), 1.16 (t, J=7.1 Hz, 3H), 1.53 (s, 3H), 1.86-1.96 (m, 2H), 1.87-2.01 (m, 2H), 2.55-2.61 (m, 2H), 2.70-2.85 (m, 6H), 3.40 (s, 3H), 3.62-3.78 (m, 1H), 3.71 (s, 2H), 3.75 (s, 3H), 3.98-4.21 (m, 3H), 6.48 (d, J=2.3 Hz, 1H), 6.49 (dd, J=8.2 and 2.3 Hz, 1H), 6.69 (d, J=2.7 Hz, 1H), 6.76 (dd, J=8.0 and 2.7 Hz, 1H), 7.06 (d, J=8.2 Hz, 1H), 7.18-7.23 (m, 3H), 8.44 (d, J=6.0 Hz, 2H).

Example 73

Synthesis of 1-ethyl-7-(3-{[2-(7-methoxy-2-oxo-3,4-dihydro-2H-quinolin-1-yl)ethyl]pyridin-4-ylmethylamino}propoxy)-3,3,5-trimethyl-1,5-dihydrobenzo[b][1,4]diazepine-2,4-dione Using an appropriate starting material and following the procedure of Example 7, the object compound was synthesized.

¹H-NMR (CDCl₃) δppm:

0.85 (s, 3H), 1.14 (t, J=7.1 Hz, 3H), 1.52 (s, 3H), 1.84-1.96 (m, 2H), 2.55-2.63 (m, 2H), 2.62-2.71 (m, 4H), 2.75-2.84 (m, 2H), 3.38 (s, 3H), 3.68 (s, 2H), 3.77 (s, 3H), 3.64-3.76 (m, 1H), 3.96-4.23 (m, 5H), 6.61-6.75 (m, 5H), 7.16-7.22 (m, 3H), 8.45 (d, J=6.0 Hz, 2H).

Example 74

Synthesis of N-(3-(1-ethyl-3,3,5-trimethyl-2,4-dioxo-2,3,4,5-tetrahydro-1H-benzo[b][1,4]diazepin-7-yloxy)propyl)-N-(2-(7-methyl-1-oxo-1H-isoquinolin-2-yl)ethyl)-2-nitrobenzenesulfonamide N,N,N',N'-Tetra methyl azodicarboxamide (TMAD) (118 mg) and tri-n-butyl phosphine (0.17 ml) were added to a THF solution (5 ml) of N-[3-(1-ethyl-3,3,5-trimethyl-2,4-dioxo-2,3,4,5-tetrahydro-1H-benzo[b][1,4]diazepin-7-yloxy)propyl]-2-nitrobenzenesulfonamide (231 mg) and 2-(2-hydroxyethyl)-7-methyl-2H-isoquinolin-1-one (93 mg), and stirred at room temperature overnight. Water was added to the reaction mixture, and extraction with dichloromethane was performed. The organic layer was dried over anhydrous sodium sulfate, and concentrated under reduced pressure. The residue was purified by silica gel column chromatography (ethyl acetate:methanol=20:1→10:1) The purified product was concentrated to dryness under reduced pressure to thereby obtain 205 mg (yield: 65%) of N-(3-(1-ethyl-3,3,5-trimethyl-2,4-dioxo-2,3,4,5-tetrahydro-1H-benzo[b][1,4]diazepin-7-yloxy)propyl)-N-(2-(7-methyl-1-oxo-1H-isoquinolin-2-yl)ethyl)-2-nitrobenzenesulfonamide as a white amorphous solid.

¹H-NMR (CDCl₃) δppm:

0.84 (3H, s), 1.14 (3H, t, J=7.1 Hz), 1.52 (3H, s), 2.04-2.19 (2H, m), 2.49 (3H, s), 3.39 (3H, s), 3.62 (2H, t, J=6.7 Hz), 3.60-3.78 (1H, m), 3.73 (2H, t, J=6.7 Hz), 3.94 (2H, t, J=5.7 Hz), 4.10-4.26 (1H, m), 4.23 (2H, t, J=6.7 Hz), 6.43 (1H, d, J=7.3 Hz), 6.68 (1H, d, J=2.7 Hz), 6.72 (1H, dd, J=2.7 and 8.9 Hz), 7.08 (1H, d, J=7.3 Hz), 7.17 (1H, d, J=8.9 Hz), 7.39 (1H, d, J=8.1 Hz), 7.46-7.54 (1H, m), 7.54-7.62 (3H, m), 7.93-8.03 (1H, m), 8.16 (1H, s).

Example 75

Synthesis of 1-ethyl-3,3,5-trimethyl-7-{3-[2-(7-methyl-1-oxo-1H-isoquinolin-2-yl)ethylamino]propoxy}-1,5-dihydrobenzo[b][1,4]diazepine-2,4-dione Using an appropriate starting material and following the procedure of Example 18, the object compound was synthesized.

¹H-NMR (CDCl₃) δppm:

0.84 (3H, s), 1.14 (3H, t, J=7.0 Hz), 1.52 (3H, s), 1.89-2.05 (2H, m), 2.48 (3H, s), 2.87 (2H, t, J=6.7 Hz), 3.06 (2H, t, J=6.2 Hz), 3.38 (3H, s), 3.61-3.76 (1H, m), 4.02 (2H, t, J=6.1 Hz), 4.14 (2H, t, J=6.2 Hz), 4.10-4.22 (1H, m), 6.44 (1H, d, J=7.3 Hz), 6.69 (1H, d, J=2.7 Hz), 6.75 (1H, dd, J=2.7 and 8.9 Hz), 7.06 (1H, d, J=7.3 Hz), 7.15 (1H, d, J=8.9 Hz), 7.40 (1H, d, J=8.0 Hz), 7.45-7.50 (1H, m), 8.22 (1H, s).

Example 76

Synthesis of 1-ethyl-3,3,5-trimethyl-7-(3-{[2-(7-methyl-1-oxo-1H-isoquinolin-2-yl)ethyl]pyridin-4-ylmethylamino}propoxy)-1,5-dihydrobenzo[b][1,4]diazepine-2,4-dione dihydrochloride Using appropriate starting materials and following the procedures of Examples 7 and 6, the object compound was synthesized. ¹H-NMR (DMSO-D₆) δppm: 0.74 (3H, s), 1.01 (3H, t, J=6.9 Hz), 1.32 (3H, s), 2.00-2.24 (2H, m), 2.44 (3H, s), 2.89-4.60 (10H, m), 3.30 (3H, s), 4.81 (2H, s), 6.62 (1H, d, J=7.1 Hz), 6.78 (1H, d, J=9.1 Hz), 6.85 (1H, s), 7.36 (1H, d, J=9.1 Hz), 7.45 (1H, d, J=7.1 Hz), 7.95-8.13 (5H, m), 8.86 (2H, d, J=6.0 Hz).

Example 77

Synthesis of 1-ethyl-3,3,5-trimethyl-7-{3-[(pyridin-4-ylmethyl)amino]propoxy}-1,5-dihydrobenzo[b][1,4]diazepine-2,4-dione 4-Pyridinecarbaldehyde (0.64 ml, 6.8 mmol) was added to a methanol solution (10 ml) of 7-(3-aminopropoxy)-1-ethyl- 3,3,5-trimethyl-1,5-dihydrobenzo[b][1,4]diazepine-2,4-dione (2.18 g, 6.8 mmol), and stirred under a nitrogen atmosphere at room temperature for 1.5 hours. The reaction mixture was cooled in an ice water bath, and sodium borohydride (257 mg, 6.8 mmol) was added thereto at 0° C. The mixture was then stirred at room temperature overnight. Water was added to the reaction mixture, and extraction with ethyl acetate was performed. The organic layer was washed with water and a saturated sodium chloride aqueous solution, in this order, dried over anhydrous magnesium sulfate, and concentrated under reduced pressure. The residue was purified by silica gel column chromatography (ethyl acetate: methanol=9:1→3:2). The purified product was concentrated under reduced pressure to thereby obtain 2.35 g (yield: 84%) of 1-ethyl-3,3,5-trimethyl-7-{3-[(pyridin-4-ylmethyl)amino]propoxy}-1,5-dihydrobenzo[b][1,4]diazepine-2,4-dione as a pale yellow oil.

$^1$H-NMR (CDCl$_3$) δppm:

0.86 (s, 3H), 1.12 (t, J=7.1 Hz, 3H), 1.52 (s, 3H), 1.97-2.09 (m, 2H), 2.84 (t, J=6.8 Hz, 2H), 3.39 (s, 3H), 3.62-3.78 (m, 1H), 3.85 (s, 2H), 4.09 (t, J=6.1 Hz, 2H), 4.06-4.24 (m, 1H), 6.71 (d, J=2.8 Hz, 1H), 6.80 (dd, J=9.0 and 2.8 Hz, 1H), 7.20 (d, J=9.0 Hz, 1H), 7.26-7.27 (m, 2H), 8.53 (d, J=6.0 Hz, 2H).

Examples 78 to 456

Using appropriate starting materials and following the procedures of the above-mentioned Examples, the compounds shown in Tables 1 to 33 were prepared.

TABLE 1

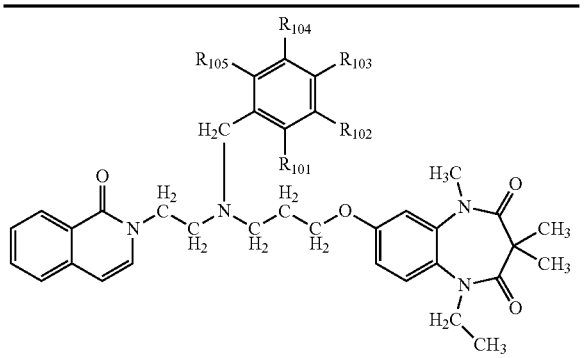

| Example | R101 | R102 | R103 | R104 | R105 | MS (M+1) |
|---|---|---|---|---|---|---|
| 78 | —H | —H | —H | —H | —H | 581 |
| 79 | —H | —H | —CO$_2$H | —H | —H | 625 |
| 80 | —H | —H | —C$_6$H$_5$ | —H | —H | 657 |
| 81 | —H | —H | —OCH$_3$ | —H | —H | 611 |
| 82 | —H | —H | —OH | —H | —H | 597 |
| 83 | —H | —H | —CH$_3$ | —H | —H | 595 |
| 84 | —H | —H | —CH(CH$_3$)$_2$ | —H | —H | 623 |
| 85 | —H | —H | —CN | —H | —H | 606 |
| 86 | —H | —H | —OC$_2$H$_5$ | —H | —H | 625 |
| 87 | —H | —OH | —H | —H | —H | 597 |
| 88 | —H | —H | —NHCOCH$_3$ | —H | —H | 638 |
| 89 | —Cl | —H | —H | —H | —H | 615 |
| 90 | —H | —Cl | —H | —H | —H | 615 |
| 91 | —H | —H | —Cl | —H | —H | 615 |
| 92 | —F | —H | —H | —H | —H | 599 |
| 93 | —CN | —H | —H | —H | —H | 606 |

TABLE 1-continued

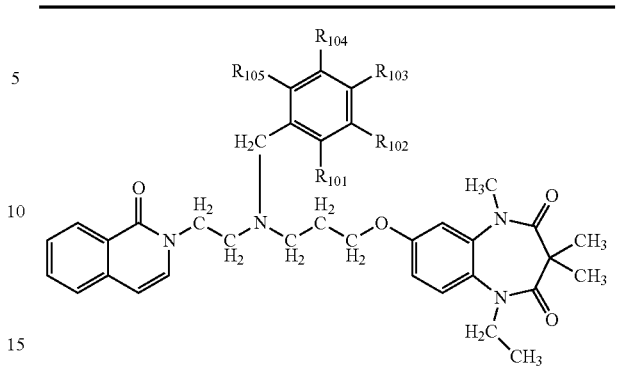

| Example | R101 | R102 | R103 | R104 | R105 | MS (M+1) |
|---|---|---|---|---|---|---|
| 94 | —CF$_3$ | —H | —H | —H | —H | 649 |
| 95 | —H | —CF$_3$ | —H | —H | —H | 649 |
| 96 | —H | —CH$_3$ | —H | —H | —H | 595 |
| 97 | —H | —H | —CF$_3$ | —H | —H | 649 |
| 98 | —H | —H | —C$_2$H$_5$ | —H | —H | 609 |
| 99 | —H | —H | —F | —H | —H | 599 |
| 100 | —CH$_3$ | —H | —H | —H | —H | 595 |
| 101 | —H | —CN | —H | —H | —H | 606 |
| 102 | —OCH$_3$ | —H | —H | —H | —H | 611 |
| 103 | —H | —H | —SCH$_3$ | —H | —H | 627 |
| 104 | —H | —H | —OCH(CH$_3$)$_2$ | —H | —H | 639 |

TABLE 2

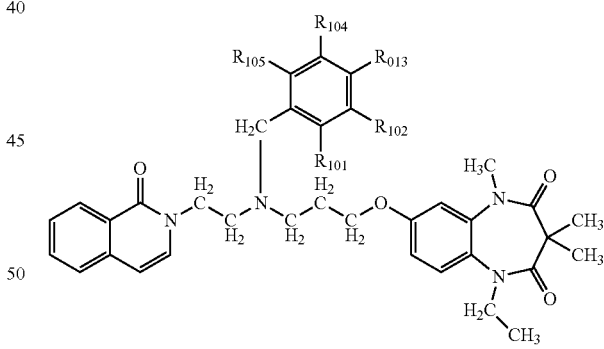

| Example | R101 | R102 | R103 | R104 | R105 | MS (M+1) |
|---|---|---|---|---|---|---|
| 105 | —H | —C$_6$H$_5$ | —H | —H | —H | 657 |
| 106 | —H | —H | -2-THIENYL | —H | —H | 663 |
| 107 | —OH | —H | —H | —H | —H | 597 |
| 108 | —H | —H | -3-PYRIDYL | —H | —H | 658 |
| 109 | —H | -3-PYRIDYL | —H | —H | —H | 658 |
| 110 | -3-PYRIDYL | —H | —H | —H | —H | 658 |
| 111 | -2-PYRIDYL | —H | —H | —H | —H | 663 |
| 112 | —H | —H | -2-FURYL | —H | —H | 647 |

TABLE 3

| Example | R101 | R102 | R103 | R104 | R105 | MS (M + 1) |
|---|---|---|---|---|---|---|
| 113 | —H | —H | (1H-1,2,4-triazol-1-yl) | —H | —H | 648 |
| 114 | —H | —H | (1H-imidazol-1-yl) | —H | —H | 647 |
| 115 | —H | —H | (piperidin-1-yl) | —H | —H | 664 |
| 116 | (4-methylpiperazin-1-yl) | —H | —H | —H | —H | 679 |
| 117 | —H | (1H-pyrazol-1-yl) | —H | —H | —H | 647 |
| 118 | —H | —H | (morpholin-4-ylmethyl) | —H | —H | 680 |
| 119 | —H | —H | (1H-imidazol-1-ylmethyl) | —H | —H | 661 |
| 120 | —H | (1H-imidazol-1-ylmethyl) | —H | —H | —H | 661 |
| 121 | —H | —H | (pyrimidin-5-yl) | —H | —H | 659 |
| 122 | —H | (pyrimidin-5-yl) | —H | —H | —H | 659 |

TABLE 4

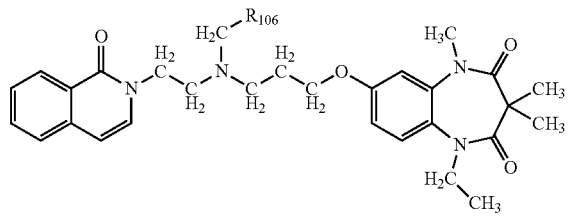

| Example | R106 | MS (M + 1) |
|---|---|---|
| 123 | -2-IMIDAZOLYL | 571 |
| 124 | -2-PYRIDYL | 582 |
| 125 | -3-THIENYL | 587 |
| 126 | -3-INDOLYL | 620 |
| 127 | -2-BENZOFURANYL | 621 |
| 128 | -4-QUINOLYL | 632 |
| 129 | -2-QUINOLYL | 632 |
| 130 | —CH=CHC₆H₅(trans) | 607 |
| 131 | -4-IMIDAZOLYL | 571 |
| 132 | -2-FURYL | 571 |
| 133 | -2-NAPHTHYL | 631 |
| 134 | -5-BENZOFURANYL | 621 |
| 135 | -3-QUINOLYL | 632 |
| 136 | —CH₂C₆H₅ | 595 |
| 137 | -8-QUINOLYL | 632 |
| 138 | —CH(CH₃)C₆H₅ | 609 |
| 139 | —(CH₂)₂C₆H₅ | 609 |

TABLE 5

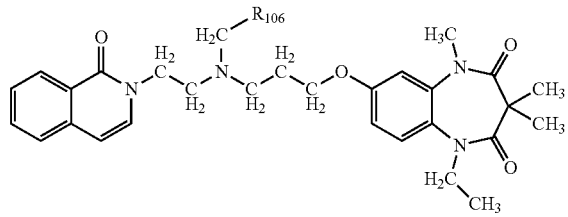

| Example | R106 | MS (M + 1) |
|---|---|---|
| 140 | 2,5-dimethylfuryl | 585 |
| 141 | 2,3-dimethylthienyl | 601 |
| 142 | 4-methyl-2-phenylimidazolyl | 647 |
| 143 | 1,2-dimethylindolyl | 634 |
| 144 | methylimidazo[1,2-a]pyridinyl | 621 |

TABLE 5-continued

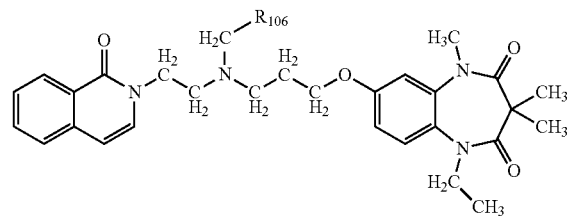

| Example | R106 | MS (M + 1) |
|---|---|---|
| 145 | methylimidazo[2,1-b]thiazolyl | 627 |
| 146 | 4-methyl-2-phenylthiazolyl | 664 |
| 147 | 2-(prop-1-enyl)furyl | 597 |
| 148 | 5-methylfuran-2-carboxyl (OH) | 615 |
| 149 | 5-methylthiophene-2-carboxyl (OH) | 631 |

TABLE 6

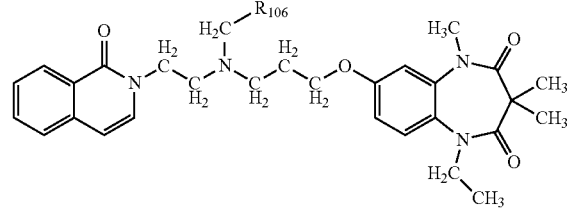

| Example | R106 | MS (M + 1) |
|---|---|---|
| 150 | 5-methylfuran-2-sulfonyl OH | 651 |
| 151 | 5-methyl-2-ethylfuryl | 599 |
| 152 | 2,3-dimethylbenzothienyl | 651 |

TABLE 6-continued

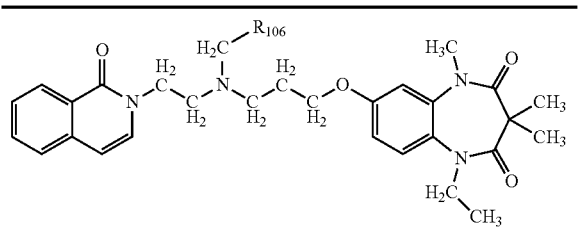

| Example | R106 | MS (M + 1) |
|---|---|---|
| 153 | 2-chloro-5-methylthiophene | 621 |
| 154 | 2,5-dimethyl-3-methylfuran | 599 |
| 155 | 1,2-dimethylimidazole | 585 |
| 156 | 1-acetyl-3-methylindole | 662 |
| 157 | 1,2-dimethylbenzimidazole | 635 |
| 158 | 2-ethyl-5-methylthiophene | 615 |

TABLE 7

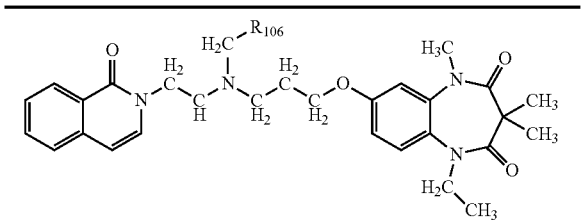

| Example | R106 | MS (M + 1) |
|---|---|---|
| 159 | 2,4-dimethyl-1H-imidazole | 585 |

TABLE 7-continued

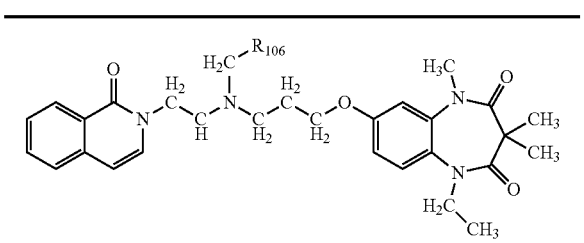

| Example | R106 | MS (M + 1) |
|---|---|---|
| 160 | 5-methylbenzo[d][1,3]dioxole | 625 |
| 161 | (E)-1-methyl-2-(4-methoxyphenyl)ethene | 637 |
| 162 | 4-methylbenzo[d][1,3]dioxole | 625 |
| 163 | 7-methyl-1H-indole | 620 |
| 164 | 2,2,6-trimethylchroman | 665 |
| 165 | 5-methyl-2,3-dihydrobenzofuran | 623 |
| 166 | 4,5-dichloro-2-methyl-1H-imidazole | 639 |
| 167 | 5-chloro-2-methylbenzofuran | 655 |

TABLE 8

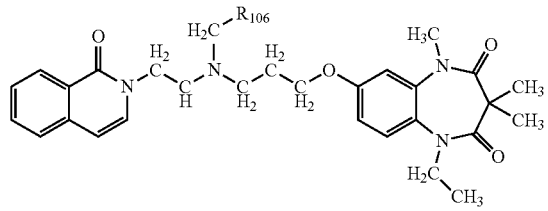

| Example | R106 | MS (M + 1) |
|---|---|---|
| 168 | 2,2-difluoro-6-methylbenzo[1,3]dioxole | 661 |
| 169 | 2,2-difluoro-4-methylbenzo[1,3]dioxole | 661 |
| 170 | 4-(prop-1-enyl)benzonitrile | 632 |
| 171 | 3-(prop-1-enyl)benzonitrile | 632 |
| 172 | 1,3,5-trimethylpyrazole | 599 |
| 173 | 4-chloro-1,3-dimethylpyrazole | 619 |
| 174 | 1,5-dimethylimidazole | 585 |
| 175 | 2-(prop-1-enyl)phenol | 623 |

TABLE 9

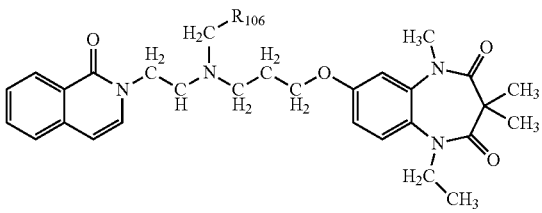

| Example | R106 | MS (M + 1) |
|---|---|---|
| 176 | (2-methylprop-1-enyl)benzene | 621 |
| 177 | 5-methyl-1H-benzimidazole | 621 |
| 178 | 5-chloro-2-methyl-1H-indole | 654 |
| 179 | 3-methylbenzothiophene | 637 |
| 180 | 2-methylbenzothiophene | 637 |
| 181 | 2,6-dimethylpyridine | 596 |
| 182 | 2,5-dimethylthiophene | 601 |
| 183 | 1,3-dimethyl-1H-indazole | 635 |
| 184 | 2,4,5-trimethyloxazole | 600 |

TABLE 10
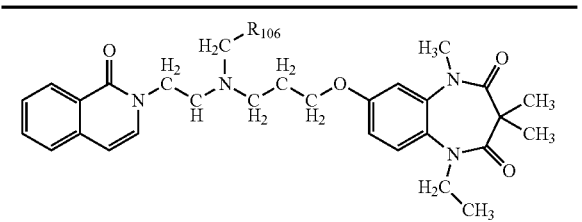
| Example | R106 | MS (M + 1) |
|---|---|---|
| 185 | 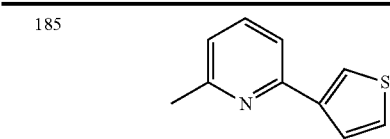 | 664 |
| 186 |  | 602 |
| 187 | 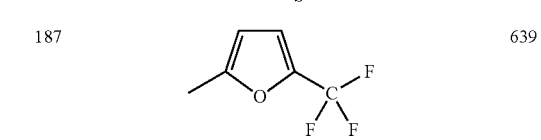 | 639 |
| 188 | 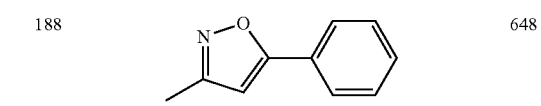 | 648 |
| 189 | 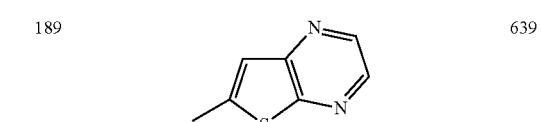 | 639 |
| 190 | 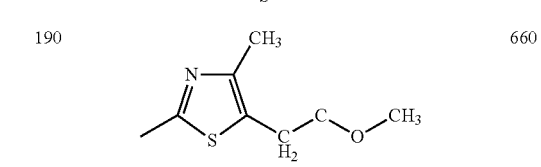 | 660 |
| 191 | 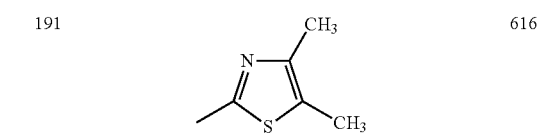 | 616 |
| 192 | 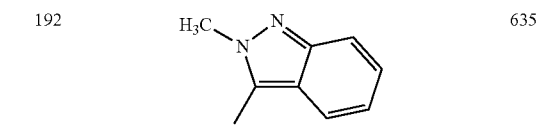 | 635 |
| 193 | 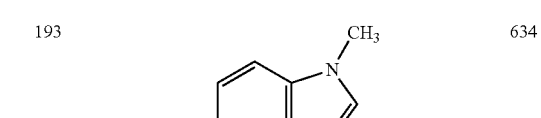 | 634 |
| 194 | 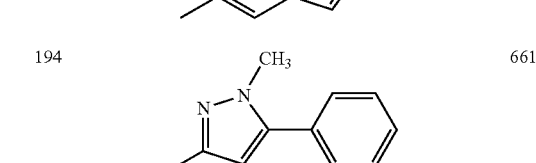 | 661 |
TABLE 11
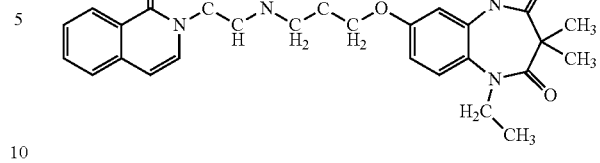
| Example | R106 | MS (M + 1) |
|---|---|---|
| 195 | 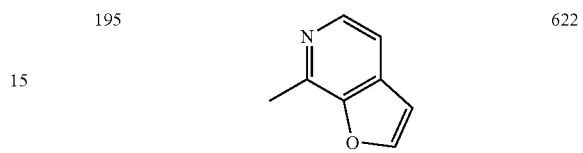 | 622 |
| 196 | 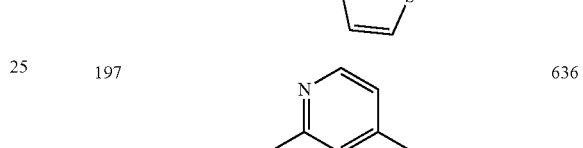 | 638 |
| 197 | 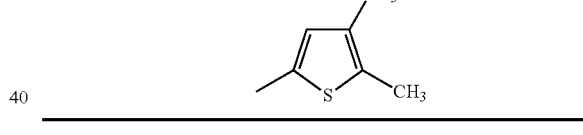 | 636 |
| 198 | 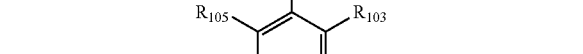 | 585 |
| 199 | 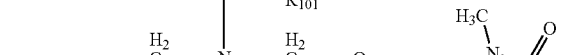 | 615 |
TABLE 12
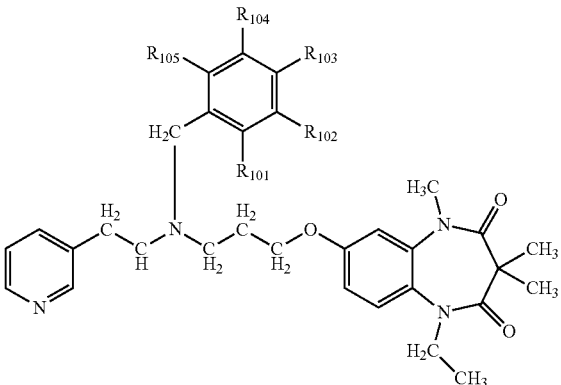
| Example | R101 | R102 | R103 | R104 | R105 | MS (M + 1) |
|---|---|---|---|---|---|---|
| 200 | —H | —H | —H | —H | —H | 515 |
| 201 | —H | —H | —CO₂H | —H | —H | 559 |
| 202 | —H | —H | —C₆H₅ | —H | —H | 591 |
| 203 | —H | —H | —OCH₃ | —H | —H | 545 |
| 204 | —H | —H | —H | —OCH₃ | —H | 545 |

TABLE 12-continued

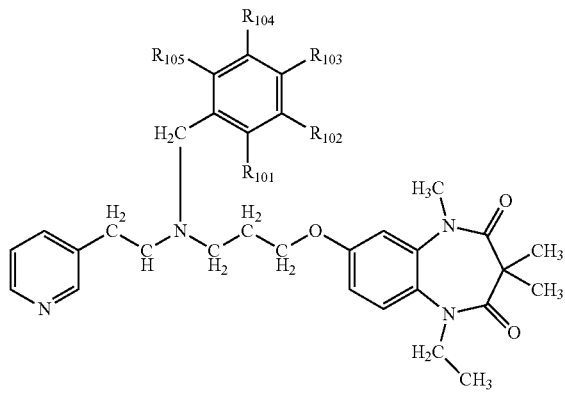

| Example | R101 | R102 | R103 | R104 | R105 | MS (M + 1) |
|---|---|---|---|---|---|---|
| 205 | —H | —H | —OH | —H | —H | 531 |
| 206 | —H | —H | —CH$_3$ | —H | —H | 529 |
| 207 | —H | —H | —CH(CH$_3$)$_2$ | —H | —H | 557 |
| 208 | —H | —H | —CN | —H | —H | 540 |
| 209 | —H | —H | —OC$_2$H$_5$ | —H | —H | 559 |
| 210 | —H | —H | —H | —OH | —H | 531 |
| 211 | —H | —H | —OH | —OH | —H | 547 |
| 212 | —H | —H | —H | —H | —CO$_2$H | 559 |
| 213 | —H | —H | —NHCOCH$_3$ | —H | —H | 572 |
| 214 | —H | —H | —O(CH$_2$)$_3$N(CH$_3$)$_2$ | —H | —H | 616 |
| 215 | —H | —H | —H | —H | —Cl | 549 |
| 216 | —H | —H | —H | —Cl | —H | 549 |

TABLE 12-continued

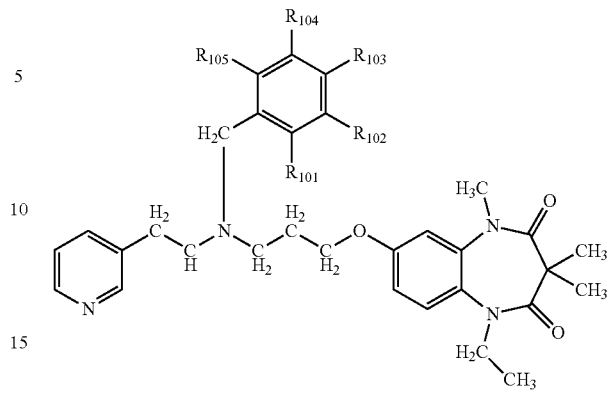

| Example | R101 | R102 | R103 | R104 | R105 | MS (M + 1) |
|---|---|---|---|---|---|---|
| 217 | —H | —H | —Cl | —H | —H | 549 |
| 218 | —H | —H | —H | —H | —F | 533 |
| 219 | —H | —H | —H | —H | —CN | 540 |
| 220 | —H | —H | —H | —H | —CF$_3$ | 583 |
| 221 | —H | —H | —H | —CF$_3$ | —H | 583 |
| 222 | —H | —H | —H | —CH$_3$ | —H | 529 |
| 223 | —H | —H | —CF$_3$ | —H | —H | 583 |
| 224 | —H | —H | —C$_2$H$_5$ | —H | —H | 543 |
| 225 | —H | —H | —F | —H | —H | 533 |
| 226 | —H | —H | —H | —H | —CH$_3$ | 529 |
| 227 | —H | —H | —CO$_2$CH$_3$ | —H | —H | 573 |

TABLE 13

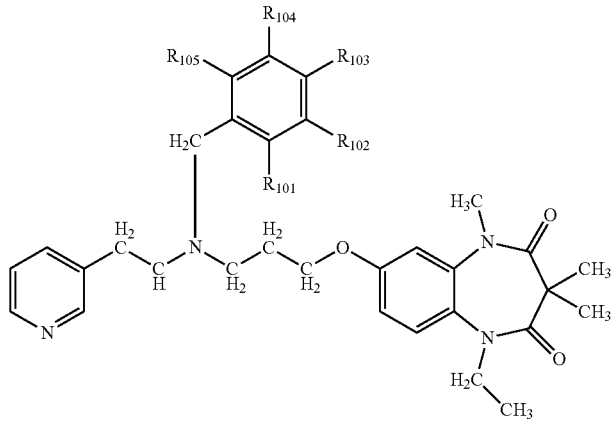

| Example | R101 | R102 | R103 | R104 | R105 | MS (M + 1) |
|---|---|---|---|---|---|---|
| 228 | —H | —H | —H | —F | —H | 533 |
| 229 | —H | —H | —H | —CN | —H | 540 |
| 230 | —H | —H | —H | —H | —OCH$_3$ | 545 |
| 231 | —H | —H | —SCH$_3$ | —H | —H | 561 |
| 232 | —H | —H | —H | —H | —CO$_2$CH$_3$ | 573 |
| 233 | —H | —H | —SO$_2$CH$_3$ | —H | —H | 593 |
| 234 | —H | —H | —OCH(CH$_3$)$_2$ | —H | —H | 573 |
| 235 | —H | —H | —H | —C$_6$H$_5$ | —H | 591 |
| 236 | —H | —H | —H | —H | —NHSO$_2$CH$_3$ | 608 |
| 237 | —H | —H | -1-IMIDAZOLYL | —H | —H | 581 |
| 238 | —H | —H | -2-THIENYL | —H | —H | 597 |
| 239 | —H | —H | —H | —H | —OH | 531 |
| 240 | —H | —H | -3-PYRIDYL | —H | —H | 592 |
| 241 | —H | —H | —H | -3-PRYIDYL | —H | 592 |
| 242 | —H | —H | —H | —H | -3-PYRIDYL | 592 |
| 243 | —H | —H | —H | —H | -2-THIENYL | 597 |
| 244 | —H | —H | -2-FURYL | —H | —H | 581 |

TABLE 14

| Example | R101 | R102 | R103 | R104 | R105 | MS (M + 1) |
|---|---|---|---|---|---|---|
| 245 | —H | —H | 1-methyl-1,2,4-triazol-3-yl | —H | —H | 582 |
| 246 | —H | —H | —H | —H | 4-methylpiperazin-1-yl | 613 |
| 247 | —H | —H | —H | 1-imidazolyl | —H | 581 |
| 248 | —H | —H | morpholinomethyl | —H | —H | 614 |
| 249 | —H | —H | (1-imidazolyl)methyl | —H | —H | 595 |
| 250 | —H | —H | —H | (1-imidazolyl)methyl | —H | 595 |
| 251 | —H | —H | pyrimidin-5-yl | —H | —H | 593 |
| 252 | —H | —H | —H | pyrimidin-5-yl | —H | 593 |
| 253 | —H | —H | 2-oxopyrrolidin-1-yl | —H | —H | 598 |

TABLE 15
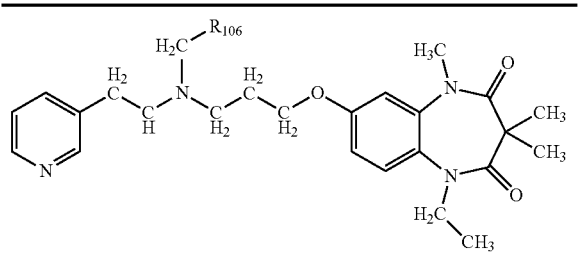
| Example | R106 | MS (M + 1) |
|---|---|---|
| 254 | -3-FURYL | 505 |
| 255 | -2-PYRIDYL | 516 |
| 256 | -2-THIENYL | 521 |
| 257 | -3-THIENYL | 521 |
| 258 | -2-BENZOFURANYL | 555 |
| 259 | -4-QUINOLYL | 566 |
| 260 | -2-QUINOLYL | 566 |
| 261 | —CH=CH$_6$H$_5$(trans) | 541 |
| 262 | -2-THIAZOLYL | 522 |
| 263 | -1-NAPHTHYL | 565 |
| 264 | -2-FURYL | 505 |
| 265 | -2-NAPHTHYL | 565 |
| 266 | -5-BENZOFURANYL | 555 |
| 267 | -3-QUINOLYL | 566 |
| 268 | —CH$_2$C$_6$H$_5$ | 529 |
| 269 | -8-QUINOLYL | 566 |
| 270 | —CH(CH$_3$)$_2$C$_6$H$_5$ | 543 |
| 271 | —(CH$_2$)$_2$C$_6$H$_5$ | 543 |
| 272 | -6-QUINOLYL | 566 |
| 273 | -2-BENZTHIAZOLYL | 572 |
TABLE 16
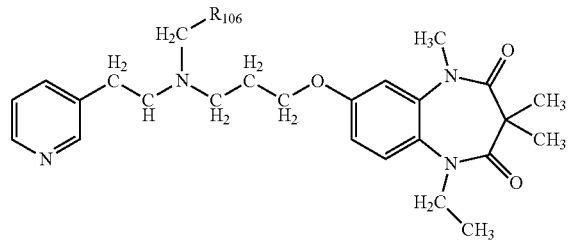
| Example | R106 | MS (M + 1) |
|---|---|---|
| 274 | 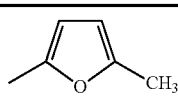 | 519 |
| 275 | 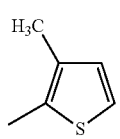 | 535 |
| 276 | 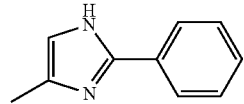 | 581 |
| 277 | 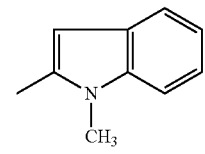 | 568 |
TABLE 16-continued
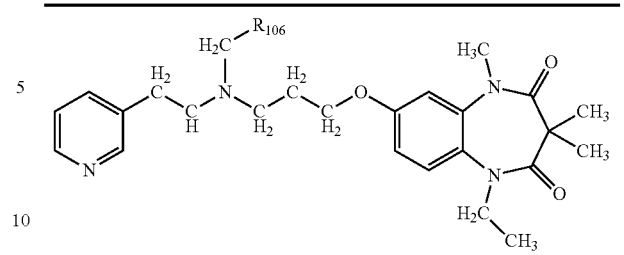
| Example | R106 | MS (M + 1) |
|---|---|---|
| 278 | 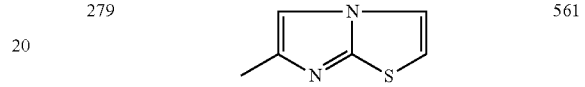 | 555 |
| 279 | 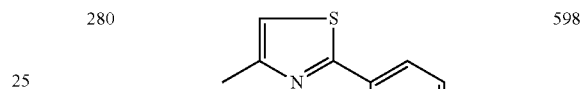 | 561 |
| 280 |  | 598 |
| 281 | 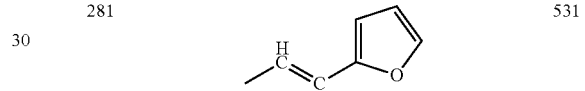 | 531 |
| 282 | 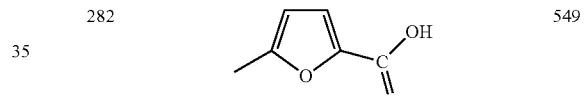 | 549 |
| 283 | 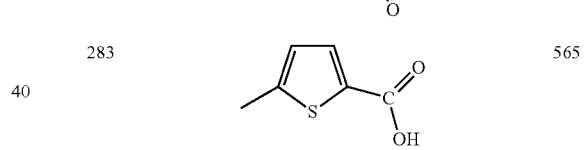 | 565 |
TABLE 17
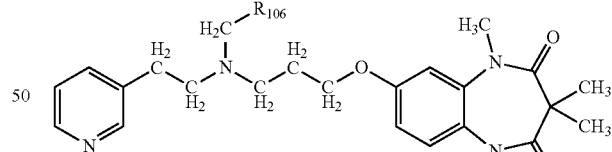
| Example | R106 | MS(M + 1) |
|---|---|---|
| 284 | 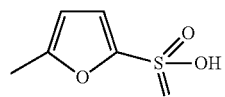 | 585 |
| 285 | 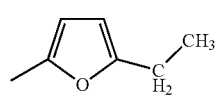 | 533 |

TABLE 17-continued
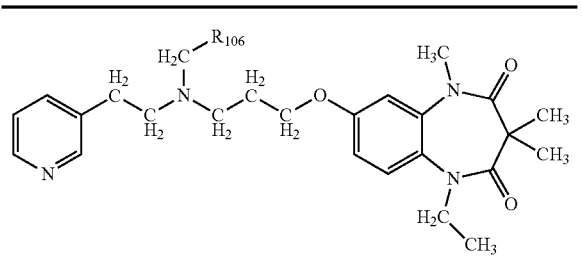
| Example | R106 | MS(M + 1) |
|---|---|---|
| 286 | 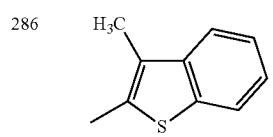 | 585 |
| 287 | 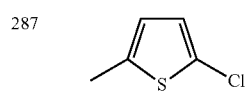 | 555 |
| 288 | 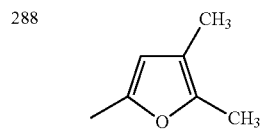 | 533 |
| 289 | 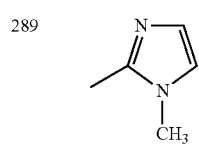 | 519 |
| 290 | 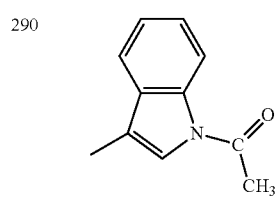 | 596 |
| 291 | 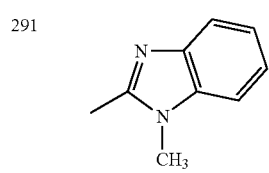 | 569 |
| 292 | 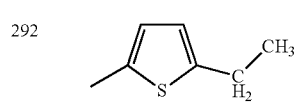 | 549 |
TABLE 18
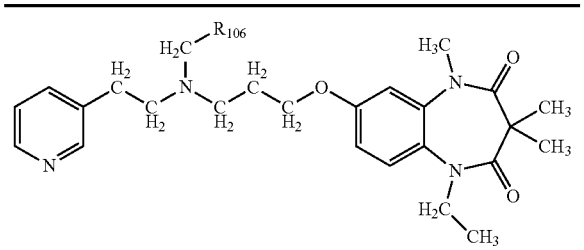
| Example | R106 | MS(M + 1) |
|---|---|---|
| 293 | 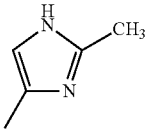 | 519 |
| 294 | 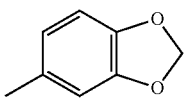 | 559 |
| 295 | 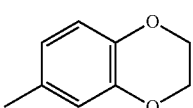 | 573 |
| 296 | 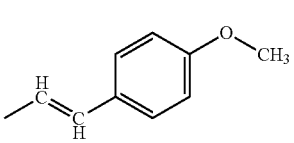 | 571 |
| 297 | 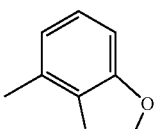 | 559 |
| 298 | 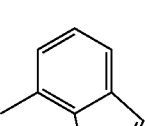 | 554 |
| 299 | 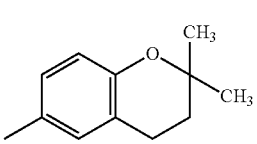 | 599 |
| 300 | 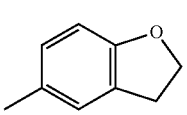 | 557 |
| 301 | 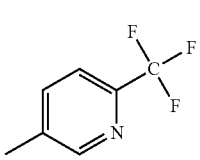 | 584 |

TABLE 19
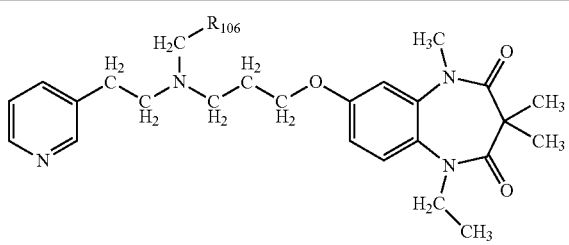
| Example | R106 | MS(M + 1) |
|---|---|---|
| 302 | 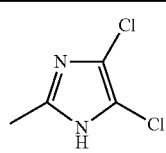 | 573 |
| 303 | 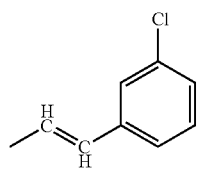 | 575 |
| 304 | 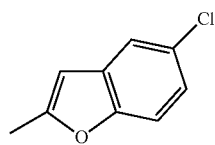 | 589 |
| 305 | 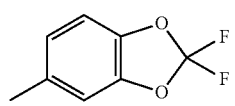 | 595 |
| 306 | 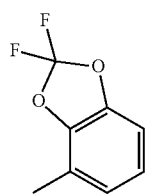 | 595 |
| 307 | 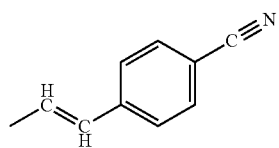 | 566 |
| 308 | 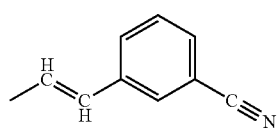 | 566 |
| 309 | 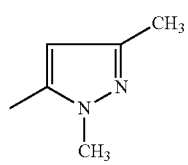 | 533 |
TABLE 20
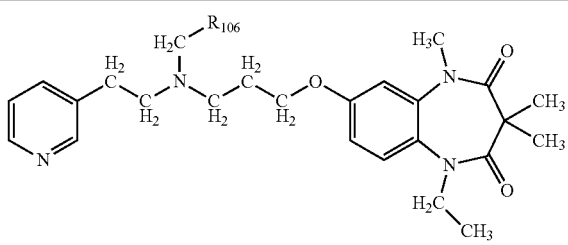
| Example | R106 | MS(M + 1) |
|---|---|---|
| 310 | 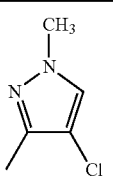 | 553 |
| 311 | 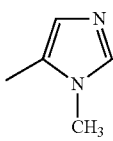 | 519 |
| 312 | 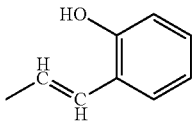 | 557 |
| 313 | 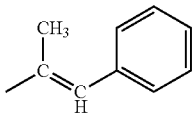 | 555 |
| 314 | 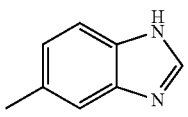 | 555 |
| 315 | 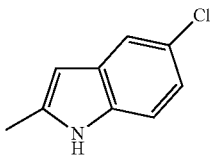 | 588 |
| 316 | 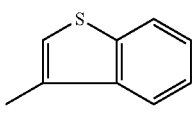 | 571 |
| 317 | 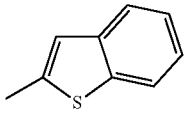 | 571 |
| 318 | 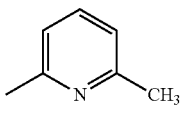 | 530 |

TABLE 21

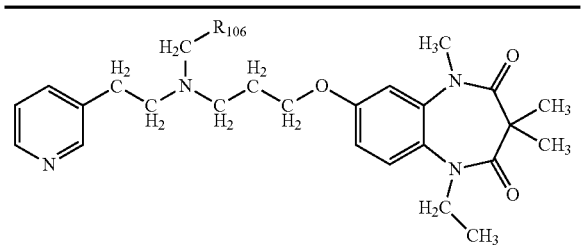

| Example | R106 | MS(M + 1) |
|---|---|---|
| 319 | 2,5-dimethylthiophene | 535 |
| 320 | 1,3-dimethyl-1H-indazole | 569 |
| 321 | 2,4,5-trimethyloxazole | 534 |
| 322 | 6-methyl-2-(thiophen-3-yl)pyridine | 598 |
| 323 | 4,5-dimethylthiazole | 536 |
| 324 | 5-methyl-2-(trifluoromethyl)furan | 573 |
| 325 | 3-methyl-5-phenylisoxazole | 582 |
| 326 | 6-methylthieno[2,3-b]pyrazine | 573 |
| 327 | 2,4-dimethyl-5-(methoxymethyl)thiazole | 594 |
| 328 | 2,4-dimethylthiazole | 550 |

TABLE 22

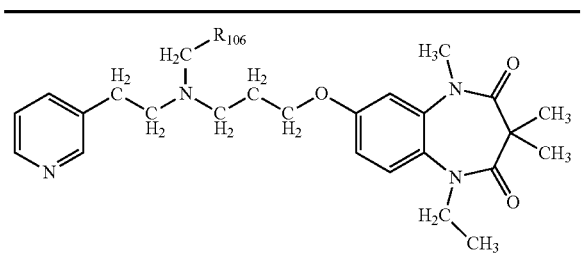

| Example | R106 | MS(M + 1) |
|---|---|---|
| 329 | 2,3-dimethyl-2H-indazole | 569 |
| 330 | 1,5-dimethyl-1H-indole | 568 |
| 331 | 1,5-dimethyl-3-phenyl-1H-pyrazole | 595 |
| 332 | 1,3-dimethyl-5-phenyl-1H-pyrazole | 595 |
| 333 | 7-methylfuro[2,3-c]pyridine | 556 |
| 334 | 4-methylthieno[3,2-c]pyridine | 572 |
| 335 | 1-methyl-5,6,7,8-tetrahydroisoquinoline | 570 |
| 336 | 1,3-dimethyl-1H-pyrazole | 519 |
| 337 | 2,3-dimethylthiophene | 549 |

TABLE 23
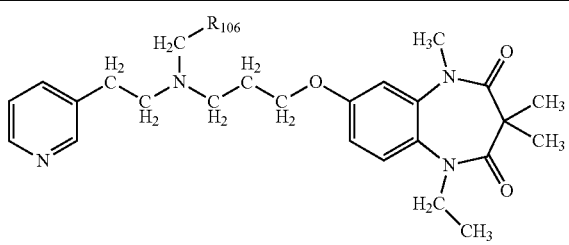
| Example | R106 | MS(M + 1) |
|---|---|---|
| 338 | 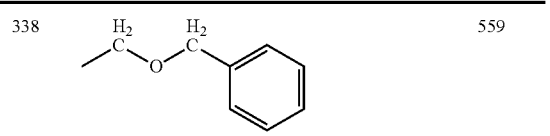 | 559 |
| 339 | 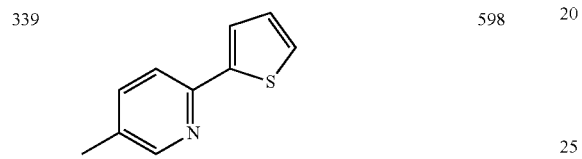 | 598 |
| 340 | 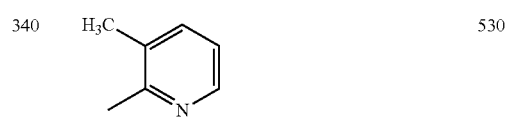 | 530 |
| 341 | 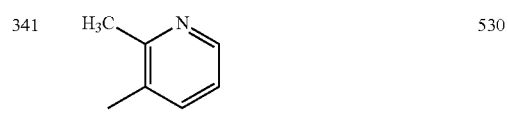 | 530 |
| 342 | 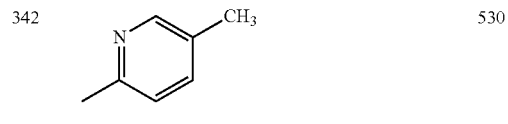 | 530 |
| 343 | 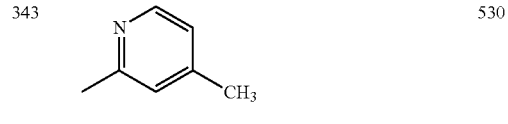 | 530 |
| 344 | 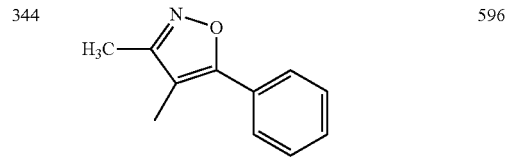 | 596 |
| 345 | 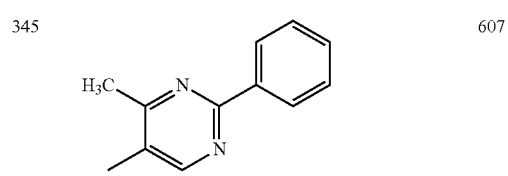 | 607 |
| 346 | 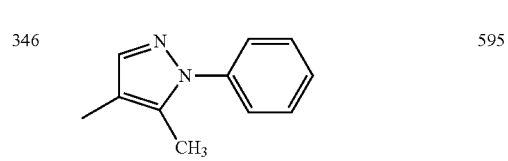 | 595 |
TABLE 24
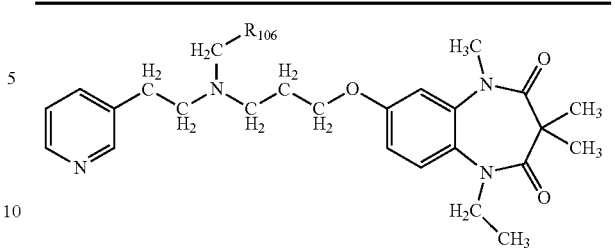
| Example | R106 | MS(M + 1) |
|---|---|---|
| 347 | 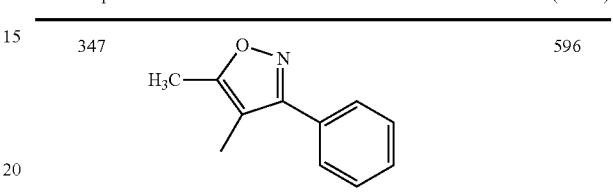 | 596 |
| 348 | 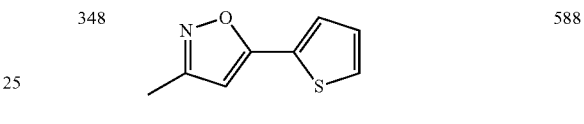 | 588 |
| 349 | 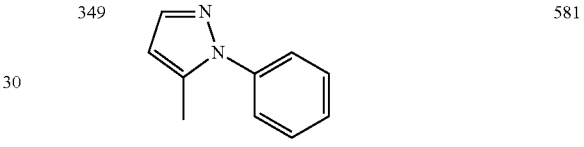 | 581 |
| 350 | 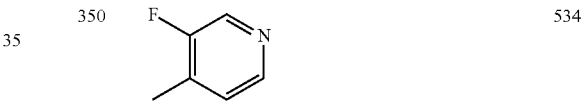 | 534 |
| 351 | 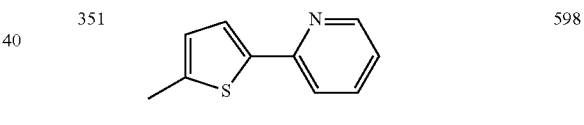 | 598 |
| 352 | 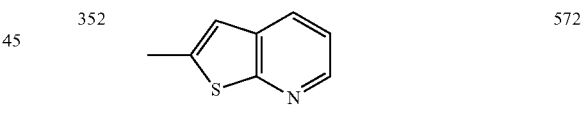 | 572 |
| 353 | 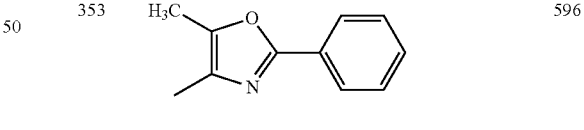 | 596 |
| 354 | 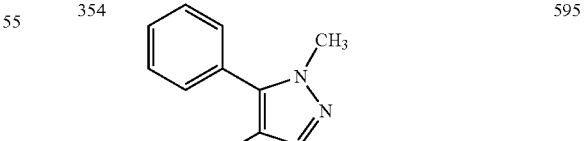 | 595 |
| 355 | 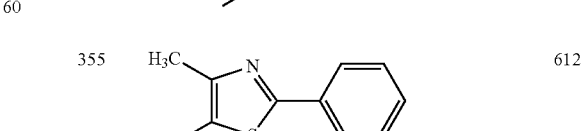 | 612 |

TABLE 25
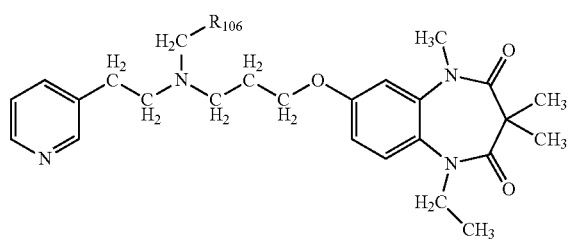
| Example | R106 | MS(M + 1) |
|---|---|---|
| 356 | 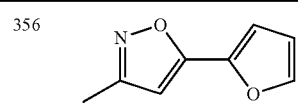 | 572 |
| 357 | 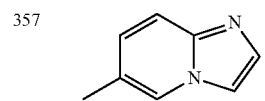 | 555 |
| 358 | 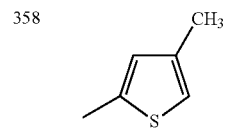 | 535 |
| 359 | 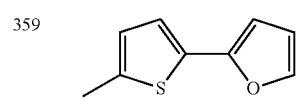 | 587 |
| 360 | 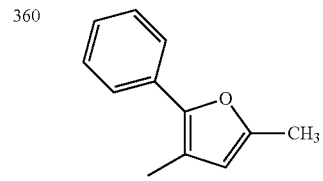 | 595 |
| 361 | 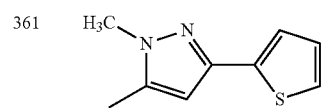 | 601 |
| 362 | 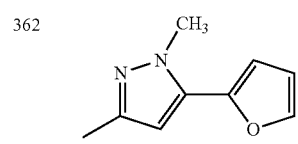 | 585 |
| 363 | 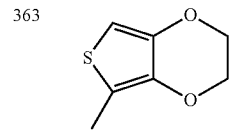 | 579 |
| 364 |  | 612 |
TABLE 26
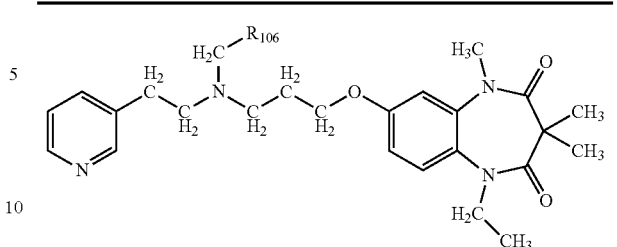
| Example | R106 | MS(M + 1) |
|---|---|---|
| 365 | 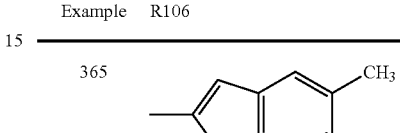 | 585 |
| 366 | 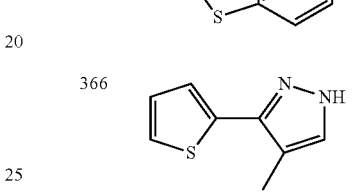 | 587 |
| 367 | 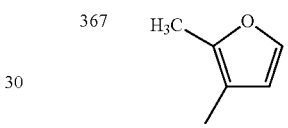 | 519 |
| 368 | 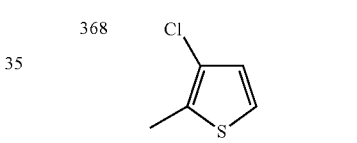 | 555 |
| 369 | 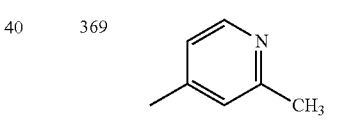 | 530 |
TABLE 27
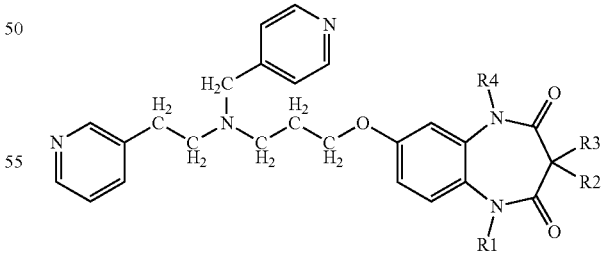
| Example | R1 | R2 | R3 | R4 | MS(M + 1) |
|---|---|---|---|---|---|
| 370 | —CH$_3$ | —H | —H | —CH$_3$ | 474 |
| 371 | —H | —H | —H | —H | 446 |

TABLE 28

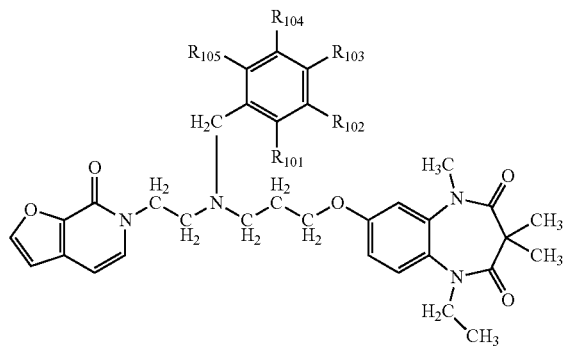

| Example | R101 | R102 | R103 | R104 | R105 | MS (M+1) |
|---|---|---|---|---|---|---|
| 372 | —H | —H | —H | —H | —H | 571 |
| 373 | —H | —H | —CO$_2$H | —H | —H | 615 |
| 374 | —H | —H | —C$_6$H$_5$ | —H | —H | 647 |
| 375 | —H | —H | —OCH$_3$ | —H | —H | 601 |
| 376 | —H | —H | —H | —OCH$_3$ | —H | 601 |
| 377 | —H | —H | —OH | —H | —H | 587 |
| 378 | —H | —H | —CH$_3$ | —H | —H | 585 |
| 379 | —H | —H | —CH(CH$_3$)$_2$ | —H | —H | 613 |
| 380 | —H | —H | —CN | —H | —H | 596 |
| 381 | —H | —H | —OC$_2$H$_5$ | —H | —H | 615 |
| 382 | —H | —H | —H | —OH | —H | 587 |
| 383 | —H | —H | —OH | —OH | —H | 603 |
| 384 | —H | —H | —H | —H | —CO$_2$H | 615 |
| 385 | —H | —H | —NHCOCH$_3$ | —H | —H | 628 |
| 386 | —H | —H | —O(CH$_2$)$_3$N(CH$_3$)$_2$ | —H | —H | 672 |
| 387 | —H | —H | —H | —H | —Cl | 605 |
| 388 | —H | —H | —H | —Cl | —H | 605 |
| 389 | —H | —H | —Cl | —H | —H | 605 |
| 390 | —H | —H | —H | —H | —F | 589 |
| 391 | —H | —H | —H | —H | —CN | 596 |
| 392 | —H | —H | —H | —H | —CF$_3$ | 639 |
| 393 | —H | —H | —H | —CF$_3$ | —H | 639 |
| 394 | —H | —H | —H | —CH$_3$ | —H | 585 |
| 395 | —H | —H | —CF$_3$ | —H | —H | 639 |
| 396 | —H | —H | —C$_2$H$_5$ | —H | —H | 599 |
| 397 | —H | —H | —F | —H | —H | 589 |
| 398 | —H | —H | —H | —H | —CH$_3$ | 585 |
| 399 | —H | —H | —CO$_2$CH$_3$ | —H | —H | 629 |

TABLE 29

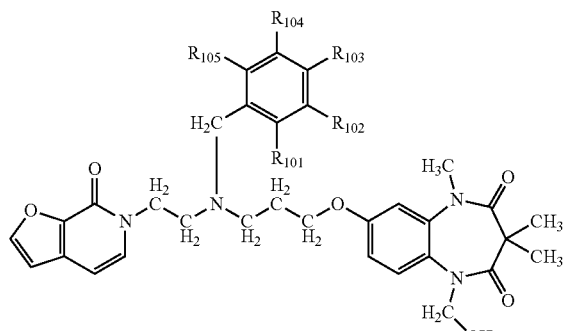

| Example | R101 | R102 | R103 | R104 | R105 | MS (M+1) |
|---|---|---|---|---|---|---|
| 400 | —H | —H | —H | —F | —H | 589 |
| 401 | —H | —H | —H | —CN | —H | 596 |
| 402 | —H | —H | —H | —H | —OCH$_3$ | 601 |
| 403 | —H | —H | —SCH$_3$ | —H | —H | 617 |

TABLE 29-continued

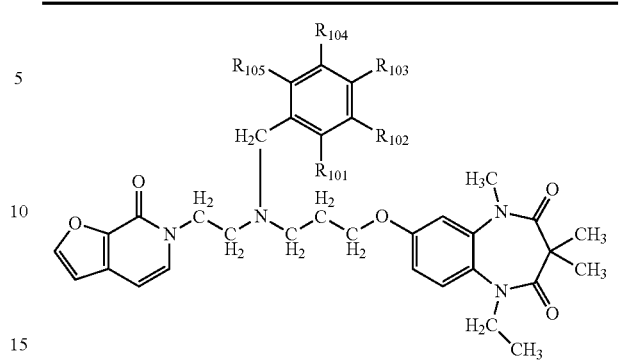

| Example | R101 | R102 | R103 | R104 | R105 | MS (M+1) |
|---|---|---|---|---|---|---|
| 404 | —H | —H | —H | —H | —CO$_2$CH$_3$ | 629 |
| 405 | —H | —H | —SO$_2$CH$_3$ | —H | —H | 649 |
| 406 | —H | —H | —OCH(CH$_3$)$_2$ | —H | —H | 629 |
| 407 | —H | —H | —H | —C$_6$H$_5$ | —H | 647 |
| 408 | —H | —H | —H | —H | —NHSO$_2$CH$_3$ | 664 |
| 409 | —H | —H | -1-IMIDAZOLYL | —H | —H | 637 |
| 410 | —H | —H | -2-THIENYL | —H | —H | 653 |
| 411 | —H | —H | ![1,2,4-triazol-1-yl] | —H | —H | 638 |
| 412 | —H | —H | ![piperidin-1-yl] | —H | —H | 654 |

TABLE 30

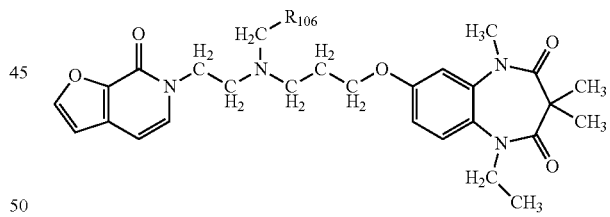

| Example | R106 | MS(M+1) |
|---|---|---|
| 413 | -3-FURYL | 561 |
| 414 | -2-IMIDAZOLYL | 561 |
| 415 | -2-PYRIDYL | 572 |
| 416 | -3-PYRIDYL | 572 |
| 417 | -2-THIENYL | 577 |
| 418 | -3-THIENYL | 577 |
| 419 | -2-BENZOFURANYL | 611 |
| 420 | -4-QUINOLYL | 622 |
| 421 | -2-QUINOLYL | 622 |
| 422 | —CH=CHC$_6$H$_5$(trans) | 597 |
| 423 | -2-THIAZOLYL | 578 |
| 424 | -4-IMIDAZOLYL | 561 |
| 425 | -1-NAPHTHYL | 621 |
| 426 | -2-FURYL | 561 |
| 427 | -2-NAPHTHYL | 621 |
| 428 | -5-BENZOFURANYL | 611 |

TABLE 31
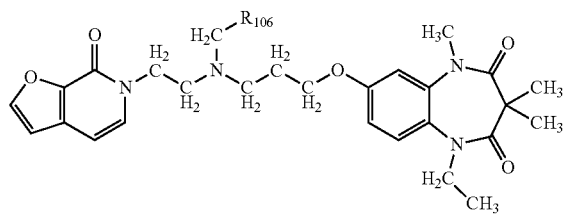
| Example | R106 | MS(M + 1) |
|---|---|---|
| 429 | 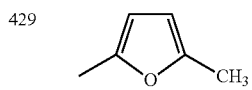 | 575 |
| 430 | 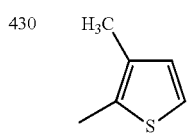 | 591 |
| 431 | 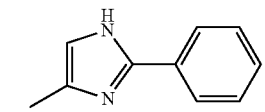 | 637 |
| 432 | 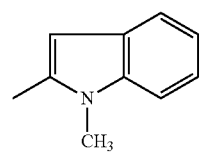 | 624 |
| 433 | 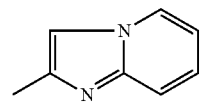 | 611 |
| 434 | 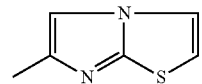 | 617 |
| 435 | 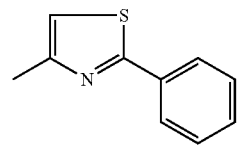 | 654 |
| 436 | 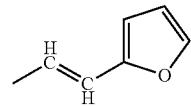 | 587 |
| 437 | 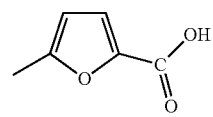 | 605 |
| 438 | 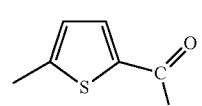 | 621 |
TABLE 32
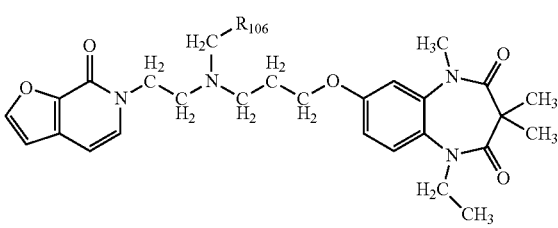
| Example | R106 | MS(M + 1) |
|---|---|---|
| 439 | 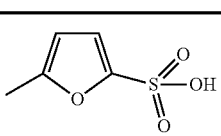 | 641 |
| 440 | 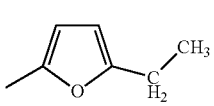 | 589 |
| 441 | 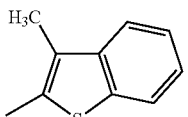 | 641 |
| 442 | 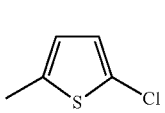 | 611 |
| 443 | 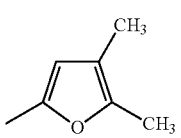 | 589 |
| 444 | 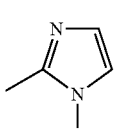 | 575 |
| 445 | 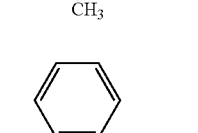 | 652 |
| 446 | 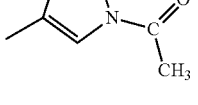 | 625 |
| 447 | 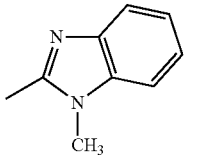 | 605 |

TABLE 33

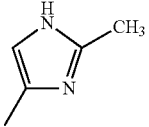

| Example | R106 | MS(M + 1) |
|---|---|---|
| 448 | 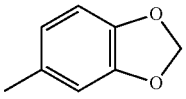 | 575 |
| 449 | 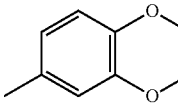 | 615 |
| 450 | 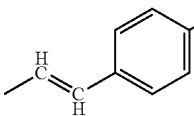 | 629 |
| 451 | 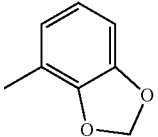 | 627 |
| 452 | 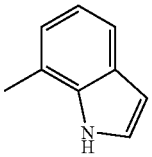 | 615 |
| 453 | 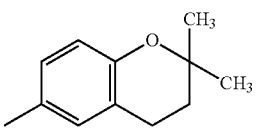 | 610 |
| 454 | 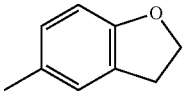 | 655 |
| 455 | 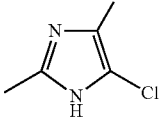 | 613 |
| 456 |  | 629 |

Using appropriate starting materials and following the procedures of Reference Examples 1 to 62, the following object compounds were synthesized.

Reference Example 63

(1-Oxo-1H-isoquinolin-2-yl)acetaldehyde $^1$H-NMR (CDCl$_3$) δppm:
4.78 (s, 2H), 6.59 (d, J=7.3 Hz, 1H), 7.00 (d, J=7.3 Hz, 1H), 7.52-7.59 (m, 2H), 7.68-7.73 (m, 1H), 8.44 (d, J=8.9 Hz, 1H), 9.76 (s, 1H).

Reference Example 64

(2-Oxo-2H-quinolin-1-yl)acetaldehyde $^1$H-NMR (CDCl$_3$) δppm:
5.15 (s, 2H), 6.76 (d, J=9.5 Hz, 1H), 7.05 (d, J=8.5 Hz, 1H), 7.24-7.29 (m, 1H), 7.54-7.60 (m, 1H), 7.61 (dd, J=7.7 and 1.5 Hz, 1H), 7.77 (d, J=9.5 Hz, 1H), 9.70 (s, 1H).

Reference Example 65

6-(2,2-Dihydroxyethyl)-6H-thieno[2,3-c]pyridin-7-one $^1$H-NMR (DMSO-d$_6$) δppm:
3.98 (d, J=5.3 Hz, 2H), 5.11-5.16 (m, 1H), 6.04 (d, J=6.4 Hz, 1H), 6.66 (d, J=7.1 Hz, 2H), 7.27 (d, J=5.2 Hz, 1H), 7.41 (d, J=7.1 Hz, 1H), 7.84 (d, J=5.2 H, 1H).

Reference Example 66

5-(2,2-Dihydroxyethyl)-5H-furo[3,2-c]pyridin-4-one $^1$H-NMR (DMSO-d$_6$) δppm:
3.88 (d, J=5.4 Hz, 2H), 4.95-5.03 (m, 1H), 6.08 (d, J=6.4 Hz, 2H), 6.69 (dd, J=7.4, 0.8 Hz, 1H), 6.94 (dd, J=2.1 and 0.8 Hz, 1H), 7.50 (d, J=7.4 Hz, 1H), 7.86 (d, J=2.1 Hz, 1H).

Reference Example 67

5-(2,2-Dihydroxyethyl)-5H-thieno[3,2-c]pyridin-4-one $^1$H-NMR (DMSO-d$_6$) δppm:
3.90 (d, J=6.3 Hz, 2H), 4.99-5.04 (m, 1H), 6.07 (d, J=6.3 Hz, 2H), 6.86 (d, J=7.2 Hz, 1H), 7.41-7.49 (m, 2H), 7.57-7.64 (m, 1H).

Reference Example 68

2-Bromo-5-(2,2-dihydroxyethyl)-5H-furo[3,2-c]pyridin-4-one $^1$H-NMR (DMSO-d$_6$) δppm:
3.86 (d, J=5.4 Hz, 2H), 4.95-5.03 (m, 1H), 6.07 (d, J=6.4 Hz, 2H), 6.69 (dd, J=7.4 and 0.8 Hz, 1H), 7.08 (d, J=0.8 Hz, 1H), 7.51 (d, J=7.4 Hz, 1H).

Reference Example 69

5-(2,2-Dihydroxyethyl)-2-methyl-5H-furo[3,2-c]pyridin-4-one $^1$H-NMR (DMSO-d$_6$) δppm:
2.36 (s, 3H), 3.86 (d, J=5.4 Hz, 2H), 4.94-4.98 (m, 1H), 6.04 (d, J=6.4 Hz, 2H), 6.52 (s, 1H), 6.59 (d, J=7.4 Hz, 1H), 7.41 (d, J=7.4 H, 1H).

Reference Example 70

5-(2,2-Dihydroxyethyl)-2-ethyl-5H-thieno[3,2-c]pyridin-4-one $^1$H-NMR (DMSO-d$_6$) δppm:
1.73 (t, J=7.5z, 3H), 3.31 (q, J=7.5 Hz, 2H), 4.32 (d, J=6.8 Hz, 2H), 5.40-5.51 (m, 1H), 6.53 (d, J=6.2 Hz, 2H), 7.22 (d, J=7.2 Hz, 1H), 7.65 (s, 1H), 7.82 (d, J=7.2 Hz, 1 Hz).

Reference Example 71

(7-Bromo-1-oxo-1H-isoquinolin-2-yl)acetaldehyde $^1$H-NMR (CDCl$_3$) δppm:
4.77 (s, 2H), 6.52 (d, J=7.4 Hz, 1H), 6.97 (d, J=7.4 Hz, 1H), 7.43 (d, J=8.5 Hz, 1H), 7.76 (dd, J=8.5 and 2.1 Hz, 1H), 8.55 (d, J=2.1 Hz, 1H), 9.73 (s, 1H).

Reference Example 72

(1-Oxo-5,6,7,8-tetrahydro-1H-isoquinolin-2-yl)acetaldehyde $^1$H-NMR (CDCl$_3$) δppm:
1.73-1.94 (4H, m), 2.64-2.81 (2H, m), 2.81-2.98 (2H, m), 5.04-5.17 (2H, m), 6.72-6.84 (1H, m), 7.08 (1H, d, J=6.5 Hz), 8.31 (1H, d, J=6.5 Hz).

Reference Example 73

2-Butylpyridine-3-carbaldehyde $^1$H-NMR (CDCl$_3$) δppm:
0.96 (3H, t, J=7.4 Hz), 1.41-1.48 (2H, m), 1.67-1.76 (2H, m), 3.21 (2H, t, J=8.0 Hz), 7.31 (1H, dd, J=7.8 and 4.8 Hz), 8.13 (1H, dd, J=7.8 and 1.9 Hz), 8.72 (1H, dd, J=4.8 and 1.9 Hz), 10.36 (1H, s).

Reference Example 74

1-(Ethoxycarbonyl)cyclobutanecarboxylic acid $^1$H-NMR (CDCl$_3$) δppm:
1.27 (t, J=7.1 Hz, 3H), 2.00-2.07 (m, 2H), 2.60 (t, J=8.2 Hz, 4H), 4.25 (q, J=7.1 Hz, 1H).

Reference Example 75

Ethyl 1-(2-aminophenylcarbamoyl)cyclobutanecarboxylate $^1$H-NMR (CDCl$_3$) δppm:
1.34 (t, J=7.1 Hz, 3H), 1.97-2.08 (m, 2H), 2.60-2.68 (m, 2H), 2.71-2.82 (m, 2H), 3.80 (br, 2H), 4.29 (q, J=7.1 Hz, 2H), 6.77-6.83 (m, 2H), 7.02-7.08 (m, 1H), 7.95 (br, 1H).

Reference Example 76

Spiro[benzo[b][1,4]diazepine-3,1'-cyclobutane]-2,4(1H,5H)-dione $^1$H-NMR (DMSO-d$_6$) δppm:
1.59-1.70 (m, 2H), 3.29-3.44 (m, 4H), 7.07-7.14 (m, 4H), 10.4 (br, 2H).

Reference Example 77

1,5-Dimethylspiro[benzo[b][1,4]diazepine-3,1'-cyclobutane]-2,4(1H,5H)-dione $^1$H-NMR (CDCl$_3$) δppm:
1.26-1.68 (m, 4H), 2.83-2.89 (m, 2H), 3.44 (s, 6H), 7.23-7.30 (m, 4H).

Reference Example 78

1,5-Dimethyl-7-(4,4,5,5-tetramethyl-1,3,2-dioxaborolan-2-yl)spiro[benzo[b][1,4]diazepine-3,1'-cyclobutane]-2,4(1H,5H)-dione $^1$H-NMR (CDCl$_3$) δppm: 1.26 (s, 6H), 1.60 (s, 6H), 1.62-1.69 (m, 4H), 2.06-2.89 (m, 2H), 3.45 (s, 3H), 3.48 (s, 3H), 7.26-7.28 (m, 1H), 7.65-7.70 (m, 2H).

Reference Example 79

7-Hydroxy-1,5-dimethylspiro[benzo[b][1,4]diazepine-3,1'-cyclobutane]-2,4(1H,5H)-dione $^1$H-NMR (CDCl$_3$) δppm:
1.58-1.62 (m, 4H), 2.83-2.88 (m, 2H), 3.41 (s, 3H), 3.44 (s, 3H), 7.14 (d, J=8.7 Hz, 1H), 7.36 (dd, J=8.7 and 2.1 Hz, 1H), 7.41 (d, J=2.1 Hz, 1H).

Example 457

Synthesis of 1-ethyl-3,3,5-trimethyl-7-{3-[(pyridin-4-ylmethyl)amino]propoxy}-1,5-dihydrobenzo[b][1,4]diazepine-2,4-dione sulfate Sulfuric acid (13 μl) was added to an ethyl acetate solution (5 ml) of 1-ethyl-3,3,5-trimethyl-7-{3-[(pyridin-4-ylmethyl)amino]propoxy}-1,5-dihydrobenzo[b][1,4]diazepine-2,4-dione (100 mg, 0.24 mmol), and stirred at room temperature for 15 minutes. The resultant mixture was concentrated to dryness under reduced pressure to thereby obtain 1-ethyl-3,3,5-trimethyl-7-{3-[(pyridin-4-ylmethyl)amino]propoxy}-1,5-dihydrobenzo[b][1,4]diazepine-2,4-dione sulfate as a white amorphous solid.

$^1$H-NMR (DMSO-d$_6$) δppm:
0.74 (s, 3H), 0.99 (t, J=7.0 Hz, 3H), 1.31 (s, 3H), 2.14-2.18 (m, 2H), 3.14-3.18 (m, 2H), 3.31 (s, 3H), 3.61-3.69 (m, 1H), 4.00-4.09 (m, 1H), 4.10-4.14 (m, 2H), 4.27 (s, 2H). 6.94-6.95 (m, 2H), 7.40 (d, J=9.0 Hz, 1H), 7.55-7.57 (m, 2H), 8.62-8.64 (m, 2H).

Example 458

Synthesis of 1,3,3,5-tetramethyl-7-(3-{[2-(1-oxo-3,4-dihydro-1H-isoquinolin-2-yl)ethyl]pyridin-4-ylmethylamino}-propoxy)-1,5-dihydrobenzo[b][1,4]diazepine-2,4-dione tris phosphate 85% phosphoric acid aqueous solution (0.34 ml) was added to an ethanol solution (19 ml) of 1,3,3,5-Tetramethyl-7-(3-{[2-(1-oxo-3,4-dihydro-1H-isoquinolin-2-yl)ethyl]pyridin-4-ylmethylamino}-propoxy)-1,5-dihydro-benzo[b][1,4]diazepine-2,4-dione (1.05 g, 1.84 mmol), and stirred at 50° C. for 15 minutes. The reaction mixture was cooled to room temperature. The precipitated insoluble matter was collected by filtration, washed with ethanol, and dried to thereby obtain 1.59 g (yield: 73%) of 1,3,3,5-Tetramethyl-7-(3-{[2-(1-oxo- 3,4-dihydro-1H-isoquinolin-2-yl)ethyl]pyridin-4-ylmethylamino}-propoxy)-1,5-dihydro-benzo[b][1,4]diazepine-2,4-dione tris(phosphate) as a white solid.

¹H-NMR (DMSO-d₆) δppm:
0.75 (3H, s), 1.32 (3H, s), 1.78-1.98 (2H, m), 2.55-2.77 (4H, m), 2.81-2.98 (2H, m), 3.28 (3H, s), 3.29 (3H, s), 3.51 (2H, t, 6.6 Hz), 3.62 (2H, m), 3.68 (s, 2H), 3.99 (2H, t, J=6.0 Hz), 6.75 (2H, dd, J=2.6 and 9.0 Hz), 6.82 (2H, d, 2.6 Hz), 7.21-7.38 (5H, m), 7.41-7.51 (1H, m), 8.34 (2H, d, J=5.8 Hz)

Example 459

Synthesis of N-[3-(1-ethyl-3,3,5-trimethyl-2,4-dioxo-2,3,4,5-tetrahydro-1H-benzo[b][1,4]diazepin-7-yloxy)propyl]-N-(2-pyridin-3-ylethyl)isonicotinamide N-(3-Dimethylaminopropyl)-N'-ethylcarbodiimide hydrochloride (WSC) (0.16 g, 0.85 mmol) was added to an acetonitrile solution (6 ml) of 1-ethyl-3,3,5-trimethyl-7-[3-(2-pyridin-3-ylethylamino)propoxy]-1,5-dihydrobenzo[b][1,4]diazepine-2,4-dione (0.3 g, 0.71 mmol), isonicotinic acid (96 mg, 0.78 mmol), and 1-hydroxybenzotriazole (HOBT) (0.138 g, 0.85 mmol), and then stirred at room temperature for 2 days. The solvent was concentrated under reduced pressure. Ethyl acetate and a sodium hydrogen carbonate aqueous solution were added to the reaction mixture, and stirred for 1 hour. Water was added to the reaction mixture, and extraction with ethyl acetate was conducted. The organic layer was dried over anhydrous sodium sulfate and concentrated under reduced pressure. The residue thus obtained was purified by medium pressure liquid chromatography (silica gel, dichloromethane:methanol=92:8). The purified product was concentrated under reduced pressure and crystallized from ethyl acetate, diethylether and n-hexane. The precipitated crystals were collected by filtration and dried to thereby obtain 0.21 g (yield: 56%) of N-[3-(1-ethyl-3,3,5-trimethyl-2,4-dioxo-2,3,4,5-tetrahydro-1H-benzo[b][1,4]diazepin-7-yloxy)propyl]-N-(2-pyridin-3-ylethyl)isonicotinamide as a white powder.

Melting Point 88.1 to 92.2° C.

Example 460

Synthesis of 1-ethyl-3,3,5-trimethyl-7-(3-{[2-(4-oxo-4H-thieno[3,2-c]pyridin-5-yl)ethyl]pyridin-4-ylmethylamino}-propoxy)-1,5-dihydrobenzo[b][1,4]diazepine-2,4-dione Using an appropriate starting material and following the procedure of Example 7, the object compound was synthesized.

¹H-NMR (CDCl₃) δppm:
0.88 (s, 3H), 1.17 (t, J=7.1 Hz, 3H), 1.54 (s, 3H), 1.89-1.97 (m, 2H), 2.74 (t, J=6.8 Hz, 2H), 2.83-2.95 (m, 2H), 3.39 (s, 3H), 3.69 (s, 2H), 3.68-3.74 (m, 1H), 3.89 (t, J=6.0 Hz, 2H), 4.12 (t, J=6.0 Hz, 2H), 4.11-4.21 (m, 1H), 6.53-6.70 (m, 3H), 7.05 (d, J=7.2 Hz, 1H), 7.10 (d, J=5.9 Hz, 2H), 7.20 (d, J=8.9 Hz, 1H), 7.32 (d, J=5.3 Hz, 1H), 7.63 (d, J=5.3 Hz, 1H), 8.32 (d, J=5.9 Hz, 2H).

Example 461

Synthesis of 1-ethyl-3,3,5-trimethyl-7-(3-{[2-(7-oxo-7H-thieno[2,3-c]pyridin-6-yl)ethyl]pyridin-4-ylmethylamino}-propoxy)-1,5-dihydrobenzo[b][1,4]diazepine-2,4-dione Using an appropriate starting material and following the procedure of Example 7, the object compound was synthesized.

¹H-NMR (CDCl₃) δppm:
0.88 (s, 3H), 1.17 (t, J=7.1 Hz, 3H), 1.54 (s, 3H), 1.89-1.97 (m, 2H), 2.74 (t, J=6.8 Hz, 2H), 2.83-2.95 (m, 2H), 3.39 (s, 3H), 3.68-3.74 (m, 3H), 3.90 (t, J=6.0 Hz, 2H), 4.05-4.21 (m, 3H), 6.56 (d, J=7.1 Hz, 1H), 6.60-6.70 (m, 2H), 7.03-7.10 (m, 3H), 7.16-7.23 (m, 2H), 7.73 (d, J=5.2 Hz, 1H), 8.31 (d, J=5.9 Hz, 2H).

Example 462

Synthesis of 1-ethyl-3,3,5-trimethyl-7-(3-{[2-(4-oxo-4H-furo[3,2-c]pyridin-5-yl)ethyl]pyridin-4-ylmethylamino}propoxy)-1,5-dihydrobenzo[b][1,4]diazepine-2,4-dione Using an appropriate starting material and following the procedure of Example 7, the object compound was synthesized.

White Powder
Melting Point 93.8° C.
¹H-NMR (CDCl₃) δppm:
0.87 (s, 3H), 1.16 (t, J=7.1 Hz, 3H), 1.53 (s, 3H), 1.82-1.95 (m, 2H), 2.72 (t, J=6.8 Hz, 2H), 2.76-2.89 (m, 2H), 3.38 (s, 3H), 3.68 (s, 2H), 3.63-3.78 (m, 1H), 3.87 (t, J=6.0 Hz, 2H), 4.10 (t, J=6.0 Hz, 2H), 4.11-4.20 (m, 1H), 6.43 (d, J=7.4 Hz, 1H), 6.60 (d, J=2.8 Hz, 1H), 6.67 (dd, J=9.0 and 2.8 Hz, 1H), 6.96 (d, J=2.9 Hz, 1H), 7.05-7.11 (m, 3H), 7.19 (d, J=9.0 Hz, 1H), 7.50 (d, J=2.9 Hz, 1H), 8.35 (d, J=6.0 Hz, 2H).

Example 463

Synthesis of 7-(3-{[2-(2-bromo-4-oxo-4H-furo[3,2-c]pyridine-5-yl)ethyl]pyridin-4-ylmethylamino}propoxy)-1-ethyl-3,3,5-trimethyl-1,5-dihydrobenzo[b][1,4]diazepine-2,4-dione dihydrochloride Using an appropriate starting material and following the procedure of Example 7 and Example 6, the object compound was synthesized.

Amorphous
¹H-NMR (DMSO-d₆) δppm:
0.75 (s, 3H), 1.01 (t, J=7.1 Hz, 3H), 1.32 (s, 3H), 2.15 (br, 2H), 2.95-3.40 (m, 2H), 3.32 (s, 3H), 3.61-3.73 (m, 3H), 4.01-4.09 (m, 3H), 4.34 (br, 4H), 6.81 (br, 2H), 6.88 (br, 1H), 7.10 (s, 1H), 7.39 (d, J=9.0 Hz, 1H), 7.74 (br, 1H), 8.13 (br, 2H), 8.86 (br, 2H).

Example 464

Synthesis of 1-ethyl-3,3,5-trimethyl-7-(3-{[2-(2-methyl-4-oxo-4H-furo[3,2-c]pyridin-5-yl)ethyl]pyridin-4-ylmethylamino}propoxy)-1,5-dihydrobenzo[b][1,4]diazepine-2,4-dione dihydrochloride Using an appropriate starting material and following the procedure of Example 6, the object compound was synthesized.

Amorphous
¹H-NMR (DMSO-d₆) δppm:
0.75 (s, 3H), 1.01 (t, J=7.1 Hz, 3H), 1.32 (s, 3H), 2.00-2.22 (m, 2H), 2.22 (s, 3H), 3.11-3.39 (m, 7H), 3.60-3.71 (m, 1H), 4.02-4.07 (m, 3H), 4.30-4.45 (m, 2H), 4.51-4.71 (m, 2H), 6.55 (s, 1H), 6.72 (d, J=7.3 Hz, 1H), 6.84-6.90 (m, 2H), 7.40 (d, J=9.0 Hz, 1H), 7.64 (d, J=7.3 Hz, 1H), 8.21 (br, 2H), 8.89 (br, 2H).

Example 465

Synthesis of 1-ethyl-3,3,5-trimethyl-7-(3-{[2-(2-methyl-4-oxo-4H-furo[3,2-c]pyridin-5-yl)ethyl]pyridin-4-ylmethylamino}propoxy)-1,5-dihydrobenzo[b][1,4]diazepine-2,4-dione Using an appropriate starting material and following the procedure of Example 7, the object compound was synthesized.
$^1$H-NMR (CDCl$_3$) δppm:
0.87 (s, 3H), 1.16 (t, J=7.1 Hz, 3H), 1.53 (s, 3H), 1.83-1.96 (m, 2H), 2.42 (s, 3H), 2.72 (t, J=6.2 Hz, 2H), 2.85 (t, J=6.0 Hz, 2H), 3.39 (s, 3H), 3.68 (s, 2H), 3.66-3.79 (m, 1H), 3.89 (t, J=6.1 Hz, 2H), 4.08-4.23 (m, 3H), 6.37 (d, J=7.3 Hz, 1H), 6.49-6.54 (m, 1H), 6.63-6.69 (m, 2H), 7.01 (d, J=7.3 Hz, 1H), 7.08-7.12 (m, 2H), 7.19 (d, J=8.3 Hz, 1H), 8.35-8.37 (m, 2H).

Example 466

Synthesis of 1-ethyl-7-(3-{[2-(2-ethyl-4-oxo-4H-thieno[3,2-c]pyridin-5-yl)-ethyl]-pyridin-4-ylmethylamino}-propoxy)-3,3,5-trimethyl-1,5-dihydrobenzo[b][1,4]diazepine-2,4-dione dihydrochloride Using an appropriate starting material and following the procedure of Example 7 and Example 6, the object compound was synthesized.
Amorphous
$^1$H-NMR (DMSO-d$_6$) δppm:
0.75 (s, 3H), 1.01 (t, J=7.0 Hz, 3H), 1.28 (t, J=7.5 Hz, 3H), 1.32 (s, 3H), 2.09 (br, 2H), 2.87 (q, J=7.5 Hz, 2H), 3.10-3.21 (m, 2H), 3.30 (s, 3H), 3.51-3.69 (m, 3H), 3.90-4.09 (m, 5H), 4.30 (br, 2H), 6.71-6.88 (m, 3H), 7.18-7.20 (m, 1H), 7.36-7.43 (m, 1H), 7.52 (br, 1H), 7.86 (br, 2H), 8.69 (br, 2H).

Example 467

Synthesis of 7-(3-{[2-(2,3-dimethyl-4-oxo-4H-furo[3,2-c]pyridin-5-yl)ethyl]pyridin-4-ylmethylamino}propoxy)-1-ethyl-3,3,5-trimethyl-1,5-dihydrobenzo[b][1,4]diazepine-2,4-dione dihydrochloride Using an appropriate starting material and following the procedure of Example 7 and Example 6, the object compound was synthesized.
Pale Yellow Amorphous
$^1$H-NMR (DMSO-d$_6$) δppm:
0.74 (s, 3H), 1.01 (t, J=7.0 Hz, 3H), 1.32 (s, 3H), 2.05-2.20 (m, 2H), 2.17 (s, 3H), 2.29 (s, 3H), 3.05-3.20 (m, 2H), 3.31 (s, 3H), 3.61-3.73 (m, 3H), 3.95-4.05 (m, 3H), 4.31 (br, 4H), 6.63 (br, 1H), 6.81-6.88 (m, 2H), 7.39 (d, J=9.0 Hz, 1H), 7.56 (d, J=7.3 Hz, 1H), 8.04 (br, 2H), 8.79 (br, 2H).

Example 468

Synthesis of 1-ethyl-7-(3-{[2-(2-furan-3-yl-4-oxo-4H-furo[3,2-c]pyridin-5-yl)ethyl]pyridin-4-ylmethylamino}propoxy)-3,3,5-trimethyl-1,5-dihydrobenzo[b][1,4]diazepine-2,4-dione dihydrochloride A 2N-Sodium carbonate aqueous solution (0.3 ml) and tetrakis(triphenylphosphine)palladium(0) (37.2 mg, 0.03 mmol) were added to a dimethoxyethane solution (2 ml) of 7-(3-{[2-(2-bromo-4-oxo-4H-furo[3,2-c]pyridin-5-yl)ethyl]pyridin-4-ylmethylamino}propoxy)-1-ethyl-3,3,5-trimethyl-1,5-dihydrobenzo[b][1,4]diazepine-2,4-dione (0.20 g, 0.31 mmol) and furan-3-boronic acid (39.2 mg, 0.035 mmol), and stirred under argon atmosphere at 80° C. for 6.5 hours. The reaction mixture was cooled to room temperature, and purified by silica gel column chromatography (ethyl acetate:methanol=100:0→93:7). The purified product was concentrated under reduced pressure and the resultant residue was dissolved in ethyl acetate (10 ml). A 4N—HCl ethyl acetate solution (0.5 ml) was added to the solution, and concentrated to dryness under reduced pressure to thereby obtain 0.10 g (yield: 51%) of 1-ethyl-7-(3-{[2-(2-furan-3-yl-4-oxo-4H-furo[3,2-c]pyridin-5-yl)ethyl]pyridin-4-ylmethylamino}propoxy)-3,3,5-trimethyl-1,5-dihydrobenzo[b][1,4]diazepine-2,4-dione dihydrochloride as a pale yellow amorphous solid.
$^1$H-NMR (DMSO-d$_6$) δppm:
0.73 (s, 3H), 1.00 (t, J=7.0 Hz, 3H), 1.32 (s, 3H), 2.09 (br, 2H), 3.21-3.40 (m, 2H), 3.29 (s, 3H), 3.51-3.64 (m, 3H), 3.81-4.01 (m, 5H), 4.30 (br, 2H), 6.78 (br, 2H), 6.84 (br, 1H), 6.98 (d, J=0.74 Hz, 1H), 7.16 (s, 1H), 7.33 (d, J=8.5 Hz, 1H), 7.69 (d, J=5.9 Hz, 1H), 7.82 (s, 1H), 7.93 (br, 2H), 8.19 (s, 1H), 8.74 (br, 2H).

Example 469

Synthesis of 1-ethyl-3,3,5-trimethyl-7-(3-{[2-(4-oxo-2-pyridin-3-yl-4H-furo[3,2-c]pyridin-5-yl)ethyl]pyridin-4-ylmethylamino}-propoxy)-1,5-dihydrobenzo[b][1,4]diazepine-2,4-dione trihydrochloride Using an appropriate starting material and following the procedure of Example 468, the object compound was synthesized.
Pale Yellow Amorphous
$^1$H-NMR (DMSO-d$_6$) δppm:
0.73 (s, 3H), 0.99 (t, J=7.0 Hz, 3H), 1.31 (s, 3H), 2.13 (br, 2H), 3.10-3.30 (m, 2H), 3.30 (s, 3H), 3.70-3.85 (m, 1H), 3.92-4.03 (m, 5H), 4.38 (br, 4H), 6.80-6.87 (m, 3H), 7.35 (d, J=9.0 Hz, 1H), 7.79-7.84 (m, 3H), 8.07 (br, 2H), 8.55 (d, J=8.0 Hz, 1H), 8.72 (dd, J=1.3, 5.2 Hz, 1H), 8.82 (br, 2H), 9.23 (d, J=1.8 Hz, 1H).

Example 470

Synthesis of 1-ethyl-3,3,5-trimethyl-7-(3-{[2-(4-oxo-2-pyridin-4-yl-4H-furo[3,2-c]pyridin-5-yl)ethyl]pyridin-4-ylmethylamino}propoxy)-1,5-dihydrobenzo[b][1,4]diazepine-2,4-dione trihydrochloride Using an appropriate starting material and following the procedure of Example 468, the object compound was synthesized.
Yellow Powder
$^1$H-NMR (DMSO-d$_6$) δppm:
0.74 (s, 3H), 0.99 (t, J=7.0 Hz, 3H), 1.31 (s, 3H), 2.11 (br, 2H), 3.12-3.30 (m, 2H), 3.29 (s, 3H), 3.55-3.69 (m, 1H), 3.91-4.08 (m, 5H), 4.36 (br, 4H), 6.77-6.90 (m, 3H), 7.35 (d, J=8.9 Hz, 1H), 7.93 (br, 3H), 8.30 (br, 3H), 8.76 (br, 2H), 8.91 (d, J=5.6 Hz, 2H).

Example 471

Synthesis of 7-[3-({2-[2-(3-amino-henyl)-4-oxo-4H-furo[3,2-c]pyridin-5-yl]ethyl}pyridin-4-ylmethylamino)propoxy]-1-ethyl-3,3,5-trimethyl-1,5-dihydrobenzo[b][1,4]diazepine-2,4-dione trihydrochloride Using an appropriate starting material and following the procedure of Example 468, the object compound was synthesized.
$^1$H-NMR (DMSO-d$_6$) δppm:
0.73 (s, 3H), 0.99 (t, J=7.0 Hz, 3H), 1.31 (s, 3H), 2.10 (br, 2H), 3.02-3.20 (m, 2H), 3.30 (s, 3H), 3.55-3.70 (m, 1H), 3.95-4.03 (m, 5H), 4.39 (br, 4H), 6.78-6.88 (m, 3H), 7.15-7.80 (m, 2H), 7.53 (br, 2H), 7.62-7.81 (m, 3H), 8.06 (br, 2H), 8.82 (br, 2H).

Example 472

Synthesis of 1-ethyl-3,3,5-trimethyl-7-(3-{[2-(7-oxo-7H-furo[2,3-c]pyridin-6-yl)ethyl]pyridin-3-ylmethylamino}-propoxy)-1,5-dihydrobenzo[b][1,4]diazepine-2,4-dione Using an appropriate starting material and following the procedure of Example 7, the object compound was synthesized.
White Powder
Melting Point 125° C.

Example 473

Synthesis of 1-ethyl-3,3,5-trimethyl-7-(3-{[2-(7-oxo-7H-furo[2,3-c]pyridin-6-yl)ethyl]quinolin-4-ylmethylamino}-propoxy)-1,5-dihydrobenzo[b][1,4]diazepine-2,4-dione dihydrochloride Using an appropriate starting material and following the procedure of Example 7 and Example 6, the object compound was synthesized.
White Powder
$^1$H-NMR (DMSO-D$_6$) δppm:
0.74 (3H, s), 1.01 (3H, t, J=7.0 Hz), 1.32 (3H, s), 2.00-2.28 (2H, m), 2.70-5.31 (15H, m), 6.45-6.59 (1H, m), 6.76-6.80 (1H, m), 6.83-6.87 (2H, m), 7.37 (1H, d, J=9.0 Hz) 7.42-7.58 (1H, m), 7.72-7.88 (1H, m), 7.95-8.19 (3H, m), 8.31 (1H, d, J=8.6 Hz), 8.43-8.50 (1H, m), 9.03-9.19 (1H, m)

Example 474

Synthesis of 1-ethyl-7-(3-{(3-hydroxybenzyl)-[2-(7-oxo-7H-furo[2,3-c]pyridin-6-yl)ethyl]amino}propoxy)-3,3,5-trimethyl-1,5-dihydrobenzo[b][1,4]diazepine-2,4-dione hydrochloride Using an appropriate starting material and following the procedure of Example 7 and Example 6, the object compound was synthesized.
White Powder
$^1$H-NMR (DMSO-D$_6$) δppm:
0.75 (3H, s), 1.01 (3H, t, J=7.0 Hz), 1.32 (3H, s), 2.12-2.27 (2H, m), 3.20-3.44 (7H, m) 3.45-3.43 (2H, m), 3.63-3.70 (1H, m), 3.99-4.09 (3H, m), 4.35-4.37 (1H, m), 4.43-4.53 (1H, m) 6.68-6.71 (1H, m), 6.84-6.93 (4H, m), 6.99-7.10 (2H, m), 7.20-7.26 (1H, m), 7.40 (1H, d, J=7.7 Hz), 7.54-7.58 (1H, m), 8.17 (1H, s), 9.72-9.80 (1H, m)

Example 475

Synthesis of 1-ethyl-3,3,5-trimethyl-7-(3-{[2-(7-oxo-7H-furo[2,3-c]pyridin-6-yl)ethyl]thiazol-2-ylmethylamino}-propoxy)-1,5-dihydrobenzo[b][1,4]diazepine-2,4-dione dihydrochloride Using an appropriate starting material and following the procedure of Example 7 and Example 6, the object compound was synthesized.
White Powder
$^1$H-NMR (DMSO-D$_6$) δppm:
0.75 (3H, s), 1.00 (3H, t, J=7.1 Hz), 1.32 (3H, s), 2.05-2.28 (2H, m), 3.10-3.84 (8H, m), 3.99-4.09 (3H, m), 4.40-4.50 (2H, m), 4.72-4.88 (2H, m), 6.64-6.67 (1H, m), 6.84-6.92 (3H, m), 7.39 (1H, d, J=9.0 Hz) 7.52-7.59 (1H, m), 7.65-7.91 (2H, m), 8.14 (1H, d, J=1.9 Hz)

Example 476

Synthesis of 1-ethyl-3,3,5-trimethyl-7-(3-{[2-(4-oxo-2-phenyl-4H-furo[3,2-c]pyridin-5-yl)ethyl]pyridin-4-ylmethylamino}propoxy)-1,5-dihydrobenzo[b][1,4]diazepine-2,4-dione dihydrochloride Using an appropriate starting material and following the procedure of Example 468, the object compound was synthesized.
Amorphous
$^1$H-NMR (DMSO-d$_6$) δppm:
0.72 (s, 3H), 0.99 (t, J=7.0 Hz, 3H), 1.31 (s, 3H), 2.09 (br, 2H), 3.11-3.30 (m, 2H), 3.29 (s, 3H), 3.61-3.72 (m, 1H), 3.60-4.04 (m, 5H), 4.38 (br, 4H), 6.71-6.88 (m, 3H), 7.32 (d, J=8.6 Hz, 1H), 7.37-7.41 (m, 1H), 7.46-7.51 (m, 3H), 7.74 (br, 1H), 7.86 (d, J=7.4 Hz, 2H), 8.03 (br, 2H), 8.81 (br, 2H).

Example 477

Synthesis of 1-ethyl-7-[3-({2-[2-(4-methoxyphenyl)-4-oxo-4H-furo[3,2-c]pyridin-5-yl]ethyl}pyridin-4-ylmethylamino)-propoxy]-3,3,5-trimethyl-1,5-dihydrobenzo[b][1,4]diazepine-2,4-dione dihydrochloride Using an appropriate starting material and following the procedure of Example 468, the object compound was synthesized.
Amorphous
$^1$H-NMR (DMSO-d$_6$) δppm:
0.71 (s, 3H), 0.98 (t, J=7.0 Hz, 3H), 1.31 (s, 3H), 2.00 (br, 2H), 3.28 (s, 3H), 3.20-3.38 (m, 2H), 3.50-3.70 (m, 1H), 3.82 (s, 3H), 3.90-4.02 (m, 5H), 4.40 (br, 4H), 6.82 (br, 3H), 7.05 (d, J=8.8 Hz, 2H), 7.30 (br, 2H), 7.66 (br, 1H), 7.79 (d, J=8.8 Hz, 2H), 7.92 (br, 2H), 8.68 (br, 2H).

Example 478

Synthesis of 1-ethyl-3,3,5-trimethyl-7-[3-(pyridin-4-ylmethylpyridin-2-ylmethylamino)propoxy]-1,5-dihydrobenzo[b][1,4]diazepine-2,4-dione Using an appropriate starting material and following the procedure of Example 7, the object compound was synthesized.

Colorless Oil

¹H-NMR (CDCl₃) δppm:

0.86 (s, 3H), 1.15 (t, J=7.1 Hz, 3H), 1.53 (s, 3H), 1.91-2.08 (m, 2H), 2.66 (t, J=6.9 Hz, 2H), 3.39 (s, 3H), 3.61 (s, 2H), 3.63 (s, 2H), 3.61-3.78 (m, 1H), 3.97 (t, J=6.1 Hz, 2H), 4.03-4.20 (m, 1H), 6.60 (d, J=2.7 Hz, 1H), 6.70 (dd, J=2.7 and 9.0 Hz, 1H), 7.16-7.26 (m, 4H), 7.64-7.68 (m, 1H), 8.46-8.52 (m, 3H), 8.60 (br, 1H).

Example 479

Synthesis of 1-ethyl-3,3,5-trimethyl-7-[3-(pyridin-4-ylmethylpyridin-2-ylmethylamino)propoxy]-1,5-dihydrobenzo[b][1,4]diazepine-2,4-dione trihydrochloride Using an appropriate starting material and following the procedure of Example 6, the object compound was synthesized.

White Solid

¹H-NMR (DMSO-d₆) δppm:

0.76 (s, 3H), 1.05 (t, J=7.0 Hz, 3H), 1.33 (s, 3H), 2.09 (br, 2H), 2.75 (br, 2H), 3.31 (s, 3H), 3.61-3.73 (m, 1H), 4.03-4.30 (m, 5H), 4.53 (br, 2H), 6.81-6.82 (m, 2H), 7.34-7.37 (m, 1H), 7.94 (br, 1H), 8.15 (br, 2H), 8.64 (br, 1H), 8.80-8.87 (m, 3H), 9.01 (Br, 1H).

Example 480

Synthesis of 1-ethyl-3,3,5-trimethyl-7-[3-(pyridin-4-ylmethylpyridin-3-ylmethylamino)propoxy]-1,5-dihydrobenzo[b][1,4]diazepine-2,4-dione Using an appropriate starting material and following the procedure of Example 7, the object compound was synthesized.

Colorless Oil

¹H-NMR (CDCl₃) δppm:

0.86 (s, 3H), 1.15 (t, J=7.1 Hz, 3H), 1.53 (s, 3H), 1.91-2.04 (m, 2H), 2.71 (t, J=6.9 Hz, 2H), 3.38 (s, 3H), 3.67 (s, 2H), 3.61-3.72 (m, 1H), 3.80 (s, 2H), 3.99 (t, J=6.1 Hz, 2H), 4.05-4.20 (m, 1H), 6.61 (d, J=2.8 Hz, 1H), 6.71 (dd, J=2.8 and 9.0 Hz, 1H), 7.14-7.19 (m, 2H), 7.26-7.31 (m, 2H), 7.46 (d, J=7.8 Hz, 1H), 7.57-7.68 (m, 1H), 8.47-8.54 (m, 3H).

Example 481

Synthesis of 1-ethyl-3,3,5-trimethyl-7-[3-(pyridin-4-ylmethylpyridin-3-ylmethylamino)propoxy]-1,5-dihydrobenzo[b][1,4]diazepine-2,4-dione trihydrochloride Using an appropriate starting material and following the procedure of Example 6, the object compound was synthesized.

White Amorphous

¹H-NMR (DMSO-d₆) δppm:

0.76 (s, 3H), 1.01 (t, J=7.0 Hz, 3H), 1.32 (s, 3H), 2.14 (br, 2H), 2.96 (br, 2H), 3.30 (s, 3H), 3.61-3.73 (m, 1H), 4.03-4.10 (m, 3H), 4.27-4.32 (m, 4H), 6.81-6.85 (m, 2H), 7.38 (d, J=9.0 Hz, 1H), 7.64 (br, 1H), 7.81 (br, 1H), 8.07 (br, 3H), 8.81 (br, 3H).

Example 482

Synthesis of 7-[3-(bis-pyridin-4-ylmethylamino)propoxy]-1-ethyl-3,3,5-trimethyl-1,5-dihydrobenzo[b][1,4]diazepine-2,4-dione Using an appropriate starting material and following the procedure of Example 7, the object compound was synthesized.

Colorless Oil

¹H-NMR (CDCl₃) δppm:

0.86 (s, 3H), 1.15 (t, J=7.1 Hz, 3H), 1.53 (s, 3H), 1.91-2.02 (m, 2H), 2.66 (t, J=6.6 Hz, 2H), 3.38 (s, 3H), 3.62 (s, 4H), 3.61-3.78 (m, 1H), 3.92-3.99 (m, 2H), 4.01-4.20 (m, 1H), 6.61 (d, J=2.8 Hz, 1H), 6.70 (dd, J=2.8 and 9.0 Hz, 1H), 7.20 (d, J=9.0 Hz, 1H), 7.28-7.30 (m, 4H), 8.50-8.53 (m, 4H).

Example 483

Synthesis of 7-[3-(bis-pyridin-4-ylmethylamino)propoxy]-1-ethyl-3,3,5-trimethyl-1,5-dihydrobenzo[b][1,4]diazepine-2,4-dione trihydrochloride Using an appropriate starting material and following the procedure of Example 6, the object compound was synthesized.

White Amorphous

¹H-NMR (DMSO-d₆) δppm:

0.75 (s, 3H), 1.02 (t, J=7.0 Hz, 3H), 1.32 (s, 3H), 2.01 (br, 2H), 2.67 (br, 2H), 3.30 (s, 3H), 3.63-3.72 (m, 1H), 4.03-4.10 (m, 7H), 6.81-6.85 (m, 2H), 7.37 (d, J=9.0 Hz, 1H), 8.10 (br, 4H), 8.84 (br, 4H).

Example 484

Synthesis of 1-ethyl-3,3,5-trimethyl-7-{3-[(5-methylfuran-2-ylmethyl)pyridin-4-ylmethylamino]propoxy}-1,5-dihydrobenzo[b][1,4]diazepine-2,4-dione Using an appropriate starting material and following the procedure of Example 7, the object compound was synthesized.

Pale Yellow Oil

¹H-NMR (CDCl₃)

0.86 (s, 3H), 1.15 (t, J=7.1 Hz, 3H), 1.53 (s, 3H), 1.91-2.05 (m, 2H), 2.27 (s, 3H), 2.67 (t, J=6.6 Hz, 2H), 3.39 (s, 3H), 3.63 (s, 2H), 3.64 (s, 2H), 3.62-3.79 (m, 1H), 4.02 (t, J=6.2 Hz, 2H), 4.07-4.22 (m, 1H), 5.87 (br, 1H), 6.04 (br, 1H), 6.66 (d, J=2.8 Hz, 1H), 6.75 (dd, J=2.8 and 9.0 Hz, 1H), 7.20 (d, J=9.0 Hz, 1H), 7.24-7.26 (m, 2H), 8.46-8.50 (m, 2H).

Example 485

Synthesis of 1-ethyl-3,3,5-trimethyl-7-{3-[(5-methylfuran-2-ylmethyl)pyridin-4-ylmethylamino]propoxy}-1,5-dihydrobenzo[b][1,4]diazepine-2,4-dione dihydrochloride Using an appropriate starting material and following the procedure of Example 6, the object compound was synthesized.

Pale Yellow Amorphous

¹H-NMR (DMSO-d₆) δppm:

0.76 (s, 3H), 1.01 (t, J=7.0 Hz, 3H), 1.32 (s, 3H), 2.21-2.30 (m, 5H), 3.05 (br, 2H), 3.32 (s, 3H), 3.62-3.72 (m, 1H), 4.02-4.11 (m, 3H), 4.23-4.58 (m, 4H), 6.10 (br, 1H), 6.57 (br, 1H), 6.87-6.91 (m, 2H), 7.40 (d, J=9.0 Hz, 1H), 8.20 (br, 2H), 8.90 (br, 2H).

Example 486

Synthesis of 1-ethyl-3,3,5-trimethyl-7-{3-[(2-methylaminoethyl)pyridin-4-ylmethylamino]propoxy}-1,5-dihydrobenzo[b][1,4]diazepine-2,4-dione trihydrochloride Using an appropriate starting material and following the procedure of Example 44, the object compound was synthesized.

$^1$H-NMR (DMSO-$d_6$) δppm:
0.76 (s, 3H), 1.01 (t, J=7.0 Hz, 3H), 1.32 (s, 3H), 2.21 (br, 2H), 2.51 (s, 3H), 3.10 (br, 2H), 3.33 (s, 3H), 3.35 (br, 2H), 3.61-3.72 (m, 1H), 4.00-4.12 (m, 5H), 4.55 (br, 2H), 6.90 (dd, J=2.6, 9.0 Hz, 1H), 6.94 (d, J=2.6 Hz, 1H), 7.40 (d, J=9.0 Hz, 1H), 8.35 (br, 2H), 8.95 (br, 2H), 9.50 (br, 2H).

Example 487

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methylbenzamide Diethyl phosphorocyanidate (0.15 g, 1.0 mmol) was added to a THF solution (5 ml) of 1-ethyl-3,3,5-trimethyl-7-{3-[(2-methylaminoethyl)pyridin-4-ylmethylamino]propoxy}-1,5-dihydrobenzo[b][1,4]diazepine-2,4-dione (0.39 g, 0.83 mmol) benzoic acid (0.14 g, 1.1 mmol), and triethylamine (0.15 ml, 1.1 mmol), and the mixture was stirred at room temperature overnight. The reaction mixture was purified by silica gel column chromatography (ethyl acetate:methanol=100:0→80:20). The purified product was concentrated under reduced pressure to thereby obtain 0.41 g (yield: 86%) of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-yl methylamino}ethyl)-N-methyl-benzamide as a colorless oil.

$^1$H-NMR (CDCl$_3$) δppm:
0.84 (s, 3H), 1.15 (t, J=7.1 Hz, 3H), 1.52 (s, 3H), 1.86-1.98 (m, 2H), 2.72 (br, 4H), 2.93 (br, 3H), 3.36 (s, 3H), 3.40-3.69 (m, 5H), 3.98 (br, 2H), 4.13-4.23 (m, 1H), 6.66 (d, J=2.8 Hz, 1H), 6.70 (dd, J=2.8 and 9.0 Hz, 1H), 7.15 (d, J=9.0 Hz, 1H), 7.17-7.27 (m, 2H), 7.30-7.39 (m, 5H), 8.47-8.50 (m, 2H).

Example 488

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methylbenzamide dihydrochloride Using an appropriate starting material and following the procedure of Example 6, the object compound was synthesized.

$^1$H-NMR (DMSO-$d_6$) δppm:
0.75 (s, 3H), 1.01 (t, J=7.0 Hz, 3H), 1.33 (s, 3H), 2.38 (br, 2H), 2.97 (s, 3H), 3.32 (br, 5H), 3.40-3.49 (m, 2H), 3.61-3.70 (m, 1H), 3.97 (br, 2H), 4.01-4.10 (m, 1H), 4.15 (br, 2H), 4.87 (br, 2H), 6.90-6.95 (m, 2H), 7.40-7.49 (m, 6H), 8.50 (br, 2H), 9.05 (br, 2H).

Example 489

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-3-methoxy-N-methylbenzamide Using an appropriate starting material and following the procedure of Example 487, the object compound was synthesized.

$^1$H-NMR (CDCl$_3$) δppm:
0.84 (s, 3H), 1.13 (t, J=7.1 Hz, 3H), 1.52 (s, 3H), 1.92 (br, 2H), 2.71 (br, 4H), 2.93 (br, 3H), 3.36 (s, 3H), 3.40-3.80 (m, 5H), 3.79 (s, 3H), 3.99 (br, 2H), 4.08-4.25 (m, 1H), 6.67 (d, J=2.8 Hz, 1H), 6.72 (dd, J=2.8 and 9.0 Hz, 1H), 6.85-6.94 (m, 3H), 7.16 (d, J=9.0 Hz, 1H), 7.12-7.30 (m, 3H), 8.47-8.50 (m, 2H).

Example 490

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-3-methoxy-N-methylbenzamide dihydrochloride Using an appropriate starting material and following the procedure of Example 6, the object compound was synthesized.

$^1$H-NMR (DMSO-$d_6$) δppm:
0.75 (br, 3H), 1.00 (br, 3H), 1.32 (s, 3H), 2.33 (br, 2H), 2.94 (s, 3H), 3.30 (br, 7H), 3.61-3.70 (m, 1H), 3.77 (s, 3H), 4.01-4.15 (m, 5H), 4.71 (br, 2H), 6.91 (br, 2H), 7.02 (br, 3H), 7.32-7.41 (m, 2H), 8.17 (br, 2H), 8.89 (br, 2H).

Example 491

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-4-methoxy-N-methylbenzamide Using an appropriate starting material and following the procedure of Example 487, the object compound was synthesized.

$^1$H-NMR (CDCl$_3$) δppm:
0.84 (s, 3H), 1.13 (t, J=7.1 Hz, 3H), 1.51 (s, 3H), 1.84-1.97 (m, 2H), 2.60-2.78 (m, 4H), 2.95 (s, 3H), 3.37 (s, 3H), 3.50-3.75 (m, 5H), 3.82 (s, 3H), 4.00 (t, J=6.2 Hz, 2H), 4.08-4.21 (m, 1H), 6.67 (d, J=2.8 Hz, 1H), 6.86 (dd, J=2.8 and 9.0 Hz, 1H), 6.85-6.88 (m, 2H), 7.16 (d, J=9.0 Hz, 1H), 7.17-7.21 (m, 2H), 7.32-7.33 (m, 2H), 8.47-8.50 (m, 2H).

Example 492

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-4-methoxy-N-methylbenzamide dihydrochloride Using an appropriate starting material and following the procedure of Example 6, the object compound was synthesized.

$^1$H-NMR (DMSO-$d_6$) δppm:
0.75 (br, 3H), 1.00 (br, 3H), 1.32 (s, 3H), 2.32 (br, 2H), 2.99 (s, 3H), 3.30 (br, 5H), 3.66 (br, 2H), 3.78 (s, 3H), 3.88 (br, 3H), 4.10 (br, 3H), 4.64 (br, 2H), 6.87-6.97 (m, 4H), 7.38-7.45 (m, 3H), 8.12 (br, 2H), 8.95 (br, 2H).

Example 493

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-2-fluoro-N-methylbenzamide Using an appropriate starting material and following the procedure of Example 487, the object compound was synthesized.
$^1$H-NMR (CDCl$_3$) δppm:
0.84 (s, 3H), 1.13 (t, J=7.1 Hz, 3H), 1.51 (s, 3H), 1.95-2.04 (m, 2H), 2.43-2.59 (m, 2H), 2.81-2.95 (m, 2H), 2.83 (s, 3H), 3.35 (s, 3H), 3.62-3.79 (m, 5H), 4.02-4.21 (m, 3H), 6.61-6.79 (m, 3H), 7.00-7.39 (m, 6H), 8.46-8.49 (m, 2H).

Example 494

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-2-fluoro-N-methylbenzamide Using an appropriate starting material and following the procedure of Example 6, the object compound was synthesized.
$^1$H-NMR (DMSO-d$_6$) δppm:
0.75 (br, 3H), 1.00 (br, 3H), 1.32 (s, 3H), 2.32 (br, 2H), 2.88 (s, 3H), 3.30 (br, 5H), 3.68 (br, 3H), 4.12 (br, 5H), 4.72 (br, 2H), 6.89-6.93 (m, 2H), 7.29 (br, 2H), 7.38-7.42 (m, 1H), 7.51 (br, 2H), 8.29 (br, 2H), 8.96 (br, 2H).

Example 495

Synthesis of N-(2-[([3-(1-ethyl-3,3,5-trimethyl-2,4-dioxo-2,3,4,5-tetrahydro-1H-benzo[b][1,4]diazepin-7-yloxy)propyl]pyridin-4-ylmethylamino]ethyl)-2,N-dimethylbenzamide Using an appropriate starting material and following the procedure of Example 487, the object compound was synthesized.
$^1$H-NMR (CDCl$_3$) δppm:
0.84 (s, 3H), 1.13 (t, J=7.1 Hz, 3H), 1.49 (s, 3H), 1.95-2.04 (m, 2H), 2.26 (s, 3H), 2.43-2.59 (m, 2H), 2.73 (s, 3H), 2.72-2.81 (m, 2H), 3.35 (s, 3H), 3.62-3.79 (m, 5H), 4.02-4.27 (m, 3H), 6.60-6.79 (m, 2H), 7.00-7.35 (m, 7H), 8.46-8.52 (m, 2H).

Example 496

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-2,N-dimethylbenzamide dihydrochloride Using an appropriate starting material and following the procedure of Example 6, the object compound was synthesized.
$^1$H-NMR (DMSO-d$_6$) δppm:
0.75 (s, 3H), 1.00 (br, 3H), 1.32 (s, 3H), 2.18 (s, 3H), 2.33 (br, 2H), 2.78 (s, 3H), 3.30 (br, 5H), 3.60-3.75 (m, 3H), 4.04-4.08 (m, 3H), 4.13 (br, 2H), 4.71 (br, 2H), 6.87-6.93 (m, 2H), 7.15-7.31 (m, 4H), 7.40-7.42 (m, 1H), 8.23 (br, 2H), 8.92 (br, 2H).

Example 497

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-4,N-dimethylbenzamide Using an appropriate starting material and following the procedure of Example 487, the object compound was synthesized.
$^1$H-NMR (CDCl$_3$) δppm:
0.84 (s, 3H), 1.13 (t, J=7.1 Hz, 3H), 1.51 (s, 3H), 1.84-1.98 (m, 2H), 2.35 (s, 3H), 2.60-2.78 (m, 4H), 2.93 (s, 3H), 3.36 (s, 3H), 3.53-3.78 (m, 5H), 4.00 (br, 2H), 4.07-4.22 (m, 1H), 6.67 (d, J=2.8 Hz, 1H), 6.70 (dd, J=2.8 and 9.0 Hz, 1H), 7.10-7.17 (m, 3H), 7.20-7.27 (m, 4H), 8.47-8.50 (m, 2H).

Example 498

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-4,N-dimethylbenzamide dihydrochloride Using an appropriate starting material and following the procedure of Example 6, the object compound was synthesized.
$^1$H-NMR (DMSO-d$_6$) δppm:
0.74 (s, 3H), 1.00 (br, 3H), 1.32 (s, 3H), 2.32 (br, 5H), 2.95 (s, 3H), 3.30 (br, 5H), 3.60-3.75 (m, 3H), 3.80-4.15 (m, 5H), 4.68 (br, 2H), 6.91 (br, 2H), 7.23 (br, 2H), 7.40-7.42 (m, 3H), 8.23 (br, 2H), 8.91 (br, 2H).

Example 499

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-2-(2-methoxyphenyl)-N-methylacetamide Using an appropriate starting material and following the procedure of Example 487, the object compound was synthesized.
$^1$H-NMR (CDCl$_3$) δppm:
0.84 (s, 3H), 1.13 (t, J=7.1 Hz, 3H), 1.52 (s, 3H), 1.84-1.99 (m, 2H), 2.60-2.73 (m, 4H), 3.04 (s, 3H), 3.37 (s, 3H), 3.41-3.53 (m, 2H), 3.65 (br, 2H), 3.61-3.70 (m, 1H), 3.83 (s, 3H), 3.93-4.00 (m, 2H), 4.06-4.21 (m, 1H), 4.68 (s, 2H), 6.63-6.73 (m, 2H), 6.80-6.97 (m, 4H), 7.10-7.24 (m, 3H), 8.47-8.49 (m, 2H).

Example 500

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-2-(2-methoxyphenyl)-N-methylacetamide dihydrochloride Using an appropriate starting material and following the procedure of Example 6, the object compound was synthesized.

¹H-NMR (DMSO-d₆) δppm:
0.74 (s, 3H), 1.01 (t, J=7.0 Hz, 3H), 1.31 (s, 3H), 2.25 (br, 2H), 3.04 (s, 3H), 3.30 (br, 5H), 3.40-3.49 (m, 2H), 3.75 (s, 3H), 3.75 (br, 1H), 3.94-4.08 (m, 5H), 4.67 (br, 2H), 4.83 (s, 2H), 6.79-6.99 (m, 6H), 3.78 (d, J=9.0 Hz, 1H), 8.05 (br, 2H), 8.83 (br, 2H).

Example 501

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-2-(3-methoxyphenyl)-N-methylacetamide Using an appropriate starting material and following the procedure of Example 487, the object compound was synthesized.
¹H-NMR (CDCl₃) δppm:
0.84 (s, 3H), 1.13 (t, J=7.1 Hz, 3H), 1.52 (s, 3H), 1.82-1.93 (m, 2H), 2.60-2.73 (m, 4H), 2.91 (s, 3H), 3.37 (s, 3H), 3.41-3.54 (m, 2H), 3.59-3.70 (m, 5H), 3.76 (s, 3H), 3.97 (t, J=6.1 Hz, 2H), 4.06-4.21 (m, 1H), 6.65-6.81 (m, 5H), 7.13-7.25 (m, 4H), 8.44-8.50 (m, 2H).

Example 502

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-2-(3-methoxyphenyl)-N-methylacetamide dihydrochloride Using an appropriate starting material and following the procedure of Example 6, the object compound was synthesized.
¹H-NMR (DMSO-d₆) δppm:
0.74 (s, 3H), 1.00 (t, J=7.0 Hz, 3H), 1.32 (s, 3H), 2.24 (br, 2H), 3.03 (s, 3H), 3.23 (br, 2H), 3.30 (s, 3H), 3.63-3.72 (m, 6H), 4.01-4.08 (m, 5H), 4.62 (br, 4H), 6.78-6.91 (m, 5H), 7.20 (t, J=7.8 Hz, 1H), 7.39 (d, J=8.9 Hz, 1H), 8.22 (br, 2H), 8.90 (br, 2H).

Example 503

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-2-(4-methoxyphenyl)-N-methylacetamide Using an appropriate starting material and following the procedure of Example 487, the object compound was synthesized.
¹H-NMR (CDCl₃) δppm:
0.84 (s, 3H), 1.13 (t, J=7.1 Hz, 3H), 1.52 (s, 3H), 1.82-1.93 (m, 2H), 2.57-2.73 (m, 4H), 2.91 (s, 3H), 3.37 (s, 3H), 3.43-3.54 (m, 2H), 3.59 (s, 2H), 3.60-3.75 (m, 3H), 3.76 (s, 3H), 3.97 (t, J=6.1 Hz, 2H), 4.06-4.21 (m, 1H), 6.65 (br, 1H), 6.73 (dd, J=8.9 and 2.8 Hz, 1H), 6.83 (d, J=8.4 Hz, 2H), 7.05-7.21 (m, 5H), 8.44-8.50 (m, 2H).

Example 504

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-2-(4-methoxyphenyl)-N-methylacetamide dihydrochloride Using an appropriate starting material and following the procedure of Example 6, the object compound was synthesized.
¹H-NMR (DMSO-d₆) δppm:
0.74 (s, 3H), 1.00 (t, J=7.0 Hz, 3H), 1.31 (s, 3H), 2.27 (br, 2H), 3.04 (s, 3H), 3.23 (br, 2H), 3.30 (s, 3H), 3.63-3.72 (m, 6H), 4.01-4.08 (m, 5H), 4.62 (br, 4H), 6.78-6.89 (m, 4H), 7.12-7.14 (m, 2H), 7.39 (d, J=9.0 Hz, 1H), 7.96 (br, 2H), 8.81 (br, 2H).

Example 505

Synthesis of 2-benzo[1,3]dioxol-5-yl-N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methylacetamide Using an appropriate starting material and following the procedure of Example 487, the object compound was synthesized.
¹H-NMR (CDCl₃) δppm:
0.84 (s, 3H), 1.13 (t, J=7.1 Hz, 3H), 1.52 (s, 3H), 1.82-1.93 (m, 2H), 2.57-2.73 (m, 4H), 2.92 (s, 3H), 3.37 (s, 3H), 3.41-3.50 (m, 2H), 3.57 (s, 2H), 3.59-3.73 (m, 3H), 3.98 (t, J=6.1 Hz, 2H), 4.07-4.20 (m, 1H), 5.89 (s, 2H), 6.64-6.77 (m, 5H), 7.07-7.25 (m, 3H), 8.44-8.49 (m, 2H).

Example 506

Synthesis of 2-benzo[1,3]dioxol-5-yl-N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methylacetamide dihydrochloride Using an appropriate starting material and following the procedure of Example 6, the object compound was synthesized.
¹H-NMR (DMSO-d₆) δppm:
0.74 (s, 3H), 1.00 (t, J=7.0 Hz, 3H), 1.32 (s, 3H), 2.25 (br, 2H), 3.03 (s, 3H), 3.23 (br, 2H), 3.30 (s, 3H), 3.63-3.71 (m, 3H), 4.01-4.08 (m, 5H), 4.58 (br, 2H), 4.69 (br, 2H), 5.97 (s, 2H), 6.67-6.69 (m, 1H), 6.80-6.83 (m, 2H), 6.89-6.91 (m, 2H), 7.39 (d, J=8.9 Hz, 1H), 8.14 (br, 2H), 8.87 (br, 2H).

Example 507

Synthesis of 1-ethyl-3,3,5-trimethyl-7-(3-{(3-methylpyridin-4-ylmethyl)-[2-(7-oxo-7H-furo[2,3-c]pyridin-6-yl)ethyl]-amino}-propoxy)-1,5-dihydrobenzo[b][1,4]diazepine-2,4-dione dihydrochloride Using an appropriate starting material and following the procedure of Example 7 and Example 6, the object compound was synthesized.
White Powder
¹H-NMR (DMSO-D₆) δppm:
0.75 (3H, s), 1.02 (3H, t, J=7.1 Hz), 1.32 (3H, s), 1.90-2.01 (2H, m), 2.35-2.45 (3H, m), 2.61-3.95 (8H, m), 3.96-4.32 (7H, m), 6.49-6.61 (1H, m), 6.81-6.89 (3H, m), 7.39 (1H, d, J=9.0 Hz), 7.41-7.51 (1H, m), 7.52-8.02 (1H, m), 8.11 (1H, s), 8.41-8.49 (1H, m), 8.65 (1H, s)

Example 508

Synthesis of 1-ethyl-3,3,5-trimethyl-7-(3-{(2-methylpyridin-4-ylmethyl)-[2-(7-oxo-7H-furo[2,3-c]pyridin-6-yl)ethyl]-amino}propoxy)-1,5-dihydrobenzo[b][1,4]diazepine-2,4-dione dihydrochloride Using an appropriate starting material and following the procedure of Example 7 and Example 6, the object compound was synthesized.

White Powder
¹H-NMR (DMSO-D₆) δppm:
0.75 (3H, s), 1.01 (3H, t, J=7.1 Hz), 1.32 (3H, s), 1.82-2.11 (2H, m), 2.61-3.81 (8H, m), 3.89-4.41 (10H, m), 6.54-6.59 (1H, m), 6.78-6.91 (3H, m), 7.39 (1H, d, J=9.0 Hz), 7.48-7.53 (1H, m), 7.52-7.99 (2H, m), 8.12 (1H, s), 8.52-8.68 (1H, m)

Example 509

Synthesis of 1-ethyl-7-(3-{(3-fluoropyridin-4-ylmethyl)-[2-(7-oxo-7H-furo[2,3-c]Pyridin-6-yl)ethyl]amino}propoxy)-3,3,5-trimethyl-1,5-dihydrobenzo[b][1,4]diazepine-2,4-dione dihydrochloride Using an appropriate starting material and following the procedure of Example 7 and Example 6, the object compound was synthesized.
White Powder
¹H-NMR (DMSO-D₆) δppm:
0.75 (3H, s), 1.01 (3H, t, J=7.1 Hz), 1.32 (3H, s), 1.99-2.27 (2H, m), 3.31 (3H, s), 3.33-3.81 (5H, m), 3.96-4.20 (3H, m), 4.25-4.45 (4H, m), 6.60-6.64 (1H, m), 6.80-6.92 (3H, m), 7.39 (1H, d, J=9.0 Hz), 7.52-7.56 (1H, m), 7.57-8.12 (1H, m), 8.14 (1H, s), 8.15-8.57 (1H, m), 8.60-8.66 (1H, m)

Example 510

Synthesis of 1-ethyl-3,3,5-trimethyl-7-(3-{(2-methylpyridin-3-ylmethyl)-[2-(7-oxo-7H-furo[2,3-c]pyridin-6-yl)ethyl]-amino}propoxy)-1,5-dihydrobenzo[b][1,4]diazepine-2,4-dione dihydrochloride Using an appropriate starting material and following the procedure of Example 7 and Example 6, the object compound was synthesized.
White Powder
¹H-NMR (DMSO-D₆) δppm:
0.75 (3H, s), 1.01 (3H, t, J=7.1 Hz), 1.32 (3H, s), 1.90-2.17 (2H, m), 2.52-3.00 (4H, m), 3.25-3.94 (9H, m), 4.01-4.35 (5H, m), 6.52-6.60 (1H, m), 6.82-6.91 (3H, m), 6.93-7.38 (1H, m), 7.40 (1H, d, J=9.0 Hz), 7.47-7.94 (2H, m), 8.12 (1H, s), 8.60-8.68 (1H, m)

Example 511

Synthesis of 1-ethyl-3,3,5-trimethyl-7-{3-[[2-(7-oxo-7H-furo[2,3-c]pyridin-6-yl)ethyl]-(4-trifluoromethylpyridin-3-ylmethyl)amino]propoxy}-1,5-dihydrobenzo[b][1,4]diazepine-2,4-dione Using an appropriate starting material and following the procedure of Example 7, the object compound was synthesized.
White Powder
Melting Point 137 to 138° C.

Example 512

Synthesis of 1-ethyl-3,3,5-trimethyl-7-{3-[[2-(7-oxo-7H-furo[2,3-c]pyridin-6-yl)ethyl]-(2-pyrrolidin-1-ylpyridin-4-ylmethyl)amino]propoxy}-1,5-dihydrobenzo[b][1,4]diazepine-2,4-dione trihydrochloride Using an appropriate starting material and following the procedure of Example 7 and Example 6, the object compound was synthesized.

White Powder
¹H-NMR (DMSO-D₆) δppm:
0.75 (3H, s), 1.01 (3H, t, J=7.1 Hz), 1.32 (3H, s), 1.91-2.03 (5H, m), 3.27-3.76 (13H, m), 3.99-4.61 (7H, m), 6.58-6.62 (1H, m), 6.91-7.24 (4H, m), 7.40 (1H, d, J=9.1 Hz), 7.43-8.09 (3H, m), 8.13 (1H, s)

Example 513

Synthesis of 2-({[3-(1-ethyl-3,3,5-trimethyl-2,4-dioxo-2,3,4,5-tetrahydro-1H-benzo[b][1,4]diazepin-7-yloxy)propyl]-[2-(7-oxo-7H-furo[2,3-c]pyridin-6-yl)ethyl]amino}methyl)-benzonitrile phosphate Using an appropriate starting material and following the procedure of Example 7 and Example 458, the object compound was synthesized.
¹H-NMR (DMSO-D₆) δppm:
0.75 (3H, s), 1.02 (3H, t, J=7.0 Hz), 1.32 (3H, s), 1.78-1.90 (2H, m), 2.65 (2H, t, J=6.5 Hz), 2.77 (2H, t, J=5.7 Hz), 3.30 (3H, s), 3.34-4.13 (8H, m), 6.46 (1H, d, J=6.7 Hz), 6.74 (1H, dd, J=2.7 and 9.0 Hz), 6.81 (1H, d, J=2.7 Hz), 6.85 (1H, d, J=2.0 Hz), 7.21-7.32 (3H, m), 7.35-7.40 (2H, m), 7.63 (1H, m), 8.07 (1H, d, J=2.0 Hz)

Example 514

Synthesis of 7-(3-{(3,5-dihydroxybenzyl)-[2-(7-oxo-7H-furo[2,3-c]pyridin-6-yl)ethyl]amino}propoxy)-1-ethyl-3,3,5-trimethyl-1,5-dihydrobenzo[b][1,4]diazepine-2,4-dione hydrochloride Using an appropriate starting material and following the procedure of Example 7 and Example 6, the object compound was synthesized.
White Powder
¹H-NMR (DMSO-D₆) δppm:
0.75 (3H, s), 1.00 (3H, t, J=7.0 Hz), 1.32 (3H, s), 2.20-2.35 (2H, m), 3.08-3.62 (7H, m), 3.63-3.72 (1H, m), 3.99-4.17 (3H, m), 4.18-4.28 (1H, m), 4.30-4.72 (3H, m), 6.34 (1H, s), 6.45 (2H, s), 6.70 (1H, d, J=7.0 Hz), 6.86-6.96 (3H, m), 7.39 (1H, d, J=8.9 Hz), 7.56 (1H, d, J=7.1 Hz), 8.16 (1H, s), 9.47 (2H, br s)

Example 515

Synthesis of 1-ethyl-7-(3-{(5-fluoropyridin-3-ylmethyl)-[2-(7-oxo-7H-furo[2,3-c]pyridin-6-yl)ethyl]amino}propoxy)-3,3,5-trimethyl-1,5-dihydrobenzo[b][1,4]diazepine-2,4-dione hydrochloride Using an appropriate starting material and following the procedure of Example 7 and Example 6, the object compound was synthesized.
White Powder
¹H-NMR (DMSO-D₆) δppm:
0.75 (3H, s), 1.00 (3H, t, J=7.1 Hz), 1.32 (3H, s), 2.17-2.32 (2H, m), 3.22-3.73 (8H, m), 3.99-4.10 (3H, m), 4.44-4.66 (4H, m), 6.68 (1H, d, J=7.0 Hz), 6.85-6.93 (3H, m), 7.41 (1H, d, J=9.0 Hz), 7.58 (1H, d, J=7.0 Hz), 8.05-8.21 (2H, m), 8.64-8.71 (2H, m)

Example 516

Synthesis of 1-ethyl-7-(2-hydroxy-3-{[2-(1-oxo-1H-isoquinolin-2-yl)ethyl]pyridin-4-ylmethylamino}propoxy)-3,3,5-trimethyl-1,5-dihydrobenzo[b][1,4]diazepine-2,4-dione Using an appropriate starting material and following the procedure of Example 7, the object compound was synthesized.
Colorless Solid
Melting Point 67 to 74° C.

Example 517

Synthesis of 1-ethyl-7-(2-hydroxy-3-{[2-(1-oxo-1H-isoquinolin-2-yl)ethyl]pyridin-3-ylmethylamino}propoxy)-3,3,5-trimethyl-1,5-dihydrobenzo[b][1,4]diazepine-2,4-dione Using an appropriate starting material and following the procedure of Example 7, the object compound was synthesized.
Colorless Solid
$^1$H-NMR (DMSO-D$_6$) δppm:
0.74 (3H, s), 1.03 (3H, t, J=7.0 Hz), 1.32 (3H, s), 2.54-3.08 (3H, m), 3.23-3.30 (3H, m), 3.49-3.92 (6H, m), 3.92-4.27 (3H, m), 4.84-4.99 (1H, m), 6.45-6.56 (1H, m), 6.56-6.79 (2H, m), 6.88-7.06 (1H, m), 7.22-7.38 (1H, m), 7.38-7.73 (5H, m), 8.16 (1H, d, J=8.1 Hz), 8.23-8.35 (1H, m), 8.42 (1H, s).

Example 518

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-3-fluoro-N-methylbenzamide Using an appropriate starting material and following the procedure of Example 487, the object compound was synthesized.
$^1$H-NMR (CDCl$_3$) δppm:
0.84 (s, 3H), 1.13 (t, J=7.1 Hz, 3H), 1.52 (s, 3H), 2.02 (br, 2H), 2.73 (br, 4H), 2.92 (s, 3H), 3.36 (s, 3H), 3.41-3.73 (m, 5H), 3.99 (br, 2H), 4.07-4.20 (m, 1H), 6.67 (d, J=2.8 Hz, 1H), 6.72 (dd, J=2.8 and 9.0 Hz, 1H), 7.03-7.40 (m, 7H), 8.48-8.51 (m, 2H).

Example 519

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-3-fluoro-N-methylbenzamide dihydrochloride Using an appropriate starting material and following the procedure of Example 6, the object compound was synthesized.
$^1$H-NMR (DMSO-d$_6$) δppm:
0.75 (s, 3H), 1.00 (t, J=7.0 Hz, 3H), 1.32 (3H, s), 2.33 (br, 2H), 2.93 (s, 3H), 3.30 (br, 5H), 3.61-3.71 (m, 3H), 4.01-4.11 (m, 5H), 4.66 (br, 2H), 6.88-6.91 (m, 2H), 7.28-7.33 (m, 2H), 7.39-7.40 (m, 2H), 7.46-7.52 (m, 1H), 8.14 (br, 2H), 8.91 (br, 2H).

Example 520

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-4-fluoro-N-methylbenzamide Using an appropriate starting material and following the procedure of Example 487, the object compound was synthesized.
$^1$H-NMR (CDCl$_3$) δppm:
0.84 (s, 3H), 1.13 (t, J=7.1 Hz, 3H), 1.52 (s, 3H), 1.95 (br, 2H), 2.73 (br, 4H), 2.94 (s, 3H), 3.37 (s, 3H), 3.42-3.77 (m, 5H), 3.98 (br, 2H), 4.07-4.20 (m, 1H), 6.67 (d, J=2.8 Hz, 1H), 6.72 (dd, J=2.8 and 9.0 Hz, 1H), 7.05 (t, J=8.6 Hz, 2H), 7.16 (d, J=9.0 Hz, 1H), 7.26 (br, 2H), 7.32-7.38 (m, 2H), 8.48-8.51 (m, 2H).

Example 521

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-4-fluoro-N-methylbenzamide dihydrochloride Using an appropriate starting material and following the procedure of Example 6, the object compound was synthesized.
$^1$H-NMR (DMSO-d$_6$) δppm:
0.74 (s, 3H), 1.00 (t, J=7.0 Hz, 3H), 1.32 (s, 3H), 2.27 (br, 2H), 2.94 (s, 3H), 3.30 (br, 5H), 3.61-3.91 (m, 5H), 4.03-4.10 (m, 3H), 4.62 (br, 2H), 6.86-6.90 (m, 2H), 7.24-7.26 (m, 2H), 7.39 (d, J=8.9 Hz, 1H), 7.56 (br, 2H), 8.00 (br, 2H), 8.82 (br, 2H).

Example 522

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-3,N-dimethylbenzamide Using an appropriate starting material and following the procedure of Example 487, the object compound was synthesized.
$^1$H-NMR (CDCl$_3$) δppm:
0.84 (s, 3H), 1.13 (t, J=7.1 Hz, 3H), 1.52 (s, 3H), 1.97 (br, 2H), 2.34 (s, 3H), 2.78 (br, 4H), 2.94 (s, 3H), 3.36 (s, 3H), 3.43-3.81 (m, 5H), 4.04 (br, 2H), 4.07-4.20 (m, 1H), 6.67 (d, J=2.8 Hz, 1H), 6.73 (dd, J=2.8 and 9.0 Hz, 1H), 7.09-7.26 (m, 5H), 7.32 (br, 2H), 8.48-8.51 (m, 2H).

Example 523

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-3,N-dimethylbenzamide dihydrochloride Using an appropriate starting material and following the procedure of Example 6, the object compound was synthesized.
$^1$H-NMR (DMSO-d$_6$) δppm:
0.75 (s, 3H), 1.00 (t, J=7.0 Hz, 3H), 1.32 (s, 3H), 2.32 (5H), 2.94 (s, 3H), 3.30 (br, 5H), 3.61-3.91 (m, 5H), 4.02-4.11

(m, 3H), 4.62 (br, 2H), 6.89-6.90 (m, 2H), 7.20-7.31 (m, 4H), 7.39 (d, J=8.9 Hz, 1H), 8.05 (br, 2H), 8.83 (br, 2H).

Example 524

Synthesis of 2-dimethylamino-N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methylbenzamide Using an appropriate starting material and following the procedure of Example 487, the object compound was synthesized.
$^1$H-NMR (CDCl$_3$) δppm:
0.84 (s, 3H), 1.13 (t, J=7.1 Hz, 3H), 1.52 (s, 3H), 1.99 (br, 2H), 2.76 (s, 6H), 2.74-2.89 (m, 4H), 3.06 (s, 3H), 3.36 (s, 3H), 3.53-3.83 (m, 5H), 3.95-4.21 (m, 3H), 6.67-6.75 (m, 2H), 6.85-6.97 (m, 2H), 7.10-7.24 (m, 3H), 7.40-7.42 (m, 2H), 8.53-8.55 (m, 2H).

Example 525

Synthesis of 2-dimethylamino-N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methylbenzamide trihydrochloride Using an appropriate starting material and following the procedure of Example 6, the object compound was synthesized.
$^1$H-NMR (DMSO-d$_6$) δppm:
0.74 (s, 3H), 1.00 (t, J=7.0 Hz, 3H), 1.32 (s, 3H), 2.32 (br, 2H), 2.84 (s, 6H), 2.94 (s, 3H), 3.01 (br, 7H), 3.64-3.70 (m, 1H), 3.93 (br, 2H), 4.03-4.14 (m, 3H), 4.69 (br, 2H), 6.85-6.93 (m, 2H), 7.12 (br, 1H), 7.23 (br, 2H), 7.39-7.42 (m, 2H), 8.22 (br, 2H), 8.92 (br, 2H).

Example 526

Synthesis of 3-dimethylamino-N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methylbenzamide trihydrochloride Using an appropriate starting material and following the procedure of Example 487, the object compound was synthesized.
White Powder
$^1$H-NMR (DMSO-d$_6$) δppm:
0.75 (s, 3H), 1.00 (t, J=7.0 Hz, 3H), 1.32 (s, 3H), 2.34 (br, 2H), 2.96 (s, 3H), 3.05 (s, 6H), 3.31 (s, 3H), 3.43 (br, 2H), 3.58-3.69 (m, 1H), 3.94 (br, 2H), 4.01-4.10 (m, 1H), 4.13 (br, 2H), 4.68 (br, 2H), 4.81 (br, 2H), 6.88-6.93 (m, 2H), 7.18 (br, 1H), 7.40 (d, J=9.0 Hz, 1H), 7.47 (br, 3H), 8.47 (br, 2H), 9.03 (br, 2H).

Example 527

Synthesis of 4-dimethylamino-N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methylbenzamide trihydrochloride Using an appropriate starting material and following the procedure of Example 487, the object compound was synthesized.
White Solid
$^1$H-NMR (DMSO-d$_6$) δppm:
0.75 (s, 3H), 1.00 (t, J=7.0 Hz, 3H), 1.32 (s, 3H), 2.31 (br, 2H), 3.00 (br, 9H), 3.22-3.48 (m, 4H), 3.31 (s, 3H), 3.61-3.70 (m, 1H), 3.89 (br, 2H), 3.99-4.14 (m, 3H), 4.80 (br, 2H), 6.87-6.93 (m, 2H), 7.12 (br, 2H), 7.40 (d, J=9.0 Hz, 1H), 7.48 (br, 2H), 8.46 (br, 2H), 9.03 (br, 2H).

Example 528

Synthesis of furan-2-carboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide Using an appropriate starting material and following the procedure of Example 487, the object compound was synthesized.
$^1$H-NMR (CDCl$_3$) δppm:
0.86 (s, 3H), 1.15 (t, J=7.1 Hz, 3H), 1.54 (s, 3H), 1.88-1.96 (m, 2H), 2.65-2.80 (m, 4H), 3.14 (s, 3H), 3.39 (s, 3H), 3.61-3.75 (m, 5H), 4.01 (t, J=6.2 Hz, 2H), 4.04-4.22 (m, 1H), 6.45-6.48 (m, 1H), 6.67-6.69 (m, 1H), 6.73 (dd, J=2.8 and 9.0 Hz, 1H), 6.99 (d, J=3.5 Hz, 1H), 7.18 (d, J=9.0 Hz, 1H), 7.24-7.26 (m, 2H), 7.60 (br, 1H), 8.49-8.50 (m, 2H).

Example 529

Synthesis of furan-2-carboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide dihydrochloride Using an appropriate starting material and following the procedure of Example 6, the object compound was synthesized.
$^1$H-NMR (DMSO-d$_6$) δppm:
0.75 (s, 3H), 1.00 (t, J=7.0 Hz, 3H), 1.32 (s, 3H), 2.29 (br, 2H), 3.10-3.40 (m, 2H), 3.32 (s, 3H), 3.59-3.70 (m, 1H), 3.80-4.11 (m, 7H), 4.70 (br, 2H), 6.63 (d, J=1.6 Hz, 1H), 6.88 (dd, J=2.7, 9.0 Hz, 1H), 6.92 (d, J=2.7 Hz, 1H), 6.96 (d, J=3.3 Hz, 1H), 7.40 (d, J=9.0 Hz, 1H), 7.86 (br, 1H), 8.38 (br, 2H), 8.94 (br, 2H).

Example 530

Synthesis of thiophene-2-carboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide Using an appropriate starting material and following the procedure of Example 487, the object compound was synthesized.
$^1$H-NMR (CDCl$_3$) δppm:
0.86 (s, 3H), 1.15 (t, J=7.1 Hz, 3H), 1.54 (s, 3H), 1.86-1.96 (m, 2H), 2.63-2.80 (m, 4H), 3.14 (s, 3H), 3.38 (s, 3H), 3.62-3.77 (m, 5H), 4.01 (t, J=6.2 Hz, 2H), 4.03-4.20 (m, 1H), 6.67 (d, J=2.8 Hz, 1H), 6.73 (dd, J=2.8 and 9.0 Hz, 1H), 7.01-7.03 (m, 1H), 7.16 (d, J=9.0 Hz, 1H), 7.24-7.26 (m, 2H), 7.30-7.32 (m, 1H), 7.59-7.61 (m, 1H), 8.48-8.50 (m, 2H).

Example 531

Synthesis of thiophene-2-carboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide dihydrochloride Using an appropriate starting material and following the procedure of Example 6, the object compound was synthesized.
$^1$H-NMR (DMSO-d$_6$) δppm:
0.75 (s, 3H), 1.00 (t, J=7.0 Hz, 3H), 1.32 (s, 3H), 2.26 (br, 3H), 3.23 (br, 2H), 3.31 (s, 3H), 3.64-3.70 (m, 3H), 3.80-3.93 (m, 2H), 4.02-4.08 (m, 3H), 4.59 (br, 2H), 6.85-6.89 (m, 2H), 7.14 (br, 1H), 7.39 (d, J=8.9 Hz, 1H), 7.58 (br, 1H), 7.79 (br, 1H), 7.95 (br, 2H), 8.80 (br, 2H).

Example 532

Synthesis of furan-3-carboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide Using an appropriate starting material and following the procedure of Example 487, the object compound was synthesized.
$^1$H-NMR (CDCl$_3$) δppm:
0.84 (s, 3H), 1.13 (t, J=7.1 Hz, 3H), 1.52 (s, 3H), 1.87-1.98 (m, 2H), 2.63-2.80 (m, 4H), 3.05 (s, 3H), 3.37 (s, 3H), 3.53-3.70 (m, 5H), 3.99 (t, J=6.2 Hz, 2H), 4.01-4.21 (m, 1H), 6.56 (s, 1H), 6.66 (d, J=2.8 Hz, 1H), 6.72 (dd, J=2.8 and 9.0 Hz, 1H), 7.16 (d, J=9.0 Hz, 1H), 7.24-7.26 (m, 2H), 7.39 (br, 1H), 7.66 (br, 1H), 8.47-8.50 (m, 2H).

Example 533

Synthesis of furan-3-carboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide dihydrochloride Using an appropriate starting material and following the procedure of Example 6, the object compound was synthesized.
$^1$H-NMR (DMSO-d$_6$) δppm:
0.75 (s, 3H), 1.00 (t, J=7.0 Hz, 3H), 1.32 (s, 3H), 2.26 (br, 2H), 3.14 (br, 3H), 3.31 (s, 5H), 3.62-3.70 (m, 3H), 3.87 (br, 2H), 4.03-4.09 (m, 3H), 4.61 (br, 2H), 6.74 (br, 1H), 6.85-6.90 (m, 2H), 7.39 (d, J=8.9 Hz, 1H), 7.74 (s, 1H), 8.09 (br, 2H), 8.14 (br, 1H), 8.85 (br, 2H).

Example 534

Synthesis of thiophene-3-carboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide Using an appropriate starting material and following the procedure of Example 487, the object compound was synthesized.
$^1$H-NMR (CDCl$_3$) δppm:
0.84 (s, 3H), 1.13 (t, J=7.1 Hz, 3H), 1.52 (s, 3H), 1.88-1.97 (m, 2H), 2.62-2.78 (m, 4H), 3.00 (s, 3H), 3.37 (s, 3H), 3.51-3.73 (m, 5H), 3.99 (t, J=6.2 Hz, 2H), 4.01-4.21 (m, 1H), 6.66 (d, J=2.8 Hz, 1H), 6.71 (dd, J=2.8 and 9.0 Hz, 1H), 7.13-7.26 (m, 4H), 7.26-7.29 (m, 1H), 7.43-7.44 (m, 1H), 8.48-8.50 (m, 2H).

Example 535

Synthesis of thiophene-3-carboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide dihydrochloride Using an appropriate starting material and following the procedure of Example 6, the object compound was synthesized.
$^1$H-NMR (DMSO-d$_6$) δppm:
0.75 (s, 3H), 1.00 (t, J=7.0 Hz, 3H), 1.32 (s, 3H), 2.28 (br, 2H), 3.06 (br, 5H), 3.31 (s, 3H), 3.61-3.70 (m, 3H), 3.87 (br, 2H), 4.03-4.09 (m, 3H), 4.61 (br, 2H), 6.86-6.90 (m, 2H), 7.28 (br, 1H), 7.39 (d, J=8.9 Hz, 1H), 7.58-7.60 (m, 1H), 7.91 (br, 1H), 8.06 (br, 2H), 8.84 (br, 2H).

Example 536

Synthesis of cyclohexanecarboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide Using an appropriate starting material and following the procedure of Example 4'87, the object compound was synthesized.
$^1$H-NMR (CDCl$_3$) δppm:
0.83 (s, 3H), 1.13 (t, J=7.1 Hz, 3H), 1.52 (s, 3H), 1.50-1.81 (m, 10H), 1.88-2.00 (m, 2H), 2.39 (br, 1H), 2.60-2.78 (m, 4H), 2.93 (s, 3H), 3.37 (s, 3H), 3.43 (br, 2H), 3.61-3.74 (m, 3H), 3.91-4.21 (m, 3H), 6.67 (d, J=2.8 Hz, 1H), 6.73 (dd, J=2.8 and 9.0 Hz, 1H), 7.15 (d, J=9.0 Hz, 1H), 7.24-7.26 (m, 2H), 8.48 (br, 2H).

Example 537

Synthesis of cyclohexanecarboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide dihydrochloride Using an appropriate starting material and following the procedure of Example 6, the object compound was synthesized.
$^1$H-NMR (DMSO-d$_6$) δppm:
0.75 (s, 3H), 1.00 (t, J=7.0 Hz, 3H), 1.08-1.28 (m, 6H), 1.32 (s, 3H), 1.66 (br, 4H), 2.26 (br, 2H), 2.55 (br, 1H), 3.03 (s, 3H), 3.21 (br, 2H), 3.32 (s, 3H), 3.64-3.71 (m, 3H), 4.02-4.10 (m, 5H), 4.59 (br, 2H), 6.87-6.92 (m, 2H), 7.40 (d, J=8.9 Hz, 1H), 8.09 (br, 2H), 8.86 (br, 2H).

Example 538

Synthesis of benzo[1,3]dioxole-5-carboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide Using an appropriate starting material and following the procedure of Example 487, the object compound was synthesized.

¹H-NMR (CDCl₃) δppm:

0.84 (s, 3H), 1.13 (t, J=7.1 Hz, 3H), 1.52 (s, 3H), 1.88-1.94 (m, 2H), 2.62-2.75 (m, 4H), 2.94 (s, 3H), 3.36 (s, 3H), 3.51 (br, 2H), 3.63 (s, 2H), 3.61-3.77 (m, 1H), 3.98 (t, J=6.2 Hz, 2H), 3.95-4.20 (m, 1H), 5.96 (s, 2H), 6.67 (d, J=2.8 Hz, 1H), 6.72-6.79 (m, 2H), 6.83-6.88 (m, 2H), 7.15 (d, J=9.0 Hz, 1H), 7.24-7.26 (m, 2H), 8.47-8.50 (m, 2H).

Example 539

Synthesis of benzo[1,3]dioxole-5-carboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide dihydrochloride Using an appropriate starting material and following the procedure of Example 6, the object compound was synthesized.

¹H-NMR (DMSO-d₆) δppm:

0.75 (s, 3H), 1.00 (t, J=7.0 Hz, 3H), 1.32 (s, 3H), 2.32 (br, 2H), 2.95 (s, 3H), 3.31 (br, 5H), 3.62-3.71 (m, 3H), 4.02-4.09 (m, 5H), 4.71 (br, 2H), 6.06 (s, 2H), 6.86-7.06 (m, 5H), 7.39 (d, J=8.9 Hz, 1H), 8.29 (br, 2H), 8.94 (br, 2H).

Example 540

Synthesis of 1-Ethyl-3,3,5-trimethyl-7-(3-{[2-(2-oxo-2H-pyridin-1-yl)ethyl]pyridin-4-ylmethylamino}propoxy)-1,5-dihydrobenzo[b][1,4]diazepine-2,4-dione dihydrochloride Using an appropriate starting material and following the procedure of Example 7, the object compound was synthesized.

Light Brown Amorphous

¹H-NMR (DMSO-d₆) δppm:

0.75 (s, 3H), 1.01 (t, J=7.0 Hz, 3H), 1.32 (s, 3H), 2.26 (br, 2H), 3.24 (br, 2H), 3.32 (s, 3H), 3.64-3.73 (m, 1H), 4.01-4.09 (m, 5H), 4.37 (br, 2H), 4.70 (br, 2H), 6.28 (t, J=6.5 Hz, 1H), 6.41 (d, J=9.0 Hz, 1H), 6.89 (dd, J=2.5, 9.0 Hz, 1H), 6.93 (d, J=2.5 Hz, 1H), 7.41 (d, J=9.0 Hz, 1H), 7.42-7.47 (m, 1H), 7.78 (d, J=6.5 Hz, 1H), 8.34 (br, 2H), 8.98 (br, 2H).

Example 541

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-2-methoxy-N-methylbenzamide dihydrochloride Using an appropriate starting material and following the procedure of Example 487, the object compound was synthesized.

White Powder

¹H-NMR (DMSO-d₆) δppm:

0.75 (s, 3H), 1.01 (t, J=7.0 Hz, 3H), 1.32 (s, 3H), 2.33 (br, 2H), 2.79 (s, 3H), 3.21-3.44 (m, 2H), 3.30 (s, 3H), 3.53-3.64 (m, 1H), 3.94 (s, 3H), 3.90-4.15 (m, 7H), 4.76 (br, 2H), 6.84-7.14 (m, 4H), 7.22 (d, J=7.4 Hz, 1H), 7.38-7.44 (m, 2H), 8.36 (br, 2H), 8.99 (br, 2H).

Example 542

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methyl-2-trifluoromethyl-benzamide dihydrochloride Using an appropriate starting material and following the procedure of Example 487, the object compound was synthesized.

Pale Yellow Powder

¹H-NMR (DMSO-d₆) δppm:

0.75 (s, 3H), 1.00 (t, J=7.0 Hz, 3H), 1.32 (s, 3H), 2.36 (br, 2H), 2.78 (s, 3H), 3.30-3.43 (m, 5H), 3.61-3.70 (m, 1H), 3.85 (br, 2H), 4.00-4.19 (m, 5H), 4.81 (br, 2H), 6.84-6.95 (m, 2H), 7.40 (d, J=9.0 Hz, 1H), 7.62-7.69 (m, 2H), 7.76 (t, J=7.7 Hz, 1H), 7.82 (d, J=7.7 Hz, 1H), 8.44 (br, 2H), 9.01 (br, 2H).

Example 543

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methyl-3-trifluoromethyl-benzamide dihydrochloride Using an appropriate starting material and following the procedure of Example 487, the object compound was synthesized.

Pale Yellow Amorphous

¹H-NMR (DMSO-d₆) δppm:

0.75 (s, 3H), 1.00 (t, J=7.0 Hz, 3H), 1.32 (s, 3H), 2.36 (br, 2H), 2.95 (s, 3H), 3.25-3.33 (m, 2H), 3.31 (s, 3H), 3.37-3.45 (m, 2H), 3.61-3.73 (m, 1H), 3.97 (br, 2H), 4.00-4.13 (m, 1H), 4.13 (br, 2H), 4.82 (br, 2H), 6.89-6.94 (m, 2H), 7.40 (d, J=9.0 Hz, 1H), 7.69 (t, J=7.6 Hz, 1H), 7.82-7.86 (m, 2H), 7.91 (s, 1H), 8.47 (br, 2H), 9.02 (br, 2H).

Example 544

Synthesis of 2-cyano-N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methyl-benzamide dihydrochloride Using an appropriate starting material and following the procedure of Example 487, the object compound was synthesized.

¹H-NMR (DMSO-d₆) δppm:

0.75 (s, 3H), 1.00 (t, J=7.0 Hz, 3H), 1.32 (s, 3H), 2.31 (br, 2H), 2.89 (s, 3H), 3.16-3.45 (m, 2H), 3.30 (s, 3H), 3.50-3.75 (m, 3H), 3.90-4.15 (m, 5H), 4.71 (br, 2H), 6.82-6.94 (m, 2H), 7.40 (d, J=9.0 Hz, 1H), 7.62-7.67 (m, 1H), 7.74 (br, 1H), 7.78-7.80 (m, 1H), 7095 (d, J=7.7 Hz, 1H), 8.29 (br, 2H), 8.94 (br, 2H).

Example 545

Synthesis of 4-cyano-N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methyl-benzamide dihydrochloride Using an appropriate starting material and following the procedure of Example 487, the object compound was synthesized.

White Solid

¹H-NMR (DMSO-d$_6$) δppm:

0.74 (s, 3H), 1.00 (t, J=7.0 Hz, 3H), 1.32 (s, 3H), 2.31 (br, 2H), 2.91 (s, 3H), 3.21-3.40 (m, 4H), 3.30 (s, 3H), 3.50-3.75 (m, 1H), 3.93 (br, 2H), 4.00-4.13 (m, 3H), 4.69 (br, 2H), 6.87-6.92 (m, 2H), 7.39 (d, J=9.0 Hz, 1H), 7.71 (d, J=7.8 Hz, 2H), 7.92 (d, J=7.8 Hz, 1H), 8.28 (br, 2H), 8.94 (br, 2H).

Example 546

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methyl-2-thiophen-2-ylacetamide dihydrochloride Using an appropriate starting material and following the procedure of Example 487, the object compound was synthesized.

White Solid

¹H-NMR (DMSO-d$_6$) δppm:

0.75 (s, 3H), 1.00 (t, J=7.0 Hz, 3H), 1.32 (s, 3H), 2.26 (br, 2H), 3.08 (s, 3H), 3.22 (br, 2H), 3.31 (s, 3H), 3.45-3.63 (m, 3H), 3.67-3.86 (m, 2H), 3.97 (s, 2H), 3.98-4.10 (m, 3H), 4.62 (br, 2H), 6.87-6.97 (m, 4H), 7.36-7.39 (m, 2H), 8.20 (br, 2H), 8.90 (br, 2H).

Example 547

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methyl-2-thiophen-3-ylacetamide dihydrochloride Using an appropriate starting material and following the procedure of Example 487, the object compound was synthesized.

White Solid

¹H-NMR (DMSO-d$_6$) ppm:

0.75 (s, 3H), 1.00 (t, J=7.0 Hz, 3H), 1.32 (s, 3H), 2.25 (br, 2H), 3.05 (s, 3H), 3.22 (br, 2H), 3.31 (s, 3H), 3.49-3.80 (m, 7H), 3.95-4.10 (m, 3H), 4.62 (br, 2H), 6.86-6.92 (m, 2H), 6.99-7.01 (m, 1H), 7.25 (br, 1H), 7.40 (d, J=9.0 Hz, 1H), 7.44-7.46 (m, 1H), 8.21 (br, 2H), 8.91 (br, 2H).

Example 548

Synthesis of thiazole-4-carboxylic acid (2-{[3-C1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide trihydrochloride Using an appropriate starting material and following the procedure of Example 487, the object compound was synthesized.

White Solid

¹H-NMR (DMSO-d$_6$) δppm:

0.75 (s, 3H), 1.00 (t, J=7.0 Hz, 3H), 1.32 (s, 3H), 2.31 (br, 2H), 3.17 (s, 3H), 3.23-3.40 (m, 2H), 3.31 (s, 3H), 3.61-3.80 (m, 3H), 3.95-4.11 (m, 5H), 4.66 (br, 2H), 6.89-6.92 (m, 2H), 7.40 (d, J=9.0 Hz, 1H), 8.23-8.32 (m, 3H), 8.96 (br, 2H), 9.15-9.17 (m, 1H).

Example 549

Synthesis of isoxazole-5-carboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide trichloride Using an appropriate starting material and following the procedure of Example 487, the object compound was synthesized.

White Solid

¹H-NMR (DMSO-d$_6$) δppm:

0.75 (s, 3H), 1.00 (t, J=7.0 Hz, 3H), 1.32 (s, 3H), 2.29 (br, 2H), 3.17 (s, 3H), 3.25 (br, 2H), 3.31 (s, 3H), 3.55-3.77 (m, 3H), 3.81-4.10 (m, 5H), 4.69 (br, 2H), 6.87-6.93 (m, 2H), 7.04 (d, J=1.8 Hz, 1H), 7.40 (d, J=9.0 Hz, 1H), 8.30 (br, 2H), 8.75-8.76 (m, 1H), 8.95 (br, 2H).

Example 550

Synthesis of 5-methyl-isoxazole-3-carboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide trihydrochloride Using an appropriate starting material and following the procedure of Example 487, the object compound was synthesized.

White Solid

¹H-NMR (DMSO-d$_6$) δppm:

0.75 (s, 3H), 1.00 (t, J=7.0 Hz, 3H), 1.32 (s, 3H), 2.27 (br, 2H), 2.46 (s, 3H), 3.11 (s, 3H), 3.21-3.47 (m, 2H), 3.32 (s, 3H), 3.50-3.95 (m, 5H), 4.00-4.13 (m, 3H), 4.67 (br, 2H), 6.50 (s, 1H), 6.87-6.93 (m, 2H), 7.40 (d, J=9.0 Hz, 1H), 8.24 (br, 2H), 8.93 (br, 2H).

Example 551

Synthesis of 1-ethyl-3,3,5-trimethyl-7-(3-{[2-(4-oxo-4H-furo[3,2-c]pyridin-5-yl)ethyl]pyridin-3-ylmethylamino}-propoxy)-1,5-dihydrobenzo[b][1,4]diazepine-2,4-dione Using an appropriate starting material and following the procedure of Example 7, the object compound was synthesized.

White Powder

Melting Point 118 to 119° C.

Example 552

Synthesis of 1-ethyl-3,3,5-trimethyl-7-(3-{[2-(4-oxo-4H-furo[3,2-c]pyridin-5-yl)ethyl]pyridin-3-ylmethylamino}-propoxy)-1,5-dihydrobenzo[b][1,4]diazepine-2,4-dione dihydrochloride Using an appropriate starting material and following the procedure of Example 6, the object compound was synthesized.

White Amorphous

¹H-NMR (DMSO-d$_6$) δppm:

0.75 (3H, s), 1.01 (3H, t, J=7.1 Hz), 1.32 (3H, s), 2.20-2.43 (2H, m), 3.08-3.40 (5H, m), 3.43-4.68 (10H, m), 6.82-6.94 (4H, m), 7.41 (1H, d, J=8.9 Hz), 7.70-7.75 (2H, m), 7.92 (1H, d, J=1.9 Hz), 8.36-8.48 (1H, m), 8.74-8.80 (1H, m), 8.94-9.02 (1H, m)

Example 553

Synthesis of 1-ethyl-3,3,5-trimethyl-7-(3-{[2-(2-methyl-4-oxo-4H-furo[3,2-c]pyridin-5-yl)ethyl]pyridin-3-ylmethylamino}propoxy)-1,5-dihydrobenzo[b][1,4]diazepine-2,4-dione Using an appropriate starting material and following the procedure of Example 7, the object compound was synthesized.
White Powder
$^1$H-NMR (CDCl$_3$) δppm:
0.86 (3H, s), 1.16 (3H, t, J=7.1 Hz), 1.53 (3H, s), 1.88-1.93 (2H, m), 2.41 (3H, s), 2.70 (2H, t, J=6.8 Hz), 2.86 (2H, t, J=6.2 Hz), 3.39 (3H, s), 3.68-3.75 (3H, m), 3.86 (2H, t, J=6.1 Hz), 4.07 (2H, t, J=6.1 Hz) 4.14-4.21 (1H, m), 6.36 (1H, d, J=7.3 Hz), 6.52 (1H, s), 6.62 (1H, s), 6.67 (1H, dd, J=9.0, 2.8 Hz), 7.00 (1H, d, J=7.4 Hz), 7.07 (1H, dd, J=7.7, 4.9 Hz), 7.17 (1H, d, J=9.0 Hz), 7.50 (1H, d, J=7.8 Hz), 8.42 (1H, d, J=4.8 Hz), 8.48 (1H, s)

Example 554

Synthesis of 1-ethyl-3,3,5-trimethyl-7-(3-{[2-(2-oxo-2H-quinolin-1-yl)ethyl]pyridin-3-ylmethylamino}-propoxy)-1,5-dihydrobenzo[b][1,4]diazepine-2,4-dione dihydrochloride Using an appropriate starting material and following the procedure of Example 7 and Example 6, the object compound was synthesized.
White Amorphous
$^1$H-NMR (DMSO-d$_6$) δppm:
0.74 (3H, s), 1.00 (3H, t, J=7.0 Hz), 1.32 (3H, s), 2.18-2.39 (2H, m), 3.04-3.79 (7H, m), 3.99-4.28 (3H, m), 4.42-4.94 (5H, m), 6.66 (1H, d, J=9.5 Hz), 6.78-6.97 (2H, m), 7.32 (1H, t, J=7.4 Hz), 7.40 (1H, d, J=8.9 Hz), 7.63 (1H, t, J=7.2 Hz), 7.70-7.84 (3H, m), 8.00 (1H, d, J=9.5 Hz), 8.39-8.52 (1H, m), 8.73-8.82 (1H, m), 8.99 (1H, s)

Example 555

Synthesis of 1-ethyl-3,3,5-trimethyl-7-(3-{[2-(2-oxo-3,4-dihydro-2H-quinolin-1-yl)ethyl]pyridin-3-ylmethylamino}-propoxy)-1,5-dihydrobenzo[b][1,4]diazepine-2,4-dione dihydrochloride Using an appropriate starting material and following the procedure of Example 7 and Example 6, the object compound was synthesized.
White Amorphous
$^1$H-NMR (DMSO-d$_6$) δppm:
0.75 (3H, s), 1.00 (3H, t, J=7.1 Hz), 1.32 (3H, s), 2.15-2.40 (2H, m), 2.57 (2H, t, J=8.2 Hz), 2.89 (2H, t, J=7.7 Hz), 3.08-3.96 (8H, m), 3.99-4.22 (3H, m), 4.29-4.51 (2H, m), 4.51-4.80 (2H, m), 6.86-6.94 (2H, m), 7.00-7.06 (1H, m), 7.20-7.32 (3H, m), 7.41 (1H, d, J=8.9 Hz), 7.72-7.85 (1H, m), 8.46-8.60 (1H, m), 8.79-8.84 (1H, m), 9.04 (1H, s)

Example 556

Synthesis of 7-(3-{[2-(7-bromo-1-oxo-1H-isoquinolin-2-yl)ethyl]pyridin-4-ylmethylamino}propoxy)-1-ethyl-3,3,5-trimethyl-1,5-dihydrobenzo[b][1,4]diazepine-2,4-dione Using an appropriate starting material and following the procedure of Example 7, the object compound was synthesized.
Pale Yellow Powder
Melting Point 146 to 147° C.

Example 557

Synthesis of 1-ethyl-7-(3-{(2-hydroxy-pyridin-4-ylmethyl)-[2-(7-oxo-7H-furo[2,3-c]pyridin-6-yl)ethyl]amino}propoxy)-3,3,5-trimethyl-1,5-dihydrobenzo[b][1,4]diazepine-2,4-dione Using an appropriate starting material and following the procedure of Example 7, the object compound was synthesized.
White Powder
Melting Point 160.5 to 161.5° C.

Example 558

Synthesis of 1-ethyl-3,3,5-trimethyl-7-{3-[(2-methylpyridin-4-ylmethyl)-(2-pyridin-3-yl-ethyl)amino]propoxy}-1,5-dihydrobenzo[b][1,4]diazepine-2,4-dione trihydrochloride Using an appropriate starting material and following the procedure of Example 7 and Example 6, the object compound was synthesized.
White Amorphous
$^1$H-NMR (DMSO-d$_6$) δppm:
0.74 (3H, s), 1.00 (3H, t, J=7.0 Hz), 1.31 (3H, s), 1.68-2.48 (2H, m), 2.64 (3H, s), 2.70-4.25 (6H, m), 3.30 (3H, s), 3.43 (2H, t, J=7.0 Hz), 3.66 (1H, dq, J=7.0, 7.0 Hz), 4.05 (1H, dq, J=7.0, 7.0 Hz), 4.23-4.99 (2H, bs), 6.80-7.00 (2H, m), 7.40 (1H, d, J=9.0 Hz), 7.48-8.23 (3H, m), 8.32 (1H, bs), 8.50-9.00 (1H, m), 8.74 (1H, d, J=5.7 Hz), 8.80 (1H, s), 12.00 (1H, bs)

Example 559

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methyl-4-trifluoromethyl-benzamide dihydrochloride Using an appropriate starting material and following the procedure of Example 487, the object compound was synthesized.
Colorless Amorphous
$^1$H-NMR (DMSO-d$_6$) δppm:
0.74 (s, 3H), 1.00 (t, J=7.0 Hz, 3H), 1.32 (s, 3H), 2.30 (br, 2H), 2.91 (s, 3H), 3.11-3.30 (m, 2H), 3.29 (s, 3H), 3.59-3.69 (m, 3H), 4.02 (br, 2H), 4.01-4.15 (m, 3H), 4.63 (br, 2H), 6.82-6.90 (m, 2H), 7.39 (d, J=8.9 Hz, 1H), 7.55-8.02 (m, 6H), 8.81 (br, 2H).

Example 560

Synthesis of 3-cyano-N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methylbenzamide dihydrochloride Using an appropriate starting material and following the procedure of Example 487, the object compound was synthesized.

Colorless Amorphous $^1$H-NMR (DMSO-d$_6$) δppm:

0.74 (s, 3H), 1.00 (t, J=7.0 Hz, 3H), 1.32 (s, 3H), 2.32 (br, 2H), 2.92 (s, 3H), 3.15-3.28 (m, 2H), 3.29 (s, 3H), 3.55-3.70 (m, 3H), 3.87 (br, 2H), 4.00-4.12 (m, 3H), 4.58 (br, 2H), 6.86-6.90 (m, 2H), 7.39 (d, J=8.9 Hz, 1H), 7.63-7.68 (m, 1H), 7.73-8.14 (m, 5H), 8.84 (br, 2H).

Example 561

Synthesis of 1H-indazole-3-carboxylic acid (2-{[3-C1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide trihydrochloride Using an appropriate starting material and following the procedure of Example 487, the object compound was synthesized.

Colorless Amorphous $^1$H-NMR (DMSO-d$_6$) δppm:

0.73 (s, 3H), 0.99 (t, J=7.0 Hz, 3H), 1.31 (s, 3H), 2.32 (br, 2H), 3.06 (br, 3H), 3.28 (br, 3H), 3.43 (br, 2H), 3.61-3.69 (m, 3H), 4.01-4.11 (m, 5H), 4.67 (br, 2H), 6.84-6.89 (m, 2H), 7.20-7.24 (m, 1H), 7.33-7.36 (m, 1H), 7.40-7.44 (m, 1H), 7.61-7.63 (m, 1H), 8.04 (br, 3H), 8.83 (br, 2H), 13.7 (br, 1H).

Example 562

Synthesis of 1H-pyrrole-3-carboxylic acid (2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)methylamide dihydrochloride Using an appropriate starting material and following the procedure of Example 487, the object compound was synthesized.

Colorless Amorphous $^1$H-NMR (DMSO-d$_6$) δppm:

0.75 (s, 3H), 1.00 (t, J=7.0 Hz, 3H), 1.32 (s, 3H), 2.26 (br, 2H), 3.10-3.25 (m, 5H), 3.31 (s, 3H), 3.57-3.69 (m, 3H), 3.87 (br, 2H), 4.02-4.08 (m, 3H), 4.60 (br, 2H), 6.15 (s, 1H), 6.63 (br, 1H), 6.83-6.94 (m, 3H), 7.39 (d, J=8.9 Hz, 1H), 7.99 (br, 2H), 8.81 (br, 2H).

Example 563

Synthesis of N-(2-{[3-(1-ethyl-3,3,5-trimethyl-2,4-dioxo-2,3,4,5-tetrahydro-1H-benzo[b][1,4]diazepin-7-yloxy)propyl]pyridin-4-ylmethylamino}ethyl)-N-methylnicotinamide trihydrochloride Using an appropriate starting material and following the procedure of Example 487, the object compound was synthesized.

Colorless Amorphous $^1$H-NMR (DMSO-d$_6$) δppm:

0.75 (s, 3H), 1.00 (t, J=7.0 Hz, 3H), 1.32 (s, 3H), 2.33 (br, 2H), 2.98 (s, 3H), 3.30 (s, 3H), 3.43 (br, 2H), 3.53-3.70 (m, 3H), 3.93-4.20 (m, 5H), 4.84 (br, 2H), 6.87-6.92 (m, 2H), 7.40 (d, J=8.9 Hz, 1H), 7.78 (br, 1H), 8.28 (br, 3H), 8.80 (br, 1H), 8.94 (br, 3H).

Example 564

Synthesis of 1-ethyl-7-(3-{(2-hydroxypyridin-4-ylmethyl)-[2-(1-oxo-1H-isoquinolin-2-yl)ethyl]amino}propoxy)-3,3,5-trimethyl-1,5-dihydrobenzo[b][1,4]diazepine-2,4-dione Using an appropriate starting material and following the procedure of Example 7, the object compound was synthesized.

White Powder

Melting Point 155 to 156° C.

Example 565

Synthesis of 1,3,3,5-Tetramethyl-7-(3-{[2-(4-oxo-4H-furo[3,2-c]pyridin-5-yl)ethyl]pyridin-4-ylmethylamino}propoxy)-1,5-dihydrobenzo[b][1,4]diazepine-2,4-dione dihydrochloride Using an appropriate starting material and following the procedure of Example 7 and Example 6, the object compound was synthesized.

Colorless Solid

Melting Point 149 to 153° C.

$^1$H-NMR (DMSO-d$_6$) δppm:

0.76 (3H, s), 1.32 (3H, s), 1.73-2.42 (2H, m), 3.30 (3H, s), 3.32 (3H, s), 2.80-3.50 (4H, m), 3.83-4.81 (6H, m), 6.65-6.90 (3H, m), 6.94 (1H, d, J=1.6 Hz), 7.35 (1H, d, J=8.9 Hz), 7.71 (1H, d, J=7.5 Hz), 7.91 (1H, d, J=2.1 Hz), 7.95-8.35 (2H, m), 8.60-9.03 (2H, m).

Example 566

Synthesis of 1-ethyl-3,3,5-trimethyl-7-(3-{[2-(2-methyl-4-oxo-4H-furo[3,2-c]pyridin-5-yl)ethyl]pyrimidin-5-ylmethylamino}-propoxy)-1,5-dihydrobenzo[b][1,4]diazepine-2,4-dione Using an appropriate starting material and following the procedure of Example 7, the object compound was synthesized.

White Powder

Melting Point 154° C.

Example 567

Synthesis of 1-Ethyl-3,3,5-trimethyl-7-{3-[[2-(2-methyl-4-oxo-4H-furo[3,2-c]pyridin-5-yl)ethyl]-(2-methylpyridin-3-ylmethyl)amino]propoxy}-1,5-dihydrobenzo[b][1,4]diazepine-2,4-dione Using an appropriate starting material and following the procedure of Example 7, the object compound was synthesized.

White Powder

Melting Point 128 to 129° C.

Example 568

Synthesis of 1-ethyl-3,3,5-trimethyl-7-(3-{[2-(4-oxo-4H-thieno[3,2-c]pyridin-5-yl)ethyl]pyridin-3-ylmethylamino}-propoxy)-1,5-dihydrobenzo[b][1,4]diazepine-2,4-dione Using an appropriate starting material and following the procedure of Example 7, the object compound was synthesized.

Ivory White Powder
Melting Point 114° C.

Example 569

Synthesis of 1-ethyl-3,3,5-trimethyl-7-{3-[[2-(2-methyl-4-oxo-4H-furo[3,2-c]pyridin-5-yl)ethyl]-(3-methylpyridin-4-ylmethyl)amino]propoxy}-1,5-dihydrobenzo[b][1,4]diazepine-2,4-dione dihydrochloride Using an appropriate starting material and following the procedure of Example 7 and Example 6, the object compound was synthesized.
White Amorphous
$^1$H-NMR (DMSO-d$_6$) δppm:
0.75 (3H, s), 1.02 (3H, t, J=7.0 Hz), 1.32 (3H, s), 1.78-2.08 (2H, m), 2.27-2.46 (5H, m), 2.60-3.07 (3H, m), 3.31 (3H, s), 3.62-3.77 (2H, m), 3.79-5.39 (8H, m), 6.39-6.58 (1H, m), 6.58-6.74 (1H, m), 6.80-6.90 (2H, m), 7.39 (1H, d, J=9.0 Hz), 7.45-7.59 (1H, m), 7.61-7.95 (1H, m), 8.30-8.61 (1H, m), 8.64-8.81 (1H, m)

Example 570

Synthesis of 1-ethyl-3,3,5-trimethyl-7-{3-[[2-(2-methyl-4-oxo-4H-furo[3,2-c]pyridin-5-yl)ethyl]-(2-methylpyridin-4-ylmethyl)amino]propoxy}-1,5-dihydrobenzo[b][1,4]diazepine-2,4-dione dihydrochloride Using an appropriate starting material and following the procedure of Example 7 and Example 6, the object compound was synthesized.
White Amorphous
$^1$H-NMR (DMSO-d$_6$) δppm:
0.75 (3H, s), 1.01 (3H, t, J=7.0 Hz), 1.33 (3H, s), 2.03-2.38 (2H, m), 2.39 (3H, s), 2.55-2.78 (3H, m), 3.00-3.54 (5H, m), 3.62-3.71 (1H, m), 3.89-4.18 (5H, m), 4.26-4.64 (4H, m), 6.55 (1H, s), 6.67-6.76 (1H, m), 6.77-6.93 (2H, m), 7.39 (1H, d, J=9.0 Hz), 7.58-7.64 (1H, m) 7.79-8.25 (2H, m), 8.60-8.78 (1H, m)

Example 571

Synthesis of 7-(3-{(5-chloro-pyridin-2-ylmethyl)-[2-(2-methyl-4-oxo-4H-furo[3,2-c]pyridin-5-yl)ethyl]-amino}-propoxy)-1-ethyl-3,3,5-trimethyl-1,5-dihydrobenzo[b][1,4]diazepine-2,4-dione dihydrochloride Using an appropriate starting material and following the procedure of Example 7 and Example 6, the object compound was synthesized.
White Amorphous
$^1$H-NMR (DMSO-d$_6$) δppm:
0.75 (3H, s), 1.01 (3H, t, J=7.1 Hz), 1.32 (3H, s), 2.20-2.32 (2H, m), 2.40 (3H, s), 3.31 (3H, s) 3.37-3.46 (2H, m), 3.49-3.58 (2H, m), 3.60-3.71 (1H, m), 3.99-4.69 (7H, m), 6.56 (1H, s), 6.78 (1H, d, J=7.4 Hz), 6.86-6.90 (2H, m), 7.38-7.43 (1H, m), 7.64 (1H, d, J=7.3 Hz), 7.68-7.73 (1H, m) 8.04-8.09 (1H, m), 8.54 (1H, s)

Example 572

Synthesis of 1-ethyl-7-(3-{(6-methoxy-pyridin-3-ylmethyl)-[2-(2-methyl-4-oxo-4H-furo[3,2-c]pyridin-5-yl)ethyl]amino}-propoxy)-3,3,5-trimethyl-1,5-dihydrobenzo[b][1,4]diazepine-2,4-dione Using an appropriate starting material and following the procedure of Example 7, the object compound was synthesized.
White Powder
Melting Point 114 to 116° C.

Example 573

Synthesis of 1-ethyl-3,3,5-trimethyl-7-{3-[[2-(2-methyl-4-oxo-4H-furo[3,2-c]pyridin-5-yl)ethyl]-(4-methylpyridin-3-ylmethyl)amino]propoxy}-1,5-dihydrobenzo[b][1,4]diazepine-2,4-dione Using an appropriate starting material and following the procedure of Example 7, the object compound was synthesized.
White Powder
Melting Point 147 to 148° C.

Example 574

Synthesis of 1-ethyl-7-(3-{(6-methoxy-pyridin-3-ylmethyl)-[2-(4-oxo-4H-furo[3,2-c]pyridin-5-yl)ethyl]amino}propoxy)-3,3,5-trimethyl-1,5-dihydrobenzo[b][1,4]diazepine-2,4-dione Using an appropriate starting material and following the procedure of Example 7, the object compound was synthesized.
White Powder
Melting Point 111 to 113° C.

Example 575

Synthesis of 1-ethyl-3,3,5-trimethyl-7-(3-{(2-methylpyridin-3-ylmethyl)-[2-(4-oxo-4H-furo[3,2-c]pyridin-5-yl)ethyl]-amino}propoxy)-1,5-dihydrobenzo[b][1,4]diazepine-2,4-dione Using an appropriate starting material and following the procedure of Example 7, the object compound was synthesized.
White Powder
Melting Point 111 to 114° C.

Example 576

Synthesis of 1-ethyl-3,3,5-trimethyl-7-(3-{[2-(1-oxo-1H-isoquinolin-2-yl)ethyl]pyridin-2-ylmethylamino}propoxy)-1,5-dihydrobenzo[b][1,4]diazepine-2,4-dione Using an appropriate starting material and following the procedure of Example 7, the object compound was synthesized.

White Solid
Melting Point 94.6 to 95.4° C.

Example 577

Synthesis of 1-ethyl-3,3,5-trimethyl-7-{3-[(2-pyridin-3-yl-ethyl)-quinolin-4-ylmethylamino]propoxy}-1,5-dihydrobenzo[b][1,4]diazepine-2,4-dione trihydrochloride Using an appropriate starting material and following the procedure of Example 7 and Example 6, the object compound was synthesized.
White Powder
Melting Point 139 to 143° C.

Example 578

Synthesis of 1-ethyl-3,3,5-trimethyl-7-(3-{(4-methylpyridin-3-ylmethyl)-[2-(7-oxo-7H-furo[2,3-c]pyridin-6-yl)ethyl]-amino}propoxy)-1,5-dihydrobenzo[b][1,4]diazepine-2,4-dione Using an appropriate starting material and following the procedure of Example 7, the object compound was synthesized.
White Powder
Melting Point 123 to 124° C.

Example 579

Synthesis of 1-ethyl-3,3,5-trimethyl-7-{3-[[2-(4-oxo-4H-furo[3,2-c]pyridin-5-yl)ethyl]-(2-pyridin-3-yl-ethyl)amino]propoxy}-1,5-dihydrobenzo[b][1,4]diazepine-2,4-dione dihydrochloride Using an appropriate starting material and following the procedure of Example 7 and Example 6, the object compound was synthesized.
White Amorphous
$^1$H-NMR (D$_2$O) δppm:
0.64 (3H, s), 0.96 (3H, t, J=7.0 Hz), 1.29 (3H, s), 2.21 (2H, quin, J=2.8 Hz), 3.25 (3H, s), 3.27-3.35 (2H, m), 3.55 (2H, t, J=7.0 Hz), 3.57-3.69 (3H, m), 3.71 (2H, t, J=5.4 Hz), 4.02 (1H, dq, J=7.0, 7.0 Hz), 4.12 (2H, t, J=5.4 Hz), 4.38-4.53 (2H, m), 6.75 (1H, s), 6.81-6.93 (3H, m), 7.33 (1H, d, J=9.0 Hz), 7.50 (1H, d, 7.5 Hz), 7.58-7.65 (1H, m), 7.77-7.90 (1H, m), 8.30-8.40 (1H, m), 8.57 (1H, d, J=5.6 Hz), 8.61 (1H, s)

Example 580

Synthesis of 1-ethyl-7-(3-{(4-methoxy-benzyl)-[2-(4-oxo-4H-furo[3,2-c]pyridin-5-yl)ethyl]amino}propoxy)-3,3,5-trimethyl-1,5-dihydrobenzo[b][1,4]diazepine-2,4-dione hydrochloride Using an appropriate starting material and following the procedure of Example 7 and Example 6, the object compound was synthesized.
White Powder
Melting Point 116.3 to 120° C. (dec.)

Example 581

Synthesis of 1-ethyl-3,3,5-trimethyl-7-(3-{(6-methylpyridin-3-ylmethyl)-[2-(7-oxo-7H-furo[2,3-c]pyridin-6-yl)ethyl]-amino}propoxy)-1,5-dihydrobenzo[b][1,4]diazepine-2,4-dione Using an appropriate starting material and following the procedure of Example 7, the object compound was synthesized.
White Powder
Melting Point 120 to 122° C.

Example 582

Synthesis of 1-ethyl-3,3,5-trimethyl-7-{3-[[2-(2-methyl-4-oxo-4H-furo[3,2-c]pyridin-5-yl)ethyl]-(6-methylpyridin-3-ylmethyl)amino]propoxy}-1,5-dihydrobenzo[b][1,4]diazepine-2,4-dione Using an appropriate starting material and following the procedure of Example 7, the object compound was synthesized.
White Powder
Melting Point 136 to 138° C.

Example 583

Synthesis of 1-ethyl-3,3,5-trimethyl-7-(3-{(6-methylpyridin-3-ylmethyl)-[2-(4-oxo-4H-furo[3,2-c]pyridin-5-yl)ethyl]-amino}propoxy)-1,5-dihydrobenzo[b][1,4]diazepine-2,4-dione Using an appropriate starting material and following the procedure of Example 7, the object compound was synthesized.
White Powder
$^1$H-NMR (CDCl$_3$) δppm:
0.86 (3H, s), 1.15 (3H, t, J=7.1 Hz), 1.53 (3H, s), 1.86-1.95 (2H, m), 2.48 (3H, s), 2.70 (2H, t, J=6.8 Hz), 2.85 (2H, t, J=6.2 Hz), 3.39 (3H, s), 3.63 (2H, s), 3.65-3.75 (1H, m), 3.86 (2H, t, J=6.1 Hz), 4.06 (2H, t, J=6.1 Hz), 4.14-4.22 (1H, m), 6.41 (1H, dd, J=7.4, 0.8 Hz), 6.62 (1H, d, J=2.7 Hz), 6.67 (1H, dd, J=9.0, 2.4 Hz), 6.90-6.95 (2H, m), 7.07 (1H, d, J=7.4 Hz), 7.18 (1H, d, J=8.9 Hz), 7.35-7.42 (1H, m), 7.47 (1H, d, J=2.1 Hz), 8.31 (1H, d, J=1.8 Hz))

Example 584

Synthesis of 1-ethyl-3,3,5-trimethyl-7-{3-[(2-pyridin-3-yl-ethyl)-quinolin-5-ylmethylamino]propoxy}-1,5-dihydrobenzo[b][1,4]diazepine-2,4-dione trihydrochloride Using an appropriate starting material and following the procedure of Example 7 and Example 6, the object compound was synthesized.
Pale Yellow White Amorphous
$^1$H-NMR (D$_2$O) δppm:
0.66 (3H, s), 0.97 (3H, t, J=7.1 Hz), 1.30 (3H, s), 2.12-2.37 (2H, m), 3.25 (3H, s), 3.36-3.57 (4H, m), 3.57-3.74 (3H, m), 3.93-4.10 (3H, m), 5.08 (2H, s), 6.69 (1H, dd, J=9.0 and 2.8 Hz), 6.71 (1H, d, J=2.8 Hz), 7.30 (1H, d, J=9.0 Hz), 7.93 (1H, dd, J=8.0 and 5.8 Hz), 7.98-8.13 (3H, m), 8.23 (1H, d, J=8.3

Hz), 8.43 (1H, d, J=8.3 Hz), 8.63 (1H, d, J=5.7 Hz), 8.67 (1H, s), 9.04-9.13 (1H, m), 9.23 (1H, d, J=8.7 Hz)

Example 585

Synthesis of 5-Ethyl-1,3,3-trimethyl-7-(3-{[2-(1-oxo-5,6,7,8-tetrahydro-1H-isoquinolin-2-yl)ethyl]pyridin-4-ylmethylamino}propoxy)-1,5-dihydrobenzo[b][1,4]diazepine-2,4-dione dihydrochloride Using an appropriate starting material and following the procedure of Example 7, the object compound was synthesized.
White Powder
$^1$H-NMR (DMSO-D$_6$) δppm:
0.75 (3H, s), 1.01 (3H, t, J=7.0 Hz), 1.32 (3H, s), 1.49-1.74 (4H, m), 2.03-2.40 (4H, m), 2.90-3.41 (4H, m), 3.32 (3H, s), 3.56-4.84 (10H, m), 6.02 (1H, d, J=6.8 Hz), 6.79-7.00 (2H, m), 7.31-7.57 (2H, m), 7.93-8.25 (2H, m), 8.68-9.08 (2H, m).

Example 586

Synthesis of 1-ethyl-3,3,5-trimethyl-7-(3-{(2-methyl-2H-pyrazol-3-ylmethyl)-[2-(1-oxo-1H-isoquinolin-2-yl)ethyl]-amino}propoxy)-1,5-dihydrobenzo[b][1,4]diazepine-2,4-dione Using an appropriate starting material and following the procedure of Example 7, the object compound was synthesized.
White Powder
Melting Point 96 to 99° C.

Example 587

Synthesis of 7-{3-[benzothiazol-2-ylmethyl-(2-pyridin-3-yl-ethyl)amino]propoxy}-1-ethyl-3,3,5-trimethyl-1,5-dihydrobenzo[b][1,4]diazepine-2,4-dione dihydrochloride Using an appropriate starting material and following the procedure of Example 7 and Example 6, the object compound was synthesized.
White Amorphous
$^1$H-NMR (D$_2$O) δppm:
0.60 (3H, s), 0.95 (3H, t, J=7.1 Hz), 1.28 (3H, s), 2.06-2.37 (2H, m), 3.07 (3H, s), 3.34-3.43 (2H, m), 3.47-3.56 (2H, m), 3.59 (1H, dq, J=7.0, 7.0 Hz), 3.63-3.73 (2H, m), 3.98 (1H, dq, J=7.0, 7.0 Hz), 4.03-4.16 (2H, m), 4.85 (1H, d, J=15.2 Hz), 4.89 (1H, d, J=15.2 Hz), 6.51 (1H, d, J=2.8 Hz), 6.71 (1H, dd, J=9.1 and 2.8 Hz), 7.20 (1H, d, J=9.1 Hz), 7.38-7.53 (2H, m), 7.83 (1H, d, J=8.0 Hz), 7.87 (1H, dd, J=8.0 and 5.8 Hz), 7.91 (1H, d, J=8.0 Hz), 8.43 (1H, d, J=8.0 Hz), 8.56 (1H, d, J=5.8 Hz), 8.66 (1H, s)

Example 588

Synthesis of 1-ethyl-3,3,5-trimethyl-7-(3-{(5-methylpyridin-3-ylmethyl)-[2-(7-oxo-7H-furo[2,3-c]pyridin-6-yl)ethyl]-amino}propoxy)-1,5-dihydrobenzo[b][1,4]diazepine-2,4-dione Using an appropriate starting material and following the procedure of Example 7, the object compound was synthesized.
White Powder
Melting Point 130 to 131° C.

Example 589

Synthesis of 1-ethyl-3,3,5-trimethyl-7-{3-[[2-(2-methyl-4-oxo-4H-furo[3,2-c]pyridin-5-yl)ethyl]-(5-methylpyridin-3-ylmethyl)amino]propoxy}-1,5-dihydrobenzo[b][1,4]diazepine-2,4-dione Using an appropriate starting material and following the procedure of Example 7, the object compound was synthesized.
White Powder
Melting Point 125 to 127° C.

Example 590

Synthesis of 1-ethyl-3,3,5-trimethyl-7-(3-{(4-methylpyridin-3-ylmethyl)-[2-(4-oxo-4H-furo[3,2-c]pyridin-5-yl)ethyl]-amino}propoxy)-1,5-dihydrobenzo[b][1,4]diazepine-2,4-dione Using an appropriate starting material and following the procedure of Example 7, the object compound was synthesized.
White Powder
$^1$H-NMR (CDCl$_3$) δppm:
0.86 (3H, s), 1.15 (3H, t, J=7.0 Hz), 1.53 (3H, s), 1.91-2.01 (2H, m), 2.25 (3H, s), 2.76 (2H, t, J=6.8 Hz), 2.87 (2H, t, J=6.5 Hz), 3.39 (3H, s), 3.65-3.74 (3H, m), 3.91 (2H, t, J=6.2 Hz), 4.02 (2H, t, J=6.4 Hz) 4.11-4.22 (1H, m), 6.41 (1H, d, J=7.3 Hz), 6.65 (1H, d, J=2.6 Hz), 6.70 (1H, dd, J=8.9, 2.7 Hz), 6.91-6.97 (3H, m), 7.17 (1H, d, J=9.0 Hz), 7.47 (1H, d, J=2.0 Hz), 8.32 (1H, d, J=4.8 Hz), 8.40 (1H, s)

Example 591

Synthesis of 1-ethyl-3,3,5-trimethyl-7-(3-{(2-methylpyridin-3-ylmethyl)-[2-(7-oxo-7H-thieno[2,3-c]pyridin-6-yl)ethyl]-amino}propoxy)-1,5-dihydrobenzo[b][1,4]diazepine-2,4-dione Using an appropriate starting material and following the procedure of Example 7, the object compound was synthesized.
White Powder
Melting Point 115 to 117° C.

Example 592

Synthesis of 7-{3-[(2,5-dimethyl-2H-pyrazol-3-ylmethyl)-(2-pyridin-3-ylethyl)amino]propoxy}-1-ethyl-3,3,5-trimethyl-1,5-dihydrobenzo[b][1,4]diazepine-2,4-dione trihydrochloride Using an appropriate starting material and following the procedure of Example 7 and Example 6, the object compound was synthesized.
White Amorphous
$^1$H-NMR (D$_2$O) δppm:
0.70 (3H, s), 0.97 (3H, t, J=7.0 Hz), 1.30 (3H, s), 2.06 (3H, s), 2.13-2.30 (2H, m), 3.29 (3H, s), 3.30-3.37 (2H, m), 3.37-3.48 (2H, m), 3.48-3.68 (3H, m), 3.73 (3H, s), 4.03 (1H, dq, J=7.0, 7.0 Hz), 4.09 (2H, t, J=5.4 Hz), 4.53 (2H, s), 6.30 (1H, s), 6.84 (1H, d, J=2.7 Hz), 6.87 (1H, dd, J=9.0 and 2.7 Hz), 7.36 (1H, d, J=9.0 Hz), 7.95 (1H, dd, J=8.0 and 5.9 Hz)), 8.44 (1H, d, J=8.0 Hz), 8.64 (1H, d, J=5.9 Hz), 8.66 (1H, s)

Example 593

Synthesis of 1-ethyl-3,3,5-trimethyl-7-{3-[(4-methyl-thiazol-5-ylmethyl)-(2-pyridin-3-yl-ethyl)amino]propoxy}-1,5-dihydrobenzo[b][1,4]diazepine-2,4-dione dihydrochloride Using an appropriate starting material and following the procedure of Example 7 and Example 6, the object compound was synthesized.
White Powder
Melting Point 175 to 185° C.

Example 594

Synthesis of 1-ethyl-3,3,5-trimethyl-7-(3-{(5-methylpyridin-3-ylmethyl)-[2-(4-oxo-4H-furo[3,2-c]pyridin-5-yl)ethyl]-amino}propoxy)-1,5-dihydrobenzo[b][1,4]diazepine-2,4-dione Using an appropriate starting material and following the procedure of Example 7, the object compound was synthesized.
White Powder
Melting Point 128 to 129° C.

Example 595

Synthesis of 1-ethyl-3,3,5-trimethyl-7-(3-{(2-methylpyridin-3-ylmethyl)-[2-(4-oxo-4H-thieno[3,2-c]pyridin-5-yl)ethyl]-amino}propoxy)-1,5-dihydrobenzo[b][1,4]diazepine-2,4-dione Using an appropriate starting material and following the procedure of Example 7, the object compound was synthesized.
White Powder
Melting Point 95 to 98° C.

Example 596

Synthesis of 1-ethyl-3,3,5-trimethyl-7-{3-[[2-(2-methyl-4-oxo-4H-furo[3,2-c]pyridin-5-yl)ethyl]-(2-methyl-2H-pyrazol-3-ylmethyl)amino]propoxy}-1,5-dihydrobenzo[b][1,4]diazepine-2,4-dione Using an appropriate starting material and following the procedure of Example 7, the object compound was synthesized.
White Powder
Melting Point 119 to 121° C.

Example 597

Synthesis of 7-(3-{(1,5-dimethyl-1H-pyrazol-4-ylmethyl)-[2-(1-oxo-1H-isoquinolin-2-yl)ethyl]amino}propoxy)-1-ethyl-3,3,5-trimethyl-1,5-dihydrobenzo[b][1,4]diazepine-2,4-dione dihydrochloride Using an appropriate starting material and following the procedure of Example 7 and Example 6, the object compound was synthesized.

White Amorphous
$^1$H-NMR (DMSO-$d_6$) δppm:
0.75 (3H, s), 1.01 (3H, t, J=7.2 Hz), 1.32 (3H, s), 2.22-2.38 (5H, m), 3.20-3.41 (5H, m), 3.41-3.49 (2H, m), 3.72 (3H, s), 4.04-4.17 (4H, m), 4.26-4.38 (2H, m), 4.40-4.47 (2H, m), 6.74 (1H, d, J=7.4 Hz), 6.88-6.95 (2H, m), 7.42 (1H, d, J=8.9 Hz), 7.51-7.56 (2H, m), 7.62 (1H, s), 7.66-7.78 (2H, m), 8.24 (1H, d, J=8.0 Hz)

Example 598

Synthesis of 1-ethyl-3,3,5-trimethyl-7-(3-{(6-methylpyridin-3-ylmethyl)-[2-(1-oxo-1H-isoquinolin-2-yl)ethyl]amino}-propoxy)-1,5-dihydrobenzo[b][1,4]diazepine-2,4-dione Using an appropriate starting material and following the procedure of Example 7, the object compound was synthesized.
White Powder
Melting Point 140 to 142° C.

Example 599

Synthesis of 1-ethyl-3,3,5-trimethyl-7-(3-{(6-methylpyridin-3-ylmethyl)-[2-(4-oxo-4H-thieno[3,2-c]pyridin-5-yl)ethyl]-amino}propoxy)-1,5-dihydrobenzo[b][1,4]diazepine-2,4-dione Using an appropriate starting material and following the procedure of Example 7, the object compound was synthesized.
White Powder
Melting Point 126 to 129° C.

Example 600

Synthesis of 1-ethyl-3,3,5-trimethyl-7-(3-{(6-methylpyridin-3-ylmethyl)-[2-(7-oxo-7H-thieno[2,3-c]pyridin-6-yl)ethyl]-amino}propoxy)-1,5-dihydrobenzo[b][1,4]diazepine-2,4-dione Using an appropriate starting material and following the procedure of Example 7, the object compound was synthesized.
White Powder
Melting Point 120 to 122° C.

Example 601

Synthesis of 1-ethyl-3,3,5-trimethyl-7-(3-{(2-methylpyridin-3-ylmethyl)-[2-(1-oxo-1H-isoquinolin-2-yl)ethyl]amino}-propoxy)-1,5-dihydrobenzo[b][1,4]diazepine-2,4-dione Using an appropriate starting material and following the procedure of Example 7, the object compound was synthesized.

147

White Powder

Melting Point 98 to 102° C.

Example 602

Synthesis of 1-ethyl-3,3,5-trimethyl-7-(3-{[2-(2-methyl-4-oxo-4H-furo[3,2-c]pyridin-5-yl)ethyl]thiazol-2-ylmethylamino}propoxy)-1,5-dihydrobenzo[b][1,4]diazepine-2,4-dione Using an appropriate starting material and following the procedure of Example 7, the object compound was synthesized.

White Powder

Melting Point 175 to 176° C.

Example 603

Synthesis of 1-ethyl-3,3,5-trimethyl-7-(3-{[2-(2-methyl-4-oxo-4H-furo[3,2-c]pyridin-5-yl)ethyl]oxazol-2-ylmethylamino}propoxy)-1,5-dihydrobenzo[b][1,4]diazepine-2,4-dione Using an appropriate starting material and following the procedure of Example 7, the object compound was synthesized.

White Powder

Melting Point 130 to 131° C.

Example 604

Synthesis of 1-ethyl-3,3,5-trimethyl-7-(3-{[2-(2-methyl-4-oxo-4H-furo[3,2-c]pyridin-5-yl)ethyl]thiazol-5-ylmethylamino}propoxy)-1,5-dihydrobenzo[b][1,4]diazepine-2,4-dione Using an appropriate starting material and following the procedure of Example 7, the object compound was synthesized.

White Powder

Melting Point 181 to 183° C.

Example 605

Synthesis of 1-ethyl-3,3,5-trimethyl-7-(3-{[2-(2-methyl-4-oxo-4H-furo[3,2-c]pyridin-5-yl)ethyl]oxazol-5-ylmethylamino}propoxy)-1,5-dihydrobenzo[b][1,4]diazepine-2,4-dione Using an appropriate starting material and following the procedure of Example 7, the object compound was synthesized.

White Powder $^1$H-NMR (CDCl$_3$) δppm:

0.86 (3H, s), 1.15 (3H, t, J=7.0 Hz), 1.53 (3H, s), 1.83-1.90 (2H, m), 2.40 (3H, s), 2.65-2.75 (2H, m), 2.83-2.92 (2H, m), 3.40 (3H, s), 3.65-3.72 (1H, m), 3.79 (2H, s), 3.82-3.88 (2H, m) 4.03-4.08 (2H, m), 4.10-4.22 (1H, m), 6.35 (1H, d, J=7.3 Hz), 6.54 (1H, s), 6.63-6.73 (2H, m), 6.92 (1H, s), 7.09 (1H, d, J=7.4 Hz), 7.18 (1H, d, J=8.9 Hz), 7.74 (1H, s)

148

Example 606

Synthesis of 1-ethyl-3,3,5-trimethyl-7-(3-[([2-(2-methyl-4-oxo-4H-furo[3,2-c]pyridin-5-yl)ethyl]thiazol-4-ylmethylamino]propoxy)-1,5-dihydrobenzo[b][1,4]diazepine-2,4-dione Using an appropriate starting material and following the procedure of Example 7, the object compound was synthesized.

White Powder

Melting Point 136 to 137° C.

Example 607

Synthesis of 1-ethyl-3,3,5-trimethyl-7-(3-{[2-(2-methyl-4-oxo-4H-furo[3,2-c]pyridin-5-yl)ethyl]oxazol-4-ylmethylamino}propoxy)-1,5-dihydrobenzo[b][1,4]diazepine-2,4-dione Using an appropriate starting material and following the procedure of Example 7, the object compound was synthesized.

White Powder

Melting Point 119 to 120° C.

Example 608

Synthesis of 1-ethyl-7-(3-{(2-ethylpyridin-3-ylmethyl)-[2-(4-oxo-4H-furo[3,2-c]pyridin-5-yl)ethyl]amino}propoxy)-3,3,5-trimethyl-1,5-dihydrobenzo[b][1,4]diazepine-2,4-dione dihydrochloride Using an appropriate starting material and following the procedure of Example 7 and Example 6, the object compound was synthesized.

White Amorphous $^1$H-NMR (DMSO-d$_6$) δppm:

0.75 (3H, s), 1.01 (3H, t, J=7.0 Hz), 1.15-1.31 (3H, m), 1.33 (3H, s), 1.75-2.41 (2H, m), 2.93-3.26 (3H, m), 3.31 (3H, s), 3.54-4.93 (11H, m), 6.58-7.03 (4H, m), 7.39 (1H, d, J=8.9 Hz), 7.46-7.85 (2H, m), 7.90 (1H, s), 8.42-8.92 (2H, m)

Example 609

Synthesis of 1-ethyl-7-(3-{(2-ethylpyridin-3-ylmethyl)-[2-(2-methyl-4-oxo-4H-furo[3,2-c]pyridin-5-yl)ethyl]amino}-propoxy)-3,3,5-trimethyl-1,5-dihydrobenzo[b][1,4]diazepine-2,4-dione dihydrochloride Using an appropriate starting material and following the procedure of Example 7 and Example 6, the object compound was synthesized.

White Amorphous $^1$H-NMR (DMSO-d$_6$) δppm:

0.75 (3H, s), 1.01 (3H, t, J=7.0 Hz), 1.15-1.31 (3H, m), 1.32 (3H, s), 1.82-2.00 (2H, m), 2.39 (3H, s), 2.63-2.92 (2H, m), 2.93-3.20 (2H, m), 3.31 (3H, s), 3.51-4.88 (10H, m), 6.38-

6.53 (2H, m), 6.54-6.92 (2H, m), 7.39 (1H, d, J=9.0 Hz), 7.40-7.77 (2H, m), 8.09-8.80 (2H, m)

Example 610

Synthesis of 1-ethyl-3,3,5-trimethyl-7-{3-[[2-(4-oxo-4H-furo[3,2-c]pyridin-5-yl)ethyl]-(2-propylpyridin-3-ylmethyl)amino]propoxy}-1,5-dihydrobenzo[b][1,4]diazepine-2,4-dione dihydrochloride Using an appropriate starting material and following the procedure of Example 7 and Example 6, the object compound was synthesized.
White Amorphous
$^1$H-NMR (DMSO-$D_6$) δppm:
0.76 (3H, s), 0.90 (3H, t, J=6.7 Hz), 1.02 (3H, t, J=7.0 Hz), 1.33 (3H, s), 1.51-1.72 (2H, m), 1.73-2.00 (2H, m), 2.61-3.12 (4H, m), 3.31 (3H, s), 3.33-4.10 (10H, m), 6.55-7.03 (4H, m), 7.39 (1H, d, J=9.0 Hz), 7.43-7.68 (2H, m), 7.85-7.95 (1H, m), 8.10-8.78 (2H, m)

Example 611

Synthesis of 1-ethyl-3,3,5-trimethyl-7-{3-[[2-(2-methyl-4-oxo-4H-furo[3,2-c]pyridin-5-yl)ethyl]-(2-propylpyridin-3-ylmethyl)amino]propoxy}-1,5-dihydrobenzo[b][1,4]diazepine-2,4-dione dihydrochloride Using an appropriate starting material and following the procedure of Example 7 and Example 6, the object compound was synthesized.
White Amorphous
$^1$H-NMR (DMSO-$d_6$) δppm:
0.75 (3H, s), 0.91 (3H, t, J=7.1 Hz), 1.02 (3H, t, J=7.0 Hz), 1.33 (3H, s), 1.55-1.76 (2H, m), 2.39 (3H, s), 2.51-2.88 (2H, m), 2.90-3.19 (2H, m), 3.31 (3H, s), 3.55-4.81 (12H, m), 6.42-6.70 (2H, m), 6.78-6.92 (2H, m), 7.39 (1H, d, J=8.9 Hz), 7.43-7.88 (2H, m), 7.92-8.89 (2H, m)

Example 612

Synthesis of 1-ethyl-3,3,5-trimethyl-7-{3-[(2-pyridin-3-yl-ethyl)thiazol-5-ylmethylamino]propoxy}-1,5-dihydrobenzo[b][1,4]diazepine-2,4-dione dihydrochloride Using an appropriate starting material and following the procedure of Example 7 and Example 6, the object compound was synthesized.
White Powder
Melting Point 163 to 166° C.

Example 613

Synthesis of 7-{3-[(2,5-dimethyl-oxazol-4-ylmethyl)-(2-pyridin-3-yl-ethyl)amino]propoxy}-1-ethyl-3,3,5-trimethyl-1,5-dihydrobenzo[b][1,4]diazepine-2,4-dione dihydrochloride Using an appropriate starting material and following the procedure of Example 7 and Example 6, the object compound was synthesized.
$^1$H-NMR (DMSO-$d_6$) δppm:
0.74 (3H, s), 0.99 (3H, t, J=7.0 Hz), 1.31 (3H, s), 2.20-2.30 (2H, m), 2.36 (3H, s), 2.38 (3H, s), 2.70-3.85 (6H, m), 3.31 (3H, s), 3.66 (1H, dq, J=7.0, 7.0 Hz), 4.05 (1H, dq, J=7.0, 7.0 Hz), 4.12 (2H, t, J=6.0 Hz), 4.33 (2H, bs), 6.92 (1H, dd, J=8.9 and 2.8 Hz), 6.94 (1H, d, J=2.8 Hz), 7.42 (1H, d, J=8.9 Hz), 7.71 (1H, bs), 8.13 (1H, bs), 8.61-8.70 (1H, m), 8.72 (1H, s), 10.60 (1H, bs)

Example 614

Synthesis of N-(2-{[[3-(1-ethyl-3,3,5-trimethyl-2,4-dioxo-2,3,4,5-tetrahydro-1H-benzo[b][1,4]diazepin-7-yloxy)propyl]-(2-pyridin-3-yl-ethyl)amino]methyl}phenyl)methanesulfonamide dihydrochloride Using an appropriate starting material and following the procedure of Example 7 and Example 6, the object compound was synthesized.
White Amorphous
$^1$H-NMR (DMSO-$d_6$) δppm:
0.73 (3H, s), 0.99 (3H, t, J=7.0 Hz), 1.30 (3H, s), 2.2-2.35 (2H, m), 3.04 (3H, s), 3.05-3.95 (6H, m), 3.30 (3H, s), 3.65 (1H, dq, J=7.0, 7.0 Hz), 4.04 (1H, dq, J=7.0, 7.0 Hz), 4.04-4.20 (2H, m), 4.59 (2H, bs), 6.82-6.95 (2H, m), 7.33-7.50 (3H, m), 7.50-7.60 (1H, m), 7.60-7.75 (1H, m), 7.84 (1H, d, J=6.8 Hz), 7.96-8.16 (1H, m), 8.57-8.70 (1H, m), 8.68 (1H, bs)), 10.37 (1H, bs)

Example 615

Synthesis of 1-ethyl-3,3,5-trimethyl-7-(4-{(2-methylpyridin-3-ylmethyl)-[2-(4-oxo-4H-furo[3,2-c]pyridin-5-yl)ethyl]-amino}butoxy)-1,5-dihydrobenzo[b][1,4]diazepine-2,4-dione dihydrochloride Using an appropriate starting material and following the procedure of Example 7 and Example 6, the object compound was synthesized.
White Amorphous
$^1$H-NMR (DMSO-$d_6$) δppm:
0.75 (3H, s), 1.01 (3H, t, J=7.1 Hz), 1.32 (3H, s), 1.62-2.14 (4H, m), 2.39 (3H, s), 2.50-2.53 (3H, m), 2.73-3.08 (4H, m), 3.14-4.85 (11H, m), 6.70-6.85 (1H, m), 6.86-7.02 (3H, m), 7.40 (1H, d, J=8.9 Hz), 7.67-7.99 (3H, m), 8.51-9.03 (2H, m)

Example 616

Synthesis of 1-ethyl-3,3,5-trimethyl-7-{4-[[2-(2-methyl-4-oxo-4H-furo[3,2-c]pyridin-5-yl)ethyl]-(2-methylpyridin-3-ylmethyl)amino]butoxy}-1,5-dihydrobenzo[b][1,4]diazepine-2,4-dione dihydrochloride Using an appropriate starting material and following the procedure of Example 7 and Example 6, the object compound was synthesized.
White Amorphous
$^1$H-NMR (DMSO-$d_6$) δppm:
0.75 (3H, s), 1.01 (3H, t, J=7.0 Hz), 1.32 (3H, s), 1.53-2.15 (4H, m), 2.39 (3H, s), 2.42-2.96 (7H, m), 3.26-4.88 (11H, m), 6.41-6.63 (1H, m), 6.65-6.84 (1H, m), 6.87-6.95 (2H, m), 7.40 (1H, d, J=8.8 Hz), 7.52-7.89 (2H, m), 8.46-8.88 (2H, m)

Example 617

Synthesis of 1-ethyl-3,3,5-trimethyl-7-(4-{(2-methylpyridin-3-ylmethyl)-[2-(1-oxo-1H-isoquinolin-2-yl)ethyl]amino}-butoxy)-1,5-dihydrobenzo[b][1,4]diazepine-2,4-dione dihydrochloride Using an appropriate starting material and following the procedure of Example 7 and Example 6, the object compound was synthesized.

White Amorphous
¹H-NMR (DMSO-d₆) δppm:
0.75 (3H, s), 1.01 (3H, t, J=7.1 Hz), 1.32 (3H, s), 1.60-2.14 (4H, m), 2.47-3.08 (7H, m), 3.16-4.77 (11H, m), 6.58-6.80 (1H, m), 6.83-7.00 (2H, m), 7.39 (1H, d, J=8.9 Hz), 7.43-7.62 (2H, m), 7.63-7.99 (3H, m), 8.12-8.30 (1H, m), 8.55-9.02 (2H, m)

Example 618

Synthesis of 1-ethyl-3,3,5-trimethyl-7-(4-{[2-(4-oxo-4H-furo[3,2-c]pyridin-5-yl)ethyl]pyridin-4-ylmethylamino}-butoxy)-1,5-dihydrobenzo[b][1,4]diazepine-2,4-dione dihydrochloride Using an appropriate starting material and following the procedure of Example 7 and Example 6, the object compound was synthesized.
White Amorphous
¹H-NMR (DMSO-d₆) δppm:
0.75 (3H, s), 1.01 (3H, t, J=7.1 Hz), 1.32 (3H, s), 1.42-1.91 (4H, m), 3.31 (3H, s), 3.33-4.71 (12H, m), 6.63-6.98 (4H, m), 7.39 (1H, d, J=8.7 Hz), 7.61-7.70 (1H, m), 7.77-7.94 (3H, m), 8.66-8.82 (2H, m)

Example 619

Synthesis of 1-ethyl-3,3,5-trimethyl-7-(4-{[2-(2-methyl-4-oxo-4H-furo[3,2-c]pyridin-5-yl)ethyl]pyridin-4-ylmethylamino}butoxy)-1,5-dihydrobenzo[b][1,4]diazepine-2,4-dione dihydrochloride Using an appropriate starting material and following the procedure of Example 7 and Example 6, the object compound was synthesized.
White Amorphous
¹H-NMR (DMSO-d₆) δppm:
0.75 (3H, s), 1.01 (3H, t, J=7.1 Hz), 1.31 (3H, s), 1.57-1.99 (4H, m), 2.49 (3H, s), 3.08-4.62 (15H, s), 6.53-6.58 (1H, m), 6.69-6.76 (1H, m), 6.86-6.94 (2H, m), 7.39 (1H, d, J=8.8 Hz), 7.58-7.65 (1H, m), 7.83-8.13 (2H, m), 8.72-8.89 (2H, m)

Example 620

Synthesis of 1-ethyl-3,3,5-trimethyl-7-(4-{[2-(1-oxo-1H-isoquinolin-2-yl)ethyl]pyridin-4-ylmethylamino}butoxy)-1,5-dihydrobenzo[b][1,4]diazepine-2,4-dione dihydrochloride Using an appropriate starting material and following the procedure of Example 7 and Example 6, the object compound was synthesized.
White Amorphous
¹H-NMR (DMSO-d₆) δppm:
0.75 (3H, s), 1.01 (3H, t, J=7.1 Hz), 1.32 (3H, s), 1.60-1.99 (4H, m), 3.07-4.70 (15H, m), 6.69 (1H, d, J=7.3 Hz), 6.83-6.98 (2H, m), 7.39 (1H, d, J=8.8 Hz) 7.48-7.55 (2H, m), 7.65-7.76 (2H, m), 7.82-8.12 (2H, m), 8.20 (1H, d, J=7.9 Hz), 8.70-8.93 (2H, m)

Example 621

Synthesis of 7-(3-{(2-chloro-pyridin-3-ylmethyl)-[2-(2-methyl-4-oxo-4H-furo[3,2-c]pyridin-5-yl)ethyl]amino}-propoxy)-1-ethyl-3,3,5-trimethyl-1,5-dihydrobenzo[b][1,4]diazepine-2,4-dione dihydrochloride Using an appropriate starting material and following the procedure of Example 7 and Example 6, the object compound was synthesized.

White Amorphous
¹H-NMR (DMSO-d₆) δppm:
0.75 (3H, s), 1.01 (3H, t, J=7.0 Hz), 1.32 (3H, s), 2.08-2.33 (2H, m), 2.39 (3H, s), 3.17-4.85 (15H, m), 6.57 (1H, s), 6.70-6.94 (3H, m), 7.40 (1H, d, J=9.0 Hz) 7.42-7.74 (2H, m), 8.21-8.57 (2H, m)

Example 622

Synthesis of 1-ethyl-3,3,5-trimethyl-7-(3-[([2-(2-methyl-4-oxo-4H-thieno[3,2-c]pyridin-5-yl)ethyl]pyridin-4-ylmethylamino]propoxy)-1,5-dihydrobenzo[b][1,4]diazepine-2,4-dione ¹H-NMR (CDCl₃) δppm:
0.87 (s, 3H), 1.16 (t, J=7.1 Hz, 3H), 1.53 (s, 3H), 1.81-1.94 (m, 2H), 2.56 (s, 3H), 2.72 (t, J=6.2 Hz, 2H), 2.83-2.90 (m, 2H), 3.38 (s, 3H), 3.67 (s, 2H), 3.66-3.78 (m, 1H), 3.88 (t, J=6.1 Hz, 2H), 4.08-4.23 (m, 3H), 6.48 (d, J=7.1 Hz, 1H), 6.53-6.62 (m, 3H), 6.96 (d, J=7.1 Hz, 1H), 7.07-7.08 (m, 2H), 7.19 (d, J=8.9 Hz, 1H), 8.28-8.32 (m, 2H).

Example 623

Synthesis of 1-ethyl-3,3,5-trimethyl-7-(3-{[2-(3-methyl-4-oxo-4H-furo[3,2-c]pyridin-5-yl)ethyl]pyridin-4-ylmethylamino}propoxy)-1,5-dihydrobenzo[b][1,4]diazepine-2,4-dione dihydrochloride Using an appropriate starting material and following the procedure of Example 7, the object compound was synthesized.
¹H-NMR (DMSO-d₆) δppm:
0.75 (s, 3H), 1.01 (t, J=7.0 Hz, 3H), 1.32 (s, 3H), 2.08 (br, 2H), 2.22 (s, 3H), 3.20-3.40 (m, 2H), 3.30 (s, 3H), 3.53-3.70 (m, 3H), 3.89-4.13 (m, 5H), 4.24 (br, 2H), 6.67 (br, 1H), 6.70-6.83 (m, 2H), 7.38 (d, J=9.0 Hz, 1H), 7.62 (br, 2H), 7.89 (br, 2H), 8.71 (br, 2H).

Example 624

Synthesis of 1-ethyl-3,3,5-trimethyl-7-(3-{[2-(4-methyl-7-oxo-7H-furo[2,3-c]pyridin-6-yl)ethyl]pyridin-4-ylmethylamino}propoxy)-1,5-dihydrobenzo[b][1,4]diazepine-2,4-dione dihydrochloride Using an appropriate starting material and following the procedure of Example 7, the object compound was synthesized.
¹H-NMR (DMSO-d₆) δppm:
0.75 (s, 3H), 1.01 (t, J=7.0 Hz, 3H), 1.32 (s, 3H), 2.10 (br, 2H), 2.17 (s, 3H), 3.20-3.39 (m, 2H), 3.30 (s, 3H), 3.61-3.72 (m, 3H), 3.83-4.11 (m, 5H), 4.16 (br, 2H), 6.77 (br, 1H), 6.85 (br, 1H), 6.96 (s, 1H), 7.31 (br, 1H), 7.38 (d, J=9.0 Hz, 1H), 7.80 (br, 2H), 8.14 (s, 1H), 8.68 (br, 2H).

Example 625

Synthesis of 7-(3-{(2-butylpyridin-3-ylmethyl)-[2-(2-methyl-4-oxo-4H-furo[3,2-c]pyridin-5-yl)ethyl]amino}propoxy)-1-ethyl-3,3,5-trimethyl-1,5-dihydrobenzo[b][1,4]diazepine-2,4-dione dihydrochloride Using an appropriate starting material and following the procedure of Example 7 and Example 6, the object compound was synthesized.

White Amorphous $^1$H-NMR (DMSO-D$_6$) δppm:

0.76 (3H, s), 0.86 (3H, t, J=7.3 Hz), 1.02 (3H, t, J=7.0 Hz), 1.21-1.40 (5H, m), 1.47-1.67 (2H, m), 1.83-2.06 (2H, m), 2.39 (3H, s), 2.60-3.01 (6H, m), 3.17 (3H, s), 3.22-4.19 (8H, m) 6.35-6.67 (2H, m), 6.69-6.92 (2H, m), 7.39 (1H, d, J=8.9 Hz) 7.42-7.71 (2H, m), 8.17-8.42 (1H, m), 8.53-8.65 (1H, m)

Example 626

Synthesis of 7-{3-[(2,4-dimethyl-thiazol-5-ylmethyl)-(2-pyridin-3-yl-ethyl)amino]propoxy}-1-ethyl-3,3,5-trimethyl-1,5-dihydrobenzo[b][1,4]diazepine-2,4-dione dihydrochloride Using an appropriate starting material and following the procedure of Example 7 and Example 6, the object compound was synthesized.

White Amorphous $^1$H-NMR (DMSO-d$_6$) δppm:

0.74 (3H, s), 0.99 (3H, t, J=7.0 Hz), 1.31 (3H, s), 2.26 (2H, bs), 2.39 (3H, s), 2.59 (3H, s), 3.11-3.61 (6H, m), 3.31 (3H, s), 3.67 (1H, t, dq=7.0, 7.0 Hz), 4.05 (1H, dq, J=7.0, 7.0 Hz), 4.09-4.17 (2H, m), 4.62 (2H, bs), 6.84-6.95 (2H, m), 7.41 (1H, d, J=8.9 Hz), 7.89 (1H, dd, J=7.8 and 5.6 Hz), 8.35 (1H, d, J=7.8 Hz), 8.76 (1H, d, J=5.6 Hz), 8.84 (1H, s), 11.2 (1H, bs)

Example 627

Synthesis of 1-ethyl-3,3,5-trimethyl-7-(3-{[2-(4-oxo-4H-furo[3,2-c]pyridin-5-yl)ethyl]pyridazin-4-ylmethylamino}-propoxy)-1,5-dihydrobenzo[b][1,4]diazepine-2,4-dione Using an appropriate starting material and following the procedure of Example 7, the object compound was synthesized.

White Powder $^1$H-NMR (CDCl$_3$) δppm:

0.86 (3H, s), 1.16 (3H, t, J=7.1 Hz), 1.53 (3H, s), 1.87-1.97 (2H, m), 2.73 (2H, t, J=6.8 Hz), 2.87-2.95 (2H, m), 3.39 (3H, s), 3.66-3.77 (3H, m), 3.85 (2H, t, J=5.9 Hz), 4.10-4.24 (3H, m), 6.48 (1H, d, J=7.4 Hz), 6.59 (1H, d, J=2.7 Hz), 6.65 (1H, dd, J=2.7 and 9.0 Hz), 6.95 (1H, t, J=0.8 Hz), 7.09 (1H, d, J=7.4 Hz), 7.19 (1H, d, J=9.0 Hz), 7.25-7.28 (1H, m), 7.51 (1H, d, J=2.1 Hz), 8.89 (1H, dd, J=1.2 and 5.2 Hz), 9.08 (1H, s)

Example 628

Synthesis of N-[3-(1-ethyl-3,3,5-trimethyl-2,4-dioxo-2,3,4,5-tetrahydro-1H-benzo[b][1,4]diazepin-7-yloxy)propyl]-N-(2-pyridin-3-ylethyl)benzenesulfonamide hydrochloride Using an appropriate starting material and following the procedure of Example 4 and Example 6, the object compound was synthesized.

White Amorphous $^1$H-NMR (DMSO-d$_6$) δppm:

0.74 (3H, s), 1.01 (3H, t, J=7.0 Hz), 1.32 (3H, s), 1.85-1.97 (2H, m), 3.03 (2H, t, J=7.0 Hz), 3.03-3.62 (4H, m), 3.31 (3H, s), 3.67 (1H, dq, J=7.0, 7.0 Hz), 3.98 (2H, t, t=7.0 Hz), 4.06 (1H, dq, J=7.0, 7.0 Hz), 6.84-6.95 (2H, m), 7.41 (1H, d, J=8.9 Hz), 7.54-7.63 (2H, m), 7.63-7.72 (1H, m), 7.75-7.84 (2H, m), 7.84-7.92 (1H, m), 8.34 (1H, d, J=7.4 Hz), 8.74 (1H, d, J=5.2 Hz), 8.78 (1H, bs)

Example 629

Synthesis of 7-(3-{(2,6-dimethylpyridin-3-ylmethyl)-[2-(4-oxo-4H-furo[3,2-c]pyridin-5-yl)ethyl]amino}propoxy)-1-ethyl-3,3,5-trimethyl-1,5-dihydrobenzo[b][1,4]diazepine-2,4-dione dihydrochloride Using an appropriate starting material and following the procedure of Example 7 and Example 6, the object compound was synthesized.

White Amorphous $^1$H-NMR (DMSO-d$_6$) δppm:

0.75 (3H, s), 1.01 (3H, t, J=7.0 Hz), 1.32 (3H, s), 1.99-3.04 (12H, m), 3.05-4.82 (11H, m), 6.55-7.04 (4H, m), 7.41 (1H, d, J=8.9 Hz) 7.44-7.82 (2H, m), 7.91 (1H, s), 8.38-8.92 (1H, m)

Example 630

Synthesis of 7-(3-{(2,6-dimethylpyridin-3-ylmethyl)-[2-(2-methyl-4-oxo-4H-furo[3,2-c]pyridin-5-yl)ethyl]amino}-propoxy)-1-ethyl-3,3,5-trimethyl-1,5-dihydrobenzo[b][1,4]diazepine-2,4-dione Using an appropriate starting material and following the procedure of Example 7, the object compound was synthesized.

White Powder

Melting Point 114 to 116° C.

Example 631

Synthesis of N-[3-(1-ethyl-3,3,5-trimethyl-2,4-dioxo-2,3,4,5-tetrahydro-1H-benzo[b][1,4]diazepin-7-yloxy)propyl]-N-[2-(2-methyl-4-oxo-4H-furo[3,2-c]pyridin-5-yl)ethyl]benzenesulfonamide Using an appropriate starting material and following the procedure of Example 4, the object compound was synthesized.

White Powder

Melting Point 179.6 to 182.5° C.

Example 632

Synthesis of 1-ethyl-3,3,5-trimethyl-7-(3-{[2-(7-methyl-4-oxo-4H-furo[3,2-c]pyridin-5-yl)ethyl]pyridin-4-ylmethylamino}propoxy)-1,5-dihydrobenzo[b][1,4]diazepine-2,4-dione dihydrochloride Using an appropriate starting material and following the procedure of Example 7, the object compound was synthesized.

$^1$H-NMR (DMSO-d$_6$) δppm:

0.75 (s, 3H), 1.01 (t, J=7.0 Hz, 3H), 1.32 (s, 3H), 2.00 (br, 2H), 2.16 (s, 3H), 3.21-3.35 (m, 2H), 3.30 (s, 3H), 3.53-3.70 (m, 3H), 3.93 (br, 4H), 4.00-4.19 (m, 3H), 6.70-6.81 (m, 2H), 6.95 (s, 1H), 7.37 (d, J=9.0 Hz, 1H), 7.45 (br, 1H), 7.78 (br, 2H), 7.93 (br, 1H), 8.67 (br, 2H).

Example 633

Synthesis of N-[3-(1-ethyl-3,3,5-trimethyl-2,4-di-oxo-2,3,4,5-tetrahydro-1H-benzo[b][1,4]diazepin-7-yloxy)propyl]-N-(2-pyridin-3-ylethyl)benzamide hydrochloride Benzoyl chloride (0.091 ml, 0.78 mmol) was added to an acetonitrile solution (3 ml) of 1-ethyl-3,3,5-trimethyl-7-[3-(2-pyridin-3-ylethylamino)propoxy]-1,5-dihydrobenzo[b][1,4]diazepine-2,4-dione (0.39 g, 0.71 mmol) and triethylamine (0.12 ml, 0.86 mmol) while cooling in an ice-bath, and the mixture was stirred at room temperature overnight. Water was added to the reaction mixture, and extraction with ethyl acetate was conducted. The organic layer was dried over anhydrous sodium sulfate and concentrated under reduced pressure. The residue thus obtained was purified by medium pressure liquid chromatography (silica gel, ethyl acetate:isopropyl alcohol=100:0→92:8). The purified product was concentrated under reduced pressure and the resultant residue was dissolved in ethyl acetate (10 ml). A 1N—HCl ethanol solution (0.65 ml) was added to the solution, and concentrated under reduced pressure. The residue was recrystallized from ethyl acetate to thereby obtain 0.28 g (yield: 54%) of N-[3-(1-ethyl-3,3,5-trimethyl-2,4-dioxo-2,3,4,5-tetrahydro-1H-benzo[b][1,4]diazepin-7-yloxy)propyl]-N-(2-pyridin-3-ylethyl)benzamide hydrochloride as a white powder. Melting Point 179 to 191° C.

Example 634

Synthesis of N-[3-(1-ethyl-3,3,5-trimethyl-2,4-di-oxo-2,3,4,5-tetrahydro-1H-benzo[b][1,4]diazepin-7-yloxy)propyl]-N-[2-(1-oxo-1H-isoquinolin-2-yl)ethyl]benzenesulfonamide Using an appropriate starting material and following the procedure of Example 4, the object compound was synthesized.
White Powder
Melting Point 134 to 137° C.

Example 635

Synthesis of pyridine-3-sulfonic acid [3-(1-ethyl-3,3,5-trimethyl-2,4-dioxo-2,3,4,5-tetrahydro-1H-benzo[b][1,4]diazepin-7-yloxy)propyl]-[2-(1-oxo-1H-isoquinolin-2-yl)ethyl]amide Using an appropriate starting material and following the procedure of Example 4, the object compound was synthesized.
White Powder
Melting Point 160 to 164° C.

Example 636

Synthesis of 1-ethyl-3,3,5-trimethyl-7-(3-{[2-(4-methyl-7-oxo-7H-thieno[2,3-c]pyridin-6-yl)ethyl]pyridin-4-ylmethylamino}propoxy)-1,5-dihydrobenzo[b][1,4]diazepine-2,4-dione dihydrochloride Using an appropriate starting material and following the procedure of Example 7, the object compound was synthesized.
$^1$H-NMR (DMSO-$d_6$) δppm:
0.75 (s, 3H), 1.01 (t, J=7.0 Hz, 3H), 1.32 (s, 3H), 2.05 (br, 2H), 2.24 (s, 3H), 3.30-3.40 (m, 2H), 3.30 (s, 3H), 3.63-3.70 (m, 3H), 3.82 (br, 4H), 3.95-4.10 (m, 1H), 4.25 (br, 2H), 6.72 (br, 1H), 6.80 (br 1H), 7.35-7.43 (m, 3H), 7.85 (br, 2H), 8.07-8.11 (m, 1H), 8.66 (br, 2H).

Example 637

Synthesis of pyridine-3-sulfonic acid [3-(1-ethyl-3,3,5-trimethyl-2,4-dioxo-2,3,4,5-tetrahydro-1H-benzo[b][1,4]diazepin-7-yloxy)propyl]-[2-(2-methyl-4-oxo-4H-furo[3,2-c]pyridin-5-yl)ethyl]amide Using an appropriate starting material and following the procedure of Example 4, the object compound was synthesized.
White Powder
Melting Point 163.3 to 166.3° C.

Example 638

Synthesis of 1-ethyl-3,3,5-trimethyl-7-(2-{(2-methylpyridin-3-ylmethyl)-[2-(4-oxo-4H-furo[3,2-c]pyridin-5-yl)ethyl]-amino}ethoxy)-1,5-dihydrobenzo[b][1,4]diazepine-2,4-dione dihydrochloride Using an appropriate starting material and following the procedure of Example 7 and Example 6, the object compound was synthesized.
White Amorphous
$^1$H-NMR (DMSO-$d_6$) δppm:
0.75 (3H, s), 1.02 (3H, t, J=7.0 Hz), 1.33 (3H, s), 2.61 (3H, s), 2.77-3.05 (4H, m), 3.32 (3H, s), 3.48-3.71 (3H, m), 3.94-4.16 (5H, m), 6.63 (1H, d, J=7.3 Hz), 6.83-6.91 (3H, m), 7.39 (1H, d, J=8.8 Hz), 7.55 (1H, d, J=7.6 Hz), 7.65 (1H, t, J=6.2 Hz), 7.84 (1H, d, J=2.1 Hz), 8.34-8.38 (1H, m), 8.51 (1H, d, J=5.9 Hz)

Example 639

Synthesis of pyridine-3-sulfonic acid [3-(1-ethyl-3,3,5-trimethyl-2,4-dioxo-2,3,4,5-tetrahydro-1H-benzo[b][1,4]diazepin-7-yloxy)propyl]-(2-pyridin-3-ylethyl)amide 2 phosphate Using an appropriate starting material and following the procedure of Example 4 and Example 458, the object compound was synthesized.
White Amorous
$^1$H-NMR (DMSO-dd δppm:
0.74 (3H, s), 1.01 (3H, t, J=7.0 Hz), 1.32 (3H, s), 1.89-2.08 (2H, m), 2.80-2.98 (2H, m), 3.31 (3H, s), 3.31-5.00 (8H, m), 6.84-6.96 (2H, m), 7.30 (1H, dd, J=8.0 and 4.8 Hz), 7.40 (1H, d, J=8.7 Hz), 7.54-7.74 (2H, m), 8.18-8.27 (1H, m), 8.42 (1H, dd, J=4.8 and 1.5 Hz), 8.44 (1H, d, J=1.8 Hz), 8.83 (1H, dd, J=4.8 Hz, J=1.5 Hz), 8.99 (1H, d, J=1.8 Hz)

Example 640

Synthesis of 2,4-dimethyl-thiazole-5-sulfonic acid [3-(1-ethyl-3,3,5-trimethyl-2,4-dioxo-2,3,4,5-tetrahydro-1H-benzo[b][1,4]diazepin-7-yloxy)propyl]-(2-pyridin-3-ylethyl)amide hydrochloride Using an appropriate starting material and following the procedure of Example 4 and Example 6, the object compound was synthesized.

¹H-NMR (DMSO-d₆) δppm:

0.75 (3H, s), 1.01 (3H, t, J=7.0 Hz), 1.32 (3H, s), 1.89-2.25 (2H, m), 2.49 (3H, s), 2.62 (3H, s), 3.08 (2H, t, J=7.0 Hz), 3.32 (3H, s), 3.32-3.90 (3H, m), 3.54 (2H, t, J=7.0 Hz), 4.01 (2H, t, J=7.0 Hz), 4.01-4.20 (1H, m), 6.84-6.96 (2H, m), 7.41 (1H, d, J=8.9 Hz), 7.90 (1H, dd, J=8.0 and 5.4 Hz), 8.37 (1H, d, J=8.0 Hz), 8.75 (1H, d, J=5.4 Hz), 8.82 (1H, s)

Example 641

Synthesis of 1-ethyl-3,3,5-trimethyl-7-(3-{[2-(7-oxo-7H-thieno[2,3-c]pyridin-6-yl)ethyl]pyridin-3-ylmethylamino}-propoxy)-1,5-dihydrobenzo[b][1,4]diazepine-2,4-dione Using an appropriate starting material and following the procedure of Example 7, the object compound was synthesized.

¹H-NMR (CDCl₃) δppm:

0.85 (s, 3H), 1.14 (t, J=7.1 Hz, 3H), 1.52 (s, 3H), 1.81-1.93 (m, 2H), 2.72 (t, J=6.8 Hz, 2H), 2.89 (t, J=6.1 Hz, 2H), 3.38 (s, 3H), 3.68 (s, 2H), 3.60-3.75 (m, 1H), 3.86 (t, J=6.0 Hz, 2H), 4.05-4.21 (m, 3H), 6.55 (d, J=7.1 Hz, 1H), 6.60-6.68 (m, 2H), 6.96-7.03 (m, 1H), 7.07 (d, J=7.1 Hz, 1H), 7.12-7.18 (m, 2H), 7.42-7.50 (m, 1H), 7.66-7.70 (m, 1H), 8.35-8.37 (m, 1H), 8.47 (s, 1H).

Example 642

Synthesis of 1-ethyl-7-(3-{[2-(2-ethyl-4-oxo-4H-thieno[3,2-c]pyridin-5-yl)ethyl]pyridin-3-ylmethylamino}propoxy)-3,3,5-trimethyl-1,5-dihydrobenzo[b][1,4]diazepine-2,4-dione dihydrochloride Using an appropriate starting material and following the procedure of Example 7, the object compound was synthesized.

¹H-NMR (DMSO-d₆) δppm:

0.75 (s, 3H), 1.01 (t, J=7.0 Hz, 3H), 1.28 (t, J=7.5 Hz, 3H), 1.32 (s, 3H), 2.25 (br, 2H), 2.87 (q, J=7.5 Hz, 2H), 3.20-3.35 (m, 2H), 3.32 (s, 3H), 3.51-3.69 (m, 3H), 3.97-4.15 (m, 5H), 4.28 (br, 2H), 6.90 (br, 3H), 7.22 (s, 1H), 7.42 (d, J=9.0 Hz, 1H), 7.50-7.68 (m, 2H), 8.18 (br, 1H), 8.73 (br, 1H), 8.80 (br, 1H).

Example 643

Synthesis of 1-ethyl-7-(3-{[2-(7-methoxy-2-oxo-3,4-dihydro-2H-quinolin-1-yl)ethyl]pyridin-3-ylmethylamino}propoxy)-3,3,5-trimethyl-1,5-dihydrobenzo[b][1,4]diazepine-2,4-dione dihydrochloride Using an appropriate starting material and following the procedure of Example 7, the object compound was synthesized.

¹H-NMR (DMSO-d₆) δppm:

0.75 (s, 3H), 1.02 (t, J=7.0 Hz, 3H), 1.32 (s, 3H), 2.31 (br, 2H), 2.51-2.60 (m, 2H), 2.77-2.82 (m, 2H), 3.28 (br, 2H), 3.32 (s, 3H), 3.50-3.70 (m, 3H), 3.77 (s, 3H), 4.01-4.14 (m, 3H), 4.43 (br, 2H), 4.68 (br, 2H), 6.60 (dd, J=2.0, 8.2 Hz, 1H), 6.79 (br, 1H), 6.91 (dd, J=2.8, 9.0 Hz, 1H), 6.94 (d, J=2.8 Hz, 1H), 7.14 (d, J=8.2 Hz, 1H), 7.41 (d, J=9.0 Hz, 1H), 7.90 (br, 1H), 8.67 (br, 1H), 8.87 (br, 1H), 9.12 (br, 1H).

Example 644

Synthesis of 2,4-dimethyl-thiazole-5-sulfonic acid [3-(1-ethyl-3,3,5-trimethyl-2,4-dioxo-2,3,4,5-tetrahydro-1H-benzo[b][1,4]diazepin-7-yloxy)propyl]-[2-(1-oxo-1H-isoquinolin-2-yl)ethyl]amide Using an appropriate starting material and following the procedure of Example 4, the object compound was synthesized.

White Powder

Melting Point 76 to 84° C.

Example 645

Synthesis of 1-ethyl-3,3,5-trimethyl-7-(3-{[2-(4-oxo-2-trifluoromethyl-4H-furo[3,2-c]pyridin-5-yl)ethyl]pyridin-4-ylmethylamino}propoxy)-1,5-dihydrobenzo[b][1,4]diazepine-2,4-dione dihydrochloride Using an appropriate starting material and following the procedure of Example 7, the object compound was synthesized.

¹H-NMR (DMSO-d₆) δppm:

0.75 (s, 3H), 1.02 (t, J=7.0 Hz, 3H), 1.32 (t, J=7.5 Hz, 3H), 2.45-2.60 (m, 2H), 3.20-3.35 (m, 2H), 3.30 (s, 3H), 3.59-3.70 (m, 3H), 3.81 (br, 4H), 3.98-4.06 (m, 1H), 4.13 (br, 2H), 6.63-6.80 (m, 3H), 7.36 (d, J=9.0 Hz, 1H), 7.61-7.87 (m, 4H), 8.65 (br, 2H).

Example 646

Synthesis of 1-ethyl-3,3,5-trimethyl-7-(3-{(2-methylpyridin-3-ylmethyl)-[2-(4-oxo-2-trifluoromethyl-4H-furo[3,2-c]pyridin-5-yl)ethyl]amino}propoxy)-1,5-dihydrobenzo[b][1,4]diazepine-2,4-dione dihydrochloride Using an appropriate starting material and following the procedure of Example 7, the object compound was synthesized.

¹H-NMR (DMSO-d₆) δppm:

0.75 (s, 3H), 1.02 (t, J=7.0 Hz, 3H), 1.32 (s, 3H), 1.98 (br, 2H), 2.74 (br, 5H), 3.20-3.35 (m, 2H), 3.31 (s, 3H), 3.55-3.69 (m, 3H), 3.99-4.10 (m, 5H), 6.70-6.90 (m, 3H), 7.39 (d, J=9.0 Hz, 1H), 7.76 (br, 3H), 8.26 (br, 1H), 8.59 (br, 1H).

Example 647

Synthesis of 7-(3-{(2,4-dimethylpyridin-3-ylmethyl)-[2-(4-oxo-4H-furo[3,2-c]pyridin-5-yl)ethyl]amino}propoxy)-1-ethyl-3,3,5-trimethyl-1,5-dihydrobenzo[b][1,4]diazepine-2,4-dione dihydrochloride Using an appropriate starting material and following the procedure of Example 7, the object compound was synthesized.

¹H-NMR (DMSO-d₆) δppm:

0.76 (s, 3H), 1.02 (t, J=7.0 Hz, 3H), 1.33 (s, 3H), 1.99 (br, 2H), 2.43 (br, 3H), 2.62 (br, 3H), 2.73 (br, 4H), 3.33 (s, 3H), 3.61-3.70 (m, 3H), 3.90-4.10 (m, 5H), 6.59 (br, 1H), 6.82-6.92 (m, 3H), 7.40 (d, J=9.0 Hz, 1H), 7.49 (br, 2H), 7.87 (br, 1H), 8.40 (br, 1H).

Example 648

Synthesis of 1-ethyl-3,3,5-trimethyl-7-{3-[[2-(4-oxo-4H-furo[3,2-c]pyridin-5-yl)ethyl]-(2-trifluoromethylpyridin-3-ylmeth yl)amino]propoxy}-1,5-dihydrobenzo[b][1,4]diazepine-2,4-dione Using an appropriate starting material and following the procedure of Example 7, the object compound was synthesized.
$^1$H-NMR (CDCl$_3$) δppm:
0.86 (s, 3H), 1.15 (t, J=7.1 Hz, 3H), 1.53 (s, 3H), 1.85-1.94 (m, 2H), 2.78 (t, J=7.2 Hz, 2H), 2.89 (t, J=6.2 Hz, 2H), 3.38 (s, 3H), 3.63-3.76 (m, 1H), 3.87-3.93 (m, 4H), 4.03-4.22 (m, 3H), 6.41-6.44 (m, 1H), 6.61 (d, J=2.7 Hz, 1H), 6.67 (dd, J=9.0 and 2.7 Hz, 1H), 6.94-6.95 (m, 1H), 7.01-7.08 (m, 2H), 7.19 (d, J=9.0 Hz, 1H), 7.50-7.51 (m, 1H), 7.79-7.81 (m, 1H), 8.46 (d, J=3.6 Hz, 1H).

Example 649

Synthesis of 1-ethyl-3,3,5-trimethyl-7-{3-[[2-(2-methyl-4-oxo-4H-furo[3,2-c]pyridin-5-yl)ethyl]-(2-trifluoromethylpyridin-3-ylmethyl)amino]propoxy}-1,5-dihydrobenzo[b][1,4]diazepine-2,4-dione Using an appropriate starting material and following the procedure of Example 7, the object compound was synthesized.
$^1$H-NMR (CDCl$_3$) δppm:
0.86 (s, 3H), 1.15 (t, J=7.1 Hz, 3H), 1.53 (s, 3H), 1.87-1.95 (m, 2H), 2.43 (s, 3H), 2.78 (t, J=7.2 Hz, 2H), 2.88 (t, J=6.2 Hz, 2H), 3.38 (s, 3H), 3.63-3.76 (m, 1H), 3.86 (s, 2H), 3.92 (t, J=6.0 Hz, 2H), 4.05-4.22 (m, 3H), 6.34-6.37 (m, 1H), 6.53 (s, 1H), 6.63 (d, J=2.7 Hz, 1H), 6.68 (dd, J=9.0 and 2.7 Hz, 1H), 6.99 (d, J=7.4 Hz, 1H), 7.01-7.09 (m, 1H), 7.19 (d, J=9.0 Hz, 1H), 7.80-7.84 (m, 1H), 8.45 (d, J=3.6 Hz, 1H).

Example 650

Synthesis of 1-Ethyl-3,3,5-trimethyl-7-(3-{[3-(2-methyl-4-oxo-4H-furo[3,2-c]pyridin-5-yl)propyl]pyridin-4-ylmethylamino}propoxy)-1,5-dihydrobenzo[b][1,4]diazepine-2,4-dione dihydrochloride dihydrochloride Using an appropriate starting material and following the procedure of Example 7, the object compound was synthesized.
$^1$H-NMR (DMSO-d$_6$) δppm:
0.76 (s, 3H), 1.02 (t, J=7.0 Hz, 3H), 1.32 (s, 3H), 2.22 (br, 4H), 2.39 (s, 3H), 3.10 (br, 2H), 3.21 (br, 2H), 3.31 (s, 3H), 3.45-3.70 (m, 1H), 4.01-4.10 (m, 5H), 4.58 (br, 2H), 6.56 (s, 1H), 6.79 (d, J=7.4 Hz, 1H), 6.87-6.92 (m, 2H), 7.40 (d, J=9.0 Hz, 1H), 7.57 (d, J=7.4 Hz, 1H), 8.08 (br, 2H), 8.82 (br, 2H).

Example 651

Synthesis of pyrazine-2-carboxylic acid [3-(1-ethyl-3,3,5-trimethyl-2,4-dioxo-2,3,4,5-tetrahydro-1H-benzo[b][1,4]diazepin-7-yloxy)propyl]-(2-pyridin-3-ylethyl)amide hydrochloride Using an appropriate starting material and following the procedure of Example 45, the object compound was synthesized.
$^1$H-NMR (DMSO-D$_6$) δppm:
0.75 (3H, s), 1.01 (3H, t, J=7.0 Hz), 1.32 (3H, s), 1.89-2.25 (2H, m), 3.00-3.23 (2H, m), 3.29 and 3.32 (3H, s), 3.32-3.78 (4H, m), 3.78-3.95 (2H, m), 3.95-4.29 (2H, m), 6.67-6.80 (1H, m), 6.92-7.07 (1H, m), 7.36 and 7.42 (1H, d, J=9.5 Hz), 7.80 and 7.95 (1H, dd, J=7.7 and 5.6 Hz), 8.14 and 8.48 (1H, d, J=8.0 Hz), 8.52-9.02 (5H, m)

Example 652

Synthesis of 1-ethyl-3,3,5-trimethyl-7-{3-[[2-(4-oxo-4H-furo[3,2-c]pyridin-5-yl)ethyl]-(2,4,6-trimethylpyridin-3-ylmethyl)amino]propoxy}-1,5-dihydroenzo[b][1,4]diazepine-2,4-dione dihydrochloride Using an appropriate starting material and following the procedure of Example 7, the object compound was synthesized.
$^1$H-NMR (DMSO-d$_6$) δppm:
0.76 (s, 3H), 1.02 (t, J=7.0 Hz, 3H), 1.33 (s, 3H), 2.00 (br, 2H), 2.36 (br, 3H), 2.43-2.62 (m, 6H), 2.76 (br, 4H), 3.33 (s, 3H), 3.55-3.68 (m, 3H), 3.95 (br, 2H), 4.03-4.11 (m, 3H), 6.59 (br, 1H), 6.80-6.94 (m, 3H), 7.27 (br, 1H), 7.39-7.47 (m, 2H), 7.89 (s, 1H).

Example 653

Synthesis of N-[3-(1-ethyl-3,3,5-trimethyl-2,4-dioxo-2,3,4,5-tetrahydro-1H-benzo[b][1,4]diazepin-7-yloxy)propyl]-N-(2-pyridin-3-ylethyl)nicotinamide Using an appropriate starting material and following the procedure of Example 459, the object compound was synthesized.
White Powder
Melting Point 135.5 to 138.1° C.

Example 654

Synthesis of N-[3-(1-ethyl-3,3,5-trimethyl-2,4-dioxo-2,3,4,5-tetrahydro-1H-benzo[b][1,4]diazepin-7-yloxy)propyl]-N-pyridin-4-ylmethylnicotinamide 2.5 phosphate Using an appropriate starting material and following the procedure of Example 633 and Example 458, the object compound was synthesized.
$^1$H-NMR (DMSO-d$_6$) δppm:
0.75 (3H, s), 1.00 (3H, t, J=7.0 Hz), 1.32 (3H, s), 1.82-2.27 (2H, m), 3.29 (3H, s), 3.36-3.52 (2H, m), 3.52-4.25 (4H, m), 4.57 and 4.78 (2H, s), 6.53-7.09 (2H, m), 7.09-7.56 (4H, m), 7.69-8.05 (1H, m), 8.37-8.88 (4H, m)

Example 655

Synthesis of thiazole-4-carboxylic acid [3-(1-ethyl-3,3,5-trimethyl-2,4-dioxo-2,3,4,5-tetrahydro-1H-benzo[b][1,4]diazepin-7-yloxy)propyl]-(2-pyridin-3-ylethyl)amide hydrochloride Using an appropriate starting material and following the procedure of Example 45, the object compound was synthesized.
$^1$H-NMR (DMSO-d$_6$) δppm:
0.74 (3H, s), 1.00 (3H, t, J=7.0 Hz), 1.32 (3H, s), 1.89-2.25 (2H, m), 2.87-3.21 (2H, m), 3.31 (3H, s), 3.31-4.27 (8H, m), 6.74-6.94 (1H, m), 6.95-7.05 (1H, m), 7.28-7.47 (1H, m), 7.65-7.94 (1H, m), 8.01 (1H, bs), 8.06-8.50 (1H, m), 8.50-8.94 (2H, m), 9.05-9.22 (1H, m)

Example 656

Synthesis of N-[3-(1-ethyl-3,3,5-trimethyl-2,4-dioxo-2,3,4,5-tetrahydro-1H-benzo[b][1,4]diazepin-7-yloxy)propyl]-2-pyridin-3-yl-N-pyridin-4-ylmethylacetamide 1.5 methanesulfonate Benzotriazol-1-yloxytris(dimethylamino) phosphonium hexafluorophosphate (BOP) (0.3 g, 0.68 mmol) was added to a dichloromethane solution (6 ml) of 1-ethyl-3,3,5-trimethyl-7-{3-[(pyridin-4-ylmethyl)amino]propoxy}-1,5-dihydrobenzo[b][1,4]diazepine-2,4-dione (0.39 g, 0.73 mmol), 3-pyridylacetic acid hydrochloride (0.14 g, 0.8 mmol), and triethylamine (0.31 ml, 2.2 mmol) while cooling in an ice-bath, and the mixture was stirred at room temperature overnight. Water was added to the reaction mixture, and extraction with dichloromethane was conducted. The organic layer was dried over anhydrous sodium sulfate and concentrated under reduced pressure. The residue thus obtained was purified by medium pressure liquid chromatography (NH-silica gel, ethyl acetate:isopropyl alcohol-100:0→91:9). The purified product was concentrated under reduced pressure and the resultant residue was dissolved in ethanol (10 ml). Methanesulfonic acid (0.047 ml, 0.72 mmol) was added to the solution, and concentrated under reduced pressure. The resultant residue was washed with diethylether by decantation to thereby obtain 0.17 g (yield: 35%) of N-[3-(1-ethyl-3,3,5-trimethyl-2,4-dioxo-2,3,4,5-tetrahydro-1H-benzo[b][1,4]diazepin-7-yloxy)propyl]-2-pyridin-3-yl-N-pyridin-4-ylmethylacetamide 1.5 methanesulfonate as a pale yellow white amorphous solid.
$^1$H-NMR (DMSO-D$_6$) δppm:
0.73 (3H, s), 1.00 (3H, t, J=7.3 Hz), 1.32 (3H, s), 1.85-2.25 (2H, m), 2.35 (4.5H, s), 3.29 and 3.30 (3H, s), 3.30-3.97 (2H, m), 3.97-4.27 (6H, m), 4.79 and 4.99 (2H, s), 6.82-7.04 (2H, m), 7.33-7.48 (1H, m), 7.54-7.95 (3H, m), 8.10-8.23 (1H, m), 8.57-8.90 (4H, m)

Example 657

Synthesis of oxazole-4-carboxylic acid [3-(1-ethyl-3,3,5-trimethyl-2,4-dioxo-2,3,4,5-tetrahydro-1H-benzo[b][1,4]diazepin-7-yloxy)propyl]-(2-pyridin-3-ylethyl)amide hydrochloride Using an appropriate starting material and following the procedure of Example 45, the object compound was synthesized.
$^1$H-NMR (DMSO-D$_6$) δppm:
0.74 (3H, s), 1.00 (3H, t, J=7.3 Hz), 1.32 (3H, s), 1.98-2.25 (2H, m), 3.03-3.21 (2H, m), 3.31 (3H, s), 3.40-4.22 (8H, m), 6.74-7.05 (2H, m), 7.31-7.47 (1H, m), 7.75-8.03 (1H, m), 8.32 (1H, d, J=7.3 Hz), 8.37-8.60 (2H, m), 8.60-8.97 (2H, m)

Example 658

Synthesis of thiophene-3-carboxylic acid [3-(1-ethyl-3,3,5-trimethyl-2,4-dioxo-2,3,4,5-tetrahydro-1H-benzo[b][1,4]diazepin-7-yloxy)propyl]-(2-pyridin-3-ylethyl)amide hydrochloride Using an appropriate starting material and following the procedure of Example 633, the object compound was synthesized.
$^1$H-NMR (DMSO-D$_6$) δppm:
0.74 (3H, s), 1.00 (3H, t, J=7.2 Hz), 1.32 (3H, s), 1.88-2.25 (2H, m), 3.09 (2H, bs), 3.31 (3H, s), 3.32-4.30 (8H, m), 6.64-7.18 (3H, m), 7.39 (1H, d, J=9.3 Hz), 7.55 (1H, dd, J=4.9 and 2.9 Hz), 7.62 (1H, bs), 7.67-8.22 (1H, m), 8.22-0.18 (3H, m)

Example 659

Synthesis of furan-2-carboxylic acid [3-(1-ethyl-3,3,5-trimethyl-2,4-dioxo-2,3,4,5-tetrahydro-1H-benzo[b][1,4]diazepin-7-yloxy)propyl]-(2-pyridin-3-ylethyl)amide hydrochloride Using an appropriate starting material and following the procedure of Example 633, the object compound was synthesized.
$^1$H-NMR (DMSO-d$_6$) δppm:
0.74 (3H, s), 1.01 (3H, t, J=7.0 Hz), 1.32 (3H, s), 1.92-2.12 (2H, m), 3.01-3.21 (2H, m), 3.31 (3H, s), 3.30-3.90 (5H, m), 4.00-4.15 (3H, m), 6.56-6.62 (1H, m), 6.85-7.00 (3H, m), 7.36-7.45 (1H, m), 7.78 (1H, s), 7.85-8.00 (1H, m), 8.38 (1H, bs), 8.74 (1H, d, J=5.3 Hz), 8.82 (1H, bs)

Example 660

Synthesis of 1,3,3,5-tetramethyl-7-{3-[(pyridin-4-ylmethyl)amino]propoxy}-1,5-dihydrobenzo[b][1,4]diazepine-2,4-dione Using an appropriate starting material and following the procedure of Example 77, the object compound was synthesized.
$^1$H-NMR (CDCl$_3$) δppm:
0.87 (3H, s), 1.53 (3H, s), 1.92-2.10 (2H, m), 2.84 (2H, t, J=6.8 Hz), 3.39 (3H, s), 3.41 (3H, s), 3.85 (2H, s), 4.08 (2H, t, J=6.2), 6.71 (1H, d, J=2.7 Hz), 6.80 (1H, dd, J=2.7 and 9.0 Hz), 7.14 (1H, d, J=9.0), 7.20-7.34 (2H, m), 8.45-8.65 (2H, m).

Example 661

Synthesis of 1-ethyl-7-{2-hydroxy-3-[2-(1-oxo-1H-isoquinolin-2-yl)ethylamino]propoxy}-3,3,5-trimethyl-1,5-dihydrobenzo[b][1,4]diazepine-2,4-dione Using an appropriate starting material and following the procedure of Example 7, the object compound was synthesized.
$^1$H-NMR (CDCl$_3$) δppm:
0.84 (3H, s), 1.14 (3H, t, J=7.0 Hz), 1.52 (3H, s), 2.75-3.04 (2H, m), 3.11 (2H, t, J=6.1 Hz), 3.78 (3H, s), 3.59-3.79 (1H, m), 3.89-4.29 (6H, m), 6.52 (1H, d, J=7.3 Hz), 6.68-6.86 (2H, m), 7.11 (1H, d, J=7.3 Hz), 7.18 (1H, d, J=8.7 Hz), 7.43-7.57 (2H, m), 7.57-7.74 (1H, m), 8.42 (1H, d, J=8.2 Hz).

Example 662

Synthesis of 1-ethyl-3,3,5-trimethyl-7-{3-[(pyridin-3-ylmethyl)amino]propoxy}-1,5-dihydrobenzo[b][1,4]diazepine-2,4-dione Using an appropriate starting material and following the procedure of Example 77, the object compound was synthesized.

¹H-NMR (CDCl₃) δppm:
0.86 (3H, s), 1.14 (3H, t, J=7.1 Hz), 1.52 (3H, s), 1.96-2.06 (2H, m), 2.85 (2H, t, J=6.8 Hz), 3.39 (3H, s),3.65-3.74 (1H, m), 3.85 (2H, s), 4.07 (2H, t, J=6.1 Hz), 4.10-4.21 (1H, m), 6.71 (1H, d, J=2.8 Hz), 6.80 (1H, dd, J=9.0 and 2.8 Hz), 7.19 (1H, d, J=9.0 Hz), 7.22-7.29 (1H, m), 7.65-7.68 (1H, m), 8.50 (1H, d, J=1.6 Hz), 8.58-8.61 (1H, m)

Example 663

Synthesis of 1-ethyl-3,3,5-trimethyl-7-{3-[2-(2-methyl-4-oxo-4H-furo[3,2-c]pyridin-5-yl)ethylamino]propoxy}-1,5-dihydrobenzo[b][1,4]diazepine-2,4-dione Using an appropriate starting material and following the procedure of Example 18, the object compound was synthesized.
¹H-NMR (CDCl₃) δppm:
0.85 (3H, s), 1.14 (3H, t, J=7.1 Hz), 1.52 (3H, s), 1.92-2.00 (2H, m), 2.41 (3H, s), 2.88 (2H, t, J=6.8 Hz), 3.03 (2H, t, J=6.2 Hz) 3.39 (3H, s),3.62-3.74 (1H, m), 4.02 (2H, t, J=6.1 Hz), 4.14 (2H, t, J=6.2 Hz), 4.16-4.22 (1H, m), 6.42 (1H, d, J=9.0 Hz), 6.54 (1H, s), 6.70 (1H, d, J=2.7 Hz), 6.72-6.82 (1H, m), 7.13-7.20 (2H, m)

Example 664

Synthesis of 1-ethyl-3,3,5-trimethyl-7-{3-[(pyridin-2-ylmethyl)amino]propoxy}-1,5-dihydrobenzo[b][1,4]diazepine-2,4-dione Using an appropriate starting material and following the procedure of Example 77, the object compound was synthesized.
¹H-NMR (CDCl₃) δppm:
0.86 (3H, s), 1.14 (3H, t, J=7.1 Hz), 1.52 (3H, s), 2.03-2.09 (2H, m), 2.91 (2H, t, J=6.7 Hz), 3.48 (3H, s), 3.64-3.76 (1H, m), 3.97 (2H, s), 4.10 (2H, t, J=6.2 Hz), 4.14-4.23 (1H, m), 6.73 (1H, d, J=2.7 Hz), 6.82 (1H, dd, J=9.0 and 2.7 Hz), 7.16-7.21 (2H, m), 7.27-7.32 (1H, m), 7.85 (1H, td, J=7.7, 1.8 Hz), 8.58-8.56 (1H, m)

Example 665

Synthesis of 1-ethyl-3,3,5-trimethyl-7-{3-[2-(4-oxo-4H-furo[3,2-c]pyridin-5-yl)ethylamino]propoxy}-1,5-dihydro-benzo[b][1,4]diazepine-2,4-dione Using an appropriate starting material and following the procedure of Example 18, the object compound was synthesized.
¹H-NMR (CDCl₃) δppm:
0.86 (3H, s), 1.14 (3H, t, J=7.1 Hz), 1.52 (3H, s), 1.91-2.00 (2H, m), 2.85 (2H, t, J=6.7 Hz), 3.03 (2H, t, J=6.2 Hz), 3.39 (3H, s), 3.66-3.76 (1H, m), 4.02 (2H, t, J=6.1 Hz), 4.09-4.24 (3H, m), 6.48 (1H, d, J=7.4 Hz), 6.69 (1H, d, J=2.8 Hz), 6.76 (1H, dd, J=9.0, 2.8 Hz), 6.97 (1H, d, J=2.0 Hz), 7.16-7.24 (2H, m), 7.48 (1H, d, J=2.1 Hz)

Example 666

Synthesis of 1-ethyl-3,3,5-trimethyl-7-{3-[(2-methylpyridin-3-ylmethyl)amino]propoxy}-1,5-dihydrobenzo[b][1,4]diazepine-2,4-dione Using an appropriate starting material and following the procedure of Example 77, the object compound was synthesized.
¹H-NMR (CDCl₃) δppm:
0.86 (3H, s), 1.14 (3H, t, J=7.0 Hz), 1.53 (3H, s), 1.98-2.07 (2H, m), 2.57 (3H, s), 2.89 (2H, t, J=6.8 Hz), 3.39 (3H, s),3.62-3.73 (1H, m), 3.82 (2H, s), 4.07-4.21 (3H, m), 6.71 (1H, d, J=2.8 Hz), 6.80 (1H, dd, J=9.0 and 2.8 Hz), 7.10 (1H, dd, J=7.7 and 4.9 Hz), 7.20 (1H, d, J=9.0 Hz), 7.59-7.62 (1H, m), 8.38-8.41 (1H, m)

Example 667

Synthesis of 1-ethyl-3,3,5-trimethyl-7-{3-[(6-methylpyridin-3-ylmethyl)amino]propoxy}-1,5-dihydrobenzo[b][1,4]diazepine-2,4-dione Using an appropriate starting material and following the procedure of Example 77, the object compound was synthesized.
¹H-NMR (CDCl₃) δppm:
0.86 (3H, s), 1.14 (3H, t, J=7.1 Hz), 1.52 (3H, s), 1.95-2.07 (2H, m), 2.54 (3H, s), 2.84 (2H, t, J=6.8 Hz), 3.39 (3H, s),3.64-3.76 (1H, m), 3.80 (2H, s), 4.04-4.20 (3H, m), 6.71 (1H, d, J=2.8 Hz), 6.79 (1H, dd, J=9.0 and 2.8 Hz), 7.11 (1H, d, J=7.9 Hz), 7.19 (1H, d, J=9.0 Hz), 7.56 (1H, dd, J=7.9 and 2.3 Hz), 8.44-8.45 (1H, m)

Example 668

Synthesis of 1-ethyl-7-[3-(4-methoxybenzylamino)propoxy]-3,3,5-trimethyl-1,5-dihydrobenzo[b][1,4]diazepine-2,4-dione Using an appropriate starting material and following the procedure of Example 77, the object compound was synthesized.
¹H-NMR (CDCl₃) δppm:
0.86 (3H, s), 1.14 (3H, t, J=7.0 Hz), 1.52 (3H, s), 2.00 (2H, quin, J=6.5 Hz), 2.83 (2H, t, J=6.5H), 3.39 (3H, s), 3.70 (1H, dq, J=7.0, 7.0 Hz), 3.76 (2H, s), 3.80 (3H, s), 4.07 (2H, t, J=6.5 Hz), 4.18 (1H, dq, J=7.0, 7.0 Hz), 6.71 (1H, d, J=2.7 Hz), 6.80 (1H, dd, J=2.7 and 9.0 Hz), 6.86 (2H, d, J=8.5 Hz), 7.19 (1H, d, J=9.0 Hz), 7.24 (2H, d, J=8.5 Hz)

Example 669

Synthesis of 1-ethyl-3,3,5-trimethyl-7-{3-[(5-methylpyridin-3-ylmethyl)amino]propoxy}-1,5-dihydrobenzo[b][1,4]diazepine-2,4-dione Using an appropriate starting material and following the procedure of Example 77, the object compound was synthesized.
¹H-NMR (CDCl₃) δppm:
0.86 (3H, s), 1.14 (3H, t, J=7.1 Hz), 1.50 (3H, s), 1.98-2.05 (2H, m), 2.32 (3H, s), 2.85 (2H, t, J=6.8 Hz), 3.39 (3H, s),3.62-3.72 (1H, m), 3.81 (2H, s), 4.05-4.17 (3H, m), 6.71 (1H, s), 6.80 (1H, dd, J=9.0 and 2.8 Hz), 7.19 (1H, d, J=9.0 Hz), 7.48 (1H, s), 8.34-8.38 (2H, m)

Example 670

Synthesis of 1-ethyl-7-{3-[(2-ethylpyridin-3-ylmethyl)amino]propoxy}-3,3,5-trimethyl-1,5-dihydrobenzo[b][1,4]diazepine-2,4-dione Using an appropriate starting material and following the procedure of Example 77, the object compound was synthesized.

¹H-NMR (CDCl₃) δppm:
0.86 (3H, s), 1.14 (3H, t, J=7.1 Hz), 1.29 (3H, t, J=7.5 Hz), 1.52 (3H, s), 1.99-2.05 (2H, m), 2.82-2.91 (4H, m), 3.39 (3H, s),3.62-3.75 (1H, m), 3.84 (2H, s), 4.09 (2H, t, J=6.2 Hz) 4.10-4.23 (1H, m), 6.71 (1H, d, J=2.8 Hz), 6.80 (1H, dd, J=9.0 and 2.8 Hz), 7.09 (1H, dd, J=7.6 and 4.9 Hz), 7.20 (1H, d, J=9.0 Hz), 7.63 (1H, d, J=7.7 Hz), 8.43-8.46 (1H, m)

Example 671

Synthesis of 1-ethyl-3,3,5-trimethyl-7-{3-[(2-propylpyridin-3-ylmethyl)amino]propoxy}-1,5-dihydrobenzo[b][1,4]diazepine-2,4-dione Using an appropriate starting material and following the procedure of Example 77, the object compound was synthesized.
¹H-NMR (CDCl₃) δppm:
0.86 (3H, s), 0.99 (3H, t, J=7.4 Hz), 1.14 (3H, t, J=7.1 Hz), 1.52 (3H, s), 1.69-1.81 (2H, m), 1.99-2.07 (2H, m), 2.77-2.90 (4H, m), 3.39 (3H, s), 3.60-3.73 (1H, m), 3.84 (2H, s), 4.06-4.23 (3H, m), 6.72 (1H, s), 6.79 (1H, dd, J=9.0 and 2.8 Hz), 7.06-7.09 (1H, m), 7.20 (1H, d, J=8.0 Hz), 7.63 (1H, d, J=7.7 Hz), 8.42-8.45 (1H, m)

Example 672

Synthesis of 1-ethyl-3,3,5-trimethyl-7-{4-[(2-methylpyridin-3-ylmethyl)amino]butoxy}-1,5-dihydrobenzo[b][1,4]diazepine-2,4-dione Using an appropriate starting material and following the procedure of Example 77, the object compound was synthesized.
¹H-NMR (CDCl₃) δppm:
0.86 (3H, s), 1.14 (3H, t, J=7.1 Hz), 1.54 (3H, s), 1.67-1.75 (2H, m), 1.85-1.92 (2H, m), 2.58 (3H, s), 2.76 (2H, t, J=7.0 Hz), 3.39 (3H, s), 3.60-3.77 (1H, m), 3.80 (2H, s), 3.99 (2H, t, J=6.3 Hz), 4.11-4.22 (1H, m), 6.74 (1H, s), 6.79 (1H, dd, J=8.9 and 2.8 Hz), 7.10 (1H, dd, J=7.6 and 4.9 Hz), 7.19 (1H, d, J=9.0 Hz), 7.61 (1H, d, J=6.1 Hz), 8.38-8.41 (1H, m)

Example 673

Synthesis of 1-ethyl-3,3,5-trimethyl-7-{4-[(pyridin-4-ylmethyl)amino]butoxy}-1,5-dihydrobenzo[b][1,4]diazepine-2,4-dione Using an appropriate starting material and following the procedure of Example 77, the object compound was synthesized.
¹H-NMR (CDCl₃) δppm:
0.86 (3H, s), 1.14 (3H, t, J=7.1 Hz), 1.52 (3H, s), 1.64-1.78 (2H, m), 1.83-1.95 (2H, m), 2.72 (2H, t, J=7.1 Hz), 3.39 (3H, s), 3.63-3.73 (1H, m), 3.84 (2H, s), 3.99 (2H, t, J=6.3 Hz), 4.09-4.21 (1H, m), 6.71 (1H, s), 6.79 (1H, dd, J=9.0 and 2.8 Hz), 7.19 (1H, d, J=9.0 Hz), 7.26-7.29 (2H, m), 8.55 (2H, dd, J=4.4 and 1.6 Hz)

Example 674

Synthesis of 1-ethyl-3,3,5-trimethyl-7-{3-[(pyridazin-4-ylmethyl)amino]propoxy}-1,5-dihydrobenzo[b][1,4]diazepine-2,4-dione Using an appropriate starting material and following the procedure of Example 77, the object compound was synthesized.
¹H-NMR (CDCl₃) δppm:
0.86 (3H, s), 1.15 (3H, t, J=7.1 Hz), 1.52 (3H, s), 1.97-2.06 (2H, m), 2.85 (2H, t, J=6.7 Hz), 3.40 (3H, s), 3.65-3.75 (1H, m), 3.90 (2H, s), 4.09 (2H, t, J=6.0 Hz), 4.10-4.22 (1H, m), 6.71 (1H, d, J=2.8 Hz), 6.80 (1H, dd, J=9.0 and 2.8 Hz), 7.21 (1H, d, J=9.0 Hz), 7.46-7.49 (1H, m), 9.11 (1H, dd, J=5.2 and 1.2 Hz), 9.21 (1H, s)

Example 675

Synthesis of 7-{3-[(2,6-dimethylpyridin-3-ylmethyl)amino]propoxy}-1-ethyl-3,3,5-trimethyl-1,5-dihydrobenzo[b][1,4]diazepine-2,4-dione Using an appropriate starting material and following the procedure of Example 77, the object compound was synthesized.
¹H-NMR (CDCl₃) δppm:
0.86 (3H, s), 1.14 (3H, t, J=7.1 Hz), 1.52 (3H, s), 1.97-2.05 (2H, m), 2.50 (3H, s), 2.54 (3H, s), 2.87 (2H, t, J=6.7 Hz), 3.39 (3H, s), 3.60-3.77 (1H, m), 3.78 (2H, s), 4.06-4.24 (3H, m), 6.71 (1H, s), 6.80 (1H, dd, J=9.0 and 2.8 Hz), 6.95 (1H, d, J=7.3 Hz), 7.20 (1H, d, J=9.0 Hz), 7.48 (1H, d, J=7.7 Hz),

Example 676

Synthesis of 1-ethyl-3,3,5-trimethyl-7-{2-[(2-methylpyridin-3-yl methyl)amino]ethoxy}-1,5-dihydrobenzo[b][1,4]diazepine-2,4-dione Using an appropriate starting material and following the procedure of Example 77, the object compound was synthesized.
¹H-NMR (CDCl₃) δppm:
0.85 (3H, s), 1.14 (3H, t, J=7.1 Hz), 1.52 (3H, s), 2.59 (3H, s), 3.02-3.10 (2H, m), 3.39 (3H, s), 3.65-3.76 (1H, m), 3.89 (2H, s), 4.09-4.21 (3H, m), 6.73-6.75 (1H, m), 6.80-6.85 (1H, m), 7.10-7.14 (1H, m), 7.19-7.23 (1H, m), 7.65 (1H, dd, J=7.7 and 1.5 Hz), 8.40-8.42 (1H, m)

Example 677

Synthesis of N-[3-(1-ethyl-3,3,5-trimethyl-2,4-dioxo-2,3,4,5-tetrahydro-1H-benzo[b][1,4]diazepin-7-yloxy)propyl]-N-[2-(1-oxo-1H-isoquinolin-2-yl)ethyl]nicotinamide Using an appropriate starting material and following the procedure of Example 459, the object compound was synthesized.
White Amorphous
¹H-NMR (CDCl₃) δppm:
0.82 (3H, s), 1.13 (3H, t, J=7.0 Hz), 1.51 (3H, s), 1.88-2.45 (2H, m), 3.37 (3H, s), 3.42-3.60 (2H, m), 3.60-3.90 (3H, m), 3.95 (2H, t, J=6.2 Hz), 4.01-4.27 (1H, m), 4.40 (2H, t, J=6.2 Hz), 6.40-6.67 (2H, m), 667-7.43 (4H, m), 7.43-7.61 (2H, m), 7.61-7.76 (2H, m), 8.13-8.78 (3H, m)

Example 678

Synthesis of N-[3-(1-ethyl-3,3,5-trimethyl-2,4-dioxo-2,3,4,5-tetrahydro-1H-benzo[b][1,4]diazepin-7-yloxy)propyl]-2-methyl-N-(2-pyridin-3-ylethyl)benzamide hydrochloride Using an appropriate starting material and following the procedure of Example 633, the object compound was synthesized.

White Powder
Melting Point 155.3 to 159.3° C. (dec.)

Example 679

Synthesis of N-[3-(1-ethyl-3,3,5-trimethyl-2,4-dioxo-2,3,4,5-tetrahydro-1H-benzo[b][1,4]diazepin-7-yloxy)propyl]-2-methoxy-N-(2-pyridin-3-ylethyl)isonicotinamide Using an appropriate starting material and following the procedure of Example 459, the object compound was synthesized.
White Powder
Melting Point 112.8 to 113.9° C.

Example 680

Synthesis of cyclohexanecarboxylic acid [3-(1-ethyl-3,3,5-trimethyl-2,4-dioxo-2,3,4,5-tetrahydro-1H-benzo[b][1,4]diazepin-7-yloxy)propyl]-(2-pyridin-3-ylethyl)amide hydrochloride Using an appropriate starting material and following the procedure of Example 633, the object compound was synthesized.
White Powder
Melting Point 153.4 to 157.5° C. (dec.)

Example 681

Synthesis of N-[3-(1-ethyl-3,3,5-trimethyl-2,4-dioxo-2,3,4,5-tetrahydro-1H-benzo[b][1,4]diazepin-7-yloxy)-propyl]-N-(2-pyridin-3-yl-ethyl)-acetamide hydrochloride Using an appropriate starting material and following the procedure of Example 633, the object compound was synthesized.
White Amorphous
$^1$H-NMR (DMSO-$d_6$) δppm:
0.73 and 0.74 (3H, s), 1.01 (3H, t, J=7.0 Hz), 1.32 (3H, s), 1.85-2.12 (2H, m), 1.93 and 1.95 (3H, s), 2.92-3.11 (2H, m), 3.12-3.95 (5H, m), 3.32 (3H, s), 3.95-4.16 (3H, m), 6.88-7.00 (2H, m), 7.40 (1H, dd, J=8.8 and 2.7 Hz), 7.89 (1H, dt, J=8.1 and 5.5 Hz), 8.36 (1H, d, J=8.1 Hz), 8.74 (1H, d, J=5.5 Hz), 8.77-8.86 (1H, m)

Example 682

Synthesis of 7-(4-amino-butoxy)-1-ethyl-3,3,5-trimethyl-1,5-dihydrobenzo[b][1,4]diazepine-2,4-dione Using an appropriate starting material and following the procedure of Example 2, the object compound was synthesized.
$^1$H-NMR (CDCl$_3$) δppm:
0.86 (3H, s), 1.14 (3H, t, J=7.1 Hz), 1.52 (3H, s), 1.60-1.70 (2H, m), 1.82-1.90 (2H, m), 2.80 (2H, t, J=7.0 Hz), 3.40 (3H, s), 3.64-3.76 (1H, m), 4.00 (2H, t, J=6.3 Hz), 4.12-4.24 (1H, m), 6.72 (1H, d, J=2.7 Hz), 6.81 (1H, dd, J=9.0 and 2.7 Hz), 7.20 (1H, d, J=9.0 Hz)

Example 683

Synthesis of 7-(2-amino-ethoxy)-1-ethyl-3,3,5-trimethyl-1,5-dihydrobenzo[b][1,4]diazepine-2,4-dione Using an appropriate starting material and following the procedure of Example 2, the object compound was synthesized.
$^1$H-NMR (CDCl$_3$) δppm:
0.86 (3H, s), 1.15 (3H, t, J=7.1 Hz), 1.53 (3H, s), 3.13 (2H, t, J=5.1 Hz), 3.40 (3H, s), 3.47-3.76 (1H, m), 4.01 (2H, t, J=5.1 Hz), 4.11-4.24 (1H, m), 6.75 (1H, d, J=2.8 Hz), 6.83 (1H, dd, J=9.0 and 2.8 Hz), 7.21 (1H, d, J=9.0 Hz)

Example 684

Synthesis of 1,5-dimethyl-7-{3-[[2-(2-methyl-4-oxo-4H-furo[3,2-c]pyridin-5-yl)ethyl]-(2-methylpyridin-3-ylmethyl)amino]propoxy}spiro[benzo[b][1,4]diazepine-3,1'-cyclobutane]-2,4-dione dihydrochloride Using an appropriate starting material and following the procedure of Example 7, the object compound was synthesized.
$^1$H-NMR (DMSO-$d_6$) δppm:
1.64 (br, 4H), 2.28 (br, 2H), 2.42 (s, 3H), 2.49 (s, 3H), 2.75 (br, 2H), 2.84-2.88 (m, 4H), 3.39 (s, 3H), 3.40 (s, 3H), 3.64 (br, 2H), 3.89 (br, 2H), 4.00 (br, 2H), 6.33-6.35 (m, 1H), 6.51 (br, 1H), 6.56-6.69 (m, 2H), 6.89-6.92 (m, 2H), 7.47 (br, 1H), 8.32 (br, 2H).

Example 685

Synthesis of 7-[3-(1,3-Dioxo-1,3-dihydroisoindol-2-yl)propoxy]-1,5-dimethylspiro[benzo[b][1,4]diazepine-3,1'-cyclobutane]-2,4-dione Using an appropriate starting material and following the procedure of Example 1, the object compound was synthesized.
$^1$H-NMR (CDCl$_3$) δppm:
1.57-1.67 (m, 4H), 2.11-2.23 (m, 2H), 2.78-2.90 (m, 2H), 3.35 (s, 3H), 3.37 (s, 3H), 3.93 (t, J=6.7 Hz, 2H), 4.05 (t, J=5.9 Hz, 2H), 6.61 (d, J=2.8 Hz, 1H), 6.71 (dd, J=9.0 and 2.8 Hz, 1H), 7.12 (d, J=9.0 Hz, 1H), 7.71-7.75 (m, 2H), 7.83-7.86 (m, 2H).

Example 686

Synthesis of 7-(3-Aminopropoxy)-1,5-dimethylspiro[benzo[b][1,4]diazepine-3,1'-cyclobutane]-2,4-dione Using an appropriate starting material and following the procedure of Example 2, the object compound was synthesized.

¹H-NMR (CDCl₃) δppm:
1.63-1.68 (m, 4H), 1.96-2.01 (m, 2H), 2.78-2.83 (m, 2H), 2.93 (t, J=6.7 Hz, 2H), 3.38 (s, 3H), 3.42 (s, 3H), 4.07 (t, J=6.2 Hz, 2H), 6.74 (d, J=2.7 Hz, 1H), 6.80 (dd, J=8.9 and 2.7 Hz, 1H), 7.16 (d, J=8.9 Hz, 1H).

Example 687

Synthesis of 1,5-Dimethyl-7-{3-[(2-methylpyridin-3-ylmethyl)amino]propoxy}spiro[benzo[b][1,4]diazepine-3,1'-cyclobutane]-2,4-dione Using an appropriate starting material and following the procedure of Example 77, the object compound was synthesized.
¹H-NMR (CDCl₃) δppm:
1.62-1.68 (m, 4H), 2.00-2.05 (m, 2H), 2.57 (s, 3H), 2.82-2.91 (m, 4H), 3.39 (s, 3H), 3.41 (s, 3H), 3.82 (s, 2H), 4.08 (t, J=6.1 Hz, 2H), 6.73 (d, J=2.7 Hz, 1H), 6.79 (dd, J=8.9 and 2.7 Hz, 1H), 7.10 (dd, J=7.6 and 4.9 Hz, 1H), 7.16 (d, J=8.9 Hz, 1H), 7.62 (dd, J=7.6 and 1.4 Hz, 1H), 8.40 (dd, J=4.9 and 1.4 Hz, 1H).

Example 688

Synthesis of 1-ethyl-3,3,5-trimethyl-7-(3-{[2-(1-oxo-1H-isoquinolin-2-yl)ethyl]thiazol-2-ylmethylamino}propoxy)-1,5-dihydrobenzo[b][1,4]diazepine-2,4-dione dihydrochloride Using an appropriate starting material and following the procedure of Example 6, the object compound was synthesized.
¹H-NMR (DMSO-d₆) δppm: 0.75 (s, 3H), 1.01 (t, J=7.0 Hz, 3H), 1.32 (s, 3H), 2.20 (br, 2H), 3.30 (s, 3H), 3.21-3.58 (m, 4H), 3.61-3.71 (m, 1H), 4.00-4.11 (m, 3H), 4.42 (br, 2H), 4.81 (br, 2H), 6.69 (d, J=7.0 Hz, 1H), 6.82-6.89 (m, 2H), 7.38 (d, J=9.0 Hz, 1H), 7.50-7.54 (m, 2H), 7.66-7.75 (m, 2H), 7.89 (br, 2H), 8.21 (d, J=8.0 Hz, 1H).

Example 689

Synthesis of 1-ethyl-7-(3-{(3-fluorobenzyl)-[2-(1-oxo-1H-isoquinolin-2-yl)ethyl]amino}propoxy)-3,3,5-trimethyl-1,5-dihydrobenzo[b][1,4]diazepine-2,4-dione hydrochloride Using an appropriate starting material and following the procedure of Example 6, the object compound was synthesized.
¹H-NMR (DMSO-d₆) δppm:
0.75 (s, 3H), 1.01 (t, J=7.0 Hz, 3H), 1.32 (s, 3H), 2.29 (br, 2H), 3.31 (s, 3H), 3.50 (br, 4H), 3.61-3.68 (m, 1H), 4.02-4.18 (m, 3H), 4.48-4.60 (m, 4H), 6.72 (d, J=7.2 Hz, 1H), 6.85-6.90 (m, 2H), 7.30-7.42 (m, 2H), 7.46-7.81 (m, 7H), 8.23 (d, J=8.0 Hz, 1H).

Example 690

Synthesis of 1-ethyl-7-(3-{(3-methoxybenzyl)-[2-(1-oxo-1H-isoquinolin-2-yl)ethyl]amino}propoxy)-3,3,5-trimethyl-1,5-dihydrobenzo[b][1,4]diazepine-2,4-dione hydrochloride Using an appropriate starting material and following the procedure of Example 6, the object compound was synthesized.
¹H-NMR (DMSO-d₆) δppm:
0.75 (s, 3H), 1.01 (t, J=7.0 Hz, 3H), 1.32 (s, 3H), 2.27 (br, 2H), 3.21-3.30 (m, 5H), 3.42 (s, 3H), 3.51 (br, 2H), 3.61-3.72 (m, 1H), 4.02-4.18 (m, 3H), 4.38-4.61 (m, 4H), 6.73 (d, J=7.2 Hz, 1H), 6.86-6.90 (m, 2H), 7.01 (d, J=8.8 Hz, 1H), 7.18 (d, J=7.6 Hz, 1H), 7.31-7.42 (m, 3H), 7.51-7.56 (m, 2H), 7.68-7.77 (m, 2H), 8.21 (d, J=8.0 Hz, 1H).

Example 691

Synthesis of 1-ethyl-3,3,5-trimethyl-7-(3-{[2-(1-oxo-1H-isoquinolin-2-yl)ethyl]thiophen-2-ylmethylamino}propoxy)-1,5-dihydrobenzo[b][1,4]diazepine-2,4-dione hydrochloride Using an appropriate starting material and following the procedure of Example 6, the object compound was synthesized.
¹H-NMR (DMSO-d₆) δppm:
0.75 (s, 3H), 1.01 (t, J=7.0 Hz, 3H), 1.32 (s, 3H), 2.29 (br, 2H), 3.21-3.29 (m, 5H), 3.49 (br, 4H), 3.62-3.70 (m, 1H), 4.01-4.29 (m, 3H), 4.48 (br, 2H), 6.72 (d, J=7.1 Hz, 1H), 6.86-6.93 (m, 2H), 7.15 (br, 1H), 7.40 (d, J=8.9 Hz, 1H), 7.50-7.55 (m, 3H), 7.67-7.74 (m, 3H), 8.21 (d, J=8.0 Hz, 1H).

Example 692

Synthesis of 7-(3-{bis-[2-(1-oxo-1H-isoquinolin-2-yl)ethyl]amino}propoxy)-1-ethyl-3,3,5-trimethyl-1,5-dihydrobenzo[b][1,4]diazepine-2,4-dione hydrochloride Using an appropriate starting material and following the procedure of Example 6, the object compound was synthesized.
¹H-NMR (DMSO-d₆) δppm:
0.74 (s, 3H), 1.00 (t, J=7.0 Hz, 3H), 1.32 (s, 3H), 2.28 (br, 2H), 3.29 (s, 3H), 3.61 (br, 2H), 3.61-3.71 (m, 5H), 3.95-4.09 (m, 1H), 4.17 (br, 2H), 4.45 (br, 4H), 6.71-6.74 (m, 2H), 6.91-6.97 (m, 2H), 7.40 (d, J=9.0 Hz, 1H), 7.49-7.57 (m, 4H), 7.67-7.74 (m, 4H), 8.15 (d, J=8.2 Hz, 2H).

Example 693

Synthesis of 1-ethyl-7-(3-{[2-(7-methoxy-2-oxo-3,4-dihydro-2H-quinolin-1-yl)ethyl]pyridin-4-ylmethylamino}propoxy)-3,3,5-trimethyl-1,5-dihydrobenzo[b][1,4]diazepine-2,4-dione dihydrochloride Using an appropriate starting material and following the procedure of Example 6, the object compound was synthesized.
¹H-NMR (DMSO-d₆) δppm:
0.74 (s, 3H), 1.00 (t, J=7.0 Hz, 3H), 1.32 (s, 3H), 2.25 (br, 4H), 3.01-3.31 (m, 4H), 3.31 (s, 3H), 3.61-3.70 (m, 1H), 4.00-4.12 (m, 5H), 4.61 (br, 2H), 6.65 (d, J=7.4 Hz, 1H), 6.86-6.91 (m, 2H), 7.39 (d, J=8.9 Hz, 1H), 7.47-7.53 (m, 2H), 7.65-7.74 (m, 2H), 8.08 (br, 2H), 8.21 (d, J=8.0 Hz, 1H), 8.80 (br, 2H).

Example 694

Synthesis of 1-ethyl-3,3,5-trimethyl-7-(3-{[2-(2-oxo-2H-quinolin-1-yl)ethyl]pyridin-4-ylmethylamino}propoxy)-1,5-dihydrobenzo[b][1,4]diazepine-2,4-dione dihydrochloride Using an appropriate starting material and following the procedure of Example 6, the object compound was synthesized.

¹H-NMR (DMSO-d₆) δppm:
0.74 (s, 3H), 1.00 (t, J=7.0 Hz, 3H), 1.32 (s, 3H), 2.28 (br, 2H), 3.21-3.49 (m, 5H), 3.60-3.70 (m, 3H), 4.01-4.19 (m, 3H), 4.78 (br, 4H), 6.64 (d, J=7.4 Hz, 1H), 6.88 (br, 2H), 7.30 (br, 1H), 7.39 (d, J=8.9 Hz, 1H), 7.55-8.20 (m, 6H), 8.82 (br, 2H).

Example 695

Synthesis of 1-ethyl-7-{3-[(2-(6-methoxy-2-oxo-2H-quinolin-1-yl(ethyl)pyridin-4-ylmethylamino]propoxy}-3,3,5-trimethyl-1,5-dihydrobenzo[b][1,4]diazepine-2,4-dione dihydrochloride Using an appropriate starting material and following the procedure of Example 6, the object compound was synthesized.
¹H-NMR (DMSO-d₆) δppm:
0.74 (s, 3H), 1.00 (t, J=7.0 Hz, 3H), 1.32 (s, 3H), 2.17 (br, 2H), 3.01-3.35 (m, 5H), 3.53-3.70 (m, 3H), 3.82 (s, 3H), 4.01-4.12 (m, 3H), 4.67 (br, 4H), 6.63 (d, J=7.4 Hz, 1H), 6.83-6.89 (m, 2H), 7.21 (d, J=9.2 Hz, 1H), 7.32 (s, 1H), 7.39 (d, J=9.0 Hz, 1H), 7.70 (br, 1H), 7.91 (d, J=9.5 Hz, 1H), 8.00 (br, 2H), 8.82 (br, 2H).

Example 696

Synthesis of 1-ethyl-7-(3-{[2-(6-methoxyquinolin-2-yloxy)ethyl]pyridin-4-ylmethylamino}propoxy)-3,3,5-trimethyl-1,5-dihydrobenzo[b][1,4]diazepine-2,4-dione trihydrochloride Using an appropriate starting material and following the procedure of Example 6, the object compound was synthesized.
¹H-NMR (DMSO-d₆) δppm:
0.74 (s, 3H), 1.00 (t, J=7.0 Hz, 3H), 1.32 (s, 3H), 2.09 (br, 2H), 3.01 (br, 2H), 3.31 (s, 3H), 3.70-3.90 (m, 4H), 3.98-4.18 (m, 5H), 4.33 (br, 2H), 4.80 (br, 2H), 6.50 (d, J=9.6 Hz, 1H), 6.79-6.90 (m, 2H), 7.21-7.25 (m, 1H), 7.30-7.39 (m, 2H), 7.85 (d, J=9.6 Hz, 1H), 8.20 (d, J=8.9 Hz, 1H), 8.21 (br, 2H), 8.88 (br, 2H).

Example 697

Synthesis of 1-ethyl-3,3,5-trimethyl-7-(3-{[2-(2-oxo-3,4-dihydro-2H-quinolin-1-yl)ethyl]pyridin-4-ylmethylamino}propoxy)-1,5-dihydrobenzo[b][1,4]diazepine-2,4-dione dihydrochloride Using an appropriate starting material and following the procedure of Example 6, the object compound was synthesized.
¹H-NMR (DMSO-d₆) δppm:
0.74 (s, 3H), 1.00 (t, J=7.0 Hz, 3H), 1.32 (s, 3H), 2.10 (br, 2H), 2.51-2.60 (m, 2H), 2.85 (br, 4H), 3.31 (s, 3H), 3.10-3.35 (m, 2H), 3.52-3.70 (m, 3H), 4.01-4.11 (m, 3H), 4.22 (br, 2H), 6.85-6.89 (m, 2H), 7.00-7.02 (m, 1H), 7.13 (br, 1H), 7.19-7.24 (m, 2H), 7.40 (d, J=8.8 Hz, 1H), 7.82 (br, 2H), 8.73 (br, 2H).

Example 698

Synthesis of 1-ethyl-3,3,5-trimethyl-7-{3-[(2-(4-oxo-4H-thieno[3,2-c]pyridin-5-yl)ethyl)pyridin-4-ylmethylamino]propoxy}-1,5-dihydrobenzo[b][1,4]diazepine-2,4-dione dihydrochloride Using an appropriate starting material and following the procedure of Example 6, the object compound was synthesized.
¹H-NMR (DMSO-d₆) δppm:
0.74 (s, 3H), 1.00 (t, J=7.0 Hz, 3H), 1.32 (s, 3H), 2.08 (br, 2H), 3.05 (br, 2H), 3.31 (s, 3H), 3.53-3.70 (m, 1H), 3.95-4.09 (m, 5H), 4.31 (br, 4H), 6.71-6.83 (m, 2H), 6.95 (br, 1H), 7.39 (d, J=8.9 Hz, 1H), 7.45-7.47 (m, 1H), 7.57-7.64 (m, 2H), 7.88 (br, 2H), 8.72 (br, 2H).

Example 699

Synthesis of 1-ethyl-3,3,5-trimethyl-7-(3-{[2-(7-oxo-7H-thieno[2,3-c]pyridin-6-yl)ethyl]pyridin-4-ylmethylamino}propoxy)-1,5-dihydrobenzo[b][1,4]diazepine-2,4-dione dihydrochloride Using an appropriate starting material and following the procedure of Example 6, the object compound was synthesized.
¹H-NMR (DMSO-d₆) δppm:
0.74 (s, 3H), 1.00 (t, J=7.0 Hz, 3H), 1.32 (s, 3H), 2.32 (br, 2H), 3.33 (s, 3H), 3.26-3.37 (m, 2H), 3.43 (br, 2H), 3.62-3.70 (m, 1H), 4.00-4.13 (m, 3H), 4.53 (br, 2H), 4.82 (br, 2H), 6.82-6.89 (m, 2H), 6.92-6.93 (m, 1H), 7.38-7.42 (m, 2H), 7.69 (d, J=7.2 Hz, 1H), 8.09 (d, J=5.2 Hz, 1H), 8.44 (br, 2H), 9.00 (br, 2H).

Example 700

Synthesis of 1-ethyl-7-(3-{[2-(8-methoxy-2-oxo-2H-quinolin-1-yl)ethyl]pyridin-4-ylmethylamino}propoxy)-3,3,5-trimethyl-1,5-dihydrobenzo[b][1,4]diazepine-2,4-dione dihydrochloride Using an appropriate starting material and following the procedure of Example 6, the object compound was synthesized.
¹H-NMR (DMSO-d₆) δppm:
0.74 (s, 3H), 1.01 (t, J=7.0 Hz, 3H), 1.32 (s, 3H), 2.33 (br, 2H), 3.32 (s, 3H), 3.25-3.38 (m, 2H), 3.53-3.69 (m, 3H), 3.86 (s, 3H), 4.03-4.10 (m, 1H), 4.14 (br, 2H), 4.65 (br, 2H), 4.81 (br, 2H), 6.64 (d, J=9.4 Hz, 1H), 6.89-6.95 (m, 2H), 7.21-7.33 (m, 3H), 7.41 (d, J=8.9 Hz, 1H), 7.92 (d, J=9.4 Hz, 1H), 8.14 (br, 2H), 8.68 (br, 2H).

Example 701

Synthesis of 1-ethyl-7-(3-{[2-(8-methoxyquinolin-2-yloxy)ethyl]pyridin-4-ylmethylamino}propoxy)-3,3,5-trimethyl-1,5-dihydrobenzo[b][1,4]diazepine-2,4-dione trihydrochloride Using an appropriate starting material and following the procedure of Example 6, the object compound was synthesized.
¹H-NMR (DMSO-d₆) δppm:
0.74 (s, 3H), 1.00 (t, J=7.0 Hz, 3H), 1.32 (s, 3H), 2.26 (br, 2H), 3.15-3.21 (m, 2H), 3.31 (s, 3H), 3.58-3.65 (m, 1H), 3.90 (s, 3H), 3.98-4.12 (m, 5H), 4.51-4.80 (m, 4H), 6.52 (d, J=9.6 Hz, 1H), 6.83-6.89 (m, 2H), 7.08-7.11 (m, 1H), 7.19-7.21 (m, 1H), 7.32-7.48 (m, 2H), 7.89 (d, J=9.6 Hz, 1H), 8.00 (br, 2H), 8.80 (br, 2H).

Example 702

Synthesis of 1-ethyl-3,3,5-trimethyl-7-(3-{[2-(4-oxo-4H-furo[3,2-c]pyridin-5-yl)ethyl]pyridin-4-ylmethylamino}propoxy)-1,5-dihydrobenzo[b][1,4]diazepine-2,4-dione dihydrochloride Using an appropriate starting material and following the procedure of Example 6, the object compound was synthesized.

$^1$H-NMR (DMSO-d$_6$) δppm:
0.74 (s, 3H), 1.01 (t, J=7.0 Hz, 3H), 1.32 (s, 3H), 2.16 (br, 2H), 3.09 (br, 2H), 3.31 (s, 3H), 3.60-3.75 (m, 3H), 3.91-4.08 (m, 3H), 4.38 (br, 4H), 6.77-6.87 (m, 3H), 6.94 (br, 1H), 7.39 (d, J=9.0 Hz, 1H), 7.70 (br, 1H), 7.90 (br, 1H), 8.11 (br, 2H), 8.84 (br, 2H).

Example 703

Synthesis of 1-ethyl-7-(3-{[2-(6-methoxy-2-oxo-3,4-dihydro-2H-quinolin-1-yl)ethyl]pyridin-4-ylmethylamino}propoxy)-3,3,5-trimethyl-1,5-dihydrobenzo[b][1,4]diazepine-2,4-dione dihydrochloride Using an appropriate starting material and following the procedure of Example 6, the object compound was synthesized.

$^1$H-NMR (DMSO-d$_6$) δppm:
0.74 (s, 3H), 1.01 (t, J=7.0 Hz, 3H), 1.32 (s, 3H), 2.16 (br, 2H), 2.48-2.54 (m, 2H), 2.77 (br, 2H), 3.31 (s, 3H), 3.25-3.34 (m, 2H), 3.53-3.69 (m, 3H), 3.76 (s, 3H), 3.98-4.10 (m, 3H), 4.33 (br, 2H), 4.74 (br, 2H), 6.60 (d, J=8.3 Hz, 1H), 6.74 (br, 1H), 6.82-6.91 (m, 2H), 7.13 (d, J=8.3 Hz, 1H), 7.40 (d, J=9.0 Hz, 1H), 7.98 (br, 2H), 8.80 (br, 2H).

Example 704

Synthesis of 1-ethyl-7-(3-{[2-(7-methoxy-2-oxo-3,4-dihydro-2H-quinolin-1-yl)ethyl]pyridin-4-ylmethylamino}propoxy)-3,3,5-trimethyl-1,5-dihydrobenzo[b][1,4]diazepine-2,4-dione dihydrochloride Using an appropriate starting material and following the procedure of Example 6, the object compound was synthesized.

$^1$H-NMR (DMSO-d$_6$) δppm:
0.74 (s, 3H), 1.01 (t, J=7.0 Hz, 3H), 1.32 (s, 3H), 2.22 (br, 2H), 2.48-2.53 (m, 2H), 2.83 (br, 2H), 3.10-3.25 (m, 2H), 3.31 (s, 3H), 3.53-3.63 (m, 3H), 3.73 (s, 3H), 4.00-4.10 (m, 3H), 4.32 (br, 2H), 4.61 (br, 2H), 6.74-6.77 (m, 1H), 6.84 6.91 (m, 3H), 7.16 (br, 1H), 7.40 (d, J=8.9 Hz, 1H), 8.00 (br, 2H), 8.83 (br, 2H).

Example 704A

Synthesis of 1,3,3-trimethyl-8-(3-{[2-(1-oxo-1H-isoquinolin-2-yl)ethyl]pyridin-4-ylmethylamino}propoxy)-1,5-dihydrobenzo[b][1,4]diazepine-2,4-dione Using an appropriate starting material and following the procedure of Example 8, the object compound was synthesized.

$^1$H-NMR (CDCl$_3$) δppm:
1.05 (3H, br), 1.52 (3H, br), 1.88-1.93 (2H, m), 2.71 (2H, t, J=6.7 Hz), 2.88 (2H, t, J=6.0 Hz), 3.41 (3H, s), 3.67 (2H, s), 3.84 (2H, t, J=5.9 Hz), 4.10 (2H, t, J=6.0 Hz), 6.41 (1H, d, J=7.3 Hz), 6.52 (1H, dd, J=8.8 and 2.6 Hz), 6.61 (1H, d, J=2.6 Hz), 6.87 (1H, d, J=8.8 Hz), 6.97 (1H, d, J=7.3 Hz), 7.08 (2H, d, J=5.7 Hz), 7.49-7.53 (2H, m), 7.64-7.69 (1H, m), 7.78 (1H, br), 8.26 (2H, d, J=5.7 Hz), 8.38 (1H, d, J=7.3 Hz).

Example 704B

Synthesis of 1,3,3-trimethyl-8-{3-[2-(1-oxo-1H-isoquinolin-2-yl)ethylamino]propoxy}-1,5-dihydrobenzo[b][1,4]diazepine-2,4-dione Using an appropriate starting material and following the procedure of Example 18, the object compound was synthesized.

$^1$H-NMR (CDCl$_3$) δppm:
1.05 (3H, br), 1.55 (3H, br), 1.93-1.99 (2H, m), 2.86 (2H, t, J=6.7 Hz), 3.06 (2H, t, J=6.2 Hz), 3.43 (3H, s), 4.01 (2H, t, J=6.2 Hz), 4.09-4.15 (3H, m), 6.46 (1H, d, J=7.4 Hz), 6.66-6.72 (2H, m), 6.87 (1H, d, J=8.6 Hz), 7.11 (1H, d, J=7.3 Hz), 7.46-7.51 (2H, m), 7.61-7.67 (1H, m), 7.87 (1H, br), 8.41 (1H, d, J=8.0 Hz).

Using appropriate starting materials and following the procedures of the above-mentioned Examples, the compounds shown in Tables 34 to 76 were prepared.

TABLE 34

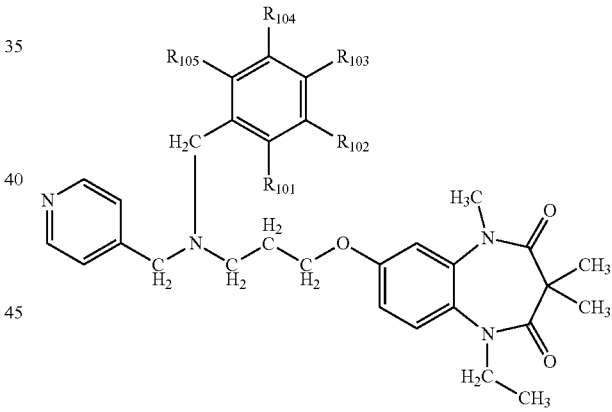

| Example No. | R101 | R102 | R103 | R104 | R105 | MS (M + 1) |
|---|---|---|---|---|---|---|
| Example 705 | —H | —H | —H | —H | —H | 501 |
| Example 706 | —H | —H | —C$_6$H$_5$ | —H | —H | 577 |
| Example 707 | —H | —H | —OCH$_3$ | —H | —H | 531 |
| Example 708 | —H | —OCH$_3$ | —H | —H | —H | 531 |
| Example 709 | —H | —H | —NHCOCH$_3$ | —H | —H | 558 |
| Example 710 | —Cl | —H | —H | —H | —H | 535 |
| Example 711 | —H | —Cl | —H | —H | —H | 535 |
| Example 712 | —H | —H | —Cl | —H | —H | 535 |
| Example 713 | —OCH$_3$ | —H | —H | —H | —H | 531 |
| Example 714 | —H | —C$_6$H$_5$ | —H | —H | —H | 577 |
| Example 715 | —H | —H | -2-THIENYL | —H | —H | 583 |
| Example 716 | —H | —H | -3-PYRIDYL | —H | —H | 578 |
| Example 717 | —H | -3-PYRIDYL | —H | —H | —H | 578 |
| Example 718 | -3-PYRIDYL | —H | —H | —H | —H | 578 |

TABLE 35

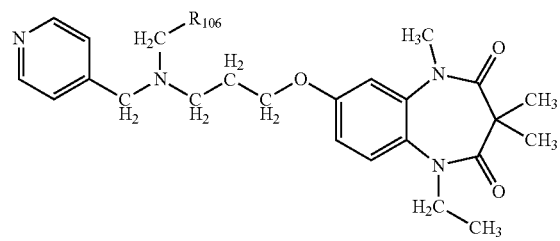

| Example No. | R101 | R102 | R103 | R104 | R105 | MS (M + 1) |
|---|---|---|---|---|---|---|
| Example 719 | —H | —H | 1-methyl-1,2,4-triazol-3-yl | —H | —H | 568 |
| Example 720 | —H | —H | 1-methylimidazol-2-yl | —H | —H | 567 |
| Example 712 | —H | 1-methylpyrazol-5-yl | —H | —H | —H | 567 |
| Example 722 | —H | —H | 5-methylpyrimidin-4-yl | —H | —H | 579 |
| Example 723 | —H | 5-methylpyrimidin-4-yl | —H | —H | —H | 579 |
| Example 724 | —H | —H | 1-methyl-2-oxopyrrolidin-3-yl | —H | —H | 584 |

TABLE 36

| Example No. | R106 | MS (M + 1) |
|---|---|---|
| Example 725 | -3-FURYL | 491 |
| Example 726 | -2-PYRIDYL | 502 |
| Example 727 | -3-PYRIDYL | 502 |
| Example 728 | -4-PYRIDYL | 502 |
| Example 729 | -2-THIENYL | 507 |
| Example 730 | -3-THIENYL | 507 |
| Example 731 | —CH=CHC$_6$H$_5$ (trans) | 527 |
| Example 732 | -2-FURYL | 491 |
| Example 733 | —CH$_2$C$_6$H$_5$ | 515 |
| Example 734 | —CH(CH$_3$)C$_6$H$_5$ | 529 |
| Example 735 | —(CH$_2$)$_2$C$_6$H$_5$ | 529 |
| Example 736 | -2-BENZTHIAZOLYL | 558 |

TABLE 37
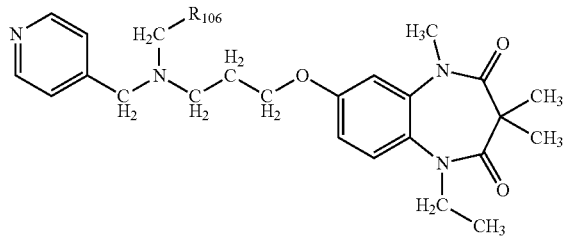
| Example No. | R106 | MS (M + 1) |
|---|---|---|
| Example 737 | 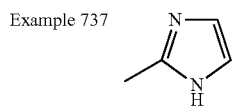 | 491 |
| Example 738 | 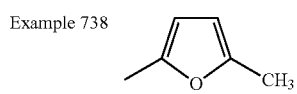 | 505 |
| Example 739 | 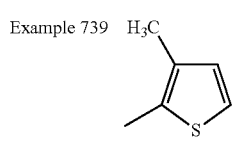 | 521 |
| Example 740 | 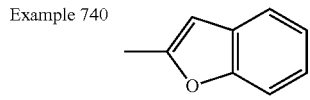 | 541 |
| Example 741 | 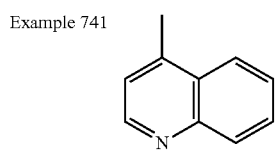 | 552 |
| Example 742 | 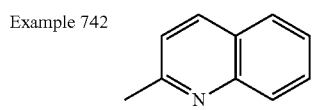 | 552 |
| Example 743 | 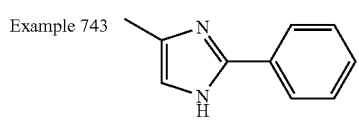 | 567 |
| Example 744 | 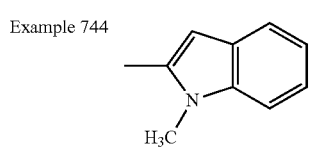 | 554 |
| Example 745 | 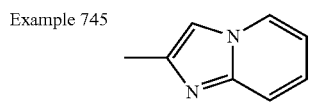 | 541 |
TABLE 38
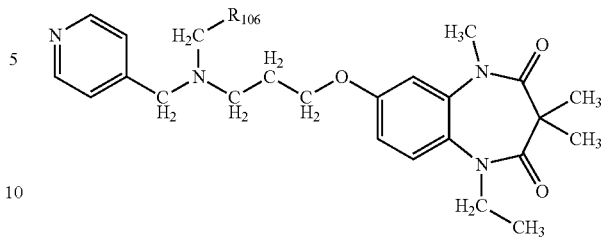
| Example No. | R106 | MS (M + 1) |
|---|---|---|
| Example 746 | 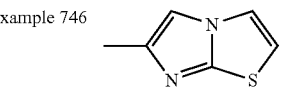 | 547 |
| Example 747 | 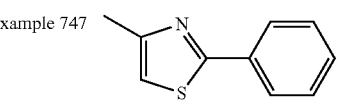 | 584 |
| Example 748 | 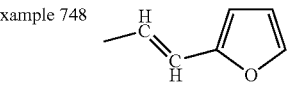 | 517 |
| Example 749 | 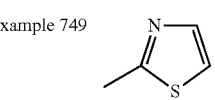 | 508 |
| Example 750 | 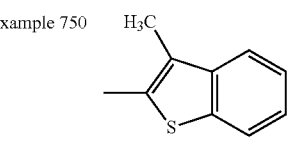 | 571 |
| Example 751 | 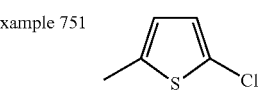 | 541 |
| Example 753 | 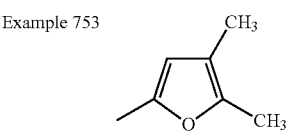 | 519 |
| Example 753 | 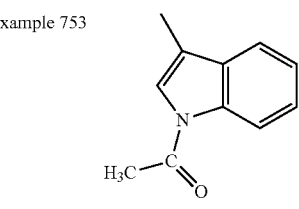 | 582 |

TABLE 39
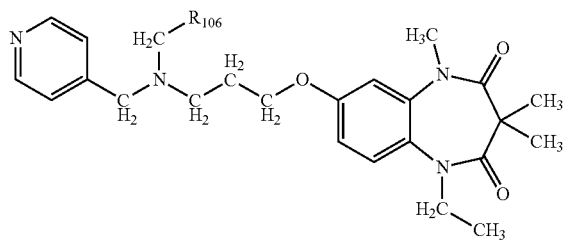
| Example No. | R106 | MS (M + 1) |
|---|---|---|
| Example 754 | 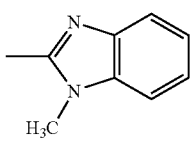 | 555 |
| Example 755 | 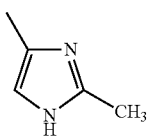 | 505 |
| Example 756 | 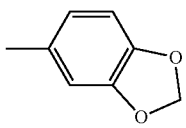 | 545 |
| Example 757 | 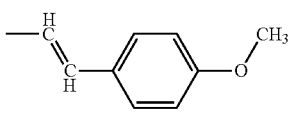 | 557 |
| Example 758 | 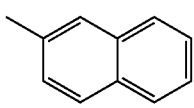 | 551 |
| Example 759 | 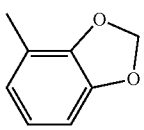 | 545 |
| Example 760 | 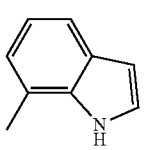 | 540 |
| Example 761 | 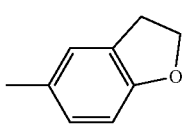 | 543 |
TABLE 40
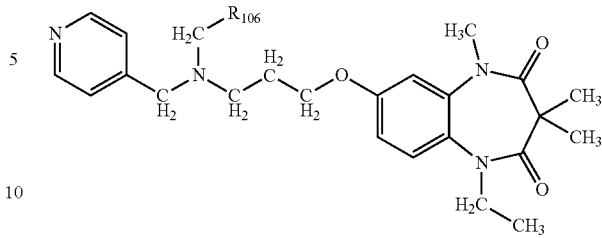
| Example No. | R106 | MS (M + 1) |
|---|---|---|
| Example 762 | 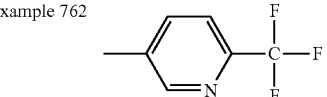 | 570 |
| Example 763 | 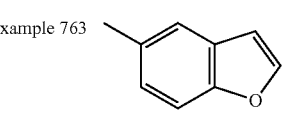 | 541 |
| Example 764 | 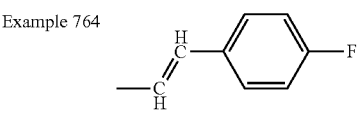 | 545 |
| Example 765 | 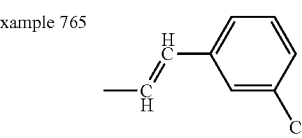 | 561 |
| Example 766 | 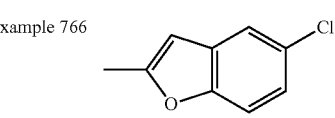 | 575 |
| Example 767 | 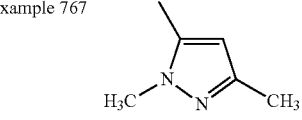 | 519 |
| Example 768 | 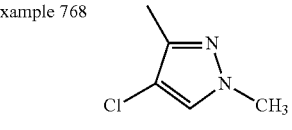 | 539 |
| Example 769 | 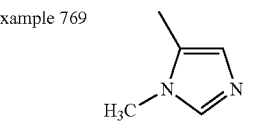 | 505 |
| Example 770 | 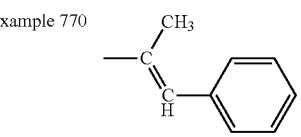 | 541 |

TABLE 41
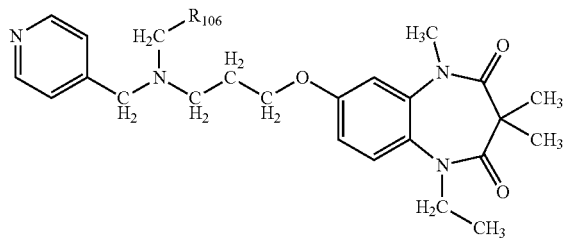
| Example No. | R106 | MS (M + 1) |
|---|---|---|
| Example 771 | 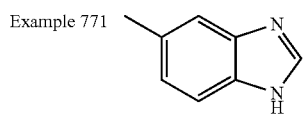 | 541 |
| Example 772 | 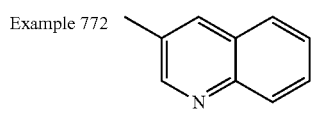 | 552 |
| Example 773 | 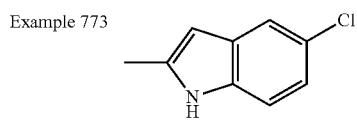 | 574 |
| Example 774 | 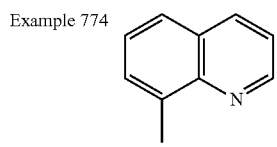 | 552 |
| Example 775 | 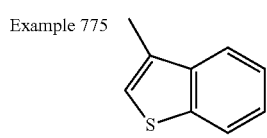 | 557 |
| Example 776 | 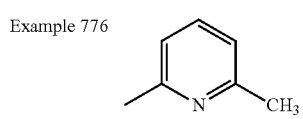 | 516 |
| Example 777 | 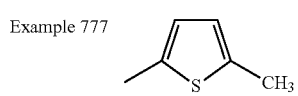 | 521 |
| Example 778 | 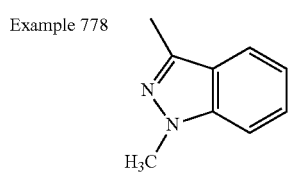 | 555 |
TABLE 42
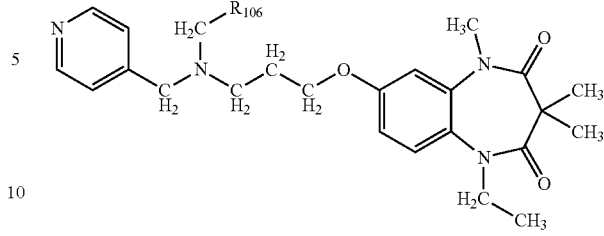
| Example No. | R106 | MS (M + 1) |
|---|---|---|
| Example 779 | 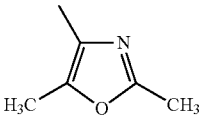 | 520 |
| Example 780 | 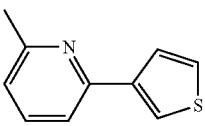 | 584 |
| Example 781 | 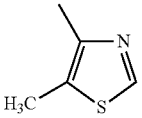 | 522 |
| Example 782 | 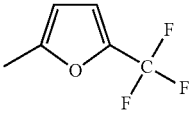 | 559 |
| Example 783 | 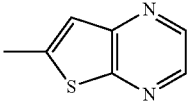 | 559 |
| Example 784 | 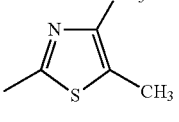 | 536 |
| Example 785 | 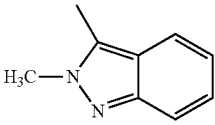 | 555 |
| Example 786 | 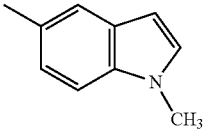 | 554 |
| Example 787 | 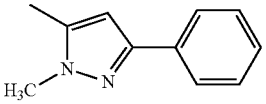 | 581 |

TABLE 43
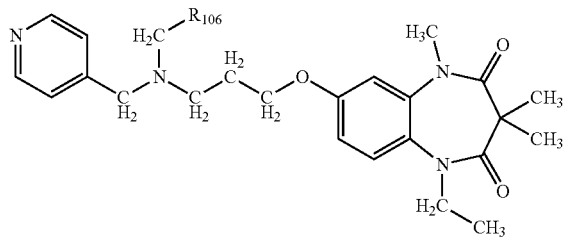
| Example No. | R106 | MS (M + 1) |
|---|---|---|
| Example 788 | 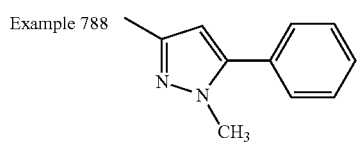 | 581 |
| Example 789 | | 542 |
| Example 790 | | 558 |
| Example 791 | | 556 |
| Example 792 | | 505 |
| Example 793 | | 545 |
| Example 794 | | 584 |
TABLE 44
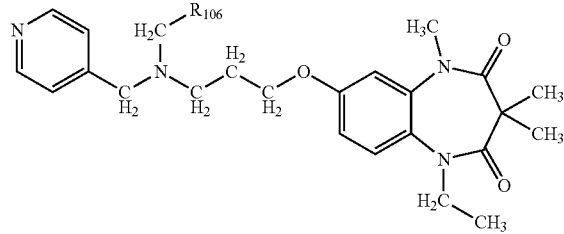
| Example No. | R106 | MS (M + 1) |
|---|---|---|
| Example 795 | 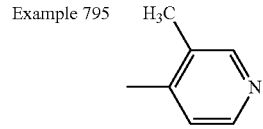 | 516 |
| Example 796 | 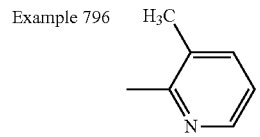 | 516 |
| Example 797 | 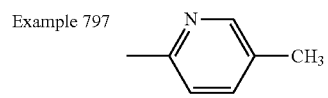 | 516 |
| Example 798 | 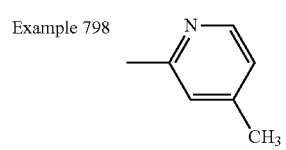 | 516 |
| Example 799 | 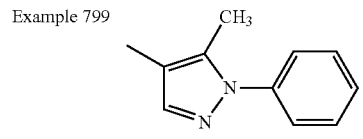 | 581 |
| Example 800 | 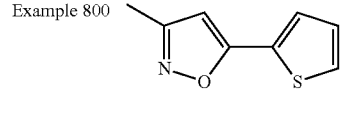 | 574 |
| Example 801 | 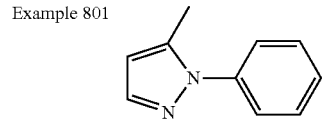 | 567 |
| Example 802 | 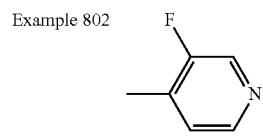 | 520 |
| Example 803 | 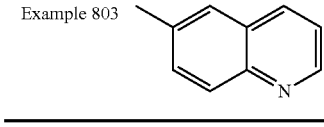 | 552 |

TABLE 45
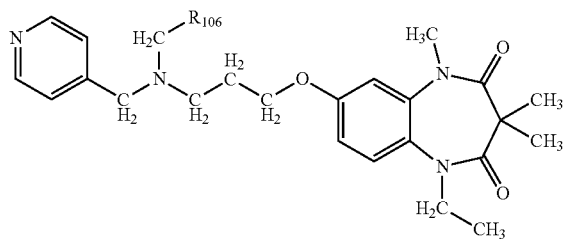
| Example No. | R106 | MS (M + 1) |
|---|---|---|
| Example 804 | 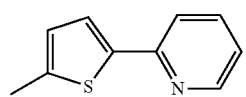 | 584 |
| Example 805 | 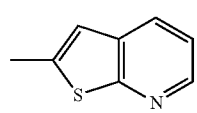 | 558 |
| Example 806 | 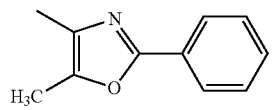 | 582 |
| Example 807 | 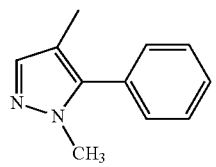 | 581 |
| Example 808 | 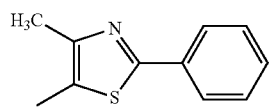 | 598 |
| Example 809 | 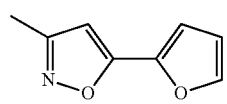 | 558 |
| Example 810 | 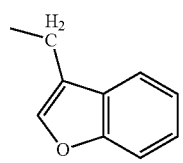 | 555 |
| Example 811 | 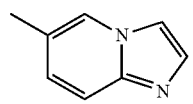 | 541 |
TABLE 46
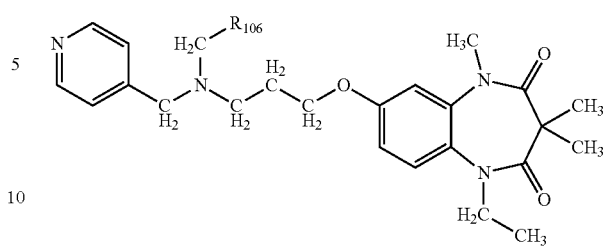
| Example No. | R106 | MS (M + 1) |
|---|---|---|
| Example 812 | 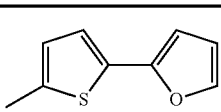 | 573 |
| Example 813 | 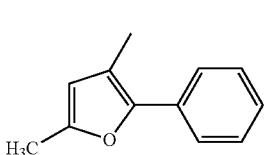 | 581 |
| Example 814 | 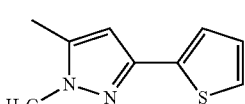 | 587 |
| Example 815 | 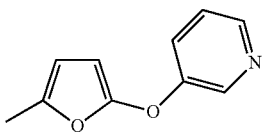 | 584 |
| Example 816 | 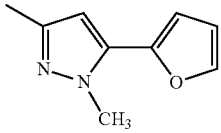 | 571 |
| Example 817 | 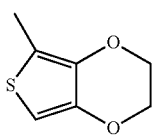 | 565 |
| Example 818 | 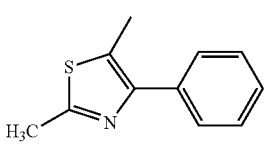 | 598 |
| Example 819 | 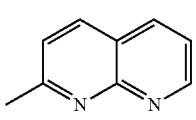 | 553 |

TABLE 47
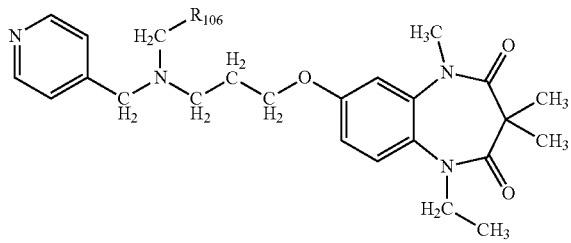
| Example No. | R106 | MS (M + 1) |
|---|---|---|
| Example 820 | 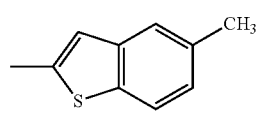 | 571 |
| Example 821 | 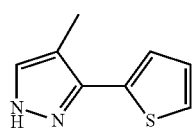 | 573 |
| Example 822 | 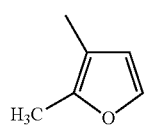 | 505 |
| Example 823 | 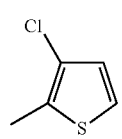 | 541 |
| Example 824 | 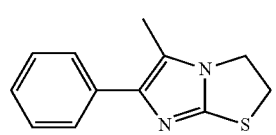 | 625 |
| Example 825 | 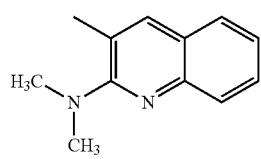 | 595 |
| Example 826 | 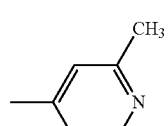 | 516 |
| Example 827 | 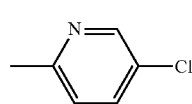 | 536 |
TABLE 48
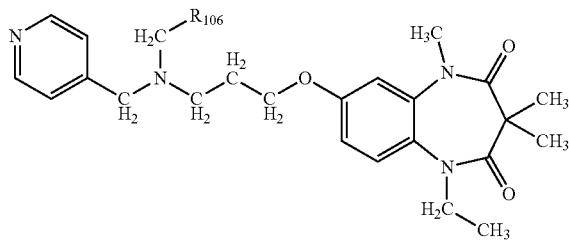
| Example No. | R106 | MS (M + 1) |
|---|---|---|
| Example 828 | 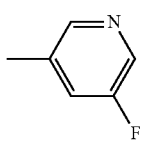 | 520 |
| Example 829 | 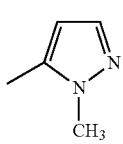 | 505 |
TABLE 49
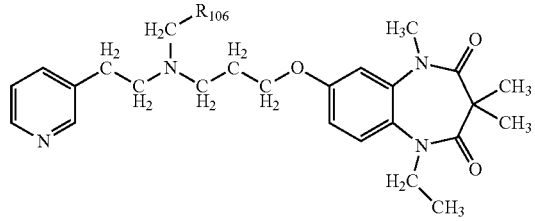
| Example No. | R106 | MS (M + 1) |
|---|---|---|
| Example 830 | 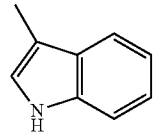 | 554 |
| Example 831 | 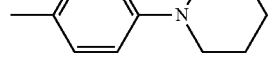 | 598 |
| Example 832 | 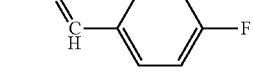 | 559 |
| Example 833 | 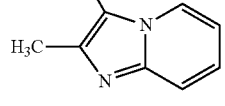 | 569 |
| Example 834 | 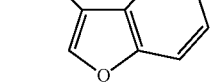 | 569 |

TABLE 49-continued

[Structure: pyridine-CH2-CH2-N(CH2-R106)-CH2-CH2-CH2-O-benzodiazepine-dione with N-CH3, C(CH3)2, N-CH2CH3]

| Example No. | R106 | MS (M + 1) |
| --- | --- | --- |
| Example 835 | 5-methyl-furan-2-yl-oxy-pyridin-3-yl | 598 |
| Example 836 | 4,5-dimethyl-1-(4-methoxyphenyl)pyrazol-3-yl | 625 |
| Example 837 | 2-methyl-1,8-naphthyridin-3-yl | 567 |

TABLE 50

[Structure: pyridine-CH2-CH2-N(CH2-R106)-CH2-CH2-CH2-O-benzodiazepine-dione with N-CH3, C(CH3)2, N-CH2CH3]

| Example No. | R106 | MS (M + 1) |
| --- | --- | --- |
| Example 838 | 5-methyl-2-(pyrrolidin-1-yl)pyridin-3-yl | 585 |
| Example 839 | 3-methyl-2-(pyrrolidin-1-yl)pyridin-3-yl | 585 |
| Example 840 | 3-methyl-2-(dimethylamino)quinolin-... | 609 |
| Example 841 | 2-methyl-5-chloro-pyridin-3-yl | 550 |

TABLE 50-continued

[Structure: pyridine-CH2-CH2-N(CH2-R106)-CH2-CH2-CH2-O-benzodiazepine-dione with two N-CH3, C(CH3)2, N-CH2CH3]

| Example No. | R106 | MS (M + 1) |
| --- | --- | --- |
| Example 842 | 5-fluoro-3-methyl-pyridin-... | 534 |
| Example 843 | 4-(trifluoromethyl)-3-methyl-pyridin-... | 584 |
| Example 844 | 3,5-dichloro-4-methyl-pyridin-... | 584 |
| Example 845 | 1-ethyl-8-methoxy-quinolin-2(1H)-one-... | 626 |

TABLE 51

[Structure: pyridine-CH2-CH2-N(CH2-R106)-CH2-CH2-CH2-O-benzodiazepine-dione with N-CH3, C(CH3)2, N-CH2CH3]

| Example No. | R106 | MS (M + 1) |
| --- | --- | --- |
| Example 846 | 2-(8-methoxyquinolin-2-yloxy)methyl | 626 |
| Example 847 | 1,5-dimethyl-1H-pyrazol-3-yl | 519 |

TABLE 51-continued

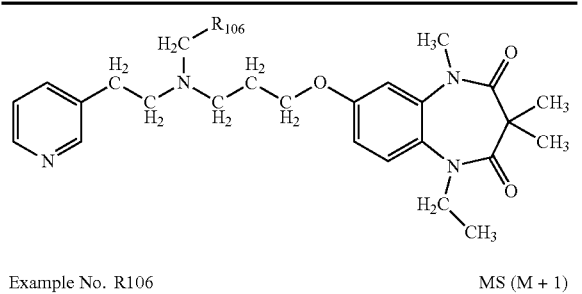

| Example No. | R106 | MS (M + 1) |
|---|---|---|
| Example 848 | 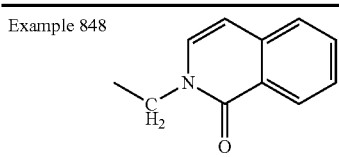 | 596 |

TABLE 52

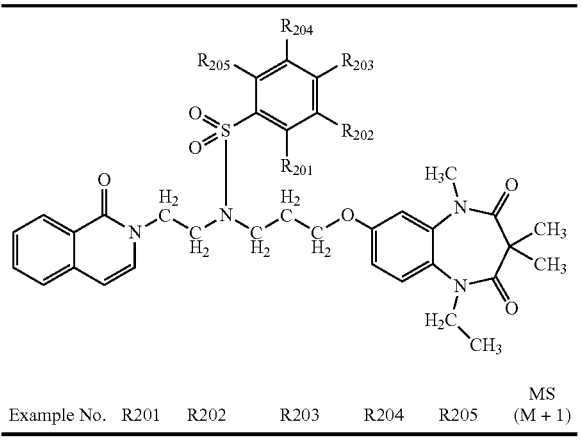

| Example No. | R201 | R202 | R203 | R204 | R205 | MS (M + 1) |
|---|---|---|---|---|---|---|
| Example 849 | —H | —H | —OCH₃ | —H | —H | 661 |
| Example 850 | —H | —H | —Cl | —H | —H | 665 |

TABLE 52-continued

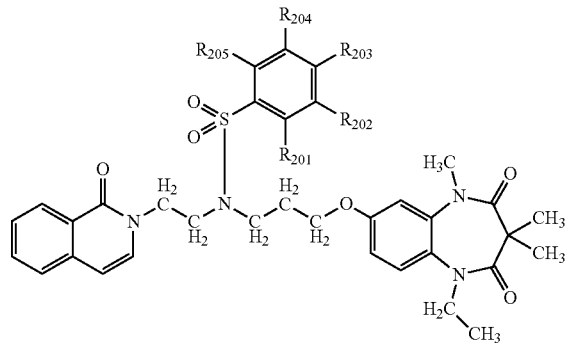

| Example No. | R201 | R202 | R203 | R204 | R205 | MS (M + 1) |
|---|---|---|---|---|---|---|
| Example 851 | —H | —H | —H | —H | —CH₃ | 645 |
| Example 852 | —H | —H | —F | —H | —H | 649 |
| Example 853 | —H | —H | —H | —H | —Cl | 665 |
| Example 854 | —H | —H | —H | —H | —CO₂CH₃ | 689 |
| Example 855 | —CN | —H | —H | —H | —H | 656 |
| Example 856 | —H | —OCH₃ | —H | —H | —H | 661 |
| Example 857 | —H | —F | —H | —H | —H | 649 |
| Example 858 | —H | —H | —H | —H | —F | 649 |
| Example 859 | —H | —CH₃ | —H | —H | —H | 645 |
| Example 860 | —H | —Cl | —H | —H | —H | 665 |
| Example 861 | —H | —H | —H | —H | —H | 631 |
| Example 862 | —H | —H | —NHCOCH₃ | —H | —H | 688 |
| Example 863 | —H | —H | —CH₃ | —H | —H | 645 |
| Example 864 | —H | —CO₂H | —H | —H | —H | 675 |
| Example 865 | —H | —CN | —H | —H | —H | 656 |
| Example 866 | —H | —H | —CN | —H | —H | 656 |

TABLE 53

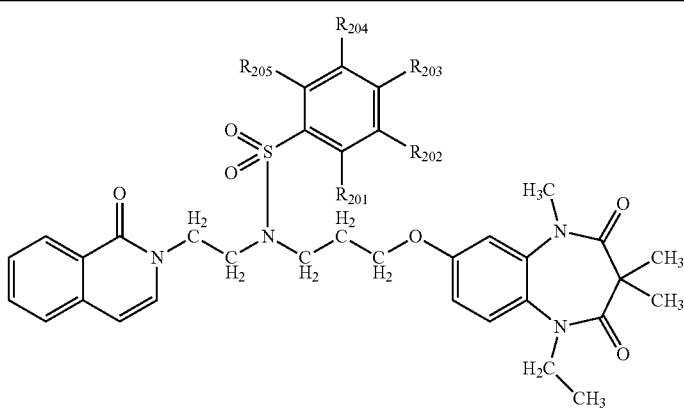

| Example No. | R201 | R202 | R203 | R204 | R205 | MS (M + 1) |
|---|---|---|---|---|---|---|
| Example 867 | —H | —H | 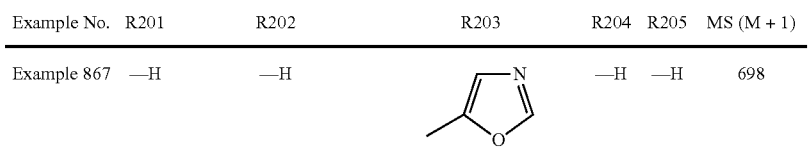 | —H | —H | 698 |

TABLE 53-continued
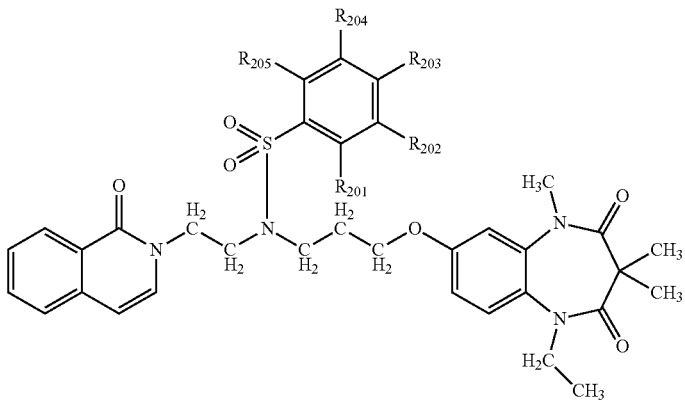
| Example No. | R201 | R202 | R203 | R204 | R205 | MS (M + 1) |
|---|---|---|---|---|---|---|
| Example 868 | —H | —H | 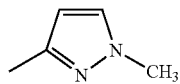 | —H | —H | 711 |
| Example 869 | —H | —H | 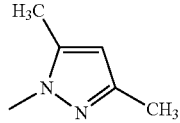 | —H | —H | 725 |
| Example 870 | —H | 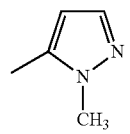 | —H | —H | —H | 711 |
| Example 871 | —H | —H | 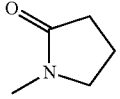 | —H | —H | 714 |
| Example 872 | —H | 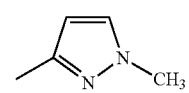 | —H | —H | —H | 711 |
| Example 873 | —H | 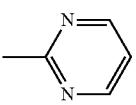 | —H | —H | —H | 709 |

TABLE 54
| Example No. | R201 | R202 | R203 | R204 | R205 | MS (M + 1) |
|---|---|---|---|---|---|---|
| Example 874 | —H | 2-methyl-4-thiazolyl | —H | —H | —H | 728 |
| Example 875 | —H | —H | 2-methylpyrimidin-yl | —H | —H | 709 |
| Example 876 | —H | —H | 2-methyl-4-thiazolyl | —H | —H | 728 |
| Example 877 | —H | 2,4-dimethylpyrimidinyl | —H | —H | —H | 723 |
TABLE 55
| Example No. | R206 | MS (M + 1) |
|---|---|---|
| Example 878 | -2-THIENYL | 637 |
| Example 879 | —CH$_2$C$_6$H$_5$ | 645 |
| Example 880 | -3-THIENYL | 637 |
| Example 881 | -2-FURYL | 621 |
TABLE 56
| Example No. | R206 | MS (M + 1) |
|---|---|---|
| Example 882 | 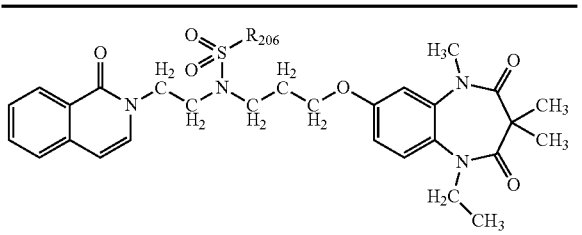 8-methylquinolinyl | 682 |

TABLE 56-continued

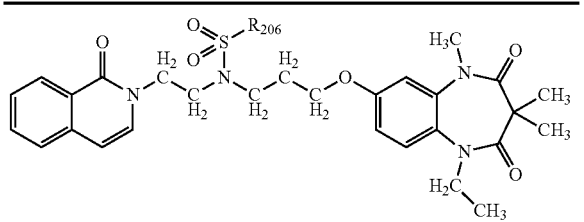

| Example No. | R206 | MS (M + 1) |
|---|---|---|
| Example 883 | 1-methyl-4-imidazolyl | 635 |
| Example 884 | 7-methyl-2,3-dihydro-1,4-benzodioxinyl | 689 |
| Example 885 | 5-methyl-2-chlorothienyl | 671 |
| Example 886 | 7-methyl-4-methyl-3,4-dihydro-2H-benzo[1,4]oxazinyl | 702 |
| Example 887 | 3-methyl-8-methylquinolinyl | 696 |
| Example 888 | 5-methylisoquinolinyl | 682 |

TABLE 57

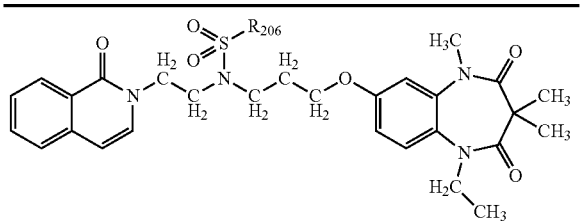

| Example No. | R206 | MS (M + 1) |
|---|---|---|
| Example 889 | 4-methyl-5-chloro-1-methylpyrazolyl | 683 |
| Example 890 | 3,4-dimethyl-5-methylisoxazolyl | 650 |
| Example 891 | 3-methyl-2,5-dichlorothienyl | 705 |
| Example 892 | 4-methyl-5-acetamidothiazolyl | 709 |
| Example 893 | 3-methyl-2-methoxycarbonylthienyl | 695 |
| Example 894 | 7-methyl-1-methylindolyl | 684 |
| Example 895 | 3,4-dimethyl-2,5-dimethylthienyl | 665 |

TABLE 58

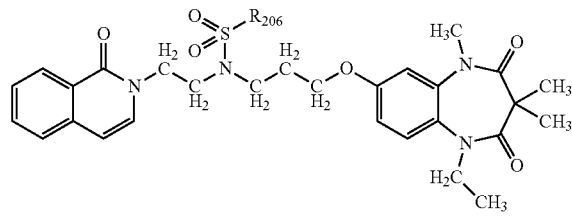

| Example No. | R206 | MS (M + 1) |
|---|---|---|
| Example 896 | 2,5-dimethylthienyl | 651 |

TABLE 58-continued
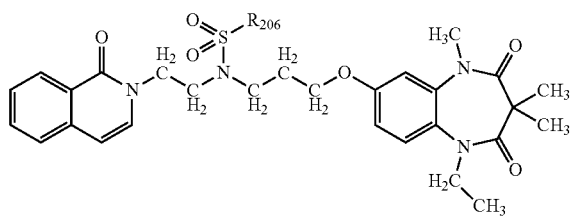
| Example No. | R206 | MS (M + 1) |
| --- | --- | --- |
| Example 897 | 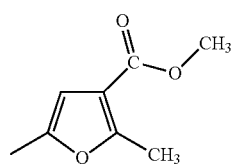 | 693 |
| Example 898 | 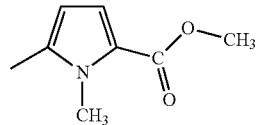 | 692 |
| Example 899 | 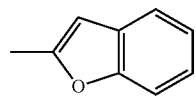 | 671 |
| Example 900 | 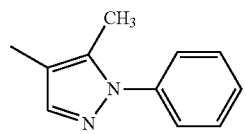 | 711 |
| Example 901 | 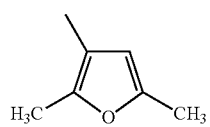 | 649 |
| Example 902 | 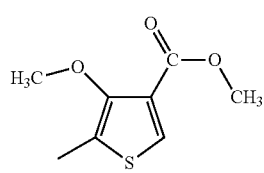 | 725 |
| Example 903 | 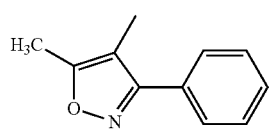 | 712 |
TABLE 59
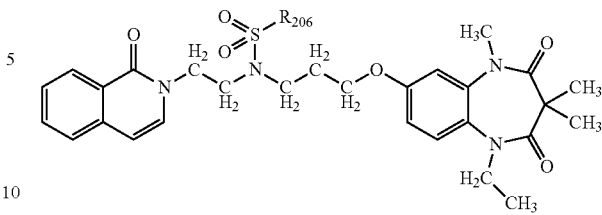
| Example No. | R206 | MS (M + 1) |
| --- | --- | --- |
| Example 904 | 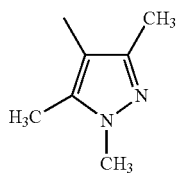 | 663 |
| Example 905 | 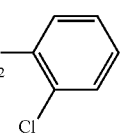 | 679 |
| Example 906 | 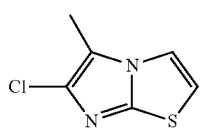 | 711 |
| Example 907 | 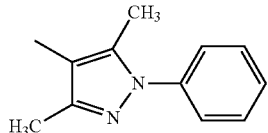 | 725 |
| Example 908 | 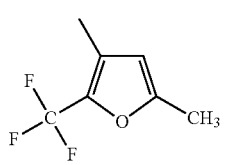 | 703 |
| Example 909 | 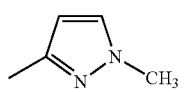 | 635 |
| Example 910 | 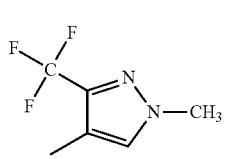 | 703 |

TABLE 60

[Structure: isoquinolinone-CH2-CH2-N(SO2-R206)-CH2-CH2-O-benzodiazepinedione with N-CH3, gem-diCH3, and N-CH2CH3 substituents]

| Example No. | R206 | MS (M + 1) |
|---|---|---|
| Example 911 | 1,5-dimethyl-1H-pyrazol-3-yl | 635 |
| Example 912 | 1,4-dimethyl-1H-indol-? | 684 |
| Example 913 | 2,4-dimethylthiazol-5-yl (with CH3) | 666 |
| Example 914 | 2-methylbenzyl | 659 |
| Example 915 | 4-chlorobenzyl | 679 |
| Example 916 | 2-fluorobenzyl | 663 |
| Example 917 | 6-morpholinopyridin-3-yl | 717 |
| Example 918 | benzo[d][1,3]dioxol-5-yl | 675 |

TABLE 61

[Structure: isoquinolinone-CH2-CH2-N(SO2-R206)-CH2-CH2-O-benzodiazepinedione with N-CH3, gem-diCH3, and N-CH2CH3 substituents]

| Example No. | R206 | MS (M + 1) |
|---|---|---|
| Example 919 | 2,3-dihydrobenzofuran-5-yl | 673 |
| Example 920 | 5-(5-methylthiophen-2-yl)oxazol-2-yl | 704 |
| Example 921 | 3,4-dimethylisoxazol-5-yl | 636 |
| Example 922 | 1,5-dimethyl-1H-indol-? | 684 |
| Example 923 | 4-methyl-3,4-dihydro-2H-pyrido[3,2-b][1,4]oxazin-7-yl | 703 |
| Example 924 | 2-oxoindolin-5-yl | 686 |
| Example 925 | 3-fluorobenzyl | 663 |

TABLE 62
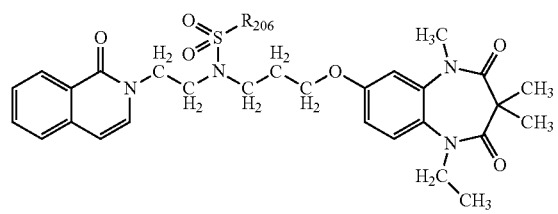
| Example No. | R206 | MS (M + 1) |
|---|---|---|
| Example 926 | 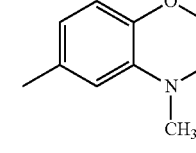 | 714 |
| Example 927 | 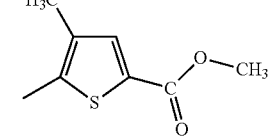 | 700 |
| Example 928 | 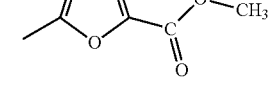 | 702 |
| Example 929 | 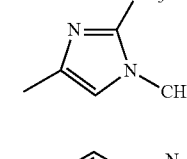 | 703 |
| Example 930 | 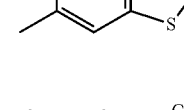 | 702 |
| Example 931 | 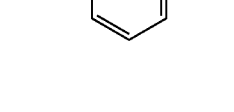 | 663 |
| Example 932 | 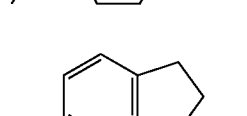 | 707 |
TABLE 63
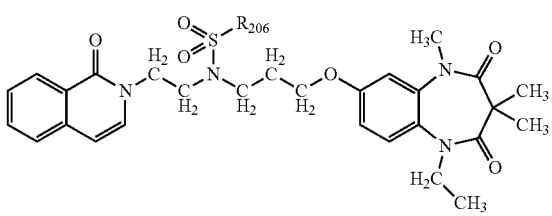
| Example No. | R206 | MS (M + 1) |
|---|---|---|
| Example 933 | 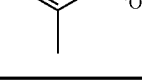 | 702 |
| Example 934 | | 709 |
| Example 935 | | 679 |
| Example 936 | | 649 |
| Example 937 | | 688 |
| Example 938 | | 670 |
| Example 939 | | 670 |
| Example 940 | | 673 |

TABLE 64

| Example No. | R301 | R302 | R303 | R304 | R305 | MS (M + 1) |
|---|---|---|---|---|---|---|
| Example 941 | —H | —H | —H | —H | —H | 529 |
| Example 942 | —H | —H | —CH$_3$ | —H | —H | 543 |
| Example 943 | —H | —H | —Cl | —H | —H | 563 |
| Example 944 | —H | —H | —F | —H | —H | 547 |
| Example 945 | —H | —H | —OCH$_3$ | —H | —H | 559 |
| Example 946 | —OCH$_3$ | —H | —H | —H | —H | 559 |
| Example 947 | —Cl | —H | —H | —H | —H | 563 |
| Example 948 | —CH$_3$ | —H | —H | —H | —H | 543 |
| Example 949 | —F | —H | —H | —H | —H | 547 |
| Example 950 | —H | —OCH$_3$ | —H | —H | —H | 559 |
| Example 951 | —H | —Cl | —H | —H | —H | 563 |
| Example 952 | —H | —CH$_3$ | —H | —H | —H | 543 |
| Example 953 | —H | —F | —H | —H | —H | 547 |

TABLE 65

| Example No. | R306 | MS (M + 1) |
|---|---|---|
| Example 954 | —CH$_2$OC$_6$H$_5$ | 559 |
| Example 955 | —(CH$_2$)$_2$C$_6$H$_5$ | 557 |
| Example 956 | —CH=CHC$_6$H$_5$ (trans) | 555 |
| Example 957 | -2-PYRIDYL | 530 |
| Example 958 | -3-PYRIDYL | 530 |
| Example 959 | -4-PYRIDYL | 530 |
| Example 960 | -2-FURYL | 519 |
| Example 961 | -2-THIENYL | 535 |
| Example 962 | -3-FURYL | 519 |
| Example 963 | -3-THIENYL | 535 |
| Example 964 | -2-BENZTHIAZOLYL | 586 |

TABLE 66

| Example No. | R306 | MS (M + 1) |
|---|---|---|
| Example 965 | —CH$_2$CH$_2$-(3-pyridyl) | 558 |
| Example 966 | —CH$_2$-(2-pyridyl) | 544 |
| Example 967 | —CH$_2$-(3-pyridyl) | 544 |
| Example 968 | —CH$_2$-(4-pyridyl) | 544 |
| Example 969 | —CH$_2$-(2-thienyl) | 549 |
| Example 970 | —CH$_2$-(3-thienyl) | 549 |
| Example 971 | 2-(chroman-2-yl) | 585 |
| Example 972 | —CH=CH-(3-pyridyl) | 556 |
| Example 973 | —CH=CH-(4-pyridyl) | 556 |

TABLE 67

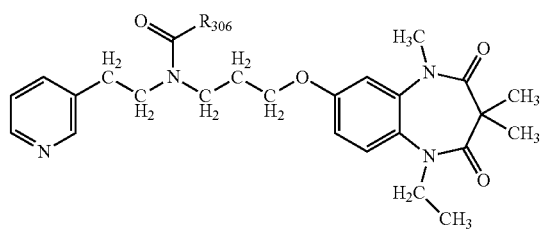

| Example No. | R306 | MS (M + 1) |
|---|---|---|
| Example 974 | 2-methyl-1H-indol-yl | 568 |
| Example 975 | 3-methyl-1H-indol-yl | 568 |
| Example 976 | 2-methylquinolin-yl | 580 |
| Example 977 | 3-methylquinolin-yl | 580 |
| Example 978 | 4-methylquinolin-yl | 580 |
| Example 979 | 6-methylquinolin-yl | 580 |
| Example 980 | 1-methylisoquinolin-yl | 580 |
| Example 981 | 3-methylisoquinolin-yl | 580 |

TABLE 68

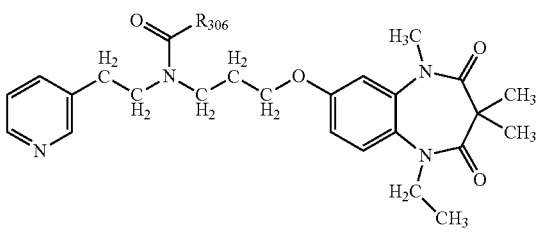

| Example No. | R306 | MS (M + 1) |
|---|---|---|
| Example 982 | 2-methylbenzofuran-yl | 569 |
| Example 983 | 3-(CH2)-1H-indol-yl | 582 |
| Example 984 | 1,2-dimethyl-1H-indol-yl | 582 |
| Example 985 | 2-(CH=CH)-pyridinyl | 556 |
| Example 986 | 6-methyl-3,4-dihydroquinolin-2(1H)-one-yl | 598 |
| Example 987 | 1-methyl-3-(CH2)-1H-indol-yl | 596 |
| Example 988 | 6-methylbenzothiazol-yl | 586 |
| Example 989 | 1,2-dimethyl-1H-pyrrol-yl | 532 |

TABLE 69
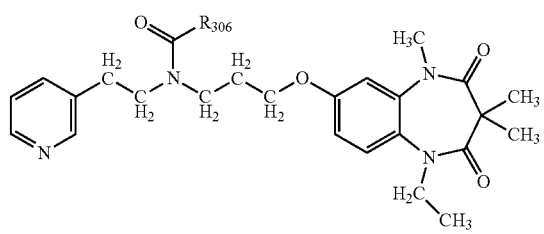
| Example No. | R306 | MS (M + 1) |
|---|---|---|
| Example 990 | 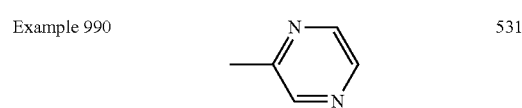 | 531 |
| Example 991 | 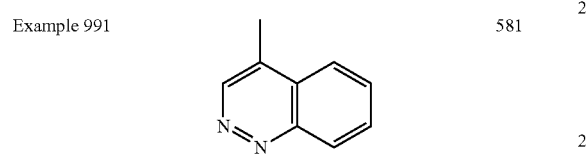 | 581 |
| Example 992 | 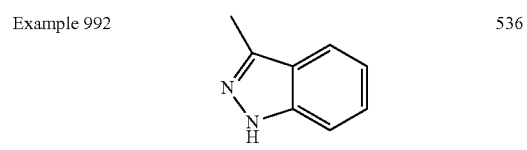 | 536 |
| Example 993 | 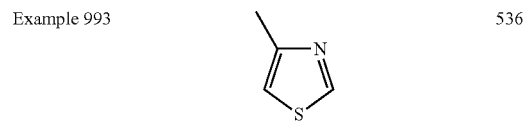 | 536 |
| Example 994 | 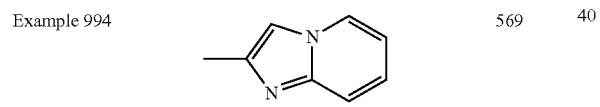 | 569 |
| Example 995 | 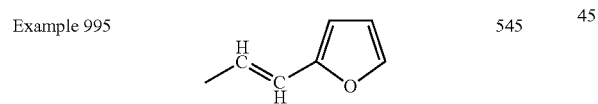 | 545 |
| Example 996 | 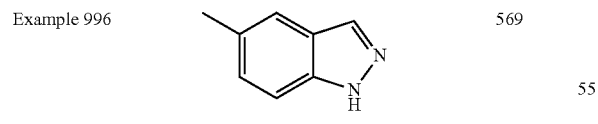 | 569 |
| Example 997 | 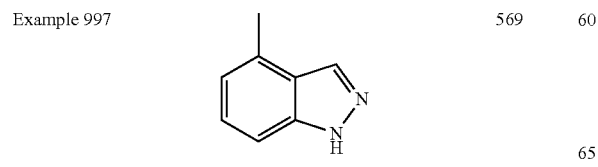 | 569 |
TABLE 70
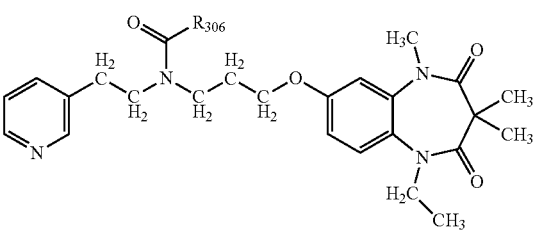
| Example No. | R306 | MS (M + 1) |
|---|---|---|
| Example 998 | 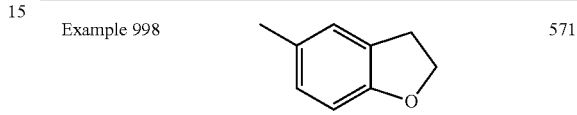 | 571 |
| Example 999 | 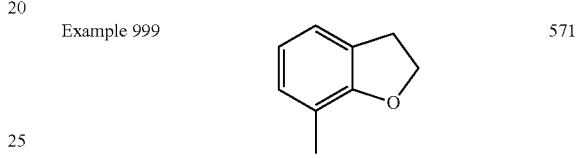 | 571 |
| Example 1000 | 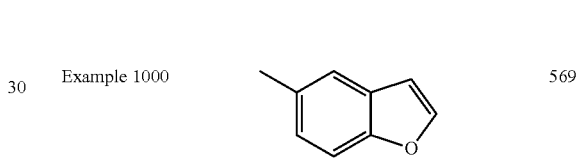 | 569 |
| Example 1001 | 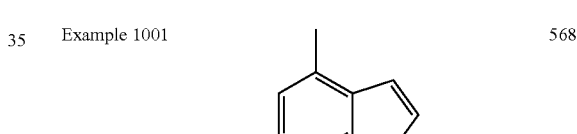 | 568 |
| Example 1002 |  | 568 |
| Example 1003 | 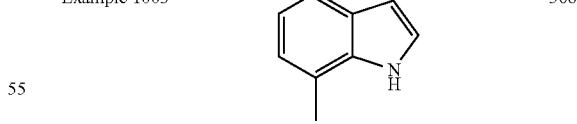 | 568 |
| Example 1004 | 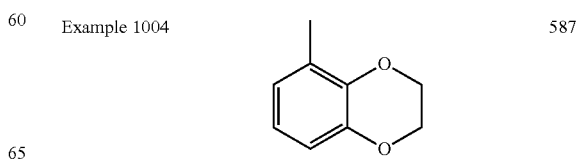 | 587 |

TABLE 71
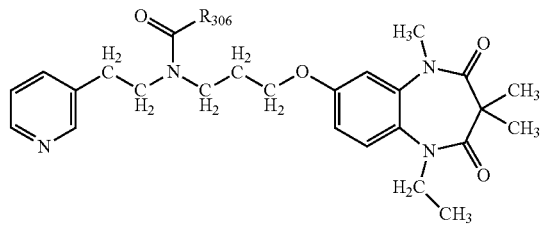
| Example No. | R306 | MS (M + 1) |
|---|---|---|
| Example 1005 | 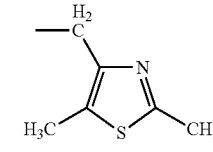 | 581 |
| Example 1006 | 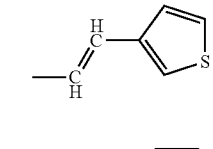 | 581 |
| Example 1007 | 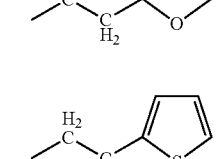 | 587 |
| Example 1008 |  | 600 |
| Example 1009 | 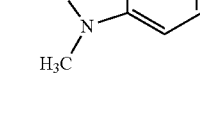 | 533 |
| Example 1010 | 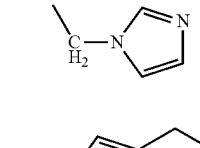 | 533 |
| Example 1011 | 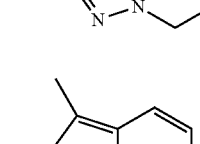 | 584 |
| Example 1012 | 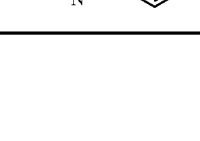 | 533 |
TABLE 72
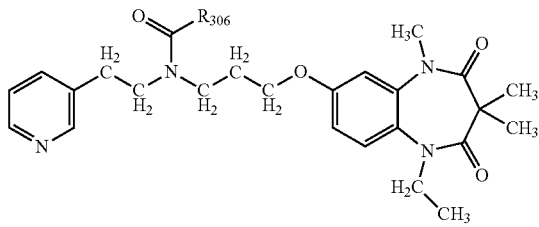
| Example No. | R306 | MS (M + 1) |
|---|---|---|
| Example 1013 | | 578 |
| Example 1014 | | 561 |
| Example 1015 | | 547 |
| Example 1016 | | 563 |
| Example 1017 | | 583 |
| Example 1018 | | 533 |
| Example 1019 | | 569 |
| Example 1020 | | 569 |

TABLE 73
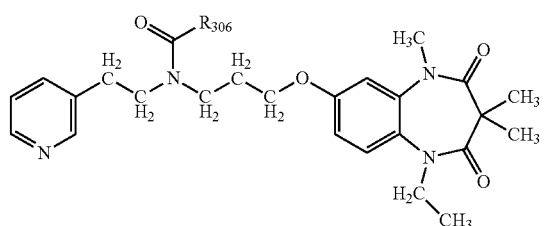
| Example No. | R306 | MS (M + 1) |
|---|---|---|
| Example 1021 | 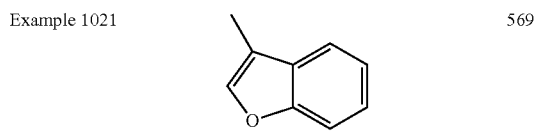 | 569 |
| Example 1022 | 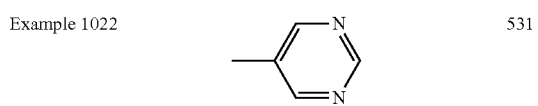 | 531 |
| Example 1023 | 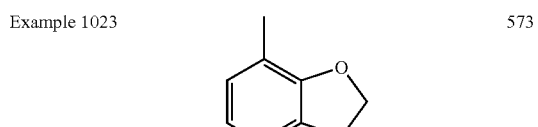 | 573 |
| Example 1024 | 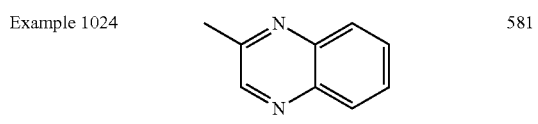 | 581 |
| Example 1025 | 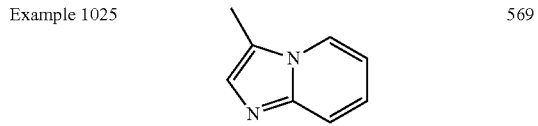 | 569 |
| Example 1026 | 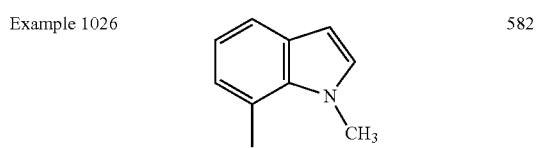 | 582 |
| Example 1027 | 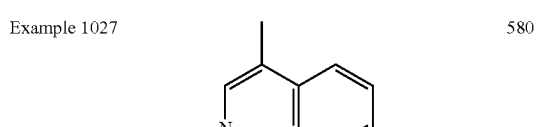 | 580 |
| Example 1028 | 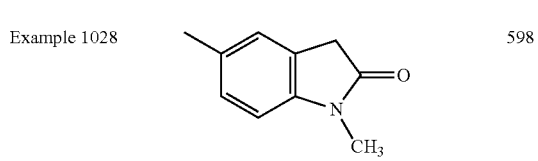 | 598 |
TABLE 74
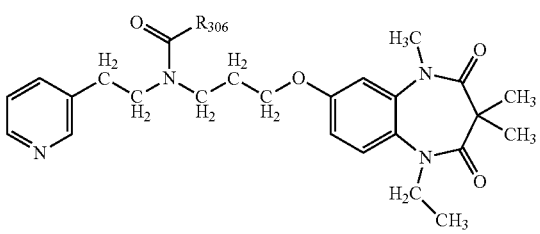
| Example No. | R306 | MS (M + 1) |
|---|---|---|
| Example 1029 | 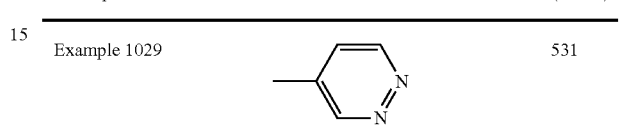 | 531 |
| Example 1030 | 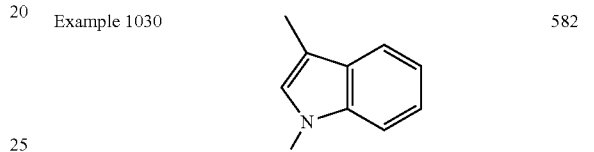 | 582 |
| Example 1031 | 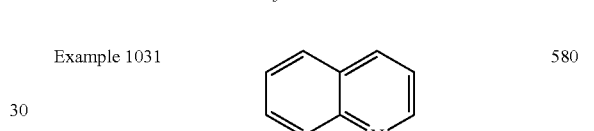 | 580 |
| Example 1032 | 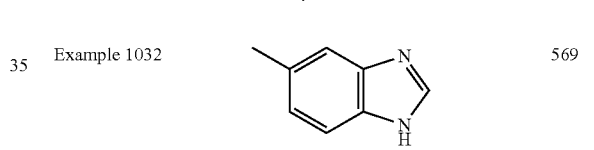 | 569 |
| Example 1033 |  | 545 |
| Example 1034 | 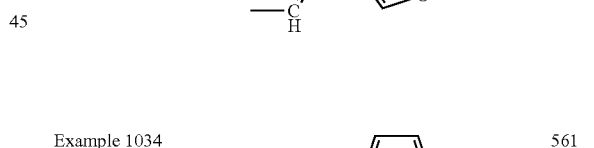 | 561 |
| Example 1035 | 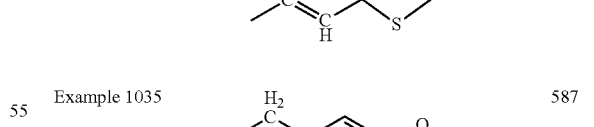 | 587 |
| Example 1036 | 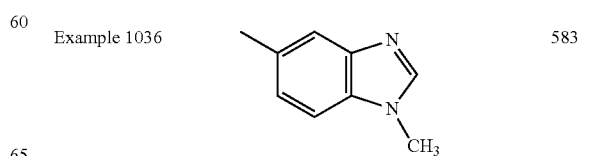 | 583 |

TABLE 75

[Structure shown with R306 group attached via amide to a chain connected to a benzodiazepinedione bearing N-CH3, gem-dimethyl, and N-ethyl groups, with pyridin-3-ylmethyl on the other end]

| Example No. | R306 | MS (M + 1) |
|---|---|---|
| Example 1037 | 6-methyl-1-methyl-indol-2-yl | 582 |
| Example 1038 | 4-methyl-1-methyl-indol-2-yl | 582 |
| Example 1039 | 3-methyl-1-methyl-pyrazol-5-yl | 533 |
| Example 1040 | 5-methyl-1-methyl-indolin-2-yl | 584 |
| Example 1041 | 2-methyl-1,8-naphthyridin-3-yl | 581 |
| Example 1042 | 2-methyl-pyrimidin-4-yl | 531 |
| Example 1043 | 7-methyl-quinolin-2-yl | 580 |

TABLE 76

[Structure shown with R306 group attached via amide linkage to chain connected to a benzodiazepine-2,4-dione bearing N-methyl, gem-dimethyl, and N-ethyl groups, with pyridin-3-ylmethyl substituent]

| Example No. | R306 | MS (M + 1) |
|---|---|---|
| Example 1044 | 5-methyl-quinolin-2-yl | 580 |
| Example 1045 | 2-methyl-indolizin-3-yl | 568 |
| Example 1046 | 4,5-dimethyl-1-methyl-triazol-? | 548 |
| Example 1047 | 4-methyl-1-methyl-pyrazol-3-yl | 533 |

Pharmacological Test 1

(1) Production of Human Kv1.5-Expressing CHO-K1 Cell Lines

CHO-K1 cell lines stably expressing human Kv1.5 channels were prepared in the following manner.

Full-length human Kv1.5 cDNA was cloned from a human heart cDNA library (produced by Stratagene). The obtained human Kv1.5 sequence corresponds to the sequence described in FASEB J. 5, 331-337 (1991).

The obtained human Kv1.5 cDNA was inserted into a plasmid encoding a CMV promoter and a G418 resistance marker to produce a Kv1.5 expression vector. The human Kv1.5 expression vector was transfected into CHO-K1 cells by the lipofectamine method. After culturing the cells in an F-12 medium (produced by Invitrogen Corp.) containing 10% FBS (produced by Invitrogen Corp.) for 3 or 4 days, the medium was replaced with a FBS-containing F-12 medium that included 1,000 µg/ml of G418 (produced by Invitrogen Corp.), and single colonies were isolated. The amount of Kv1.5 channel expression in the single colonies was quantified at the mRNA level by RT-PCR and then quantified at the protein level by western blotting. Finally, the expressed current was analyzed by patch clamp method. Cell lines expressing a current of 200 pA or more per cell were selected as channel-expressing cell lines for activity measurement by patch clamp method.

(2) Production of CHO Cell Line Expressing Human GIRK1/4

CHO cell lines stably expressing human GIRK1/4 channels were prepared in the following manner.

Full-length human GIRK1 cDNA was cloned from HuH cell- and HeLa cell-derived cDNA libraries. Full-length GIRK4 cDNA was amplified from a human heart cDNA library (produced by Clontech Laboratories, Inc.) by PCR using synthetic primers shown in Table 1, and cloned into the Eco-RI restriction enzyme site of pCR-Blunt (produced by Invitrogen Corporation) or into the HincII site of pUC118 (produced by Takara Bio, Inc.).

TABLE 77

| Primer | Sequence | |
|---|---|---|
| hGIRK1-S | 5'-ATGTCTGCACTCCGAAGGAAATTTG-3' | SEQ ID No. 1 |
| hGIRK1-A | 5'-TTATGTGAAGCGATCAGAGTTC-3' | SEQ ID No. 2 |
| hGIRK1-F2 | 5'-GCAGGGTACCCCTTCGTATTATGTCTGCACTCC-3' | SEQ ID No. 3 |
| hGIRK1-A3 | 5'-GGTGTCTGCCGAGATTTGA-3' | SEQ ID No. 4 |
| hGIRK1-A4 | 5'-CCGAGTGTAGGCGATCACCC-3' | SEQ ID No. 5 |
| hGIRK4-S | 5'-ATGGCTGGCGATTCTAGGAATGCC-3' | SEQ ID No. 6 |
| hGIRK4-A | 5'-TCTCACCGAGCCCCTGGCCTCCC-3' | SEQ ID No. 7 |
| hGIRK4-S2 | 5'-AACCAGGACATGGAGATTGG-3' | SEQ ID No. 8 |
| hGIRK4-A2 | 5'-GAGAACAGGAAAGCGGACAC-3' | SEQ ID No. 9 |

The obtained human GIRK1 and GIRK4 cDNA sequences correspond to known sequences (NCBI database: GIRK1 (NM_002239) and GIRK4 (NM_000890) respectively). The obtained GIRK1 and GIRK4 cDNA sequences were cloned into the Eco-RI restriction enzyme site of pCR-Blunt (available from Invitrogen Corporation) or into the HincII site of pUC118 (available from Takara Bio, Inc.). A GIRK4 expression vector was constructed by insertion into the BamHI-XhoI site of pcDNA5/FRT. A GIRK1 expression vector was constructed by insertion into the KpnI-XhoI site of pcDNA3.1(+) or pCAG_neo. FLP-IN-CHO cells (produced by Invitrogen Corporation) were transfected with human GIRK1 and GIRK4 expression vectors by using Lipofectamine 2000 (produced by Invitrogen Corporation) according to the protocol enclosed with the reagent or using an electronic induction method ("Nucleofector Kit-T", produced by Amaxa). First, the cells transfected with the GIRK4 expression vector were cultured in a 10% serum-containing F12 medium (produced by Sigma) supplemented with 600 µg/ml of hygromycin in an incubator with 5% carbon dioxide at 37° C. Then the cells expressing GIRK4 were transfected with the GIRK1 expression vector and were cultured in 10% serum-containing F12 medium supplemented with 350 µg/ml of G418 and 600 µg/ml of hygromycin in an incubator with 5% carbon dioxide at 37° C. to select GIRK1/4 expressing cell lines. Cell populations whose growth was observed after about 2 weeks were isolated using cloning rings, and the obtained single colonies were proliferated. RNA was extracted from single colonies, and single-stranded cDNA was synthesized by a cDNA synthesis kit (produced by Invitrogen Corporation), and the amount of expression was quantified at the mRNA level by real-time PCR (Applied Biosystems, Ltd.). Finally, the expressed current was analyzed by patch clamp method described below. The cell lines expressing a current of 500 pA or more per cell were selected as channel-expressing cell lines for activity measurement by patch clamping method.

(3) Measurement of Ion Channel Current by Patch Clamp Method (Human Kv1.5-Expressing CHO-K1 Cell Line)

An experiment was carried out using a patch clamp setup at room temperature (20 to 26° C.). A perfusion chamber having a diameter of 20 mm (flow rate: about 5 ml/min) was mounted on the stage of a phase-contrast inverted microscope (produced by Nikon Corporation) placed on a vibration isolated table. A poly-L-lysine (produced by Sigma)-coated coverslip (diameter: 15 mm, produced by Matsunami Glass Ind., Ltd.) on which human Kv1.5-expressing cells were cultured was placed in the perfusion chamber.

Depolarizing stimulation pulses were applied and ionic current was recorded by using a patch clamp amplifier (EPC-7 or EPC-7 PLUS, produced by HEKA) and a personal computer (manufactured by IBM Corp.) in which software for data acquisition and analysis of ion channel current (PULSE 8.77, produced by HEKA) was installed. The current was measured in the whole-cell configuration of the patch-clamp technique. The tip (resistance: 2 to 4 MΩ) of a borosilicate glass pipette (produced by Sutter Instrument Co.) was gently placed on the cell membrane by using a three-dimensional mechanical micromanipulator (produced by Shoshin EM Corporation). Weak suction resulted in giga seal formation (the pipette resistance increased to more than 1 GΩ). Subsequently, stronger suction was applied to break the cell membrane. The capacitative current derived from the cell membrane was corrected using a patch clamp amplifier. Subsequently, the series resistance (Rs) between the pipette and the interior of the cell was measured and corrected.

The composition of the extracellular solution used is shown below. Unless otherwise specified, these components were obtained from Wako Pure Chemical Industries, Ltd.

| | |
|---|---|
| NaCl | 140 mM, |
| KCl | 40 mM, |
| $CaCl_2$ | 1.8 mM, |
| $MgCl_2$ | 1 mM, |
| $NaH_2PO_4$ | 0.33 mM, |
| HEPES | 5 mM |
| Glucose | 5.5 mM (pH = 7.4) |

Each test compound was prepared as a 1000-fold concentrated stock solution that was dissolved in DMSO and then diluted in the extracellular solution.

The composition of the electrode internal solution used is shown below. Unless otherwise specified, these components were obtained from Wako Pure Chemical Industries, Ltd.

| | |
|---|---|
| KOH | 100 mM, |
| KCl | 40 mM, |
| Aspartic acid | 70 mM, |
| $MgCl_2$ | 1 mM, |
| MgATP | 5 mM, |
| $K_2$ creatine phosphate | 5 mM, |
| HEPES | 5 mM |
| EGTA | 5 mM (pH = 7.2) |

(4) Measurement of Ion Channel Current by Patch Clamp Method (Human GIRK1/4-Expressing CHO-K1 Cell Line)

An experiment was carried out using a patch clamp setup at room temperature (20 to 26° C.). A perfusion chamber having a diameter of 20 mm (flow rate: about 5 ml/min) was mounted on the stage of a phase-contrast inverted microscope (produced by Nikon Corporation) placed on a vibration isolation table. A poly-L-lysine (produced by Sigma)-coated coverslip (diameter: 15 mm, produced by Matsunami Glass Ind., Ltd.) on which human GIRK1/4-expressing cells were cultured was placed in the perfusion chamber.

Hyperpolarizing stimulation pulses were applied and ionic current was recorded using a patch clamp amplifier (EPC-7 or EPC-7 PLUS, manufactured by HEKA) and a personal computer (manufactured by IBM Corp.) in which software for data acquisition and analysis of ion channel current (PULSE 8.77, manufactured by HEKA) was installed. The current was measured in the whole-cell configuration of the patch-clamp technique. The tip (resistance: 2 to 4 MΩ) of a borosilicate glass pipette (produced by Sutter Instrument Co.) was gently placed on the cell membrane by using a three-dimensional mechanical micromanipulator (produced by Shoshin EM Corporation). Weak suction resulted in giga seal formation (the pipette resistance increased to more than 1 GΩ). Subsequently, stronger suction was applied to break the cell membrane. The capacitative current derived from the cell membrane was corrected using a patch clamp amplifier. Subsequently, the series resistance (Rs) between the pipette and the interior of the cell was measured and corrected.

The composition of the extracellular solution used is shown below. Unless otherwise specified, these components were obtained from Wako Pure Chemical Industries, Ltd.

| | |
|---|---|
| NaCl | 140 mM, |
| KCl | 4 mM, |
| $CaCl_2$ | 1.8 mM, |
| $MgCl_2$ | 1 mM, |
| $NaH_2PO_4$ | 0.33 mM, |
| HEPES | 5 mM |
| Glucose | 5.5 mM (pH = 7.4) |

Each test compound was prepared as a 1000-fold concentrated stock solution that was dissolved in DMSO and then diluted in the extracellular solution.

The composition of the electrode internal solution used is shown below. Unless otherwise specified, these components were obtained from Wako Pure Chemical Industries, Ltd.

| | |
|---|---|
| KOH | 100 mM, |
| KCl | 40 mM, |
| Aspartic acid | 70 mM, |
| $MgCl_2$ | 1 mM, |
| MgATP | 5 mM, |
| $K_2$ creatine phosphate | 5 mM, |
| HEPES | 5 mM |
| EGTA | 5 mM (pH = 7.2) |

(5) Measurement of Human Kv1.5 Current

While the membrane potential was bolded at −80 mV, depolarizing pulses (−80 mV for 0.05 seconds→+40 mV for 0.2 seconds →−40 mV for 0.2 seconds→−80 mV for 0.05 seconds) were applied at a stimulation frequency of 1 Hz to measure Kv1.5 channel current. More specifically, first, while perfusing an extracellular solution containing 0.1% DMSO and holding the membrane potential at −80 mV, depolarizing pulses were applied. The current obtained during the pulse application was recorded as a current in the absence of the test compounds. Subsequently, while perfusing an extracellular solution containing 0.1 μM of a test compound and holding the membrane potential at −80 mV, depolarizing pulses were applied. After the inhibitory effect of the test compound had been stabilized, the current was recorded. The same procedure was repeated using an extracellular solution containing 1 μM of the test compound and then using an extracellular solution containing 10 μM of the test compound. The current obtained using the solution containing the test compound at each concentration was recorded.

The data was analyzed by using the step end current recorded during the +40 mV depolarizing stimulation. The "step end current" refers to the average current flowing for a period of 195 to 199 milliseconds from the start of the +40 mV depolarizing pulse stimulation.

Using the step end current in the presence of the test compound and the step end current in the absence of the test compound, the relative current in the solution containing the test compound at each concentration was calculated according to the following formula:

Relative current=(Step end current in the presence of the test compound)/(Step end current in the absence of the test compound)

(6) Measurement of Human GIRK1/4 Current

While the membrane potential was held at −80 mV, hyperpolarizing pulses (−80 mV for 0.05 seconds→−120 mV for 0.2 seconds→−80 mV for 0.05 seconds) were applied at a stimulation frequency of 1 Hz to measure GIRK1/4 channel current. More specifically, first, while perfusing an extracellular solution containing 0.1% DMSO and maintaining the membrane potential at −80 mV, hyperpolarizing pulses were applied. The current obtained during the pulse application was recorded as the current in the absence of the test compounds. Subsequently, while perfusing an extracellular solution containing 0.1 μM of a test compound and maintaining the membrane potential at −80 mV, hyperpolarizing pulses were applied. After the inhibitory effect of the test compound had been stabilized, the current was recorded. The same procedure was repeated using an extracellular solution containing 1 μM of the test compound and then using an extracellular solution containing 10 μM of the test compound. The current obtained using the solution containing the test compound at each concentration were recorded.

The data was analyzed by using the step end current recorded during the −120 mV depolarizing stimulation. The "step end current" refers to the average current flowing for a period of 195 to 199 milliseconds from the start of the −120 mV depolarizing pulse stimulation.

Using the step end current in the presence of the test compound and the step end current in the absence of the test compound, the relative current in the solution containing the test compound at each concentration was calculated according to the following formula:

Relative current=(Step end current in the presence of the test compound)/(Step end current in the absence of the test compound)

(7) Calculation of Inhibitory Activity on Kv1.5 Channel Ionic Current and GIRK1/4 Channel Current The concentration for 50% inhibition of Kv1.5 channel current or GIRK1/4 channel current ($IC_{50}$ value) was calculated according to the following nonlinear regression equation:

Relative current=$1/(1+[\text{Concentration of the compound}]/IC_{50})^{nH}$ wherein nH is the Hill coefficient.

Table 78 shows the test results.

TABLE 78

| Test Compound | KV1.5 $IC_{50}$ (μM) | GIRK1/4 $IC_{50}$(μM) |
|---|---|---|
| Compound of Example 8 | 0.40 | 0.93 |
| Compound of Example 10 | 0.58 | 3.6 |
| Compound of Example 14 | 0.58 | 0.72 |
| Compound of Example 19 | 0.54 | 1.4 |
| Compound of Example 23 | 0.18 | 0.25 |
| Compound of Example 31 | 1.30 | 2.90 |
| Compound of Example 45 | 0.69 | 2.15 |
| Compound of Example 50 | 0.25 | 0.46 |
| Compound of Example 51 | 0.21 | 1.5 |
| Compound of Example 54 | 0.28 | 0.97 |
| Compound of Example 63 | 0.24 | 0.92 |
| Compound of Example 68 | 0.38 | 5.1 |
| Compound of Example 85 | 0.15 | 0.15 |
| Compound of Example 125 | 0.19 | 0.091 |
| Compound of Example 132 | 0.27 | 0.27 |
| Compound of Example 200 | 0.29 | 0.59 |
| Compound of Example 229 | 0.16 | 0.69 |
| Compound of Example 242 | 0.18 | 0.22 |
| Compound of Example 380 | 0.16 | 0.49 |
| Compound of Example 395 | 0.19 | 0.33 |
| Compound of Example 398 | 0.22 | 0.49 |
| Compound of Example 417 | 0.18 | 0.98 |
| Compound of Example 464 | 0.44 | 3.20 |
| Compound of Example 551 | 0.39 | 5.20 |
| Compound of Example 568 | 0.42 | 0.05 |
| Compound of Example 573 | 0.33 | 1.50 |
| Compound of Example 575 | 0.44 | 0.50 |
| Compound of Example 590 | 0.46 | 2.40 |
| Compound of Example 595 | 0.50 | 0.79 |
| Compound of Example 611 | 0.31 | 0.37 |
| Compound of Example 628 | 0.98 | 2.50 |
| Compound of Example 629 | 0.76 | 0.17 |
| Compound of Example 633 | 1.10 | 8.40 |
| Compound of Example 634 | 0.36 | 0.49 |

The invention claimed is:
1. A benzodiazepine compound of Formula (1)

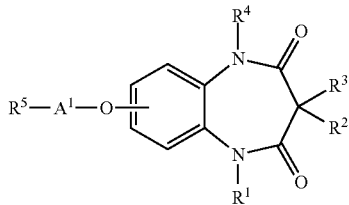

or a pharmaceutically acceptable salt thereof,
wherein $R^1$, $R^2$, $R^3$, and $R^4$ are each independently or lower alkyl;
$R^2$ and $R^3$ may be linked to form lower alkylene;
$A^1$ is lower alkylene optionally substituted with one or more hydroxy; and
$R^5$ is group represented by

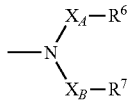

wherein $X_A$ and $X_B$ are each independently bond, lower alkenylene, —CO—, —SO$_2$—, —SO$_2$-lower alkylene, —CO-lower alkenylene, lower alkylene-N(lower alkyl)-CO-lower alkylene, lower alkylene-N(lower alkyl)-, lower alkylene-N(lower alkyl)-CO—or lower alkylene-O—,
wherein $R^6$ and $R^7$ are each independently hydrogen, lower alkyl, cyclo lower alkyl, phenyl, naphthyl, furyl, thienyl, pyrazolyl, oxazolyl, isoxazolyl, thiazolyl, pyrrolyl, triazolyl, pyridyl, pyrimidinyl, pyridazinyl, pyrazinyl, imidazo[2,1-b]thiazolyl, thieno[2,3-b]pyrazinyl, 2,3-dihydroimidazo[2,1-b]thiazolyl, benzothiazolyl, indolyl, imidazo[1,2-a]pyridyl, benzothienyl, benzimidazolyl, 2,3-dihydrobenzo[b]furyl, benzofuryl, indazolyl, furo[2,3-c]pyridyl, furo[3,2-c]pyridyl, thieno[2,3-c]pyridyl, thieno[3,2-c]pyridyl, thieno[2,3-b]pyridyl, benzo[1,3]dioxolyl, benzisoxazolyl, pyrazolo[2,3-a]pyridyl, indolizinyl, 2,3-dihydroindolyl, isoquinolyl, 1,2,3,4-tetrahydro-1H-isoquinolyl, carbostyril, 3,4-dihydrocarbostyril, quinolyl, chromanyl, 5,6,7,8-tetrahydroisoquinolyl, 3,4-dihydro-1H-isoquinolyl, naphthyridinyl, 1,4-benzodioxanyl, cinnolinyl, quinoxalinyl, or 2,3-dihydrobenz-1,4-oxazinyl, each of which is optionally substituted.

2. The benzodiazepine compound of Formula (1) or a pharmaceutically acceptable salt thereof according to claim 1 which is selected from the group consisting of the following compounds:
1-ethyl-3,3,5-trimethyl-7-{3-[(2-pyridin-3-ylethyl)pyridin-4-ylmethylamino]propoxy}-1,5-dihydrobenzo[b][1,4]diazepine-2,4-dione,
3,3,5-trimethyl-1-propyl-7-{3-[(2-pyridin-3-ylethyl)pyridin-4-ylmethylamino]propoxy}-1,5-dihydrobenzo[b][1,4]diazepine-2,4-dione,
1,5-diethyl-3,3-dimethyl-7-{3-[(2-pyridin-3-ylethy)pyridin-4-ylmethylamino]propoxy}-1,5-dihydrobenzo[b][1,4]diazepine-2,4-dione,
1,3,3,5-tetramethyl-7-{3-[(2-pyridin-3-ylethyl)pyridin-4-ylmethylamino]propoxy}-1,5-dihydrobenzo[b][1,4]diazepine-2,4-dione,
1-ethyl-3,3,5-trimethyl-7-(3-{[2-(1-oxo-1H-isoquinolin-2-yl)ethyl]pyridin-4-ylmethylamino}propoxy)-1,5-dihydrobenzo[b][1,4]diazepine-2,4-dione,
1-ethyl-3,3,5-trimethyl-7-(3-{[2-(7-oxo-7H-furo[2,3-c]pyridin-6-yl)ethyl]pyridin-4-ylmethylamino}propoxy)-1,5-dihydrobenzo[b][1,4]diazepine-2,4-dione,
N-methyl-N-(2-{pyridin-4-ylmethyl-[3-(1,3,3,5-tetramethyl-2,4-dioxo-2,3,4,5-tetrahydro-1H-benzo[b][1,4]diazepin-7yloxy)propyl]amino}ethyl)benzamide,
1,3,3,5-tetramethyl-7-{3-[(2-methylbenzyl)-(2-pyridin-3-ylethyl)amino]propoxy}-1,5-dihydrobenzo[b][1,4]diazepine-2,4-dione,
1,3,3,5-tetramethyl-7-{3-[(2-pyridin-3-ylethyl)-(quinolin-4-ylmethyl)amino]propoxy}-1,5-dihydrobenzo[b][1,4]diazepine-2,4-dione,
1-ethyl-3,3,5-trimethyl-7-{3-[(3-methylpyridin-4-ylmethyl)-(2-pyridin-3-ylethy)amino]propoxy}-1,5-dihydrobenzo[b][1,4]diazepine-2,4-dione,
1-ethyl-3,3,5-trimethyl-7-(3-{[2-(2-oxo-2H-quinolin-1-yl)ethyl]pyridin-4-ylmethylamino}propoxy)-1,5-dihydrobenzo[b][1,4]diazepine-2,4-dione,
1-ethyl-3,3,5-trimethyl-7-(3-{[2-(7-oxo-7H-thieno[2,3-c]pyridin-6-yl(ethyl]pyridin-4-ylmethylamino}propoxy)-1,5-dihydrobenzo[b][1,4]diazepine-2,4-dione,
4-({[3-(1-ethyl-3,3,5-trimethyl-2,4-dioxo-2,3,4,5-tetrahydro-1H-benzo[b][1,4]diazepin-7-yloxy)propyl]-[2-(1-oxo-1H-isoquinolin-2-yl)ethyl]amino}methyl)benzonitrile,
1-ethyl-3,3,5-trimethyl-7-(3-{[2-(1-oxo-1H-isoquinolin-2-yl)ethyl]thiophen-3-ylmethylamino}propoxy)-1,5-dihydrobenzo[b][1,4]dazepine-2,4-dione,
1-ethyl-7-(3-{furan-2-ylmethyl-[2-(1-oxo-1H-isoquinolin-2-)ethyl]amino}propoxy)-3,3,5-trimethyl-1,5-dihydrobenzo[b][1,4]diazepine-2,4-dione,
7-{3-[benzyl-(2-pyridin-3-ylethyp)amino]propoxy}-1-ethyl-3,3,5-trimethyl-1,5-dihydrobenzo[b][1,4]diazepine-2,4-dione,
3-{[[3-(1-ethyl-3,3,5-trimethyl-2,4-dioxo-2,3,4,5-tetranydro-1H-benzo[b][1,4]diazepin-7-yloxy)propyl]-(2-pyridin-3-ylethyl)amino]methyl}benzonitrile,
1-ethyl-3,3,5-trimethyl-7-{3-[(2-pyridin-3-ylbenzyl)-(2-pyridin-3-ylethyl)amino]propoxy}-1,5-dihydrobenzo[b][1,4]diazepine-2,4-dione,
4-({[3-(1-ethyl-3,3,5-trirnethyl-2,4-dioxo-2,3,4,5-tetrahydro-1H-benzo[b][1,4]diazepin-7-yloxy)propyl]-[2-(7-oxo-7H-furo[2,3-c]pyridin-6-yl)ethyl]amino}methyl)benzonitrile,
1-ethyl-3,3,5-trimethyl-7-{3-[[2-(7-oxo-7H-furo[2,3-c]pyridin-6yl)-ethyl]-(4-trifluoromethylbenzy)amino]propoxy}-1,5-dihydro-benzo[b][1,4]diazepine-2,4-dione,
1-ethyl-3,3,5-trimethyl-7-(3-{(2-methylbenzyl)-[2-(7-oxo-7H-furo[2,3-o]pyridin-6-yl)ethyl]amino}propoxy)-1,5-dihydrobenzo[b][1,4]diazepine-2,4-dione,
1-ethyl-3,3,5-trimethyl-7-(3-{[2-(7-oxo-7H-furo[2,3-c]pyridin-6-yl)ethyl]thiophen-2-ylmethylamino}propoxy)-1,5-dihydrobenzo[b][1,4]diazepine-2,4-dione,
1-ethyl-3,3,5-trimethyl-7-(3-{[2-(2-methyl-4-oxo-4H-furo[3,2-c]pyridin-5-yl)ethyl]pyridin-4-ylmethylamino}propoxy)-1,5-dihydrobenzo[b][1,4]diazepine-2,4-dione, 1-ethyl-3,3,5-trimethyl-7-(3-{[2-(4-oxo-4H-furo[3,2-c]pyridin-5-yl)ethyl]pyridin-3-ylmethylamino}propoxy)-1.5-dihydrobenzo[b][1,4]diazepine-2,4-dione, 1-ethyl-3,3,5-trimethyl-7-(3-{[2-(4-oxo-4H-thieno[3,2-c]pyridin-5-yl)ethyl]pyridin-3-ylmethylamino}propoxy)-1,5-dihydrobenzo[b][1,4]diazepine-2,4-dione, 1-ethyl-3,3,5-trimethyl-7-{3[[2-(2-methyl-4-oxo-4H-furo[3,2-c]pyridin-5-yl)ethyl]-(4-methylpyridin-3-ylmethyl)amino]propoxy}-1,5-dihydrobenzo[b][1,4]diazepine-2,4-dione, 1-ethyl-3,3,5-trimethyl-7-(3-{(2-methylpyridin-3-ylmethyl)-[2-(4-oxo-4H-furo[3,2-c]pyridin-5-yl)ethyl]amino}propoxy)-1,5-dihydrobenzo[b][1,4]diazepine-2,4-dione, 1-ethyl-3,3,5-trimethyl-7-(3-{(4-methylpyridin-3-ylmethyl)-[2-(4-oxo-4H-furo[3,2-c]pyridin-5-yl)ethyl]amino}propoxy)-1,5-dihydrobenzo[b][1,4]diazepine-2,4-dione, 1-ethyl-3,3,5-trimethyl-7-(3-{(2-methylpyridin-3-ylmethyl)12-(4-oxo-4H-thieno[3,2-c]pyridin-5-yl)ethyl]amino}propoxy)-1,5-dihydrobenzo[b][1,4]diazepine-2,4-dione, 1-ethyl-3,3,5-trimethyl-7-{3-[[2-(2-methyl-4-oxo-4H-furo[3,2-c]pyridin-5-yl)ethyl]-(2-propylpyridin-3-ylmethyl)amino]propoxy}-1,5-dihydrobenzo[b][1,4]diazepine-2,4-dione, N-[3-(1-ethyl-3,3,5-trimethyl-2,4-dioxo-2,3,4,5-tetrahydro-1H-benzo[b][1,4]diazepin-7-yloxy)propyl]-N-(2-pyridin-3-ylethyl}benzenesulfonamide, 7-(3-{(2,6-dimethylpyridin-3-ylmethyl)-[2-(4-oxo-4H-furo[3,2-c]pyridin-5-yl)ethyl]amino}propoxyl-1-ethyl-3,3,5-trimethyl-1,5-dihydrobenzo[b][1,4]diazepine-2,4-done, N-[3-(1-ethyl-3,3,5-trimethyl-2,4-dioxo-2,3,4,5-tetrahydro-1H-benzo[b][1,4]diazepin-7-yloxy)propyl]-(2-pyridin-3-ylethyl)benzamide, N-[3-(1-ethyl-3,3,5-trimethyl-2,4-dioxo-2,3,4,5-tetrahydro-1H-benzo[b][1,4]diazepin-7-yloxy)propyl]-N-[2-(1-oxo-1H-isoquinolin-2-yl)ethyl]benzenesulfonamide, and a pharmaceutically acceptable salt of any one of the aforementioned compounds.

\* \* \* \* \*

UNITED STATES PATENT AND TRADEMARK OFFICE
CERTIFICATE OF CORRECTION

PATENT NO. : 8,664,217 B2
APPLICATION NO. : 13/591361
DATED : March 4, 2014
INVENTOR(S) : Kunio Oshima et al.

It is certified that error appears in the above-identified patent and that said Letters Patent is hereby corrected as shown below:

Title Page, item [57] Abstract, Line 9, "$A^{l}$" should read as --$A^1$--.

In the Claims

Claim 1, Col. 225, Line 16, "independently or" should read as --independently hydrogen or--.
Claim 1, Col. 225, Line 19, "$A^{l}$" should read as --$A^1$--.

Claim 2, Col. 226, Lines 36-38,
"1-ethyl-7-(3-{furan-2-ylmethyl-[2-(1-oxo-1H-isoquinolin-2-)ethyl]amino}propoxy)-3,3,5-trimethyl-1,5-dihydrobenzo[b][1,4]diazepine-2,4-dione,"
should read as
--1-ethyl-7-(3-{furan-2-ylmethyl-[2-(1-oxo-1H-isoquinolin-2-yl)ethyl]amino}propoxy)-3,3,5-trimethyl-1,5-dihydrobenzo[b][1,4]diazepine-2,4-dione,--.

Claim 2, Col. 226, Lines 39-41, "7-{3-[benzyl-(2-pyridin-3-ylethyp)amino]propoxy}-1-ethyl-3,3,5-trimethyl-1,5-dihydrobenzo[b][1,4]diazepine-2,4-dione,"
should read as
--7-{3-[benzyl-(2-pyridin-3-ylethyl)amino]propoxy}-1-ethyl-3,3,5-trimethyl-1,5-dihydrobenzo[b][1,4]diazepine-2,4-dione,--.

Claim 2, Col. 226, Lines 42-44, "3-{[[3-(1-ethyl-3,3,5-trimethyl-2,4-dioxo-2,3,4,5-tetranydro-1H-benzo[b][-1,4]diazepin-7-yloxy)propyl]-(2-pyridin-3-ylethyl)amino]methyl}benzonitrile,"
should read as
--3-{[[3-(1-ethyl-3,3,5-trimethyl-2,4-dioxo-2,3,4,5-tetrahydro-1H-benzo[b][- 1,4]diazepin-7-yloxy)propyl]-(2-pyridin-3-ylethyl)amino]methyl}benzonitrile,--.

Claim 2, Col. 226, Lines 52-55, "1-ethyl-3,3,5-trimethyl-7-{3-[[2-(7-oxo-7H-furo[2,3-c]pyridin-6yl)-ethyl]-(4-trifluoromethylbenzy)amino]propoxy}-1,5-dihydro-benzo[b][1,4]diazepine-2,4-dione,"
should read as Signed and Sealed this
Twenty-ninth Day of July, 2014

Michelle K. Lee
*Deputy Director of the United States Patent and Trademark Office*

CERTIFICATE OF CORRECTION (continued)
U.S. Pat. No. 8,664,217 B2

--1-ethyl-3,3,5-trimethyl-7-{3-[[2-(7-oxo-7H-furo[2,3-c]pyridin-6-yl)-ethyl]-(4-trifluoromethylbenzy)amino]propoxy}-1,5-dihydrobenzo[b][1,4]diazepine-2,4-dione,--.

Claim 2, Col. 227, Lines 1-4, "1-ethyl-3,3,5-trimethyl-7-(3-{[2-(4-oxo-4H-furo[3,2-c]pyridin-5-yl)ethyl]- pyridin-3-ylmethylamino}propoxy)-1.5-dihydrobenzo[b][1,4)diazepine-2,4-dione," should read as
--1-ethyl-3,3,5-trimethyl-7-(3-{[2-(4-oxo-4H-furo[3,2-c]pyridin-5-yl)ethyl]- pyridin-3-ylmethylamino}propoxy)-1,5-dihydrobenzo[b][1,4]diazepine-2,4-dione,--.

Claim 2, Col. 227, Line 20, "1-ethyl-3,3,5-trimethyl-7-(3-{(2-methylpyridin-3-ylmethyl)12-(4-oxo-4H-thieno[3,2-c]pyridin-5-yl)ethyl]amino}propoxy)-1,5-dihydrobenzo[b][1,4]diaze-pine-2,4-dione," should read as
--1-ethyl-3,3,5-trimethyl-7-(3-{(2-methylpyridin-3-ylmethyl)-[2-(4-oxo-4H-thieno[3,2-c]pyridin-5-yl)ethyl]amino}propoxy)-1,5-dihydrobenzo[b][1,4]diaze-pine-2,4-dione,--.

Claim 2, Col. 228, Line 8, "7-(3-{(2,6-dimethylpyridin-3-ylmethyl)-[2-(4-oxo-4H-furo[3,2-c]pyridin-5--yl)ethyl]amino}propoxyl-1-ethyl-3,3,5-trimethyl-1,5-dihydrobenzo[b][1,4]diazepine-2,4-done," should read as
--7-(3-{(2,6-dimethylpyridin-3-ylmethyl)-[2-(4-oxo-4H-furo[3,2-c]pyridin-5--yl)ethyl]amino}propoxyl-1-ethyl-3,3,5-trimethyl-1,5-dihydrobenzo[b][1,4]diazepine-2,4-dione,--.

SEQUENCE LISTING

```
<160> NUMBER OF SEQ ID NOS: 9

<210> SEQ ID NO 1
<211> LENGTH: 25
<212> TYPE: DNA
<213> ORGANISM: artificial sequence
<220> FEATURE:
<223> OTHER INFORMATION: Primer

<400> SEQUENCE: 1
atgtctgcac tccgaaggaa atttg                                         25

<210> SEQ ID NO 2
<211> LENGTH: 22
<212> TYPE: DNA
<213> ORGANISM: artificial sequence
<220> FEATURE:
<223> OTHER INFORMATION: Primer

<400> SEQUENCE: 2
ttatgtgaag cgatcagagt tc                                            22

<210> SEQ ID NO 3
<211> LENGTH: 33
<212> TYPE: DNA
<213> ORGANISM: artificial sequence
<220> FEATURE:
<223> OTHER INFORMATION: Primer

<400> SEQUENCE: 3
gcagggtacc ccttcgtatt atgtctgcac tcc                                33

<210> SEQ ID NO 4
<211> LENGTH: 19
```

```
<212> TYPE: DNA
<213> ORGANISM: artificial sequence
<220> FEATURE:
<223> OTHER INFORMATION: Primer

<400> SEQUENCE: 4
ggtgtctgcc gagatttga                                               19

<210> SEQ ID NO 5
<211> LENGTH: 20
<212> TYPE: DNA
<213> ORGANISM: artificial sequence
<220> FEATURE:
<223> OTHER INFORMATION: Primer

<400> SEQUENCE: 5
ccgagtgtag gcgatcaccc                                              20

<210> SEQ ID NO 6
<211> LENGTH: 24
<212> TYPE: DNA
<213> ORGANISM: artificial sequence
<220> FEATURE:
<223> OTHER INFORMATION: Primer

<400> SEQUENCE: 6
atggctggcg attctaggaa tgcc                                         24

<210> SEQ ID NO 7
<211> LENGTH: 23
<212> TYPE: DNA
<213> ORGANISM: artificial sequence
<220> FEATURE:
<223> OTHER INFORMATION: Primer

<400> SEQUENCE: 7
tctcaccgag cccctggcct ccc                                          23

<210> SEQ ID NO 8
<211> LENGTH: 20
<212> TYPE: DNA
<213> ORGANISM: artificial sequence
<220> FEATURE:
<223> OTHER INFORMATION: Primer

<400> SEQUENCE: 8
aaccaggaca tggagattgg                                              20

<210> SEQ ID NO 9
<211> LENGTH: 20
<212> TYPE: DNA
<213> ORGANISM: artificial sequence
<220> FEATURE:
<223> OTHER INFORMATION: Primer

<400> SEQUENCE: 9
gagaacagga aagcggacac                                              20
```